(12) United States Patent
Moslin et al.

(10) Patent No.: US 11,021,475 B2
(45) Date of Patent: *Jun. 1, 2021

(54) AMIDE-SUBSTITUTED HETEROCYCLIC COMPOUNDS USEFUL AS MODULATORS OF IL-12, IL-23 AND/OR IFN ALPHA RESPONSES

(71) Applicant: Bristol-Myers Squibb Company, Princeton, NJ (US)

(72) Inventors: Ryan M. Moslin, Princeton, NJ (US); David S. Weinstein, San Diego, CA (US); Stephen T. Wrobleski, Flemington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/687,279

(22) Filed: Nov. 18, 2019

(65) Prior Publication Data

US 2020/0071315 A1 Mar. 5, 2020

Related U.S. Application Data

(63) Continuation of application No. 15/979,770, filed on May 15, 2018, now Pat. No. 10,526,321, which is a continuation of application No. 15/289,437, filed on Oct. 10, 2016, now Pat. No. 10,000,480, which is a continuation of application No. 14/441,183, filed as application No. PCT/US2013/068846 on Nov. 7, 2013, now Pat. No. 9,505,748.

(60) Provisional application No. 61/723,840, filed on Nov. 8, 2012.

(51) Int. Cl.

| C07D 417/14 | (2006.01) |
|---|---|
| C07D 417/12 | (2006.01) |
| C07B 59/00 | (2006.01) |
| C07D 413/12 | (2006.01) |
| C07D 403/14 | (2006.01) |
| C07D 237/24 | (2006.01) |
| C07D 401/12 | (2006.01) |
| C07D 413/14 | (2006.01) |
| C07D 401/14 | (2006.01) |
| C07D 403/12 | (2006.01) |

(52) U.S. Cl.
CPC .......... *C07D 417/14* (2013.01); *C07B 59/002* (2013.01); *C07D 237/24* (2013.01); *C07D 401/12* (2013.01); *C07D 401/14* (2013.01); *C07D 403/12* (2013.01); *C07D 403/14* (2013.01); *C07D 413/12* (2013.01); *C07D 413/14* (2013.01); *C07D 417/12* (2013.01); *C07B 2200/05* (2013.01)

(58) Field of Classification Search
CPC .. C07D 417/12; C07D 413/12; C07D 403/14; C07D 237/24; C07D 401/12; C07D 413/14; C07D 401/14; C07D 403/12
USPC ........................................................ 544/326
See application file for complete search history.

(56) References Cited

U.S. PATENT DOCUMENTS

| 9,505,748 B2 * | 11/2016 | Moslin .................... A61P 19/02 |
| 9,540,333 B2 * | 1/2017 | Santella ............... C07D 239/48 |
| RE47,929 E * | 4/2020 | Moslin ................. C07D 413/12 |
| 2002/0061865 A1 | 5/2002 | Kramer et al. |
| 2004/0142930 A1 | 7/2004 | Yamada et al. |

FOREIGN PATENT DOCUMENTS

| EP | 1184376 A1 | 3/2002 |
| WO | WO-0075113 A1 | 12/2000 |
| WO | WO-0076980 A1 | 12/2000 |
| WO | WO-2004007682 A2 | 1/2004 |
| WO | WO 2004/106293 A2 | 12/2004 |
| WO | WO-2011113802 A2 | 9/2011 |
| WO | WO-2012035039 A1 | 3/2012 |
| WO | WO 2012/066061 A1 | 5/2012 |
| WO | WO-2013047813 A1 | 4/2013 |
| WO | WO-2013104573 A1 | 7/2013 |
| WO | WO-2013171690 A1 | 11/2013 |
| WO | WO-2013192049 A2 | 12/2013 |

(Continued)

OTHER PUBLICATIONS

Barder, T. E. et al., "Catalysts for Suzuki-Miyaura Coupling Processes: Scope and Studies of the Effect of Ligand Structure," *Journal of the American Chemical Society*, 127:4685-4696 (2005).

(Continued)

*Primary Examiner* — Tracy Vivlemore
*Assistant Examiner* — Ebenezer O Sackey
(74) *Attorney, Agent, or Firm* — Covington & Burling LLP

(57) ABSTRACT

Compounds having the following formula I:

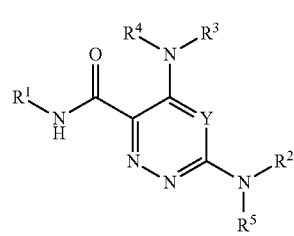

or a stereoisomer or pharmaceutically-acceptable salt thereof, where $R^1$, $R^2$, $R^3$, $R^4$, and $R^5$ are as defined herein, are useful in the modulation of IL-12, IL-23 and/or IFNα, by acting on Tyk-2 to cause signal transduction inhibition.

16 Claims, No Drawings

Specification includes a Sequence Listing.

(56) References Cited

FOREIGN PATENT DOCUMENTS

| | | |
|---|---|---|
| WO | WO-2014060371 A1 | 4/2014 |
| WO | WO-2014074660 A1 | 5/2014 |
| WO | WO-2014074661 A1 | 5/2014 |
| WO | WO-2014074670 A1 | 5/2014 |
| WO | WO-2015069310 A1 | 5/2015 |
| WO | WO-2018183649 A1 | 10/2018 |

OTHER PUBLICATIONS

Bave, U. et al., "Activation of the Type I Interferon System in Primary Sjogren's Syndrome: A Possible Etiopathogenic Mechanism," *Arthritis Rheum.*, 52:1185-1195 (2005).

Bengtsson, A. A. et al., "Activation of type I interferon system in systemic lupus erythematosus correlates with disease activity but not with antiretroviral antibodies," *Lupus*, 9:664-671 (2000).

Bennett, L. et al., "Interferon and Granulopoiesis Signatures in Systemic Lupus Erythematosus Blood," *The Journal of Experimental Medicine*, 197:711-723 (2003).

Bundgaard, H., ed., Design of Prodrugs, Elsevier (1985).

Bundgaard, H., "Design and Application of Prodrugs," Krosgaard-Larsen, P. et al eds., *A Textbook of Drug Design and Development*, 113-191, Harwood Academic Publishers (1991).

Bundgaard, H., "Penetration Enhancement for Polypeptides through Epithelia: (C) Means to Enhance Penetration," *Advanced Drug Delivery Reviews*, 8:1-38 (1992).

Caron, S., "Synthesis of Common Aromatic Heterocycles," *Practical Synthetic Organic Chemistry*, 609-647 (2011).

Chinchilla, R. et al., "The Sonogashira Reaction: A Booming Methodology in Synthetic Organic Chemistry," *Chemical Reviews* 107:874-923 (2007).

Chinchilla, R. et al., "Recent advances in Sonogashira reactions," *The Royal Society of Chemistry*, 40:5084-5121 (2011).

Cho, J. H. et al., "Recent insights into the genetics of inflammatory bowel disease," *Gastroenterology*, 140:1704-1712 (2011).

Couturier, N. et al., "Tyrosine kinase 2 variant influences T lymphocyte polarization and multiple sclerosis susceptibility," *Brain*, 134:693-703 (2011).

Cua, D. J. et al., "Interleukin-23 rather than interleukin-12 is the critical cytokine for autoimmune inflammation of the brain," *Nature*, 421:744-748 (2003).

Deng, Y. et al., "Genetic susceptibility to systemic lupus erythematosus in the genomic era," *Nat. Rev. Rheumatol.*, 6:683-692 (2010).

Dyckman et al., "Imidazo[4,5-d]thiazolo[5,4-b]pyridine based inhibitors of IKK2: Synthesis, SAR, PK/PD and activity in a preclinical model of rheumatoid arthritis," *Bioorganic and Medicinal Chemistry Letters*, 383-386 (2011).

El-Ahl, A-A. S. et al., "A novel approach for the synthesis of 5-substituted tetrazole derivatives from primary amides in mild one-step method," *Tetrahedron Letters*, 38:1257-1260 (1997).

Ellinghaus, D. et al., "Combined Analysis of Genome-wide Association Studies for Crohn Disease and Psoriasis Identifies Seven Shared Susceptibility Loci," *The American Society of Human Genetics*, 90:636-647 (2012).

Extended European Search Report dated Feb. 22, 2019, issued in Application No. 18197550.9-1116.

Eyre, S. et al., "High-density genetic mapping identifies new susceptibility loci for rheumatoid arthritis," *Nat. Genet.*, 44:1336-1340 (2012).

Garnier, E. et al., "New Polynitrogen Materials Based on Fused 1,2,4-Triazines," *Synlett*, 472-474 (2006).

Gottlieb, A. et al., "Ustekinumab, a human interleukin 12/23 monoclonal antibody, for psoriatic arthritis: randomized, double-blind, placebo-controlled, crossover trial," *Lancet*, 373:633-640 (2009).

Gracie, J. A. et al., "Interleukin-12 induces interferon-gamma-dependent switching of IgG alloantibody subclass," *Eur. J. Immunol.*, 26:1217-1221 (1996).

Graham, D. et al., "Association of polymorphisms across the tyrosine kinase gene, TYK2 in UK SLE families," *Rheumatology (Oxford)*, 46:927-930 (2007).

Grecian, S. et al., "Ruthenium-Catalyzed Cycloaddition of Nitrile Oxides and Alkynes: Practical Synthesis of Isoxazoles," *Angew. Chem. Int. Ed.*, 47:8285-8287 (2008).

Hall, J. C. et al., "Type I interferons: crucial participants in disease amplification in autoimmunity," *Nat. Rev. Rheumatol.*, 6:40-49 (2010).

Hong, K. et al., "IL-12, Independently of Ifn-$\gamma$, Plays a Crucial Role in the Pathogenesis of a Murine Psoriasis-Like Skin Disorder," *The Journal of Immunology*, 162:7480-7491 (1999).

Huang, X. et al., "Dysregulated expression of interleukin-23 and interleukin-12 subunits in systemic lupus erythematosus patients," *Mod. Rheumatol.*, 17:220-223 (2007).

Hue, S. et al., "Interleukin-23 drives innate and T cell-mediated intestinal inflammation," *J. Exp. Med.*, 203:2473-2483 (2006).

Ishiyama, T. et al., "Palladium(0)-Catalyzed Cross-Coupling Reaction of Alkoxydiboron with Haloarenes: A Direct Procedure for Arylboronic Esters," *The Journal of Organic Chemistry*, 60:7508 (1995).

Ishizaki, M. et al., "Involvement of Tyrosine Kinase-2 in Both the IL-12/Th1 and IL-23/Th17 Axes In Vivo," *The Journal of Immunology*, 187:181-189 (2011).

Kim, D. et al., "Induction of Interferon-$\alpha$ by Scleroderma Sera Containing Autoantibodies to Topoisomerase I: Association of Higher Interferon-$\alpha$ Activity With Lung Fibrosis," *Arthritis Rheum.*, 58:2163-2173 (2008).

Kolb, H. C. et al., "Click Chemistry: Diverse Chemical Function from a Few Good Reactions," *Angew. Chem. Int. Ed.*, 40:2004-2021 (2001).

Kyttaris, V. C. et al., "Cutting Edge: IL-23 Receptor Deficiency Prevents the Development of Lupus Nephritis in C57BL/6-Ipr/Ipr mice," *The Journal of Immunology*, 184:4605-4609 (2010).

Lee, E. et al., "Increased Expression of Interleukin 23 p19 and p40 in Lesional Skin of Patients with Psoriasis Vulgaris," *The Journal of Experimental Medicine*, 199:125-130 (2004).

Lees, C. W. et al., "New IBD genetics: common pathways with other diseases," *Gut*, 60:1739-1753 (2011).

Leonardi, C. L. et al., "Efficacy and safety of ustekinumab, a human interleukin-12/23 monoclonal antibody, in patients with psoriasis: 76-week results from a randomised, double-blind, 40 placebo-controlled trial (PHOENIX 1)," *Lancet*, 371:1665-1674 (2008).

McGeachy, M. J. et al., "The link between IL-23 and Th17 cell-mediated immune pathologies," *Semin. Immunol.*, 19:372-376 (2007).

Meldal, M. et al., "Cu-Catalyzed Azide-Alkyne Cycloaddition" *American Chemical Society*, 108:2952-3015 (2008).

Minegishi, Y. et al., "Human Tyrosine Kinase 2 Deficiency Reveals its Requisite Roles in Multiple Cytokine Signals Involved in Innate and Acquired Immunity," *Immunity*, 25:745-755 (2006).

Miyaura, N. et al., "Palladium-Catalyzed Cross-Coupling Reactions of Organoboron Compounds," *American Chemical Society*, 95:2457-2483 (1995).

Monnier, F. et al., "Catalytic C—C, C—N, and C—O Ullmann-Type Coupling Reactions," *Angew. Chem. Int. Ed.*, 48:6954-6971 (2009).

Murphy, C. A. et al., "Divergent Pro- and Anti-Inflammatory Roles for IL-23 and IL-12 in Joint Autoimmune Inflammation," *The Journal of Experimental Medicine*, 198:1951-1957 (2003).

Oyamada, A. et al., "Tyrosine Kinase 2 Plays Critical Roles in the Pathogenic CD4 T Cell Responses for the Development of Experimental Autoimmune Encephalomyelitis," *The Journal of Immunology*, 183:7539-7546 (2009).

Peterson, K. S. et al., "Characterization of Heterogeneity in the Molecular Pathogenesis of Lupus Nephritis from Transcriptional Profiles of Laser-captured Glomeruli," *The Journal of Clinical Investigation*, 113:1722-1733 (2004).

Prchal-Murphy, M. et al., "TYK2 Kinase Activity is Required for Functional Type I Interferon Responses In Vivo," *PLoS One*, 7:e39141 (2012).

Sandborn, W. J. et al., "Ustekinumab Crohn's Disease Study Group. A randomized trial of Ustekinumab, A Human Interleukin-12/23

(56) References Cited

OTHER PUBLICATIONS

Monoclonal Antibody, in Patients with Moderate-to-Severe Crohn's Disease," *Gastroenterology*, 135:1130-1141 (2008).

Sandling, J. K. et al., "A Candidate Gene Study of the Type I Interferon Pathway Implicates IKBKE and IL8 as Risk Loci for SLE," *European Journal of Human Genetics*, 19:479-484 (2011).

Santiago-Raber, M. L. et al., "Type-I interferon Receptor Deficiency Reduces Lupus-Like Disease in NZB Mice," *J. Exp. Med.*, 197:777-788 (2003).

Schroder, K. et al., "Interferon-γ: an overview of signals, mechanisms and functions," *J. Leukoc. Biol.*, 75(2):163-189 (2004).

Stanforth, S. P., "Catalytic Cross-coupling Reactions in Biaryl Synthesis," *Tetrahedron*, 54:263-303 (1998).

Surry, D.S. et al., "Dialkylbiaryl phosphines in Pd-catalyzed amination: a user's guide," *Chemical Science*, 2:27-50 (2011).

Tao, J. H. et al., "Meta-analysis of TYK2 gene polymorphisms association with susceptibility to autoimmune and inflammatory diseases," *Mol. Biol. Rep.*, 38:4663-4672 (2011).

Tucci, M. et al., "Overexpression of interleukin-12 and T helper 1 predominance in lupus nephritis," *Clinical Experimental Immunology*, 154:247-254 (2008).

Tzartos, J. S. et al., "Interleukin-17 Production in Central Nervous System Infiltrating T Cells and Glial Cells is Associated with Active Disease in Multiple Sclerosis," *The American Journal of Pathology*, 172:146-155 (2008).

Widder, K. et al., eds., *Methods in Enzymology*, 112:309-396, Academic Press (1985).

\* cited by examiner

AMIDE-SUBSTITUTED HETEROCYCLIC COMPOUNDS USEFUL AS MODULATORS OF IL-12, IL-23 AND/OR IFN ALPHA RESPONSES

FIELD OF THE INVENTION

This invention relates to compounds useful in the modulation of IL-12, IL-23 and/or IFNα by acting on Tyk-2 to cause signal transduction inhibition. Provided herein are amide-substituted heterocyclic compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", *Semin. Immunol.*, 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", *Eur. J. Immunol.*, 26:1217-1221 (1996); Schroder, K. et al., "Interferon-gamma: an overview of signals, mechanisms and functions", *J. Leukoc. Biol.*, 75(2): 163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", *J. Immunol.*, 184:4605-4609 (2010); Hong, K. et al., "IL-12, independently of IFN-gamma, plays a crucial role in the pathogenesis of a murine psoriasis like skin disorder", *J. Immunol.*, 162:7480-7491 (1999); Hue, S. et al., "Interleukin-23 drives innate and T cell-mediated intestinal inflammation", *J. Exp. Med.*, 203:2473-2483 (2006); Cua, D. J. et al., "Interleukin-23 rather than interleukin-12 is the critical cytokine for autoimmune inflammation of the brain", Nature, 421:744-748 (2003); Murphy, C. A. et al., "Divergent pro- and anti-inflammatory roles for IL-23 and IL-12 in joint autoimmune inflammation", *J. Exp. Med.*, 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", *J. Exp. Med.*, 199:125-130 (2004); Tzartos, J. S. et al., "Interleukin-17 production in central nervous system infiltrating T cells and glial cells is associated with active disease in multiple sclerosis", *Am. J. Pathol.*, 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", *Mod. Rheumatol.*, 17:220-223 (2007)), and T cells from lupus patients have a predominant Th1 phenotype (Tucci, M. et al., "Overexpression of interleukin-12 and T helper 1 predominance in lupus nephritis", *Clin. Exp. Immunol.*, 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", *Gut*, 60:1739-1753 (2011); Tao, J. H. et al., "Meta-analysis of TYK2 gene polymorphisms association with susceptibility to autoimmune and inflammatory diseases", *Mol. Biol. Rep.*, 38:4663-4672 (2011); Cho, J. H. et al., "Recent insights into the genetics of inflammatory bowel disease", *Gastroenterology*, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", *Lancet*, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", *Gastroenterology*, 135:1130-1141 (2008); Gottlieb, A. et al., "Ustekinumab, a human interleukin 12/23 monoclonal antibody, for psoriatic arthritis: randomized, double-blind, placebo-controlled, crossover trial", *Lancet*, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.*, 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.*, 187:181-189 (2011); Prchal-Murphy, M. et al., "TYK2 kinase activity is required for functional type I interferon responses in vivo", *PLoS One*, 7:e39141 (2012)) and humans (Minegishi, Y. et al., "Human tyrosine kinase 2 deficiency reveals its requisite roles in multiple cytokine signals involved in innate and acquired immunity", *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.*, 187:181-189 (2011); Oyamada, A. et al., "Tyrosine kinase 2 plays critical roles in the pathogenic CD4 T cell responses for the development of experimental autoimmune encephalomyelitis", *J. Immunol.*, 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility", *Brain*, 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.*, 90:636-647 (2012); Graham, D. et al., "Association of polymorphisms across the tyrosine kinase gene, TYK2 in UK SLE families", *Rheumatology (Oxford)*, 46:927-930 (2007); Eyre, S. et al., "High-density genetic mapping identifies new susceptibility loci for rheumatoid arthritis", *Nat. Genet.*, 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

An alternate preferred embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE EMBODIMENTS OF THE INVENTION

Provided herein is at least one chemical entity chosen from compounds of formula I:

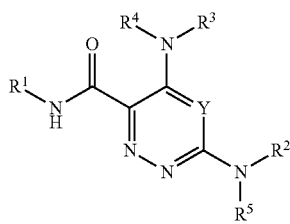

I or stereoisomers, tautomers, pharmaceutically-acceptable salts, solvates, or prodrugs thereof, wherein:

Y is N or $CR^6$;

$R^1$ is H, $C_{1-3}$alkyl or $C_{3-6}$cycloalkyl, each optionally substituted by 0-7 $R^{1a}$;

$R^{1a}$ at each occurrence is independently hydrogen, deuterium, F, Cl, Br or CN;

$R^2$ is $C_{1-6}$alkyl, $-(CH_2)_r$-3-14 membered carbocycle substituted with 0-1 $R^{2a}$ or a 5-14 membered heterocycle containing 1-4 heteroatoms selected from N, O, and S, each group substituted with 0-4 $R^{2a}$ (for the sake of clarity, $R^2$ is intended to include substituted methyl groups such as $-C(O)R^{2a}$);

$R^{2a}$ at each occurrence is independently hydrogen, =O, halo, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CH_2)_r$-3-14 membered carbocycle substituted with 0-1 $R^a$ or a $-(CH_2)_r$-5-7 membered heterocycle comprising carbon atoms or 1-4 heteroatoms selected from N, O, and $S(O)_p$ substituted with 0-2 $R^a$;

$R^3$ is $C_{3-10}$ cycloalkyl, $C_{6-10}$ aryl or a 5-10 membered heterocycle containing 1-4 heteroatoms selected from N, O, and S, each group substituted with 0-4 $R^{3a}$;

$R^{3a}$ at each occurrence is independently hydrogen, =O, halo, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CH_2)_r$-3-14 membered carbocycle substituted with 0-3 $R^a$ or a $-(CH_2)_r$-5-10 membered heterocycle comprising carbon atoms and 1-4 heteroatoms selected from N, O, and $S(O)_p$ substituted with 0-3 $R^a$;

or two $R^{3a}$, together with the atoms to which they are attached, combine to form a fused ring wherein said ring is selected from phenyl and a heterocycle comprising carbon atoms and 1-4 heteroatoms selected from N, O, and $S(O)_p$, each fused ring substituted with 0-3 $R^{a1}$;

$R^4$ and $R^5$ are independently hydrogen, $C_{1-4}$ alkyl substituted with 0-1 $R^f$, $(CH_2)_r$-phenyl substituted with 0-3 $R^d$ or a $-(CH_2)$-5-7 membered heterocycle comprising carbon atoms and 1-4 heteroatoms selected from N, O, and $S(O)_p$;

$R^6$ is hydrogen, halo, $C_{1-4}$alkyl, $C_{1-4}$haloalkyl, $OC_{1-4}$haloalkyl, $OC_{1-4}$alkyl, CN, $NO_2$ or OH;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or $-(CH_2)_r$-5-7 membered heterocycle comprising carbon atoms and 1-4 heteroatoms selected from N, O, and $S(O)_p$ substituted with 0-3 $R^d$;

$R^a$ and $R^{a1}$ at each occurrence are independently hydrogen, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, $-(CH_2)_r$-3-14 membered carbocycle or $-(CH_2)_r$-5-7 membered heterocycle comprising carbon atoms and 1-4 heteroatoms selected from N, O, and $S(O)_p$ substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or $-(CH_2)_r$-5-7 membered heterocycle comprising carbon atoms and 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$-$C_{3-6}$ cycloalkyl substituted with 0-3 $R^f$ or $(CH_2)_r$-phenyl substituted with 0-3 $R^f$;

$R^d$ at each occurrence is independently hydrogen, F, Cl, Br, $OCF_3$, $CF_3$, CN, $NO_2$, $-OR^e$, $-(CH_2)_rC(O)R^c$, $-NR^eR^e$, $-NR^eC(O)OR^c$, $C_{1-6}$ alkyl or $(CH_2)_r$-phenyl substituted with 0-3 $R^f$;

$R^e$ at each occurrence is independently selected from hydrogen, $C_{1-6}$ alkyl, $C_{3-6}$ cycloalkyl and $(CH_2)_r$-phenyl substituted with 0-3 $R^f$;

$R^f$ independently at each occurrence is hydrogen, halo, CN, $NH_2$, OH, $C_{3-6}$ cycloalkyl, $CF_3$, $O(C_{1-6}$alkyl) or a $-(CH_2)_r$-5-7 membered heterocycle comprising carbon atoms and 1-4 heteroatoms selected from N, O, and $S(O)_p$;

p is 0, 1, or 2; and r is 0, 1, 2, 3, or 4.

In another embodiment are provided compounds of formula I, or a stereoisomer or pharmaceutically-acceptable salt thereof, wherein $R^2$ is $-C(O)R^{2a}$; or $C_{1-6}$alkyl, $C_{3-6}$cycloalkyl, phenyl, pyrazolyl, thiazolyl, pyridyl, pyrimidinyl, pyridazinyl, pyrazinyl, quinolinyl or pyrrolopyridinyl, each group substituted by 0-4 groups selected from $R^{2a}$.

In an alternate embodiment there are provided compounds of formula I, or a stereoisomer or pharmaceutically-acceptable salt thereof, wherein $R^2$ is $-C(O)R^{2a}$; or $C_{1-6}$alkyl, $C_{3-6}$cycloalkyl, or phenyl, each group substituted by 0-4 groups selected from $R^{2a}$.

In yet another embodiment there are provided compounds of formula I, or a stereoisomer or pharmaceutically-acceptable salt thereof, where $R^2$ is pyrazolyl, thiazolyl, pyridyl, pyrimidinyl, pyridazinyl, pyrazinyl, quinolinyl or pyrrolopyridinyl, each group substituted by 0-4 groups selected from $R^{2a}$.

In another embodiment, there is provided a compound of formula I, or a stereoisomer or pharmaceutically-acceptable salt thereof, wherein both $R^4$ and $R^5$ are hydrogen.

In another embodiment, there is provided a compound of formula I, wherein

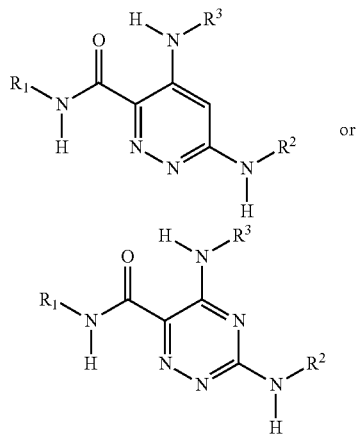

or a stereoisomer or pharmaceutically-acceptable salt thereof, wherein:

$R^1$ is H or $C_{1-3}$alkyl substituted by 0-7 $R^{1a}$;

$R^{1a}$ at each occurrence is independently hydrogen, deuterium or halogen (preferably H, D or F);

$R^2$ is $C_{1-6}$alkyl, $C_{3-6}$ cycloalkyl, phenyl, pyridyl, pyrimidinyl, pyridazinyl, pyrazinyl, quinolinyl or pyrrolopyridinyl, each group substituted by 0-4 groups selected from $R^{2a}$;

$R^{2a}$ at each occurrence is independently hydrogen, =O, halo, CN, —$(CH_2)_rOR^b$, —$(CH_2)_rC(O)R^b$, —$(CH_2)_rC(O)NR^{11}R^{11}$, —$S(O)_pNR^{11}R^{11}$, —$C_{1-6}$alkyl substituted with 0-3 $R^a$, $C_{1-6}$ haloalkyl, —$(CH_2)_r$-3-14 membered carbocycle substituted with 0-1 $R^a$ or a —$(CH_2)_r$-5-7 membered heterocycle comprising carbon atoms and 1-4 heteroatoms selected from N, O, and $S(O)_p$ substituted with 0-2 $R^a$;

$R^3$ is $C_{3-10}$ cycloalkyl, a $C_{6-10}$ aryl, or a 5-10 membered heterocycle containing 1-4 heteroatoms selected from N, O, and S, each group substituted with 0-4 $R^{3a}$;

$R^{3a}$ at each occurrence is independently hydrogen, halo, $OCF_3$, $CF_3$, $CHF_2$, CN, —$(CH_2)_rOR^b$, —$(CH_2)_rSR^b$, —$(CH_2)_rC(O)R^b$, —$(CH_2)_rNR^{11}R^{11}$, —$(CH_2)_rC(O)NR^{11}R^{11}$, —$(CH_2)_rNR^bC(O)R^c$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, a —$(CH_2)_r$-3-14 membered carbocycle substituted with 0-3 $R^a$ or a —$(CH_2)_r$-5-10 membered heterocycle comprising carbon atoms and 1-4 heteroatoms selected from N, O, and $S(O)_p$ substituted with 0-3 $R^a$;

or two $R^{3a}$, together with the atoms to which they are attached, combine to form a fused ring wherein that ring is selected from phenyl and a 5-7 membered heterocycle comprising carbon atoms and 1-4 heteroatoms selected from N, S or O, each fused ring substituted by 0-3 $R^{a1}$;

$R^{11}$ at each occurrence is independently hydrogen, $C_{1-4}$ alkyl substituted with 0-3 $R^f$ or $C_{3-10}$cycloalkyl substituted with 0-1 $R^f$;

$R^a$ and $R^{a1}$ at each occurrence are independently hydrogen, =O, F, —$(CH_2)_rOR^b$ or $C_{1-6}$alkyl substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle comprising carbon atoms and 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$;

$R^d$ at each occurrence is independently hydrogen, halo (preferably F), or —OH;

$R^f$ at each occurrence is independently hydrogen, halo, CN, OH or $O(C_{1-6}alkyl)$;

p is 0, 1 or 2; and r is 0, 1 or 2.

In an alternate embodiment,

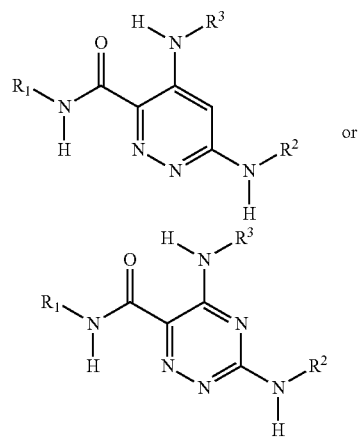

or a stereoisomer or pharmaceutically-acceptable salt thereof, wherein:

$R^1$ is H or $C_{1-3}$alkyl substituted by 0-7 $R^{1a}$;

$R^{1a}$ at each occurrence is independently hydrogen, deuterium or halogen;

$R^2$ is —$C(O)R^{2a}$; or $C_{1-6}$alkyl, $C_{3-6}$cycloalkyl, phenyl, pyrazolyl, thiazolyl, pyridyl, pyrimidinyl, pyridazinyl, pyrazinyl, quinolinyl or pyrrolopyridinyl, each group substituted by 0-4 groups selected from $R^{2a}$;

$R^{2a}$ at each occurrence is independently hydrogen, =O, halo, CN, —$(CH_2)_rOR^b$, —$(CH_2)_rC(O)R^b$, —$NR^bC(O)R^c$, —$C(O)OR^b$, —$(CH_2)_rC(O)NR^{11}R^{11}$, —$S(O)_pNR^{11}R^{11}$, —$C_{1-6}$alkyl substituted with 0-3 $R^a$, $C_{1-6}$ haloalkyl, —$(CH_2)_r$-3-14 membered carbocycle substituted with 0-1 $R^a$ or a —$(CH_2)_r$-5-7 membered heterocycle comprising carbon atoms and 1-4 heteroatoms selected from N, O, and $S(O)_p$ substituted with 0-2 $R^a$; $R^3$ is $C_{3-10}$ cycloalkyl, a $C_{6-10}$ aryl, or a 5-10 membered heterocycle containing 1-4 heteroatoms selected from N, O, and S, each group substituted with 0-4 $R^{3a}$;

$R^{3a}$ at each occurrence is independently hydrogen, halo, $OCF_3$, $CF_3$, $CHF_2$, CN, —$(CH_2)_rOR^b$, —$(CH_2)_rSR^b$, —$(CH_2)_rC(O)R^b$, —$(CH_2)_rNR^{11}R^{11}$, —$(CH_2)_rC(O)NR^{11}R^{11}$, —$(CH_2)_rNR^bC(O)R^c$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, a —$(CH_2)_r$-3-14 membered carbocycle substituted with 0-3 $R^a$ or a —$(CH_2)_r$-5-10 membered heterocycle comprising carbon atoms and 1-4 heteroatoms selected from N, O, and $S(O)_p$ substituted with 0-3 $R^a$;

or two $R^{3a}$, together with the atoms to which they are attached, combine to form a fused ring wherein that ring is selected from phenyl and a 5-7 membered heterocycle comprising carbon atoms and 1-4 heteroatoms selected from N, S or O, each fused ring substituted, as valence allows, by 0-3 $R^a$;

$R^{11}$ at each occurrence is independently hydrogen, $C_{1-4}$ alkyl substituted with 0-3 $R^f$ or $C_{3-6}$cycloalkyl substituted with 0-1 $R^f$;

$R^a$ at each occurrence is hydrogen, =O, F, —$(CH_2)_rOR^b$ or $C_{1-6}$alkyl substituted with 0-3 $R^f$;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle comprising carbon atoms and 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl or $C_{3-6}$ cycloalkyl, each group substituted with 0-3 $R^f$;

$R^d$ at each occurrence is independently hydrogen, F, Cl, Br or —OH;

$R^f$ at each occurrence is independently hydrogen, halo, CN, OH or $O(C_{1-6}alkyl)$;

p is 0, 1 or 2; and r is 0, 1 or 2.

In another embodiment, there is provided a compound of formula I having the structure:

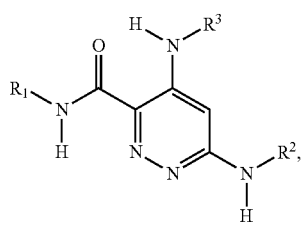

or a stereoisomer or pharmaceutically-acceptable salt thereof.

In alternate embodiment, there is provided a compound of formula I having the structure:

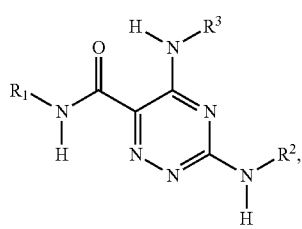

or a stereoisomer or pharmaceutically-acceptable salt thereof.

In another, preferred embodiment, there is provided a compound of formula I, or a stereoisomer or pharmaceutically-acceptable salt thereof, wherein $R^2$ is pyrazolyl, thiazolyl, pyridyl, pyrimidinyl, pyridazinyl, pyrazinyl or quinolinyl, each group substituted with 0-3 $R^{2a}$ (especially preferred embodiments are those wherein $R^{2a}$ is halo, CN or phenyl).

In an alternate preferred embodiment, there is provided a compound of formula I, or a stereoisomer or pharmaceutically-acceptable salt thereof, wherein $R^2$ is —$C(O)R^{2a}$; or $C_{1-6}$alkyl, $C_{3-6}$cycloalkyl or phenyl, each group substituted with 0-3 $R^{2a}$.

In a more preferred embodiment compounds of formula (I), or a stereoisomer or pharmaceutically-acceptable salt thereof, are provided wherein $R^2$ is selected from:

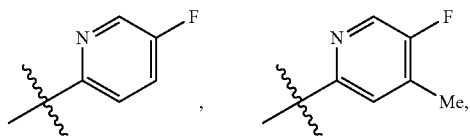

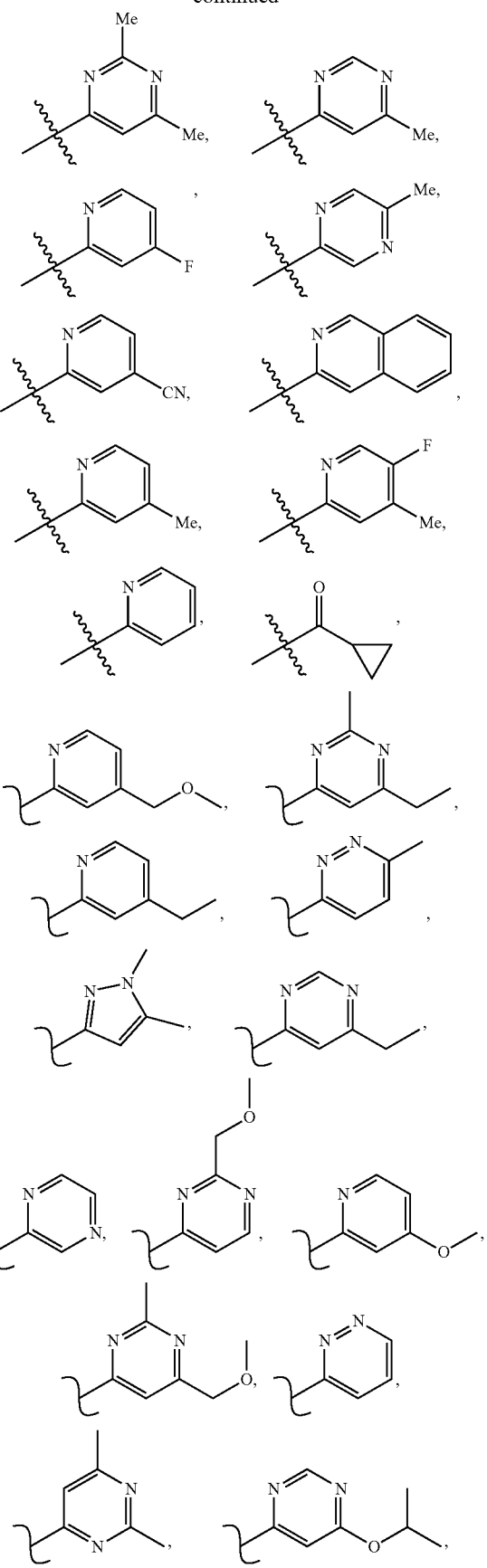

-continued

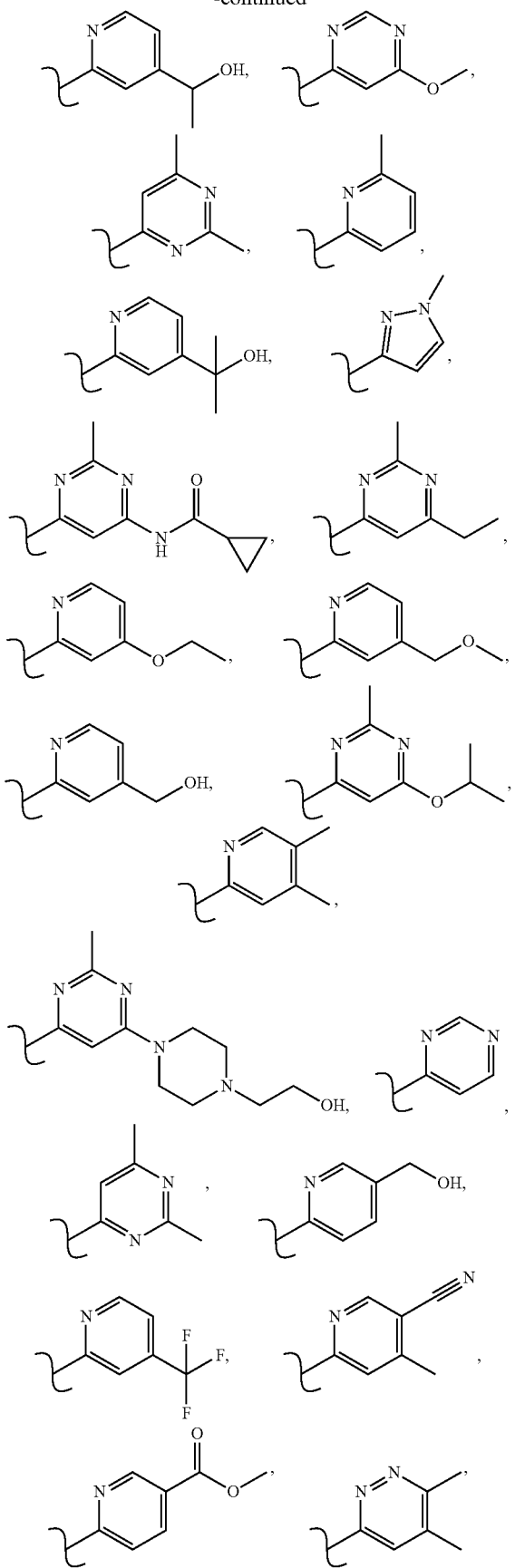
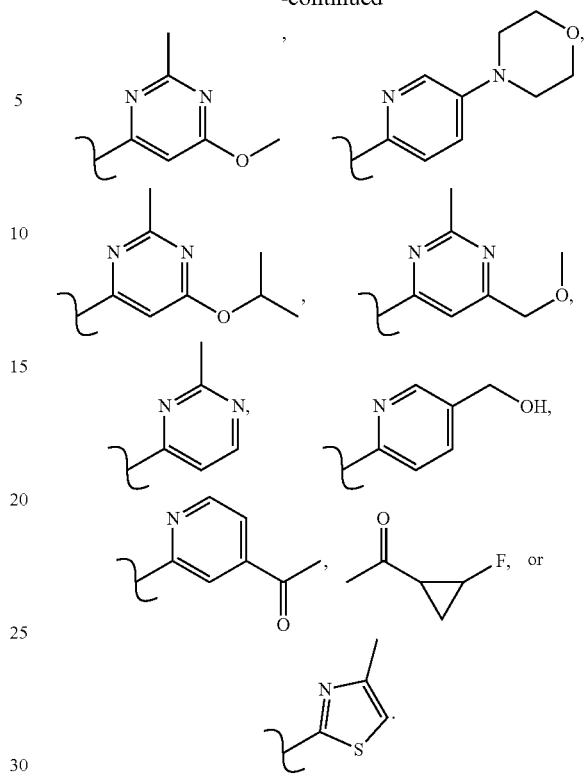

In another preferred embodiment, there is provided a compound of formula (I), or a stereoisomer or pharmaceutically-acceptable salt thereof, wherein $R^3$ is phenyl, cyclopentyl, cyclohexyl, furanyl, or pyranyl, each substituted with 0-4 $R^{3a}$ (preferably, $R^3$ is phenyl substituted with 0-3 $R^{3a}$)

In yet another, more preferred embodiment, there is provided a compound of formula (I), or a stereoisomer or pharmaceutically-acceptable salt thereof, wherein:

$R^{3a}$ at each occurrence independently is hydrogen, Ph, CN, $NH_2$, $OCF_3$, $OR^b$, halo, cycloalkyl, $C(O)NR^{11}R^{11}$, $S(O)_2NR_{11}R_{11}$, $C(O)R^b$, $SO_pR^c$, $NR^bSO_pR^c$, $NR^bC(O)R$, haloalkyl, CN, 5-7 membered heterocycle comprising carbon atoms and 1-4 heteroatoms selected from N, S or O substituted with 0-3 $R^a$ and $C_{1-6}$ alkyl substituted with 0-3 $R^a$; or one $R^{3a}$ and a second $R^{3a}$, together with the atoms to which they are attached, combine to form a fused 5-7 membered heterocycle comprising carbon atoms and 1-4 heteroatoms selected from N, S or O or phenyl;

$R^{11}$ at each occurrence independently is hydrogen, $C_{3-6}$ cycloalkyl substituted with 0-3 $R^f$, or $C_{1-4}$alkyl substituted with 0-1 $R^f$;

$R^a$ independently at each occurrence is $C_{1-6}$ alkyl substituted with 0-3 $R^f$, halo (F) or $OR^b$;

$R^b$ independently at each occurrence is hydrogen, 5-7 membered heterocycle comprising carbon atoms and 1-4 heteroatoms selected from N, S or O substituted with 0-3 $R^f$, or $C_{1-6}$ alkyl substituted with 0-3 $R^d$;

$R^d$ independently at each occurrence is F, Cl, Br or OH;

$R^c$ independently at each occurrence is $C_{1-6}$ alkyl or $C_{3-6}$ cycloalkyl, each group substituted with 0-3 $R^f$ substituted with 0-3 $R^f$;

$R^f$ independently at each occurrence is hydrogen, halo or OH; and p is 2.

In another, preferred embodiment, there is provided a compound of formula (I), or a stereoisomer or pharmaceutically-acceptable salt thereof, wherein $R^3$ is

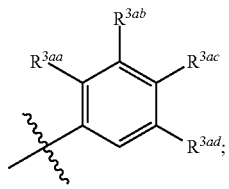

$R^{3aa}$ is $S(O)_pR^c$, $OR^b$, chloro, F, CN, $NH_2$, $C(O)NR^{11}R^{11}$, $NR^bSO_pR^c$, $NR^bC(O)R$, $C_{1-6}$ alkyl substituted with 0-3 $R^a$ or a 5- to 6-membered heteroaryl containing 1-3 heteroatoms selected from N, O, and S substituted with 0-3 $R^{3a}$; (especially, $R^{3aa}$ is $S(O)_2Me$ or OMe);

$R^{3ab}$, $R^{3ac}$, or $R^{3ad}$ are independently hydrogen, Cl, F, Br, CN, $OR^b$, $C_{1-6}$ alkyl substituted 0-3 $R^a$; $C(O)NR^{11}R^{11}$, $C(O)R^b$, $S(O)_pR^c$, or a 4-7 membered heterocycle containing 1-3 heteroatoms selected from N, O, and S substituted with 0-3 $R^a$; (especially $R^{3ab}$, $R^{3ac}$, or $R^{3ad}$ are independently, hydrogen or 5-6 membered heterocycle containing 1-3 heteroatoms selected from N, O, and S substituted with 0-2 $R^a$;

$R^{11}$ at each occurrence independently is hydrogen, cyclopropyl substituted with 0-3 $R^f$ or $C_{1-4}$alkyl substituted with 0-3 $R^f$;

$R^a$ at each occurrence independently is $C_{1-6}$ alkyl substituted with 0-3 $R^f$, $OR^b$ or halo;

$R^b$ at each occurrence independently is hydrogen, $C_{1-6}$ alkyl substituted with 0-2 $R^d$ or a 5- to 7-membered heterocycle containing 1-3 heteroatoms selected from N, O and S;

$R^c$ at each occurrence independently is $C_{1-6}$ alkyl substituted with 0-3 $R^f$;

$R^d$ at each occurrence independently is F or OH;

$R^f$ at each occurrence independently is halo or OH; and p is 0-2.

In an alternate preferred embodiment, there is provided a compound of formula I, or a stereoisomer or pharmaceutically-acceptable salt thereof, wherein:

$R^1$ is $CH_3$ or $CD_3$;

$R^2$ is —$C(O)C_{3-6}$ cycloalkyl substituted by 0-2 groups selected from $C_{1-3}$alkyl and halo; and $R^3$ is

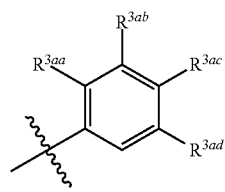

wherein $R^{3aa}$ is —$O(C_{1-3}$alkyl), $R^{3ab}$ is a triazolyl or tetrazolyl group optionally substituted with $C_{1-6}$ alkyl substituted by 0-4 groups selected from F, Cl, or Br; and $R^{3ac}$ and $R^{3ad}$ are both hydrogen.

In a further alternate embodiment, there is provided a compound of formula I, or a stereoisomer or pharmaceutically-acceptable salt thereof, wherein $R^{3aa}$ is $S(O)_pR^c$ or $C(O)NR^{11}R^{11}$ (more preferably $R^{3aa}$ is $SO_2CH_3$).

In a further embodiment, there is provided a compound of formula I, or a stereoisomer or pharmaceutically-acceptable salt thereof, wherein $R^{3aa}$ is $S(O)_pR^c$ or $C(O)NR^{11}R^{11}$ (more preferably $R^{3aa}$ is $SO_2CH_3$ or $C(O)NH_2$).

In an alternate further embodiment, there is provided a compound of formula I, or a stereoisomer or pharmaceutically-acceptable salt thereof, wherein $R^{3aa}$ is $OR^b$. More preferably $R^{3aa}$ is OH, OMe, $OCF_3$, $OCHF_2$, $OCH_2F$ or OEt. Even more preferably, $R^{3aa}$ is OMe.

In a more preferred embodiment, there is provided a compound of formula I, or a stereoisomer or pharmaceutically-acceptable salt thereof, wherein $R^3$ is selected from:

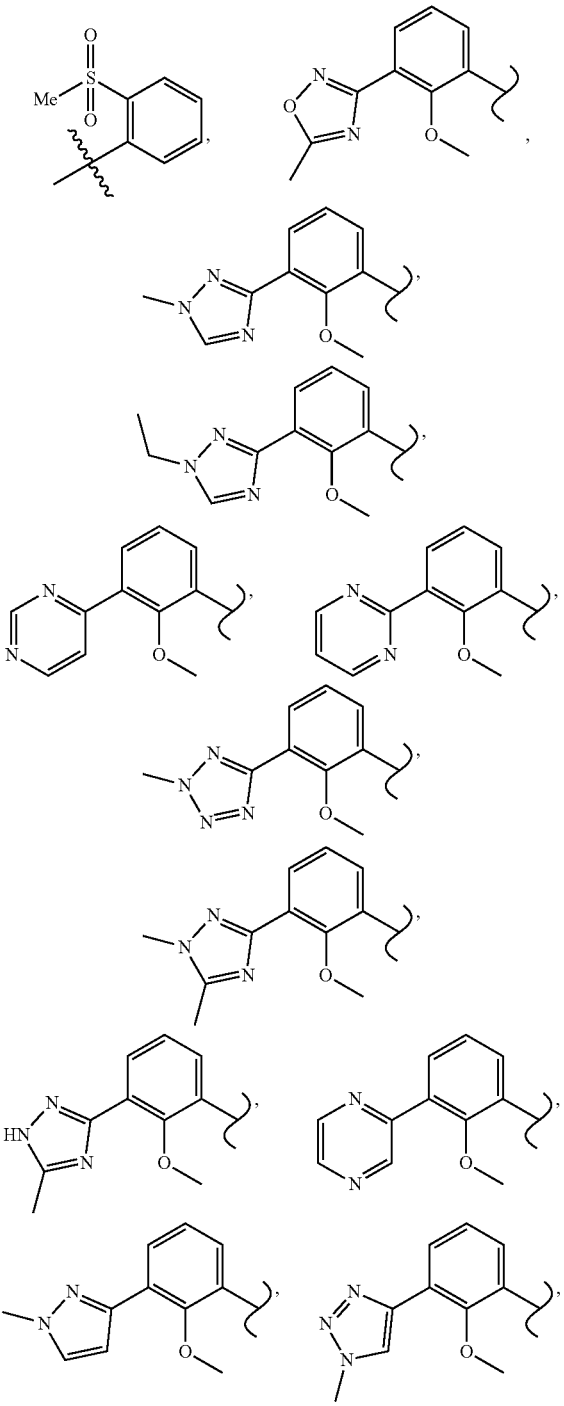

-continued

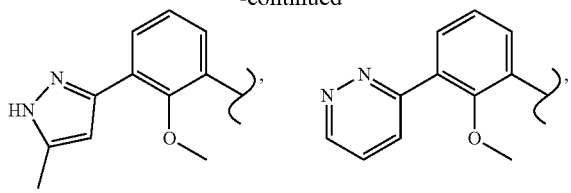
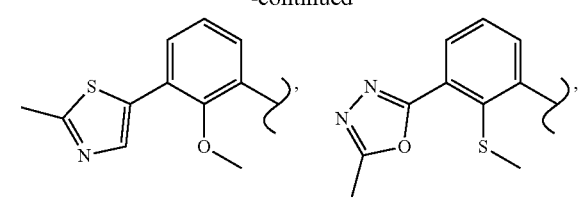
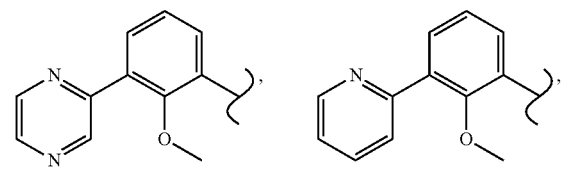
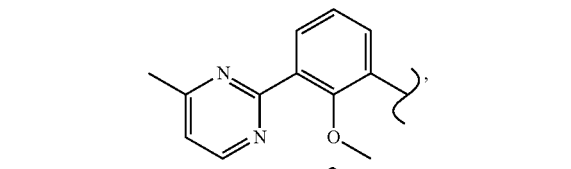
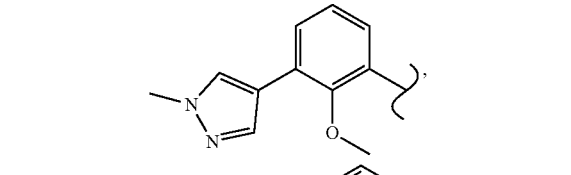
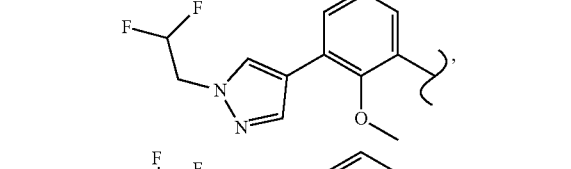
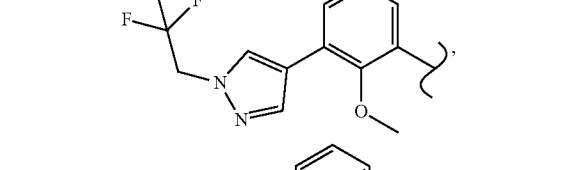
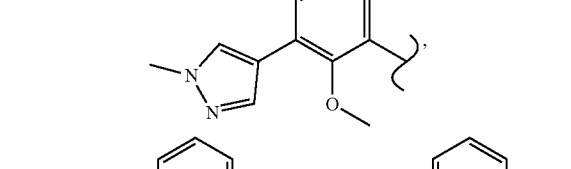
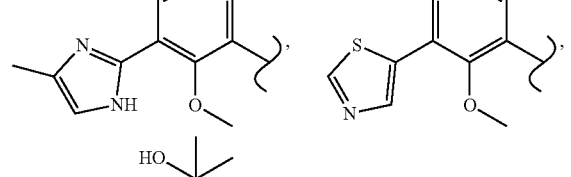
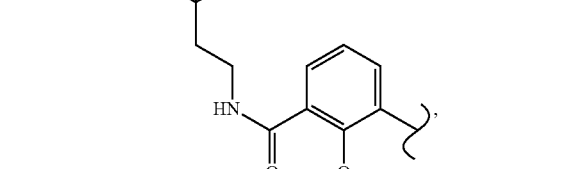
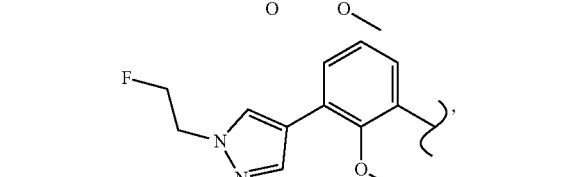
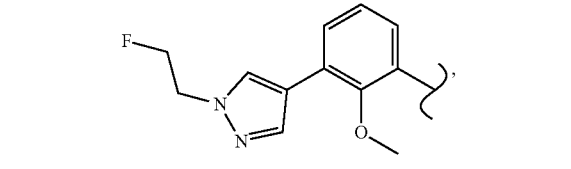
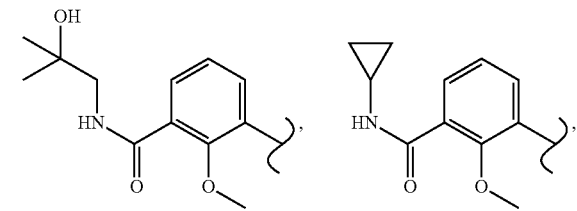

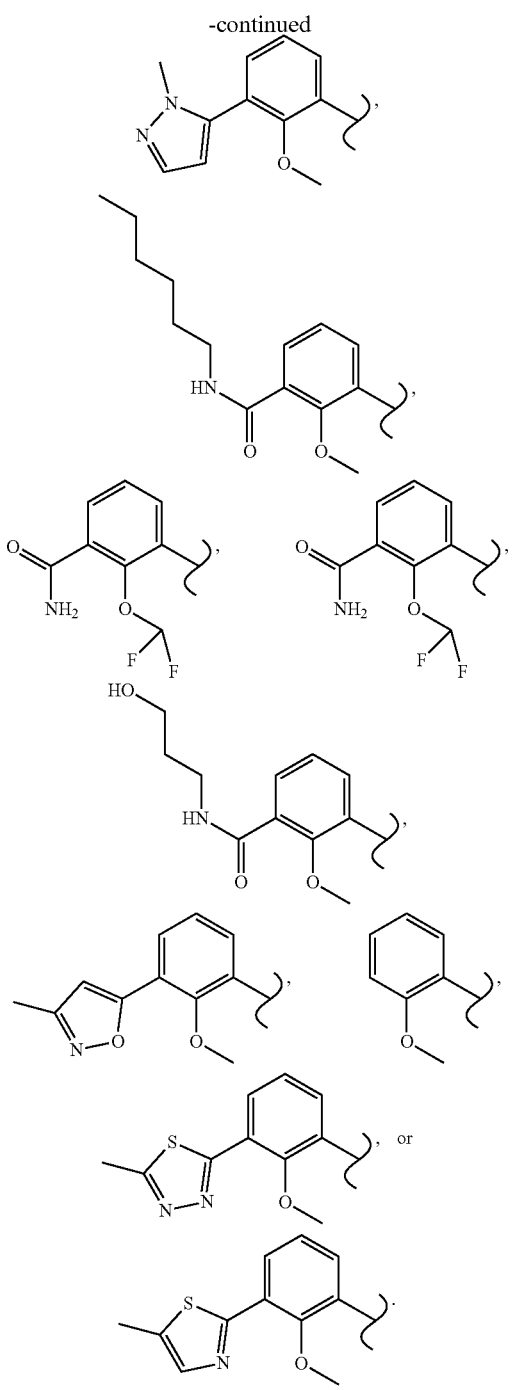

In a more preferred embodiment, there is provided a compound of formula I, or a stereoisomer or pharmaceutically-acceptable salt thereof, wherein R¹ is H, CH$_3$, C$_2$H$_5$, cyclopropyl, CD$_3$, or CD$_2$CD$_3$ (preferably CH$_3$ or CD$_3$).

In another embodiment, there is provided a pharmaceutical composition comprising one or more compounds of formula I and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of said diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating a IL-12, IL-23, and/or IFNα mediated disease (or use of the compounds of the present invention for the manufacture of a medicament for the treatment of these diseases), comprising administering to a patient in need of such treatment a therapeutically-effective amount of a compound of formula I.

The present invention also provides a method of treating a IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention for use in therapy.

In another embodiment, compounds of formula I are selected from exemplified compounds or combinations of exemplified compounds or other embodiments herein.

In another embodiment are compounds having an $IC_{50}<1000$ nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art, ⊢ is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

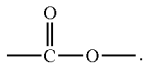

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

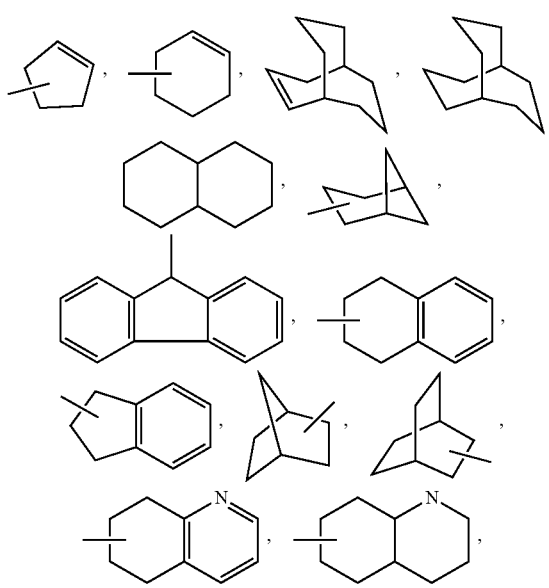

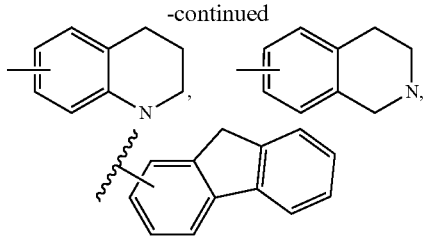

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

Thus, examples of aryl groups include:

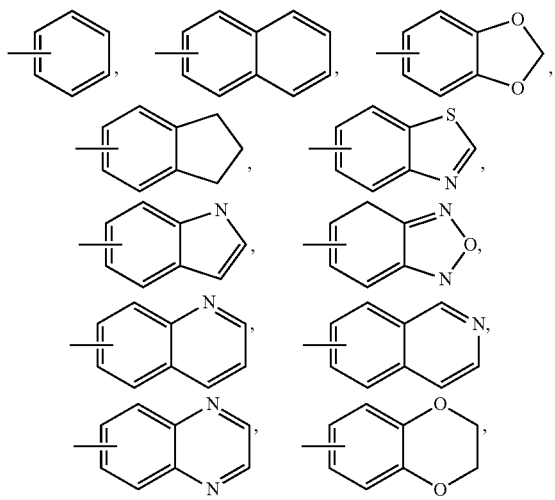

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3-to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

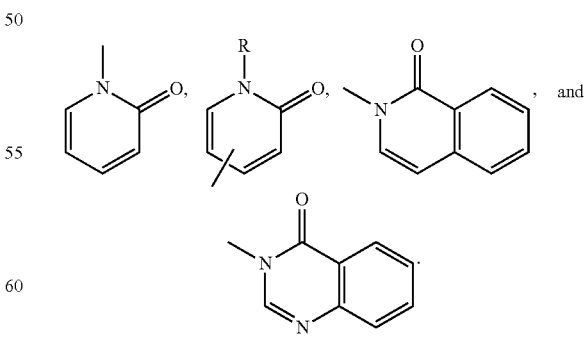

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include:

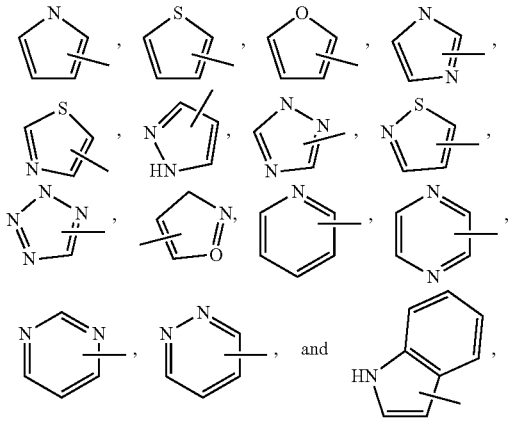

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically-acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers.

It should further be understood that solvates (e.g., hydrates) of the compounds of Formula I are also with the scope of the present invention. Methods of solvation are generally known in the art.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting on Tyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrastemal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Biological Assays

Probe Displacement Assay

The probe displacement assay is conducted as follows: In a 385 well plate, test compounds along with recombinantly expressed His-tagged protein corresponding to amino acids 575-869 of human Tyk2 (sequence shown below) at 2.5 nM, 40 nM ((R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide) (preparation described below) and 80 µg/mL Copper His-Tag scintillation proximity assay beads (Perkin Elmer, Catalog #RPNQ0095) in 50 mM HEPES, pH 7.5, containing 100 µg/mL bovine serum albumin and 5% DMSO were incubated for 30 minutes at room temperature. The amount of radiolabeled probe (preparation described below) bound to Tyk2 was then quantified by scintillation counting, and the inhibition by the test compound calculated by comparison to wells either with no inhibitor (0% inhibition) or without Tyk2 (100% inhibition). The $IC_{50}$ value is defined as the concentration of test compound required to inhibit radiolabeled probe binding by 50%.

Protein Sequence of recombinant Hig-tagged Tyk2 (575-869):

MGSSHHHHHH SSGETVRFQG HMNLSQLSFH RVDQKEITQL SHLGQ

GTRTN VYEGRLRVEG SGDPEEGKMDDEDPLVPGRD RGQELRVVLK

VLDPSHHDIA LAFYETASLM SQVSHTHLAF VHGVCVRGPE NIMVT

EYVEHGPLDVWLRRE RGHVPMAWKM VVAQQLASAL SYLENKNLVH

GNVCGRNILL ARLGLAEGTS PFIKLSDPGVGLGALSREER VERIPW

LAPE CLPGGANSLS TAMDKWGFGA TLLEICFDGE APLQSRSPSE

KEHFYQRQHRLPEPSCPQLA TLTSQCLTYE PTQRPSFRTI LRDLT

RL.

The preparation of radiolabeled probe, (R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide, was performed as described below.

2-([$^3$H]Methylsulfonyl)benzoic acid: 2-Mercaptobenzoic acid (2.3 mg, 0.015 mmol) and cesium carbonate (2 mg, 0.006 mmol) were added to a 5 mL round-bottomed flask. The flask was attached to a ported glass vacuum line and anhydrous DMF (0.5 mL) was introduced with magnetic stirring. An ampoule of tritiated methyl iodide (200 mCi, Perkin-Elmer lot 3643419) was added to the reaction flask and stirring was maintained at rt for 3 h. In-process HPLC analysis with radiometric detection indicated 80% conversion to the desired product by comparison with authentic standard. Without purification, the crude product was reacted with mCPBA (10 mg, 0.058 mmol) pre-dissolved in $CH_2Cl_2$ (1 mL) at room temperature with stirring. The reaction was stirred for 7 h and additional mCPBA (10 mg, 0.058 mmol) was added. The reaction was stirred for approximately 24 h and HPLC analysis indicated 35-40% conversion to the desired sulfonate product. The crude product was purified by semi-preparative HPLC (Luna 5 m C18 (10×250 cm); A: MeOH/$H_2O$=15/85 (0.1% TFA); B: MeOH; 270 nm; 0-8 min 0% B 1 ml/min; 8-10 min 0% B 1-3 ml/min; 10-55 min 0% B 3 ml/min; 55-65 min 0-10% B 3 ml/min; 65-75 min 10-50% B 3 ml/min; 75-80 min 50-100% B 3 ml/min) to give 81 mCi (40% radiochemical yield) of 2-([$^3$H]methylsulfonyl)benzoic acid product identified by its HPLC co-elution with an authentic standard. The radiochemical purity was measured by HPLC to be 99% (Luna 5µ C18 (4.6×150 cm); A: $H_2O$ (0.1% TFA); B: MeOH; 1.2 ml/min; 270 nm; 0-10 min 20% B; 10-15 min 20-100% B; 15-25 min 100% B. The product was dissolved in anhydrous acetonitrile to give a final solution activity of 5.8 mCi/mL.

(R)—N-(1-(3-(8-Methyl-5-(methylamino)-8H-imidazo[4,5-d]thiazolo[5,4-b]pyridin-2-yl)phenyl)ethyl)-2-([$^3$H]methylsulfonyl)benzamide: A solution of 2-([$^3$H]methylsulfonyl)benzoic acid (23.2 mCi) in acetonitrile was added to a 5 mL round-bottomed flask which was then attached to a vacuum line and carefully evaporated to dryness. (R)-2-(3-(1-Aminoethyl)phenyl)-N,8-dimethyl-8H-imidazo[4,5-d]thiazolo[5,4-b]pyridin-5-amine (prepared as described in WO 2004/106293 and Dyckman et al., *Bioorganic and Medicinal Chemistry Letters*, 383-386 (2011)) (1.1 mg, 0.0033 mmol) and PyBOP (2 mg, 0.0053 mmol) dissolved in anhydrous DMF (1.5 mL) were added to the flask followed by N,N-diisopropylethylamine (0.010 mL). The resulting clear solution was stirred at room temperature for 18 h. HPLC analysis (Luna 5. C18 (4.6×150 cm); A: $H_2O$ (0.1% TFA); B: MeOH; 1.2 ml/min; 335 nm; 0-20 min 50% B; 20-25 min 50-100% B; 25-30 min 100% B) indicated approximately a 20% conversion to the desired product by retention time comparison to a sample of non-radiolabeled (R)—N-(1-(3-(8-methyl-5-(methylamino)-8H-imidazo[4,5-d]thiazolo[5,4-b]pyridin-2-yl)phenyl)ethyl)-2-(methylsulfonyl)benzamide. The crude reaction mixture was purified by semi-preparative HPLC (Luna 5µ C18 (10×250 cm); A: MeOH/$H_2O$=50/50 (0.1% TFA); B: MeOH; 335 nm; 0-40 min 0% B 3 ml/min; 40-45 min 0-100% B 3 ml/min). The purification routine was performed a second time to yield a total of 1.7 mCi (7% radiochemical yield) of the desired product in 99.9% radiochemical purity. Mass spectral analysis of the tritiated product (m/z M+H 527.33) was used to establish the specific activity at 80.6 Ci/mmol.

| Probe Displacement Data | |
|---|---|
| Example No. | Probe Displacement ($EC_{50}$, μM) |
| 4 | 0.13 |
| 5 | 0.41 |
| 10 | 0.10 |
| 16 | 6.57E−03 |
| 51 | 7.19E−03 |
| 52 | 5.13E−03 |
| 61 | 1.66E−03 |
| 67 | 6.53E−03 |
| 69 | 0.07 |
| 70 | 5.22E−03 |
| 73 | 5.21E−03 |
| 75 | 6.18E−03 |
| 76 | 6.17E−03 |
| 84 | 1.28E−03 |
| 85 | 7.36E−03 |
| 87 | 2.02E−03 |
| 94 | 1.72E−03 |
| 102 | 1.59E−03 |
| 108 | 1.46E−03 |
| 112 | 1.94E−03 |
| 114 | 1.89E−03 |
| 125 | 0.11 |
| 134 | 5.64E−03 |
| 140 | 0.07 |
| 142 | 6.95E−03 |
| 146 | 1.70E−03 |
| 147 | 8.77E−04 |
| 151 | 7.22E−03 |
| 154 | 0.09 |
| 155 | 7.13E−03 |
| 160 | 0.07 |
| 176 | 6.35E−03 |
| 181 | 6.97E−03 |
| 183 | 5.72E−03 |
| 186 | 0.06 |
| 188 | 5.10E−03 |
| 194 | 0.08 |

Kit225 T Cell Assay

Kit225 T cells with a stably-integrated STAT-dependent luciferase reporter were plated in RPMI (Gibco) containing 10% heat-inactivated FBS (Gibco) and 100 U/mL PenStrep (Gibco). The cells were then stimulated with either 20 ng/mL human recombinant IL-23 or 200 U/mL human recombinant IFNα (PBL InterferonSource) for 5-6 hours. Luciferase expression was measured using the STEADY-GLO® Luciferase Assay System (Promega) according to the manufacturer's instructions. Inhibition data were calculated by comparison to no inhibitor control wells for 0% inhibition and non-stimulated control wells for 100% inhibition. Dose response curves were generated to determine the concentration required to inhibit 50% of cellular response ($IC_{50}$) as derived by non-linear regression analysis.

| Kit225 T Cell Inhibition Data | | |
|---|---|---|
| Example No. | IL-23 Kit225 Reporter ($IC_{50}$, nM) | IFNα Kit225 Reporter ($IC_{50}$, nM) |
| 1 | 0.03 | 0.02 |
| 2 | 0.14 | 0.05 |
| 3 | 0.10 | 0.06 |
| 4 | 2.30 | 1.15 |
| 5 | 12.50 | 6.36 |
| 6 | 0.19 | 0.11 |
| 7 | 0.07 | 0.05 |
| 8 | 0.13 | 0.09 |
| 9 | 0.06 | 0.09 |
| 10 | 0.16 | 0.40 |
| 11 | 0.10 | 0.06 |
| 12 | 0.23 | 0.10 |
| 13 | 0.02 | 0.05 |
| 14 | 0.01 | 0.01 |
| 15 | 0.04 | 0.05 |
| 16 | 0.04 | 0.02 |
| 17 | 0.57 | 0.36 |
| 18 | 0.10 | 0.03 |
| 19 | 0.09 | 0.09 |
| 20 | 0.02 | 0.02 |
| 21 | 0.08 | 0.06 |
| 22 | 0.16 | 0.10 |
| 23 | 0.10 | 0.04 |
| 24 | 0.06 | 0.05 |
| 25 | 0.14 | 0.08 |
| 26 | 0.06 | 0.05 |
| 27 | 0.01 | 0.02 |
| 28 | 0.42 | 0.61 |
| 29 | 0.14 | 0.08 |
| 30 | 0.02 | 0.01 |
| 31 | 0.08 | 0.09 |
| 32 | 0.07 | 0.05 |
| 33 | 0.66 | 0.40 |
| 34 | 0.19 | 0.17 |
| 35 | 0.21 | 0.04 |
| 36 | 0.11 | 0.03 |
| 37 | 0.54 | 0.08 |
| 38 | 0.17 | 0.10 |
| 39 | 0.34 | 0.13 |
| 40 | 0.08 | 0.12 |
| 41 | 0.16 | 0.19 |
| 42 | 0.15 | 0.26 |
| 43 | 0.46 | 0.07 |
| 44 | 0.25 | 0.10 |
| 45 | 0.42 | 0.31 |
| 46 | 0.20 | 0.06 |
| 47 | 0.05 | 0.02 |
| 48 | 0.33 | 0.11 |
| 49 | 0.56 | 0.22 |
| 50 | 0.31 | 0.49 |
| 51 | 0.04 | 0.02 |
| 52 | 0.01 | 9.21E−03 |
| 54 | 0.04 | 0.02 |
| 55 | 0.02 | 0.02 |
| 56 | 7.01E−03 | 5.45E−03 |
| 57 | 6.01E−03 | 6.48E−03 |
| 58 | 0.02 | 8.59E−03 |
| 59 | 0.02 | 0.02 |
| 60 | 0.01 | 3.38E−03 |
| 61 | 0.02 | 8.37E−03 |
| 62 | 0.03 | 0.02 |
| 63 | 0.04 | 0.06 |
| 64 | 0.25 | 0.06 |
| 65 | 0.06 | 0.02 |
| 66 | 0.02 | 0.03 |
| 67 | 0.10 | 0.07 |
| 68 | 6.56E−03 | 3.45E−03 |
| 69 | 0.38 | 0.16 |
| 70 | 0.02 | 0.02 |
| 71 | 0.01 | 5.99E−03 |
| 72 | 0.13 | 0.04 |
| 73 | 0.08 | 0.05 |
| 74 | 0.02 | 5.15E−03 |
| 75 | 0.07 | 0.04 |
| 76 | 1.99E−03 | 3.49E−03 |
| 77 | 0.07 | 0.02 |
| 78 | 0.32 | 0.07 |
| 79 | 0.08 | 0.03 |
| 80 | 0.38 | 0.19 |
| 81 | 0.24 | 0.10 |
| 82 | 0.11 | 0.06 |
| 83 | 0.05 | 0.04 |
| 84 | 0.02 | 9.39E−03 |
| 85 | 0.17 | 0.05 |
| 86 | 0.03 | 0.02 |

Kit225 T Cell Inhibition Data

| Example No. | IL-23 Kit225 Reporter (IC$_{50}$, nM) | IFNα Kit225 Reporter (IC$_{50}$, nM) |
| --- | --- | --- |
| 87 | 0.02 | 4.10E−03 |
| 88 | 0.02 | 9.97E−03 |
| 89 | 0.02 | 2.18E−03 |
| 90 | 0.54 | 0.39 |
| 91 | 0.02 | 3.62E−03 |
| 92 | 0.04 | 8.63E−03 |
| 93 | 0.05 | 0.01 |
| 94 | 0.03 | 8.59E−03 |
| 95 | 0.10 | 0.02 |
| 96 | 0.04 | 7.38E−03 |
| 97 | 0.01 | 0.02 |
| 98 | 0.03 | 9.16E−03 |
| 99 | 0.06 | 0.02 |
| 100 | 0.04 | 0.05 |
| 101 | 0.10 | 0.06 |
| 102 | 0.04 | 0.03 |
| 103 | 0.02 | 6.06E−03 |
| 104 | 0.19 | 0.04 |
| 105 | 0.18 | 0.14 |
| 106 | 0.08 | 0.08 |
| 107 | 0.09 | 0.14 |
| 108 | 8.49E−03 | 3.54E−03 |
| 109 | 0.01 | 7.13E−03 |
| 110 | 0.08 | 0.02 |
| 111 | 0.03 | 0.01 |
| 112 | 7.49E−03 | 3.72E−03 |
| 113 | 0.03 | 4.41E−03 |
| 114 | 8.29E−03 | 3.77E−03 |
| 115 | 2.96E−03 | 1.60E−03 |
| 116 | 0.02 | 0.03 |
| 117 | 0.08 | 0.03 |
| 118 | 0.03 | 0.02 |
| 119 | 0.01 | 7.37E−03 |
| 120 | 0.06 | 0.01 |
| 121 | 2.64E−03 | 2.33E−03 |
| 122 | 0.03 | 3.20E−03 |
| 123 | 5.90E−03 | 6.81E−03 |
| 124 | 0.70 | 0.49 |
| 125 | 0.17 | 0.43 |
| 126 | 0.04 | 0.03 |
| 127 | 0.03 | 0.02 |
| 128 | 6.08E−03 | 3.17E−03 |
| 129 | 0.02 | 0.01 |
| 130 | 9.70E−03 | 0.01 |
| 131 | 0.02 | 0.02 |
| 132 | 0.02 | 0.02 |
| 133 | 8.03E−03 | 3.81E−03 |
| 134 | 0.03 | 0.01 |
| 135 | 3.83E−03 | 1.40E−03 |
| 136 | 0.02 | 6.04E−03 |
| 137 | 0.01 | 6.92E−03 |
| 138 | 0.03 | 0.03 |
| 139 | 0.21 | 0.15 |
| 140 | 0.32 | 0.33 |
| 141 | 0.04 | 0.02 |
| 142 | 6.59E−03 | 4.30E−03 |
| 143 | 0.04 | 0.14 |
| 144 | 0.01 | 3.15E−03 |
| 145 | 0.01 | 8.44E−03 |
| 146 | 0.01 | 5.33E−03 |
| 147 | 1.01E−03 | 4.42E−03 |
| 148 | 0.02 | 0.01 |
| 149 | 0.17 | 0.05 |
| 150 | 0.02 | 0.01 |
| 151 | 0.02 | 0.02 |
| 152 | 0.13 | 0.03 |
| 153 | 0.15 | 0.03 |
| 154 | 0.59 | 0.43 |
| 155 | 0.03 | 0.03 |
| 156 | 0.04 | 0.01 |
| 157 | 0.23 | 0.15 |
| 158 | 0.01 | 0.02 |
| 159 | 0.11 | 0.08 |
| 160 | 0.41 | 0.31 |
| 161 | 0.21 | 0.21 |
| 162 | 0.12 | 0.06 |
| 163 | 0.04 | 0.03 |
| 164 | 0.30 | 0.17 |
| 165 | 0.34 | 0.23 |
| 166 | 0.27 | 0.21 |
| 167 | 0.31 | 0.33 |
| 168 | 0.10 | 0.08 |
| 169 | 0.04 | 0.03 |
| 170 | 0.23 | 0.39 |
| 171 | 0.05 | 0.13 |
| 172 | 5.45E−03 | 6.19E−03 |
| 173 | 0.12 | 0.02 |
| 174 | 0.02 | 6.97E−03 |
| 175 | 0.02 | 0.01 |
| 176 | 0.04 | 0.02 |
| 177 | 1.52E−03 | 1.63E−03 |
| 178 | 0.03 | 0.01 |
| 179 | 0.45 | 0.14 |
| 180 | 0.06 | 0.02 |
| 181 | 0.04 | 0.02 |
| 182 | 0.19 | 0.08 |
| 183 | 0.03 | 3.67E−03 |
| 184 | 6.41E−03 | 7.20E−03 |
| 185 | 0.28 | 0.12 |
| 186 | 0.17 | 0.08 |
| 187 | 0.05 | |
| 188 | 0.12 | 0.05 |
| 189 | 0.15 | 0.03 |
| 190 | 0.02 | 0.02 |
| 191 | 0.01 | 8.63E−03 |
| 192 | 0.04 | 0.03 |
| 193 | 0.03 | 0.04 |
| 194 | 0.63 | 0.41 |
| 195 | 0.01 | 0.02 |
| 196 | 0.07 | 0.16 |
| 197 | 0.29 | 0.26 |
| 198 | 5.22E−03 | 5.67E−03 |
| 199 | 0.19 | 0.23 |
| 200 | 0.08 | 0.03 |
| 201 | 0.02 | 4.13E−03 |
| 202 | 0.29 | 0.33 |
| 203 | 0.31 | 0.11 |
| 204 | 0.07 | 0.02 |
| 205 | 0.14 | 0.05 |
| 206 | 4.38E−03 | 7.12E−04 |

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

Scheme 1. Coupling of II/III with amine IV

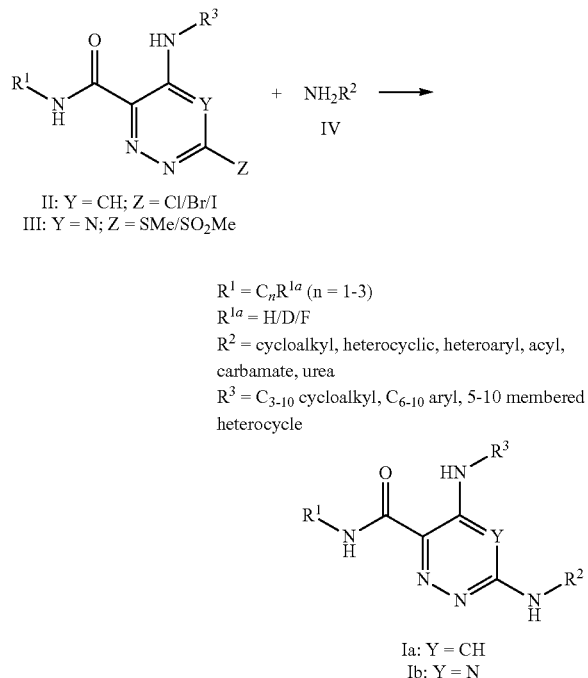

II: Y = CH; Z = Cl/Br/I
III: Y = N; Z = SMe/SO$_2$Me $R^1 = C_nR^{1a}$ (n = 1-3)
$R^{1a}$ = H/D/F
$R^2$ = cycloalkyl, heterocyclic, heteroaryl, acyl, carbamate, urea
$R^3$ = $C_{3-10}$ cycloalkyl, $C_{6-10}$ aryl, 5-10 membered heterocycle Ia: Y = CH
Ib: Y = N Scheme 1 illustrates the preparation of title compounds of the invention (I) from the intermediate pyridazine (II) or 1,2,4-triazine (III) along with an amine (IV). The coupling of the halo-pyridazine may be affected by many of the ways known to achieve displacement of 6-halo-pyridazines by amines. This includes, but is not limited to, the palladium catalyzed N-arylation of amines, and nucleophilic displacement of the halide by the amine. A variety of palladium sources can be used to affect the coupling including both palladium(II) salts (for example palladium diacetate) as well as neutral palladium (such as tetrakis triphenylphosphine palladium or tris(dibenzylideneacetone)dipalladium). A large number of catalyst ligands are suitable for this transformation including bis(diphenylphosphino)-9,9-dimethylxanthene (Xantphos) and 2-(dicyclohexylphosphino)-3,6-dimethoxy-2',4',6'-tri-i-propyl-1,1'-biphenyl (BrettPhos) and many others that those versed in synthetic chemistry are familiar with (see Surry, D. S. et al., *Chem. Sci.*, 2:27-50 (2011)). A variety of bases can be employed (such as potassium carbonate, sodium tert-butoxide, cesium carbonate and the like) as well as a number of solvents (such as 1,4-dioxane, toluene and dimethylacetamide and the like). Nucleophilic displacement is generally possible at elevated temperatures (typically >100° C.) in the presence or absence of either an acid or base catalyst. Heating can be accomplished using either a microwave or conventional heating. Amines are most typically, but not exclusively, aliphatic in such displacements. In the case of the sulfide/sulfoxide triazine (III) the displacement is best accomplished using nucleophilic displacement under thermal conditions, due to the increased electrophilicity of this position this is possible both for the electron rich aliphatic amines as well as the more electron poor anilines and related.

Scheme 2. Coupling of carboxylic acids V/VI with amine VII

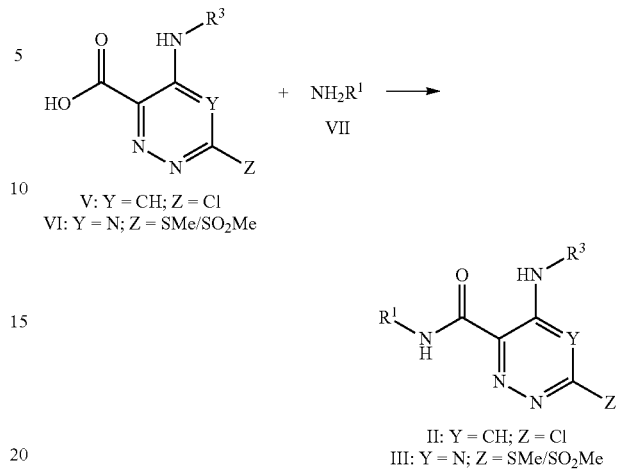

V: Y = CH; Z = Cl
VI: Y = N; Z = SMe/SO$_2$Me

II: Y = CH; Z = Cl
III: Y = N; Z = SMe/SO$_2$Me

Scheme 2 illustrates the preparation of the amides II/III from the corresponding carboxylic acids (V/VI) by coupling with an amine (VII). This coupling may be affected by many of the ways known to prepare carboxamides. For example, condensation of acid with amine (VII) may be effected by treatment of the carboxylic acid with an activating reagent, such as a water-soluble carbodiimide (EDC), in the presence of an N-hydroxy triazole (HOAt or HOBt, or the like) and amine (VII) in the presence of base (preferably triethylamine, diisopropylethylamine, or the like) in an appropriate polar aprotic solvent (N,N-dimethylformamide, acetonitrile, dichloromethane, or the like). Alternative combination reagents, reagents that combine an activating reagent and a hydroxy triazole, such as O-(7-azabenzotriazol-1-yl)-N,N,N',N'-tetramethyluronium hexafluorophosphate (HATU) or (benxotriazol-1-yloxy)tris(dimethylamino)phosphonium hexafluorophosphate (BOP) can be used in the presence of a base. The carboxylic acid may also be converted to an acid chloride by treatment with an appropriate chlorinating agent (thionyl chloride, oxalyl chloride, or the like). Similarly, the carboxylic acid may be converted to an acyl fluoride upon exposure to a fluorinating agent (such as cyanuric fluoride). Condensation of the acyl halide (chloride or fluoride) with the amine (VII) (typically carried out in the presence of a base such as pyridine or triethylamine in an aprotic solvent) may then provide the amide II/III.

Scheme 3. Saponification of esters VIII/IX

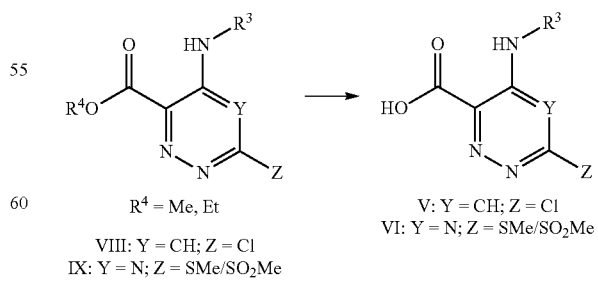

$R^4$ = Me, Et

VIII: Y = CH; Z = Cl
IX: Y = N; Z = SMe/SO$_2$Me

V: Y = CH; Z = Cl
VI: Y = N; Z = SMe/SO$_2$Me

Scheme 3 illustrates the preparation of acids V/VI via saponification of ester VIII/IX. Saponification can be accomplished using sodium, lithium, or potassium hydroxide under aqueous conditions with an organic co-solvent such as methanol and/or tetrahydrofuran.

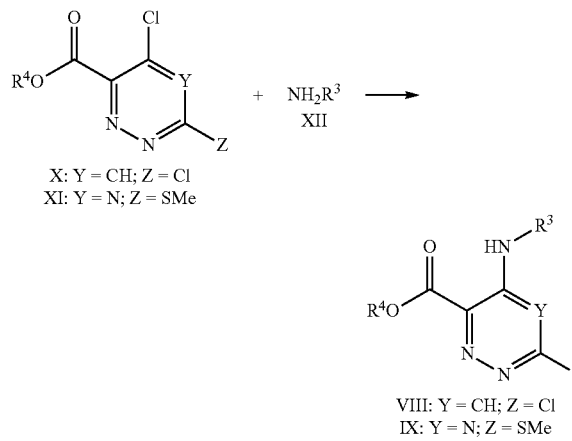

Scheme 4. Coupling of chlorides X/XI with amine XII

Scheme 4 illustrates the preparation of VIII/IX from the chloro-heterocycles X/XI via coupling with an amine (XII). In the case of pyridazine X this coupling can be accomplished using nucleophilic displacement, using either strong bases (for example lithium hexamethyldisilazide) or weak bases (for example triethylamine) in an appropriate solvent (tetrahydrofuran, acetonitrile, dimethylformamide and related). Careful monitoring of the reactions progress and appropriate solvent/base selection ensure that regioselectivity and over addition are not a concern. In the case of triazine XI the displacement is best accomplished using a palladium-catalyzed N-arylation reaction as described previously in the literature for the same compound (XI) (see: Gamier, E. et al., *Synlett*, 472-474 (2006)).

Scheme 5 illustrates the preparation of X, which was carried out in the manner previously described in US 2004/0142930 A1 (see: Yamada, K. et al., "Preparation of Heterocyclic Compounds as Selective Phosphodiesterase V Inhibitors", US 2004/0142930 A1 (Jul. 22, 2004)).

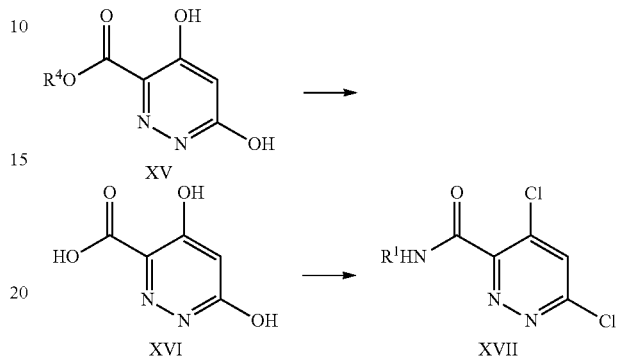

Scheme 6. Preparation of XVII

An alternative strategy that converts the ester-diol XV to the amide dichloride XVII is outlined in Scheme 6. Saponification of XV, which can be accomplished using sodium, lithium, or potassium hydroxide under aqueous conditions with an organic co-solvent such as methanol and/or tetrahydrofuran, provides XVI. Following a chlorination procedure analogous to that described in the preparation of X, material is refluxed in neat phosphorus oxychloride, see US 2004/0142930 A1, but rather than quench the reaction with water, a nucleophilic amine ($NH_2R^1$) either used in excess or in the presence of a tertiary amine base (such as triethylamine or diisopropylethylamine) are added to the crude product to provide XVII.

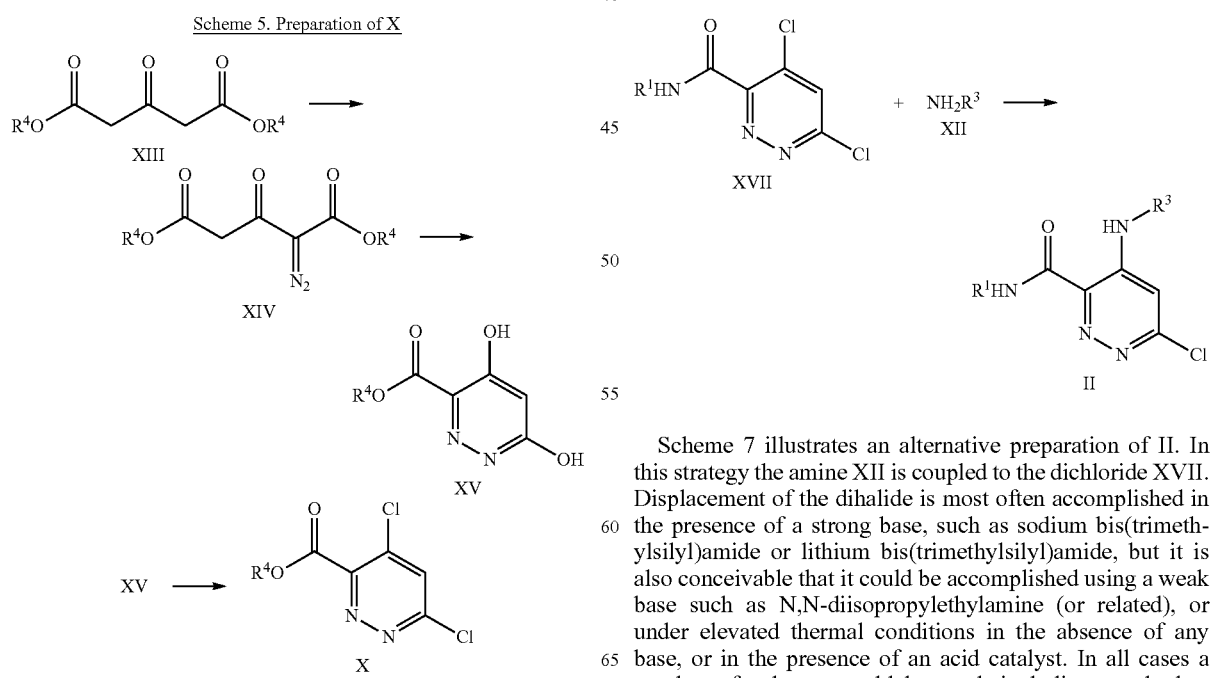

Scheme 7 illustrates an alternative preparation of II. In this strategy the amine XII is coupled to the dichloride XVII. Displacement of the dihalide is most often accomplished in the presence of a strong base, such as sodium bis(trimethylsilyl)amide or lithium bis(trimethylsilyl)amide, but it is also conceivable that it could be accomplished using a weak base such as N,N-diisopropylethylamine (or related), or under elevated thermal conditions in the absence of any base, or in the presence of an acid catalyst. In all cases a number of solvents could be used, including tetrahydrofuran, dimethylformamide and N-methyl-2-pyrrolidone.

Due to the increased reactivity of the 4-position relative to the 6-position of the 4,6-dichloropyridazine amide it is reasonable to assume that alternative strategies could also be envisioned by someone skilled in the art of chemical synthesis, including palladium catalyzed N-arylation of amines.

Scheme 8. Preparation of XI

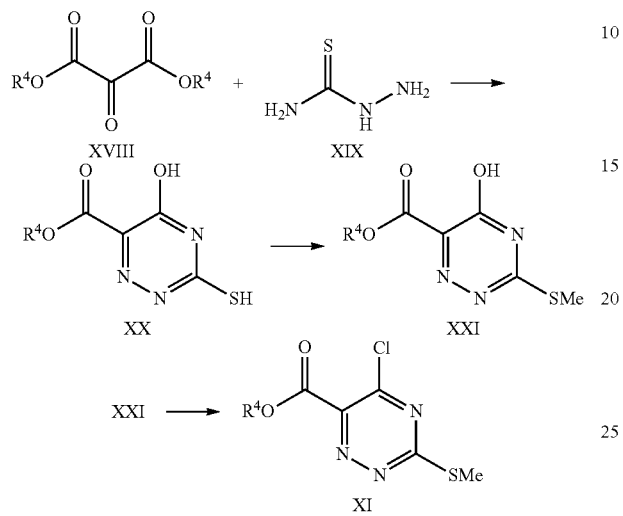

Scheme 8 illustrates the preparation of XI, which may be carried out in the manner previously described in US 2002/0061865 A1 (see: Kramer, J. B. et al., "Pyridotriazines and Pyridopyridazines", US 2002/0061865 A1 (May 23, 2002).).

Scheme 9. Oxidation of pendant sulfides

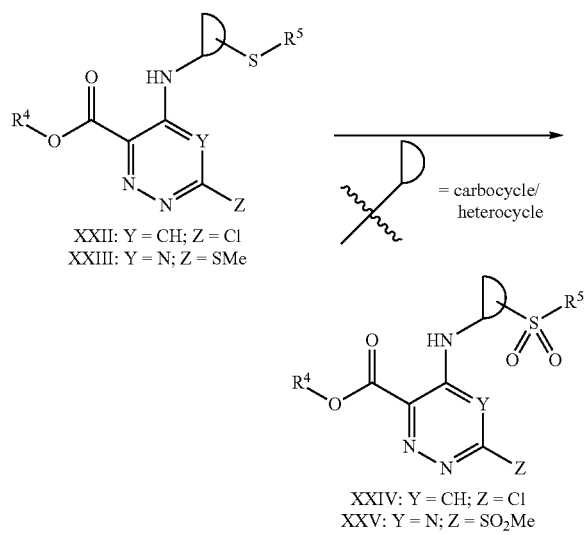

$R^5$ = acyclic aliphatic chains with or without substition, amines bearing aliphatic substituents including hydrogen Scheme 9 illustrates how pendant sulfides can be oxidized to the corresponding sulfones or (in the case of XXII) the sulfoxide (not illustrated). The sulfide (XXII/XXIII) can be oxidized to the sulfone (XXIV/XXV) using an oxidant such as sodium tungstate or 3-chloroperbenzoic acid in an organic solvent such as dichloromethane or acetic acid. The partial oxidation of XXII to the sulfoxide (not shown) generally requires more mild conditions such as hydrogen peroxide in acetic acid; however, it is possible to use the same conditions as when targeting the sulfone if one quenches the reaction at the appropriate time. To access the sulfoxide in the triazene series, the sulfide group (Z) can be displaced by VII (Scheme 2) and then partial oxidation can be performed as described above.

Scheme 10. Synthesis of anilines XII

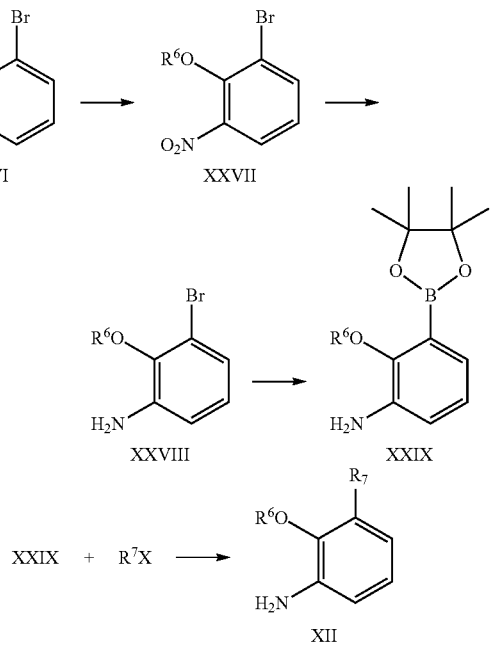

$R^6 = C_nR^{1a}$
$R^7$ = Aryl or heteraryl ring or bicycle
$X$ = halide

A large number of the anilines that were employed in Scheme 4 and Scheme 7 were commercially available; however, some were not. A strategy for the synthesis of many non-commercially available anilines is described in Scheme 10. The commercially available XXVI can be converted to the ether XXVII using the Williamson ether synthesis. The Williamson ether formation is a common protocol for the synthesis of ethers, the reaction consists of the combination of an alcohol and a base—such as potassium carbonate, sodium hydride, triethylamine, or any number of others, followed by the addition of a compatible electrophile, such as an aliphatic, benzylic or allylic functional group featuring a leaving group—most commonly a halide, but mesylates/tosylates and other groups are also compatible, is added. The reaction is typically run in a polar aprotic solvent such as tetrahydrofuran or dimethylformamide. The nitro group of XXVII is then reduced to the amine (XXVIII) using a heterogeneous catalyst such as palladium, zinc or iron and a hydrogen source such as hydrogen (gas), ammonium chloride or hydrochloric acid, such reactions are typically run in alcoholic solvents. Borylation of the aryl bromide can be accomplished using palladium catalysis (see Ishiyama, T. et al., J. Org. Chem., 60:7508 (1995)); however, metal halogen exchange followed by reaction with electrophilic borane is another common approach. The boronic ester (XXIX) can be coupled via the Suzuki coupling to a wide variety of aryl and heteroaryl halides using a number of different catalysts, ligands, bases and solvents. One common combination of reagents is 1,1'-bis(di-tert-butylphosphino)ferrocene palladium dichloride, as the catalyst, tribasic potassium phosphate (in water), as the base, reacting with an aryl bromide using dioxane as the solvent; however, a great number of potential combinations exist, for a partial description see: Barder, T. E. et al., *J Am. Chem. Soc.*, 127:4685-4696 (2005); and Miyaura, N. et al., *Chem. Rev.*, 95:2457-2483 (1995).

Scheme 11. Alternative preparation of I

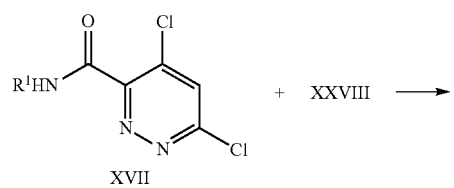

XVII

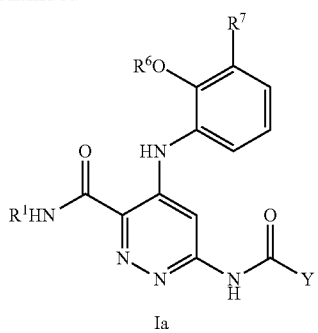

Ia

X = Halide, OH
Y = $R^2$; $N(R^8)(R^9)$
$R^8/R^9$ = independantly H, aliphatic, aryl Scheme 11 illustrates a means by which diversity at the $R^7$ (Ia) can be introduced at the end of the synthetic sequence. In this strategy XVII and XXVIII can be coupled following the same procedures described in Scheme 7. Intermediate XXX can be converted to the primary amine via the addition of a protected amine (either via thermal, or selective palladium catalyzed N-arylation conditions) followed by deprotection, for example 4-methoxyphenyl)methanamine can be introduced under strictly thermal conditions followed by deprotection with a protic acid (such as trifluoroacetic acid) to provide XXXI. Addition of XXXII to the free amine can be accomplished using the same techniques described in Scheme 2. Conversion to Ia can be accomplished using the Suzuki coupling reaction as described in Scheme 10, as well as other cross-coupling strategies such as Stille and Negishi cross-couplings (see: Stanforth, S. P., *Tetrahedron*, 54:263-303 (1998)).

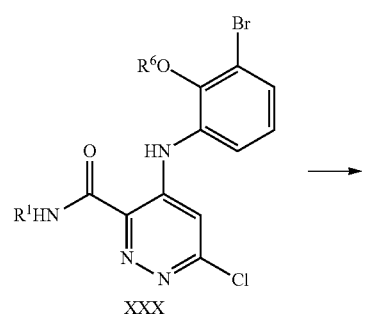

XXX

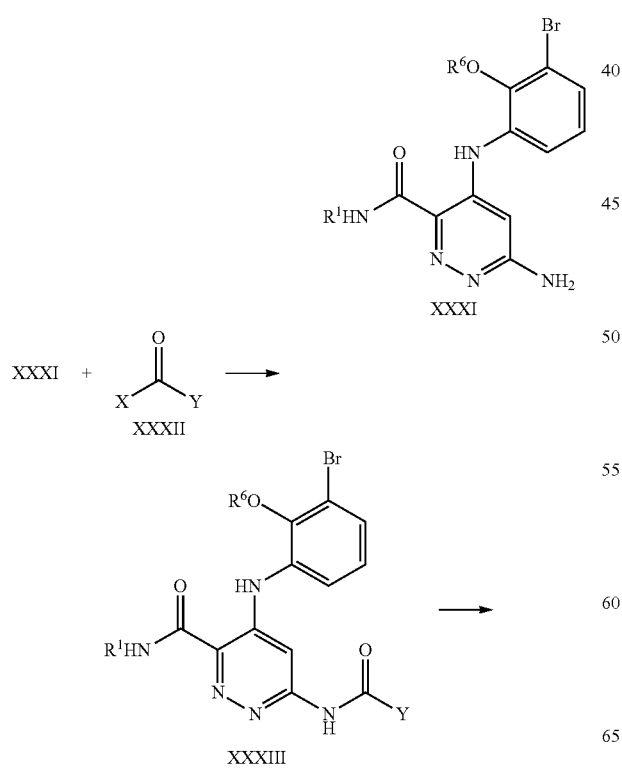

Scheme 12. Alternate synthesis of anilines XII

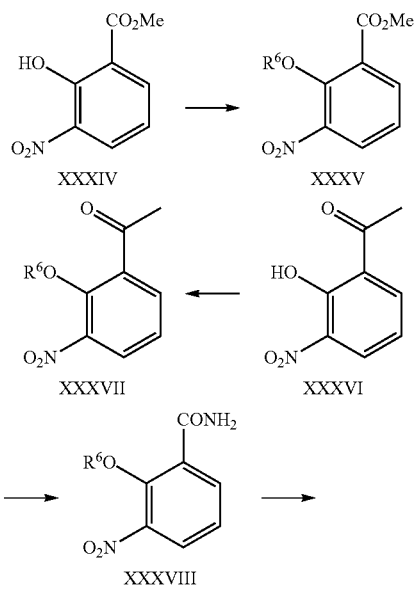

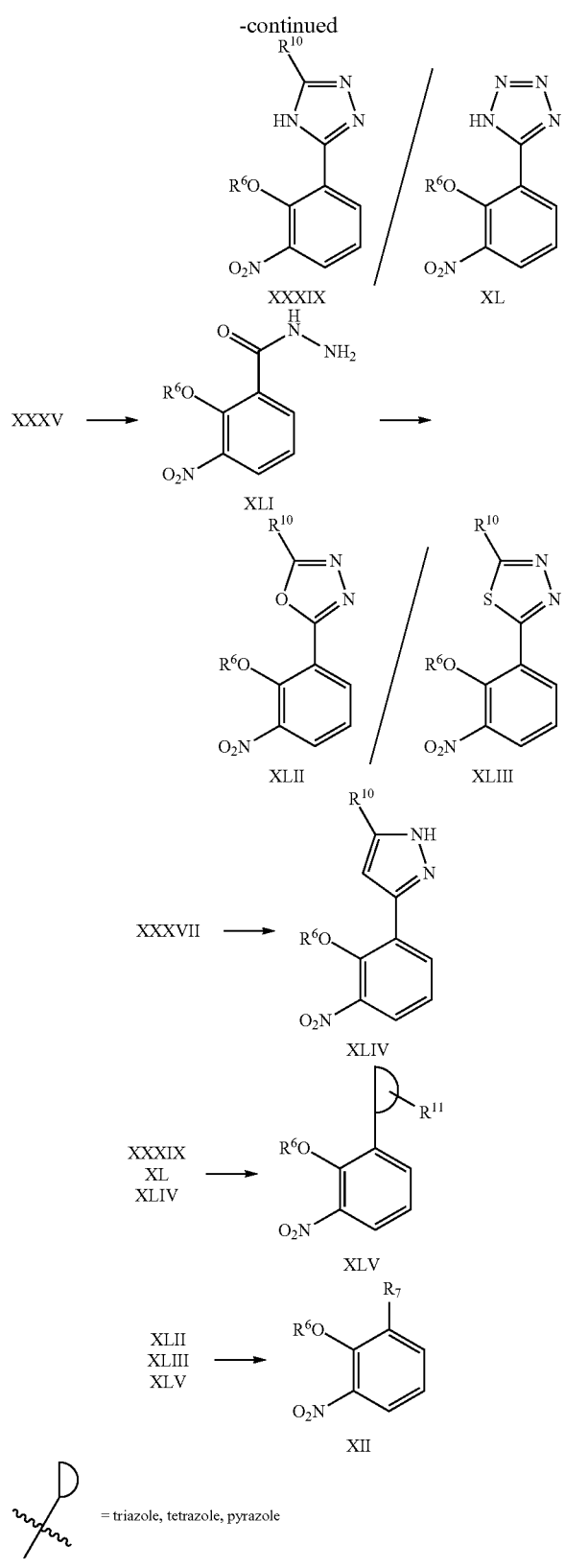

= triazole, tetrazole, pyrazole $R^{10}/R^{11}$ = independantly H, aliphatic, benzylic, allylic Scheme 12 illustrates how some of heterocycles can be built directly off of carbonyl functionality to arrive at anilines XII without the use of a transition metal catalyzed coupling reaction. The commercially available XXXIV can be converted to the ether XXXV via the techniques described in Scheme 10, similarly XXXVI can be converted to XXXVII. XXXV can be converted to the amide XXXVIII directly using ammonia and ammonium hydroxide in methanol, or via saponification and amide formation (described in Schemes 3 and 2 respectively). The amide XXXVIII can be converted to a triazole via formation of the amidine using reagents such as N,N-dimethylacetamide dimethyl acetal or N,N-dimethylformamide dimethyl acetal followed by exposure to hydrazine in the presence of acetic acid. Alternatively the tetrazole XL can be prepared from XXXVIII by reaction with triazidochlorosilane (generated in situ from tetrachlorosilane and sodium azide, see: El-Ahl, A-A. S. et al., *Tetrahedron Lett.*, 38:1257-1260 (1997).). The hydrazide XLI can be converted to the oxadiazole via a condensation reaction with an orthoformate or orthoacetate under thermal or acid catalyzed conditions, often using the orthoformate/ orthoacetate as the solvent. Alternatively the aceto variant of hydrazide XLI can be converted to the thiazole by exposure to a sulfonating reagent such as Lawesson's reagent and then condensation under thermal conditions, typically in polar aprotic solvent such as dioxane. The ketone XXXVII can be converted to the pyrazole XLIV by condensation with N,N-dimethylacetamide dimethyl acetal or N,N-dimethylformamide dimethyl acetal (or related) followed by reaction with hydrazine in the presence of acetic acid. In the cases of XXXIX, XL, and XLIV the heterocycle can further be reacted with an electrophile such as organo-halides, epoxides or activated carbonyl species (under basic conditions using an inorganic base such as potassium carbonate, a tertiary amine such as triethylamine, or a strong base such as sodium hydride) or with vinyl ethers such as ethoxyethene (under acidic conditions). Other electrophiles such as silyl halides would also be successful as would potentially a selective palladium catalyzed N-arylation. Finally the nitro compounds can be converted to the aniline XII via reduction using conditions similar to those described in Scheme 10. This list is far from an exhaustive collection of the heterocycles available from common functional group manipulations of carbonyl moieties and their derivatives (such as cyanides) see: Caron, S., *Practical Synthetic Organic Chemistry*, 609-647 (2011) and references therein.

Scheme 13. Synthesis of thioanilines XLIX

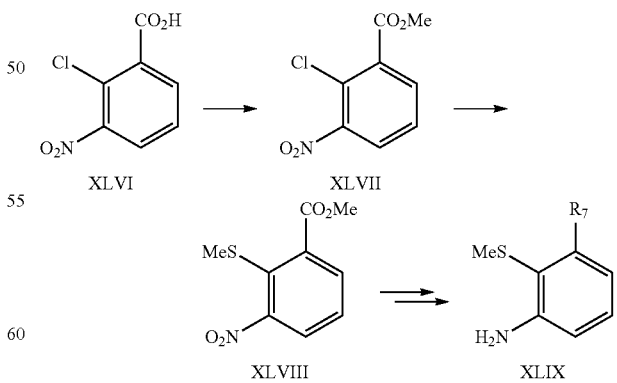

Scheme 13 illustrates the synthesis of the thio-variant of XII. Starting from the commercially available acid XLVI, which can be converted to the ester via heating with methanol in the presence of a protic acid, as well as by any number of techniques available for the synthesis of esters from acids, such as formation of the acid halide (described in Scheme 2) followed by reaction with methanol. Displacement of the chloride to provide XLVIII can be accomplished via nucleophilic addition using sodium thiomethoxide. Conversion to the functionalized aniline XLIX follows the same techniques illustrated and described in Scheme 12. Additionally the final sulfide product can be oxidized to the sulfone using the oxidation conditions described in Scheme 9.

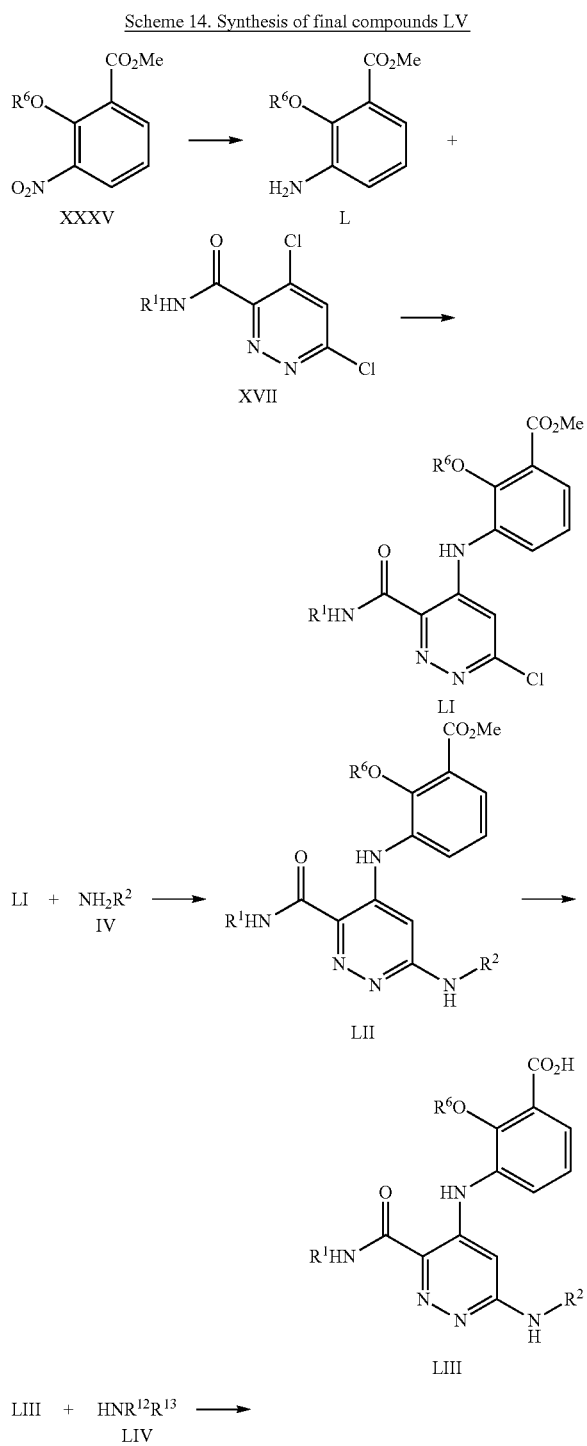

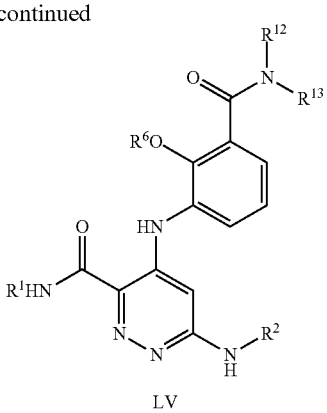

$R^{12}/R^{13}$ = independantly H, aliphatic, benzylic, allylic, also potentially linked to form a heterocycle Scheme 14 illustrates another form of the final compound Ia. In this strategy the aniline L (made via reduction of the nitro compound XXXV by analogy to Scheme 10) is added to the dichloride XVII using the techniques from Scheme 7. Conversion to LII can be accomplished using the same techniques described in Scheme 1. Saponification (described in Scheme 3) provides the acid LIII. The acid LIII can be converted to various heterocycles using the techniques described in Scheme 12, or it can be coupled with an amine to generate the amide LV as the final product as described in Scheme 2.

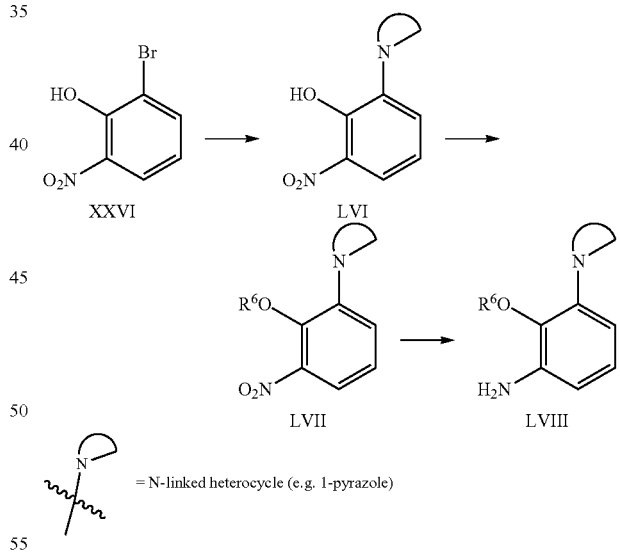

Scheme 15 illustrates another variant of XII, where the aniline has been substituted with a heterocycle via a carbon-nitrogen bond. Starting from commercially available XXVI an Ullmann condensation (for a recent review see: Mannier, F. et al., *Angew. Chem. Int. Ed.*, 48:6954-6971 (2009)) can be used. This reaction is typically performed in the presence of a copper salt (such as copper(I) oxide), an inorganic base (such as cesium carbonate) and often a ligand (although some solvents such as DMF can take the role of the ligand). The phenol LVI can be converted to the ether LVII using the Williamson ether conditions as described in Scheme 10.

Conversion to the aniline (LVIII) is accomplished by reduction of the nitro group as described in Scheme 10.

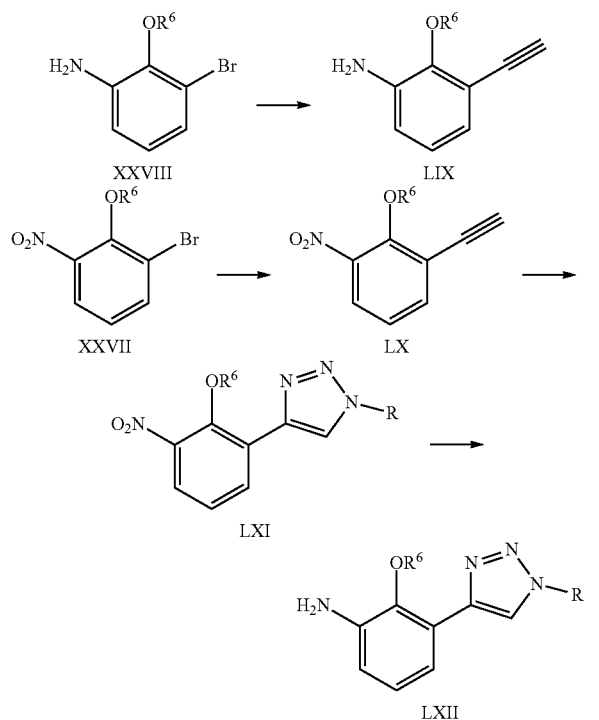

Scheme 16 describes the synthesis of anilines LIX and LXII. A Sonogashira coupling of XXVIII/XXVII with ethynyltrimethylsilane followed by removal of the silyl group using a mild base (such as potassium carbonate in a protic solvent such as methanol) or a fluoride source (such as tetrabutylammonium fluoride or potassium fluoride) can be used to provide the terminal alkynes LIX and LX. The Sonogashira coupling is performed using a palladium catalyst (such as tetrakis triphenylphosphine palladium), a copper catalyst such as copper(I) iodide, and a base (typically an amine base such as triethylamine or diisopropylamine) using either the base as the solvent or a polar solvent such as dimethylformamide; however, a great deal of work has been done running the reaction with different ligands and additives and even in the absence of the catalysts, see: Chinchilla, R. et al., *Chem. Rev.* 107:874-923 (2007); Chinchilla, R. et al., *Chem. Soc. Rev.,* 40:5084-5121 (2011). The aniline LIX can be coupled to XVII as described in Scheme 7 and then converted to the target ligand I as described in Scheme 1 or further elaborated using the techniques described for LXI (to follow). LX can be converted to the 1,2,3-triazole using the Huisgen cycloaddition (or "Click chemistry"), This reaction is run between an alkyne and an azide using a copper catalyst (commonly copper(II) sulfate), a reducing agent (such as sodium ascorbate), the reaction can be run in a number of solvents/co-solvents including water, tert-butyl alcohol, tetrahydrofuran and toluene. A great deal of work has been done describing the variety and versatility of this cycloaddition, for reviews see: Kolb, H. C. et al., *Angew. Chem. Int. Ed.,* 40:2004-2021 (2001), and Meldal, M. et al., *Chem. Rev.,* 108:2952-3015 (2008). If the Huisgen cycloaddition is performed with a removable group such as methyl pivalate this can be removed and the triazole alkylated as described in Scheme 12. Otherwise the nitro group can be reduced as described in Scheme 10 and LXII can be carried forward to react with XVII as described in Scheme 7.

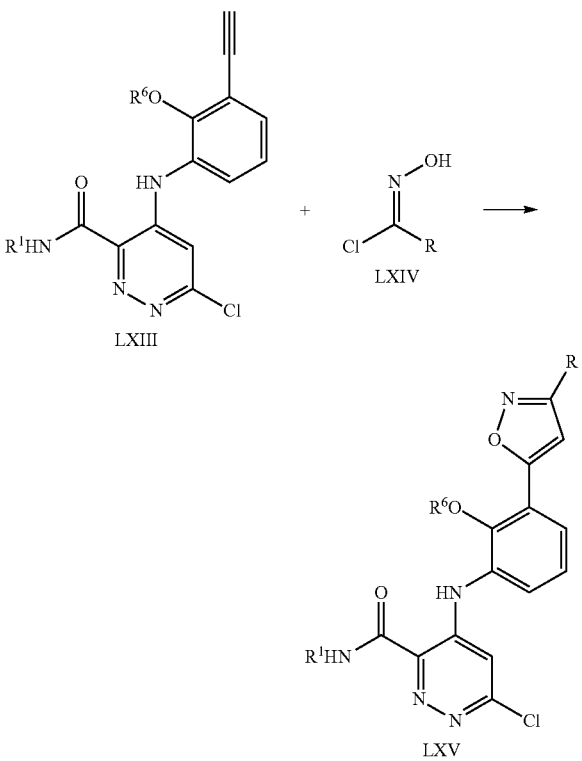

Scheme 17 illustrates the synthesis of penultimate compounds LXV (converted to target ligands using the coupling procedures described in Scheme 1). Intermediate LXIII (prepared using the techniques described in Scheme 16 and Scheme 7) can be converted to the isoxazole LXV using a [3+2] cycloaddition with a nitrile oxide (formed in situ from a N-hydroxyimidoyl chloride and a mild non-nucleophilic base). The reaction can be run thermally in aprotic solvents (such as dichloroethane) but recent work has described the utility of catalysts in the reaction, see: Grecian, S. et al., *Angew. Chem. Int. Ed.,* 47:8285-8287 (2008).

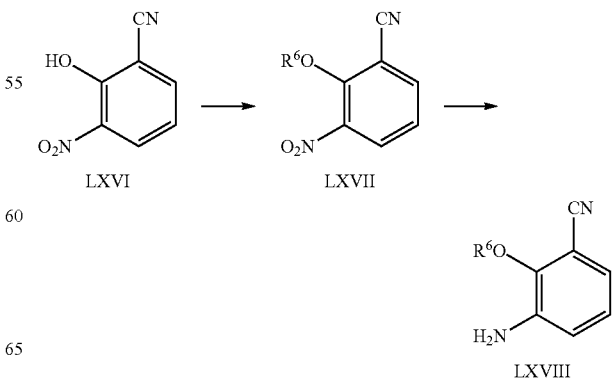

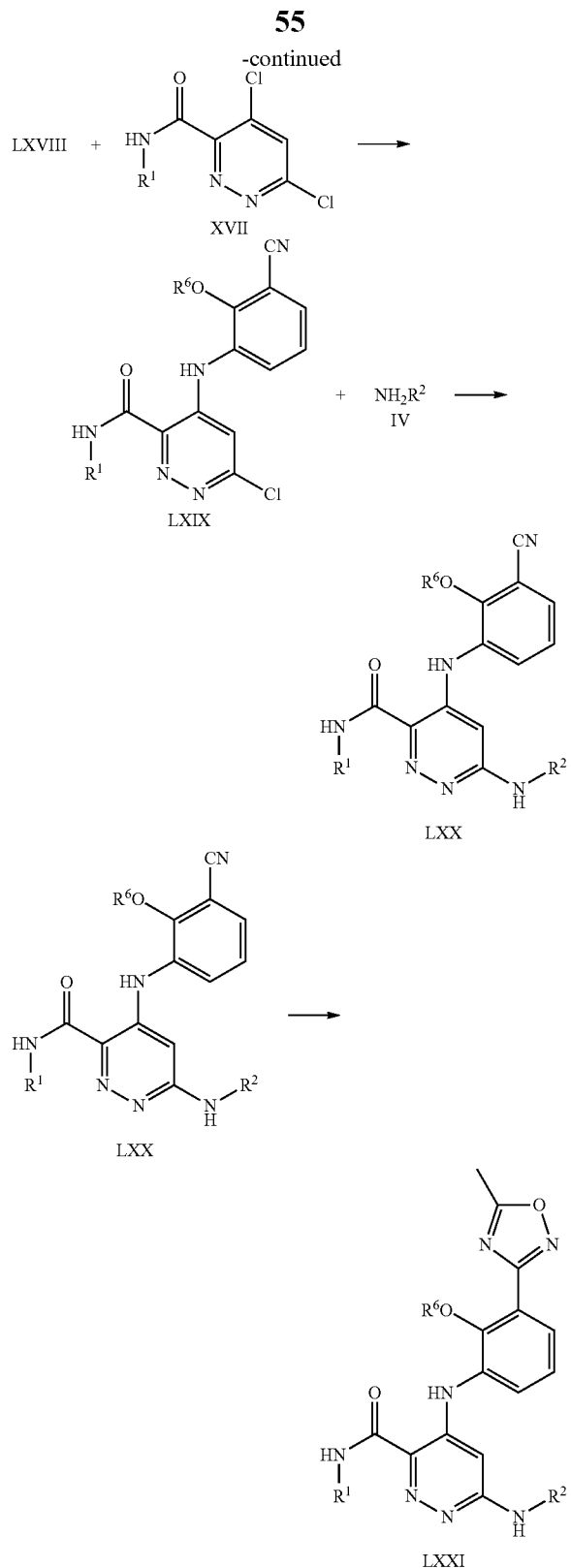

Scheme 18 illustrates the synthesis of target compounds LXX and LXXI. Commercially available LXVI can be converted to the aniline LXVIII following the strategies outlined in Scheme 10. Addition of LXVIII to XVII follows the techniques described in Scheme 7 to provide LXIX which can be coupled to amines IV following the strategies described in Scheme 1. Conversion of the cyano-containing LXX to the oxadiazole LXXI can be accomplished via the nucleophilic addition of hydroxylamine to the cyanide, performed under basic conditions typically in a polar protic solvent such as water or alcohol, followed by acylation and condensation with acetic anhydride, done by heating the intermediate with acetic anhydride in a polar aprotic solvent such as dioxane.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Chemical names were determined using ChemDraw Ultra, version 9.0.5 (CambridgeSoft). The following abbreviations are used:

$NaHCO_3$ (aq)=saturated aqueous sodium bicarbonate
brine=saturated aqueous sodium chloride
DCM=dichloromethane
DIEA=N,N-diisopropylethylamine
DMAP=4-(N,N-dimethylamino)pyridine
DMF=N,N-dimethylformamide
DMSO=dimethyl sulfoxide
EDC=N-(3-dimethylaminopropyl)-N'-ethylcarbodiimide hydrochloride
EtOAc=ethyl acetate
HOAT=1-hydroxy-7-azabenzotriazole
HOBT=1-hydroxybenzotriazole hydrate
rt=ambient room temperature (generally about 20-25° C.)
TEA=triethylamine
TFA=trifluoroacetic acid
THF=tetrahydrofuran Preparations The preparations set out below are for the synthesis of reagents that were not obtained from commercial sources and were employed for the preparation of compounds of formula I of the invention. All chiral compounds in the Tables and Schemes are racemic unless specified otherwise.

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol ("MeOH")/water mixtures in the presence of 0.1% trifluoroacetic acid ("TFA").

Analytical HPLC Method Employed in Characterization of Examples

Analytical HPLC was performed on Shimadzu LC10AS liquid chromatographs using the following methods:

Method A (used in all cases, unless otherwise indicated):
Linear gradient of 0 to 100% solvent B over 4 minutes ("min"), with 1 minute ("min") hold at 100% B
Ultraviolet ("UV") visualization at 220 nanometers ("nm")
Column: YMC S5 ODS Ballistic 4.6×50 mm
Flow rate: 4 milliliters ("mL")/min
Solvent A: 0.2% phosphoric acid, 90% water, 10% methanol
Solvent B: 0.2% phosphoric acid, 90% methanol, 10% water Method B:
Column: PHENOMENEX® Luna C18(2), 4.6×50 mm×5 m
Mobile Phase: (A) 10:90 methanol:water; (B) 90:10 methanol:water
Buffer: 0.1% TFA
Gradient Range: 0-100% B
Gradient Time: 4 min
Flow Rate: 4 mL/min
Analysis Time: 5 min
Detection:
Detector 1: UV at 220 nm
Detector 2: MS (ESI+)
Detector 3: ELSD Method C:
Column: Waters SunFire C18, 4.6×50 mm×5 m
Mobile Phase: (A) 10:90 methanol:water; (B) 90:10 methanol:water
Buffer: 0.1% TFA
Gradient Range: 0-100% B
Gradient Time: 4 min
Flow Rate: 4 mL/min
Analysis Time: 5 min
Detection:
Detector 1: UV at 220 nm
Detector 2: MS (ESI+)
Detector 3: ELSD Method D:
Column: PHENOMENEX® Luna C18(2), 4.6×50 mm×5 m
Mobile Phase: (A) 10:90 methanol:water; (B) 90:10 methanol:water
Buffer: 0.1% TFA
Gradient Range: 0-100% B
Gradient Time: 4 min
Flow Rate: 4 mL/min
Analysis Time: 5 min
Detection:
Detector 1: UV at 220 nm
Detector 2: MS (ESI+)
Detector 3: ELSD Method E:
Column: Waters Acquity UPLC BEH C18, 2.1×50 mm, 1.7 m particles
Mobile Phase: (A) 5:95 acetonitrile:water; (B) 95:5 acetonitrile:water
Buffer: 10 mM ammonium acetate
Gradient Range: 0-100% B
Gradient Time: 3 min
Flow Rate: 1.11 mL/min
Analysis Time: 4 min
Detection:
Detector 1: UV at 220 nm
Detector 2: MS (ESI+)
Detector 3: ELSD Method F:
Column: Waters SunFire C18 (4.6×150 mm), 3.5 m
Mobile Phase: (A) 5:95 acetonitrile:water; (B) 95:5 acetonitrile:water
Buffer: 0.1% TFA
Gradient Range: 0-100% B
Gradient Time: 12 min
Flow Rate: 4 mL/min
Analysis Time: 15 min
Detection:
Detector 1: UV at 220 nm
Detector 2: UV at 254 nm Method G:
Column: Waters Acquity UPLC BEH C18, 2.1×50 mm, 1.7 m particles
Mobile Phase: (A) 5:95 acetonitrile:water; (B) 95:5 acetonitrile:water
Buffer: 0.05% TFA
Gradient Range: 0-100% B
Gradient Time: 3 min
Flow Rate: 1.11 mL/min
Analysis Time: 4 min
Detection:
Detector 1: UV at 220 nm
Detector 2: MS (ESI$^+$)
Detector 3: ELSD Method H:
Column: (LCMS) Ascentis Express C18, 4.6×50 mm, 2.7 m particles
Mobile Phase: (A) 5:95 acetonitrile:water; (B) 95:5 acetonitrile:water
Buffer: 10 mM ammonium acetate
Gradient Range: 0-100% B
Gradient Time: 4 min
Flow Rate: 4 mL/min
Analysis Time: 5 min
Detection:
Detector 1: UV at 220 nm
Detector 2: MS (ESI$^+$)

Method I:
Column: Waters XBridge C18, 4.6×50 mm, 5 μm particles
Mobile Phase: (A) 5:95 acetonitrile:water; (B) 95:5 acetonitrile:water
Buffer: 0.05% TFA
Gradient Range: 0-100% B
Gradient Time: 4 min
Flow Rate: 4 mL/min
Analysis Time: 5 min
Detection:
Detector 1: UV at 220 nm
Detector 2: MS (ESI$^+$)

Method J:
Column: (LCMS) BEH C18, 2.1×50 mm, 1.7 m particles
Mobile Phase: (A) water; (B) acetonitrile
Buffer: 0.05% TFA
Gradient Range: 2%-98% B (0 to 1 min) 98% B (to 1.5 min) 98%-2% B (to 1.6 min)
Gradient Time: 1.6 min
Flow Rate: 0.8 mL/min
Analysis Time: 2.2 min Detection:
  Detector 1: UV at 254 nm
  Detector 2: MS (ESI+)
Method K:
  Column: (LCMS) BEH C18, 3.0×50 mm, 1.7 μm particles
  Mobile Phase: (A) 5:95 acetonitrile:water; (B) 95:5 acetonitrile:water
  Buffer: 10 mM ammonium acetate
  Gradient Range: 0-100% B
  Gradient Time: 1.8 min
  Flow Rate: 1.2 mL/min
  Analysis Time: 4 min
  Detection:
  Detector 1: UV at 220 nm
  Detector 2: MS (ESI+)
Method L:
  Column: (LCMS) SunFire C18 2.1×30 mm, 2.5 μm particles
  Mobile Phase: (A) 10:90 methanol:water; (B) 90:10 methanol:water
  Buffer: 0.1% TFA
  Gradient Range: 0-100% B
  Gradient Time: 2 min
  Flow Rate: 1 mL/min
  Analysis Time: 3 min
  Detection:
  Detector 1: UV at 220 nm
  Detector 2: MS (ESI+)
Method M:
  Column: (LCMS) SunFire C18 2.1×30 mm, 3.5 m particles
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 1 mL/min
  Analysis Time: 5 min
  Detection:
  Detector 1: UV at 220 nm
  Detector 2: MS (ESI+)
Method N:
  Column: Waters SunFire C18 (3×150 mm), 3.5 m
  Mobile Phase: (A) 5:95 acetonitrile:water; (B) 95:5 acetonitrile:water
  Buffer: 0.05% TFA
  Gradient Range: 0-100% B
  Gradient Time: 12 min
  Flow Rate: 0.5 mL/min
  Analysis Time: 15 min
  Detection:
  Detector 1: UV at 220 nm
  Detector 2: UV at 254 nm
Method O:
  Column: Waters SunFire C18 (4.6×150 mm), 3.5 m
  Mobile Phase: (A) 5:95 acetonitrile:water; (B) 95:5 acetonitrile:water
  Buffer: 0.05% TFA
  Gradient Range: 0-50% B (0-15 min) 50-100% B (15-18 min)
  Gradient Time: 18 min
  Flow Rate: 1 mL/min
  Analysis Time: 23 min
  Detection:
  Detector 1: UV at 220 nm
  Detector 2: UV at 254 nm
Method P:
  Column: XBridge phenyl (4.6×150 mm), 3.5 m
  Mobile Phase: (A) 5:95 acetonitrile:water; (B) 95:5 acetonitrile:water
  Buffer: 0.05% TFA
  Gradient Range: 10-100% B
  Gradient Time: 12 min
  Flow Rate: 1 mL/min
  Analysis Time: 15 min
  Detection:
  Detector 1: UV at 220 nm
  Detector 2: UV at 254 nm
Method Q:
  Column: YMC COMBISCREEN® ODS-A, 4.6×50 mm, S-5
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 4 mL/min
  Analysis Time: 5 min
  Detection:
  Detector 1: UV at 254 nm
Method R:
  Column: (LCMS) Ascentis Express C18, 2.1×50 mm, 2.7 μm particles
  Mobile Phase: (A) 2:98 acetonitrile:water; (B) 98:2 acetonitrile:water
  Buffer: 10 mM ammonium acetate
  Gradient Range: 0-100% B
  Gradient Time: 1.7 min
  Flow Rate: 1 mL/min
  Analysis Time: 4 min
  Detection:
  Detector 1: UV at 220 nm
  Detector 2: MS (ESI+)

Preparation 1

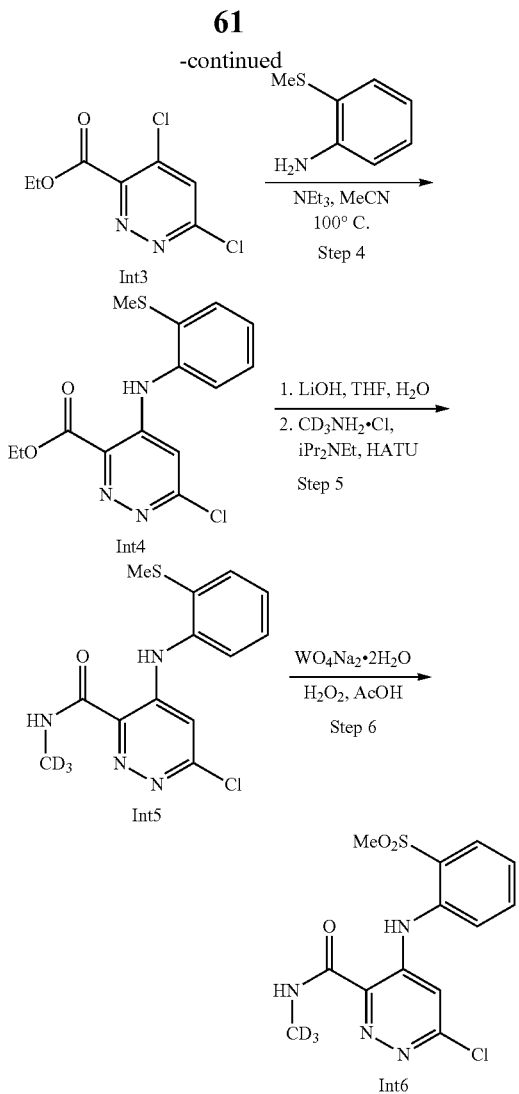

Step 1

To a cooled (0° C.) mixture of diethyl 1,3-acetonedicarboxylate (12.4 mL, 68.3 mmol) and triethylamine (10.5 mL, 75 mmol) in acetonitrile (270 mL) was added 4-acetamidobenzenesulfonylazide (16.74 g, 69.7 mmol) in portions. The reaction was warmed to room temperature and stirred for 1 hour, at which point the solids were removed by filtration, rinsing with 1:1 heptanes:diethyl ether. The filtrate was concentrated and then re-dissolved in 1:1 heptanes:diethyl ether. The slurry was stirred for 30 minutes, filtered and the filtrate concentrated once more to provide the crude product Int1 (12.2 g, 50.8 mmol). $^1$H NMR (400 MHz, chloroform-d) δ 4.31 (q, J=7.2 Hz, 2H), 4.21 (q, J=7.1 Hz, 2H), 3.87 (s, 2H), 1.33 (t, J=7.2 Hz, 3H), 1.28 (t, J=7.2 Hz, 3H).

Step 2

Int1 (12.2 g, 50.8 mmol) was dissolved in diethyl ether (100 mL) and triphenylphosphine (14 g, 53.5 mmol) was added. The reaction was stirred overnight at room temperature and then concentrated in vacuo. To the residual sludge was added acetic acid (100 mL) and water (10 mL), the vessel was equipped with a condenser and heated to reflux for 6 hours, and then concentrated in vacuo. The crude sludge was purified by automated chromatography (DCM/MeOH) and then by titration with diethyl ether (×2) to provide Int2 (5.25 g, 28.5 mmol). $^1$H NMR (400 MHz, chloroform-d) δ 12.30 (br. s., 1H), 10.59 (br. s., 1H), 6.31 (s, 1H), 4.51 (q, J=7.0 Hz, 2H), 1.47 (t, J=7.2 Hz, 3H). LC retention time 0.52 [J]. MS (E$^+$) m/z: 185 (MH$^+$).

Step 3

To a 350 mL nitrogen purged Schlenk flask containing Int2 (3.77 g, 20.47 mmol) was added phosphorus oxychloride (38 mL, 408 mmol). The vessel was sealed and heated to 100° C. for 3.5 hours. The reaction was cooled to room temperature and the excess phosphorus oxychloride was removed in vacuo. The crude oil was dissolved into chloroform, re-concentrated and then poured into ice water, rinsing with ethyl acetate. The two layers were transferred to a separatory funnel, separated and the aqueous layer extracted 3× with ethyl acetate. The combined organic layers were washed twice with water and once with brine (saturated aqueous sodium chloride) and then dried over sodium sulfate, filtered, concentrated and then purified by automated chromatography (5-90% EtOAc:hexanes), providing Int3 (3.64 g, 16.3 mmol). $^1$H NMR (400 MHz, chloroform-d) δ 7.70 (s, 1H), 4.55 (qd, J=7.1, 1.1 Hz, 2H), 1.46 (td, J=7.2, 0.9 Hz, 3H). LC retention time 0.79 [J]. MS (E$^+$) m/z: 221 (MH$^+$).

Step 4

A vial was equipped with Int3 (100 mg, 0.45 mmol), 2-(methylthio)aniline, triethylamine (0.19 mL, 1.36 mmol) and acetonitrile (0.5 mL), sealed, and heated to 100° C. overnight. The solvent was then removed under vacuum and the crude material purified by silica gel chromatography (0% to 50% EtOAc:hexanes) to provide Int4 (65 mg, 0.20 mmol). Note that the regiochemistry of the series was verified by a crystal structure of Int4. $^1$H NMR (400 MHz, chloroform-d) δ 9.66 (br. s., 1H), 7.39-7.33 (m, 2H), 6.81 (s, 1H), 4.58 (q, J=7.1 Hz, 2H), 2.46 (s, 3H), 1.52 (t, J=7.2 Hz, 3H). LC retention time 0.96 [J]. MS (E$^+$) m/z: 324 (MH$^+$).

Step 5

Int4 (65 mg, 0.20 mmol) was dissolved in tetrahydrofuran (THF, 2 mL) and lithium hydroxide (2 M in water, 0.40 mL, 0.80 mmol) was added. After stirring 30 min at room temperature, the THF was removed under reduced pressure. The residual solution was diluted with water and then acidified with 1 M hydrochloric acid. The product was extracted three times with ethyl acetate and then the combined organic layers were dried over sodium sulfate, filtered and concentrated. The residual acid was then dissolved in N,N-dimethylformamide (DMF, 0.9 mL) and deuteromethylamine (HCl salt, 16 mg, 0.23 mmol, Aldrich, catalog number 176001, 99 atom % D), triethylamine (0.10 mL, 0.58 mmol) and O-(7-azabenzotriazol-1-yl)-N,N,N',N'-tetramethyluronium hexafluorophosphate (HATU, 88 mg, 0.23 mmol) were added. The reaction was stirred for 90 minutes and then diluted with water (~15 mL) resulting in a beige precipitate. The precipitate was collected by filtration, rinsing with water and then hexanes to provide Int5 (33 mg, 0.095 mmol). $^1$H NMR (500 MHz, chloroform-d) δ 10.69 (br. s., 1H), 8.20 (br. s., 1H), 7.38-7.28 (m, 2H), 7.28-7.21 (m, 2H), 6.80 (s, 1H), 1.26 (s, 3H). LC retention time 0.97 [J]. MS (E$^+$) m/z: 312 (MH$^+$).

Step 6

Int5 (52 mg, 0.17 mmol) was dissolved in acetic acid (1.7 mL) and hydrogen peroxide (30% aqueous solution, 0.34 mL, 3.34 mmol) and sodium tungstate dihydrate (55 mg, 0.17 mmol) were added. The reaction was stirred at room temperature for 40 minutes and then water was added and the product was extracted with ethyl acetate (×3). The combined organic layers were washed with water, dried over sodium sulfate, filtered, concentrated and then purified by automated chromatography (20%-100% EtOAc:hexanes) to provide Int6. $^1$H NMR (400 MHz, chloroform-d) δ 11.49 (s, 1H), 8.20 (br. s., 1H), 8.16 (dd, J=7.9, 1.5 Hz, 1H), 7.72 (td, J=7.8, 1.4 Hz, 1H), 7.56 (d, J=7.9 Hz, 1H), 7.50-7.43 (m, 1H), 7.15 (s, 1H), 3.11 (s, 3H). LC retention time 0.81 [J]. MS (E$^+$) m/z: 344 (MH$^+$).

Alternatively Int5 can be prepared as follows:

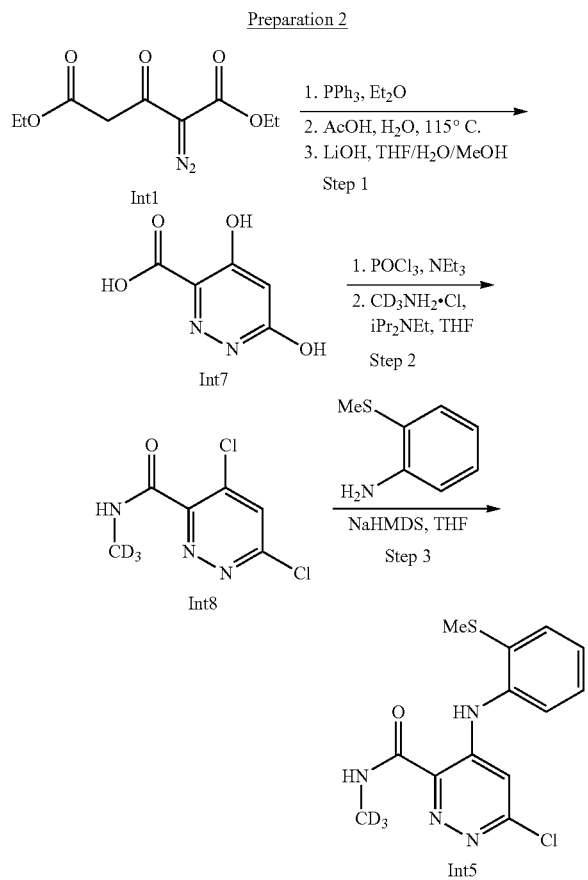

Step 1

Int1 (41.6 g, 182 mmol) was dissolved in diethyl ether (300 mL) and triphenylphosphine (47.8 g, 182 mmol) was added. The reaction was stirred overnight at room temperature and then concentrated in vacuo. To the residual sludge was added acetic acid (300 mL) and water (30 mL), the vessel was equipped with a condenser and heated to reflux for 6 hours. The reaction was concentrated and then dissolved in 1,2-dichloroethane (300 mL) and re-concentrated. The resultant slurry was dissolved in THF (600 mL) and MeOH (200 mL) and then LiOH (3M aq. 201 mL, 602 mmol) was added in portions over 5 minutes. After overnight stirring the reaction was concentrated to remove the organic solvents. Water and 1 M NaOH was added to generate a homogenous solution (total volume=400 mL, pH~12). The aqueous layer was washed 2× with diethyl ether and 2× with dichloromethane. Concentrated HCl was added until pH~7 and then the water was removed under reduced pressure, leaving a volume of ~50 mL, to this was added, at 0° C., concentrated HCl until the suspension became a densely packed solid. This solid was filtered, rinsing with 1 M HCl and then dichloromethane. After air drying (pulling air through the material on the filter pad) overnight the solid was dried for 3-5 days under vacuum in a dessicator over phosphorous pentoxide providing 27.5 g (97%) of Int7. $^1$H NMR (400 MHz, deuterium oxide) δ 6.05 (s, 1H). LC retention time 6.27 [N]. MS (E$^+$) m/z: 157 (MH$^+$).

Step 2

Int7 (10 g, 64.1 mmol) was placed in a 1 L RBF and triethylamine (8.9 mL, 64.1 mmol) was added, followed by phosphorus oxychloride (50 mL, 546 mmol). A water cooled condenser equipped with a drying tube (24/40 joint size) was then attached. The flask was placed in a room temperature oil bath and once self-reflux ceased, the temperature was raised to 80° C. Once that temperature was reached and the vigorous reflux subsided the temperature was raised again to 110° C. and the reaction run for 120 minutes. The heating was stopped and the reaction allowed to cool to ~90° C. (oil bath temperature), at which point 200 mL of anhydrous 1,2-dichloroethane was added and the flask was concentrated under reduced pressure. Caution was taken in the disposal of the condensate, which contained phosphorous oxychloride. Thus, all of the distillates were poured slowly and portionwise into a rapidly stirred ethanol/ice bath. Next, 200 mL of anhydrous 1,2-dichloroethane was added to the residue and the mixture sonicated and then concentrated. Finally 300 mL of anhydrous 1,2-dichloroethane was added and the sides of the vessel were scraped into the liqueur, the system was sonicated and stirred for ~10 minutes, and then filtered through CELITE® packed with dichloromethane and the pad rinsed with dichloromethane until the total filtrate volume was ~800 mL. This was transferred to a 2 L RBF and the solvent was removed. Next the residue was dissolved in THF (200 mL), deuteromethylamine (HCl salt, 2.26 g, 32 mmol) was then added followed by N,N'-diisopropylethylamine (18 mL, 103 mmol). After 1 hour the reaction was concentrated and the residue adsorbed onto CELITE® using dichloromethane. The CELITE® was dried and transferred onto a medium-grade glass frit, the crude product was flushed off of the CELITE® using EtOAc and the filtrate re-concentrated, and then re-adsorbed onto CELITE® using dichloromethane. This material could then be purified using automated chromatography with dry loading. Pure fractions were combined to provide 4.56 g (33%) of Int8. $^1$H NMR (500 MHz, chloroform-d) δ 7.72 (s, 1H). LC retention time 0.72 [A]. MS (E$^+$) m/z: 209 (MH$^+$).

Step 3

Int8 (3.19 g, 15.26 mmol) was dissolved in THF (100 mL) and 2-(methylthio)aniline (2.10 mL, 16.8 mmol) was added. To this solution at room temperature was added sodium bis(trimethylsilyl)amide (NaHMDS, 1 M in THF, 38 mL, 38 mmol) in a dropwise manner. The reaction was stirred for 15 minutes and then 22 mL of 1 M (aq.) HCl was added to quench the reaction. The resultant homogenous solution was poured into rapidly stirred water (600 mL) resulting in a white precipitate. The suspension was stirred for 10 minutes and then filtered, rinsing with water and then hexanes. The powder was dried and carried on as Int5. $^1$H NMR (400 MHz, DMSO-d$_6$) δ 10.76 (s, 1H), 9.34 (s, 1H), 7.47-7.41 (m, 2H), 7.37 (td, J=7.7, 1.3 Hz, 1H), 7.32-7.25 (m, 1H), 6.80 (s, 1H), 2.46 (s, 3H).

Example 1

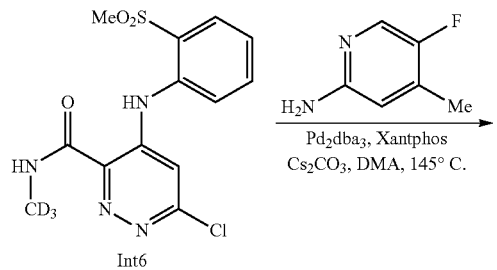

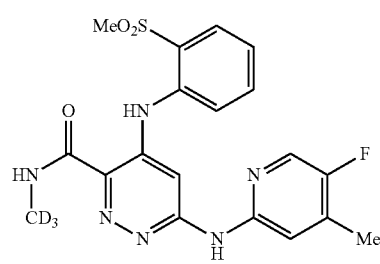

5-Fluoro-4-methylpyridin-2-amine (22 mg, 0.18 mmol) was combined with Int6 (15 mg, 0.044 mmol). To the vessel was added dimethylacetamide (DMA, 0.5 mL) followed by tris(dibenzylideneacetone)dipalladium(0) (Pd$_2$(dba)$_3$, 6.0 mg, 0.0065 mmol), 4,5-bis(diphenylphosphino)-9,9-dimethylxanthene (Xantphos, 7.6 mg, 0.013 mmol) and cesium carbonate (57 mg, 0.18 mmol). The vessel was then evacuated and backfilled with nitrogen three times and then heated to 145° C. for 4.5 hours. The crude product was diluted with DMF and filtered, and then purified using preparative HPLC. The pure fractions were pooled and concentrated in vacuo to a volume of about 2 mL at which point saturated aqueous sodium bicarbonate was added and the slurry stirred for 10 minutes. The product was extracted with ethyl acetate (×5), the combined organic layers were washed with deionized water, dried over sodium sulfate, filtered and concentrated. The residual solid was dissolved in 2:1 acetonitrile:water, frozen and then dried on a lyopholizer overnight to provide 1 (8.4 mg, 0.019 mmol). $^1$H NMR (500 MHz, DMSO-d$_6$) δ 8.21 (s, 1H), 7.88 (d, J=7.8 Hz, 1H), 7.78 (dd, J=8.0, 7.8 Hz, 1H), 7.63 (s, 1H), 7.34 (s, 1H), 7.32 (d, J=7.8 Hz, 1H), 7.00 (dd, J=8.0, 7.8 Hz, 1H), 3.09 (s, 3H), 2.82 (d, J=4.8 Hz, 3H), 2.13 (s, 3H). LC retention time 0.68 [J]. MS (E$^+$) m/z: 434 (MH$^+$).

The following Examples were prepared in a similar manner to the product of Example 1:

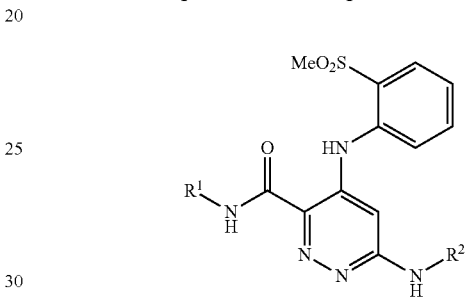

| Example No. | R$^1$ | R$^2$ | Rt (min) [Method] | m/z [M + H]$^+$ |
|---|---|---|---|---|
| 2 | H | ![pyridine-F] | 1.37 [E] | 403 |
| 3 | CH$_3$ | ![pyridine-F] | 1.46 [E] | 417 |
| 4 | Et | ![pyridine-F] | 1.50 [E] | 431 |
| 5 | cyclopropyl | ![pyridine-F] | 1.54 [A] | 443 |
| 6 | CD$_3$ | ![pyridine-F] | 0.73 [J] | 420 |

-continued
| Example No. | R¹ | R² | Rt (min) [Method] | m/z [M + H]⁺ |
|---|---|---|---|---|
| 7 | CD₃ | 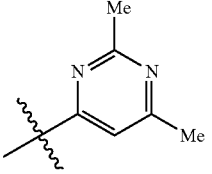 [SMILES: *c1cc(C)nc(C)n1] | 1.18 [E] | 431 |
| 8 | CD₃ | 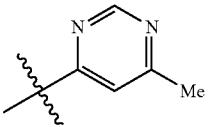 [SMILES: *c1cc(C)ncn1] | 1.14 [E] | 417 |
| 9 | CH₃ | 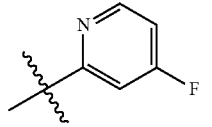 [SMILES: *c1cc(F)ccn1] | 1.28 | 417 |
| 10 | CH₃ | 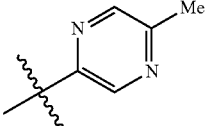 [SMILES: *c1cnc(C)cn1] | 1.08 | 414 |
| 11 | CH₃ | 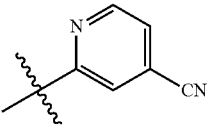 [SMILES: *c1cc(C#N)ccn1] | 1.24 | 424 |
| 12 | CH₃ | 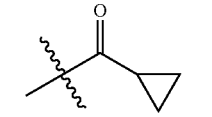 [SMILES: *C(=O)C1CC1] | 1.04 | 390 |
| 13 | CH₃ | 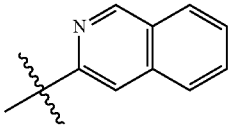 [SMILES: *c1cc2ccccc2cn1] | 1.50 | 449 |
| 14 | CH₃ | 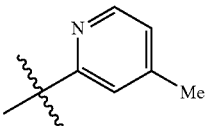 [SMILES: *c1cc(C)ccn1] | 1.30 | 413 |
| 15 | CH₃ | 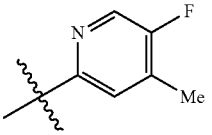 [SMILES: *c1cc(C)c(F)cn1] | 1.45 | 431 |
| 16 | CD₃ | 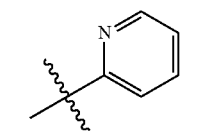 [SMILES: *c1ccccn1] | 1.30 [E] | 402 |

-continued

| Example No. | R¹ | R² | Rt (min) [Method] | m/z [M + H]⁺ |
|---|---|---|---|---|
| 17 | CD₃ | cyclopropyl ketone | 1.22 [E] | 393 |
| 18 | H | 5-fluoro-4-methylpyridin-2-yl | 6.25 [N] | 417 |
| 19 | CD₃ | 6-methylpyridazin-3-yl | 1.00 [E] | 417 |
| 20 | CD₃ | 4,5-dimethylpyridin-2-yl | 1.45 [E] | 430 |
| 21 | CD₃ | 4,6-dimethylpyridazin-3-yl | 1.08 [E] | 431 |
| 22 | CD₃ | 5-methoxypyridin-2-yl | 1.37 [E] | 432 |
| 23 | CD₃ | 4-methylpyridin-2-yl | 1.46 [E] | 416 |
| 24 | CD₃ | 1,5-dimethyl-1H-pyrazol-3-yl | 0.63 [J] | 419 |
| 25 | CD₃ | 4-cyanopyridin-2-yl | 0.64 [J] | 427 |
| 26 | CD₃ | 5-cyano-4-methylpyridin-2-yl | 1.51 [E] | 441 |

-continued

| Example No. | R¹ | R² | Rt (min) [Method] | m/z [M + H]⁺ |
|---|---|---|---|---|
| 27 | H | 2-pyridyl | 5.58 [N] | 385 |
| 28 | CD₃ | (±) trans-2-fluorocyclopropyl carbonyl | 1.08 [E] | 411 |
| 29 | CD₃ | 5-(morpholin-4-yl)pyridin-2-yl | 1.21 [E] | 487 |
| 30 | CD₃ | 6-methylpyridin-2-yl | 1.56 [E] | 416 |
| 31 | CH₃ | 2-pyridyl | 10.61 [O] | 399 |
| 32 | CD₃ | 5-(methoxycarbonyl)pyridin-2-yl | 1.46 [E] | 460 |
| 33 | CD₃ | 4-acetylpyridin-2-yl | 1.39 [E] | 444 |
| 34 | CD₃ | 4-(hydroxymethyl)pyridin-2-yl | 1.04 [E] | 432 |
| 35 | CD₃ | 4-(trifluoromethyl)pyridin-2-yl | 1.64 [E] | 470 |

-continued
| Example No. | R¹ | R² | Rt (min) [Method] | m/z [M + H]⁺ |
|---|---|---|---|---|
| 36 | CD₃ | 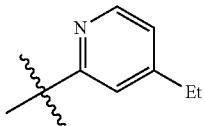 [SMILES: *c1cc(CC)ccn1] | 1.54 [E] | 430 |
| 37 | CD₃ | 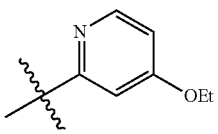 [SMILES: *c1cc(OCC)ccn1] | 1.48 [E] | 446 |
| 38 | CD₃ | 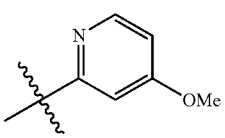 [SMILES: *c1cc(OC)ccn1] | 1.31 [E] | 432 |
| 39 | CD₃ | 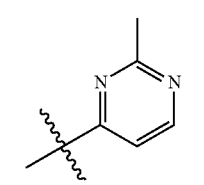 [SMILES: *c1ccnc(C)n1] | 1.02 [E] | 417 |
| 40 | CD₃ | 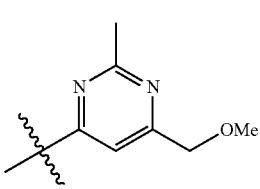 [SMILES: *c1cc(COC)nc(C)n1] | 1.13 [E] | 461 |
| 41 | CD₃ | 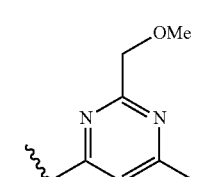 | 1.15 [E] | 461 |
| 42 | CD₃ | 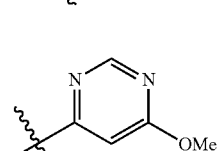 | 1.18 [E] | 433 |
| 43 | CD₃ | 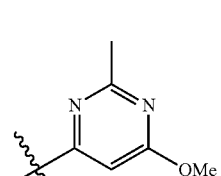 | 1.27 [E] | 447 |

-continued

| Example No. | R¹ | R² | Rt (min) [Method] | m/z [M + H]⁺ |
|---|---|---|---|---|
| 44 | CD₃ | 2-methyl-6-isopropoxypyrimidin-4-yl | 1.72 [E] | 475 |
| 45 | CD₃ | 6-isopropoxypyrimidin-4-yl | 1.59 [E] | 461 |
| 46 | CD₃ | 6-ethylpyrimidin-4-yl | 1.25 [E] | 431 |
| 47 | CD₃ | 6-ethyl-2-methylpyrimidin-4-yl | 1.32 [E] | 445 |
| 48 | CD₃ | 4-(1-hydroxyethyl)pyridin-2-yl | 1.18 [E] | 446 |
| 49 | CD₃ | 5-(hydroxymethyl)pyridin-2-yl | 0.96 [E] | 432 |
| 50 | CD₃ | 4-(2-hydroxypropan-2-yl)pyridin-2-yl | 1.18 [E] | 460 |
| 51 | CD₃ | 4-(methoxymethyl)pyridin-2-yl | 1.32 [E] | 446 |

Preparation 3

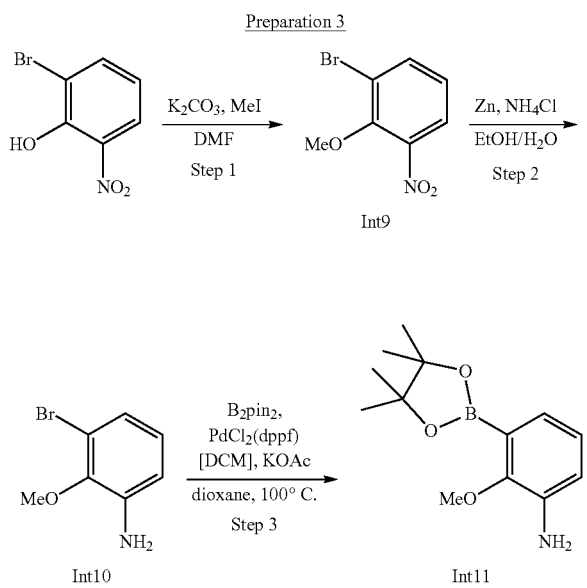

Preparation 4

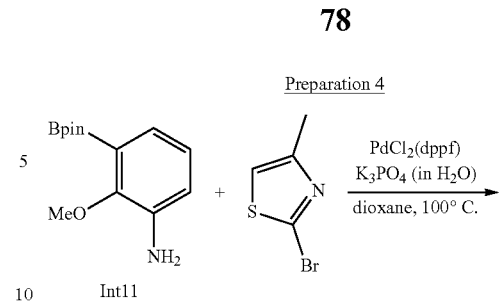

Step 1

2-Bromo-6-nitrophenol (5.0 g, 22.9 mmol) was dissolved in DMF (3 mL), potassium carbonate (4.75 g, 34.4 mmol) was added and the reaction was stirred for 30 minutes. Next iodomethane (2.15 mL, 34.4 mmol) was added and the reaction was stirred overnight. The crude reaction was filtered, diluted with ethyl acetate and washed with brine (twice) and water (twice). The organic layer was dried over sodium sulfate, filtered and concentrated to provide Int9 (5.12 g, 96%). LC retention time 0.92 [J].

Step 2

Int9 (5.12 g, 22.1 mmol) was dissolved in ethyl alcohol (150 mL) and water (50 mL). To this was added zinc (5.77 g, 88 mmol) and ammonium chloride (2.36 g, 44.1 mmol). The reaction was stirred for 1 hour, filtered and then concentrated. The crude material was dissolved in ethyl acetate and washed with water three times, the organic layer was then dried over sodium sulfate, filtered, concentrated and collected (4.3 g, 96%). LC retention time 0.75 [J]. m/z: 201.8 (MH$^+$).

Step 3

Int10 (2.0 g, 9.9 mmol) was dissolved in dioxane (40 mL) and the vessel purged with nitrogen for 5 minutes. Next bis(pinacolato)diborone (3.77 g, 14.85 mmol), [1,1'-bis(diphenylphosphino)ferrocene] dichloropalladium (II) complex with dichloromethane (404 mg, 0.49 mmol) and potassium acetate (2.91 g, 29.7 mmol) were added. The flask was evacuated and backfilled with nitrogen, and then heated to 100° C. for 15 hours. Water was added to quench the reaction and the product was then extracted with EtOAc. The combined organic layers were washed with brine (×3), dried over sodium sulfate, filtered, concentrated and purified using automated chromatography (elutes at ~40% ethyl acetate) to provide Int11 (2.0 g, 81%). $^1$H NMR (400 MHz, chloroform-d) δ 7.12 (dd, J=7.3, 1.8 Hz, 1H), 6.96-6.89 (m, 1H), 6.88-6.83 (m, 1H), 3.82 (s, 3H), 1.37 (s, 12H). LC retention time 0.65 [J]. m/z: 250 (MH$^+$).

A stirred mixture of 2-bromo-4-methylthiazole (201 mg, 1.13 mmol), Int11 (309 mg, 1.24 mmol) and 1,1'-bis(di-tert-butylphosphino)ferrocene palladium dichloride (36.8 mg in dioxane (8 mL) was degassed by bubbling nitrogen through the mixture for 5 minutes. Subsequently tribasic potassium phosphate (2M in water, 1.69 mL, 3.39 mmol) was added and the reaction mixture heated at 100° C. for one hour. The reaction mixture was cooled to room temperature, diluted with ethyl acetate (75 mL) and then dried over sodium sulfate, filtered, concentrated and purified by automated chromatography providing Int12 (218 mg, 83%). $^1$H NMR (400 MHz, chloroform-d) δ 7.63 (dd, J=7.9, 1.6 Hz, 1H), 7.02 (t, J=7.8 Hz, 1H), 6.96 (d, J=1.0 Hz, 1H), 6.80 (dd, J=7.8, 1.5 Hz, 1H), 3.88 (br. s., 2H), 3.80 (s, 3H), 2.53 (d, J=1.0 Hz, 3H). LC retention time 0.65 [J]. m/z: 221 (MH$^+$).

Preparation 5

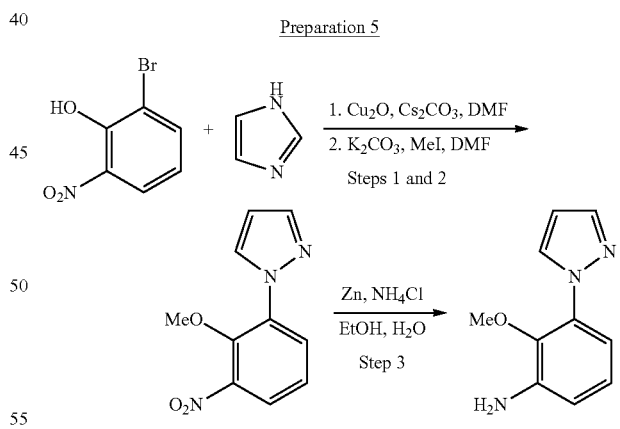

Step 1

A vial containing 2-bromo-6-nitrophenol (290 mg, 1.33 mmol), 1H-pyrazole (136 mg, 2.00 mmol) and copper(I) oxide (190 mg, 1.33 mmol) in DMF (3 mL) was purged with nitrogen for 5 minutes. Cesium carbonate (867 mg, 2.66 mmol) was then added and the vessel was sealed and heated to 100° C. overnight. The reaction was filtered, concentrated and carried on without further purification.

Step 2

The crude product of Step 1 was dissolved in DMF (3 mL), potassium carbonate (269 mg, 2.0 mmol) was added and the reaction was stirred for 30 minutes. Next iodomethane (0.12 mL, 2.0 mmol) was added and the reaction was stirred for 2 hours. The crude product was filtered, concentrated and purified by automated chromatography providing 1-(2-methoxy-3-nitrophenyl)-1H-pyrazole (115 mg, 39% yield). LC retention time 1.34 [J].

Step 3

1-(2-Methoxy-3-nitrophenyl)-1H-pyrazole (230 mg, 1.05 mmol) was dissolved in ethanol (3 mL). To this was added zinc (274 mg, 4.2 mmol), ammonium chloride (112 mg, 2.10 mmol) and water (1 mL). The reaction was stirred for 2 hours, filtered, concentrated and purified by automated chromatography to provide 2-methoxy-3-(1H-pyrazol-1-yl)aniline (150 mg, 76% yield). LC retention time 0.68 [J]. 190 (MH+).

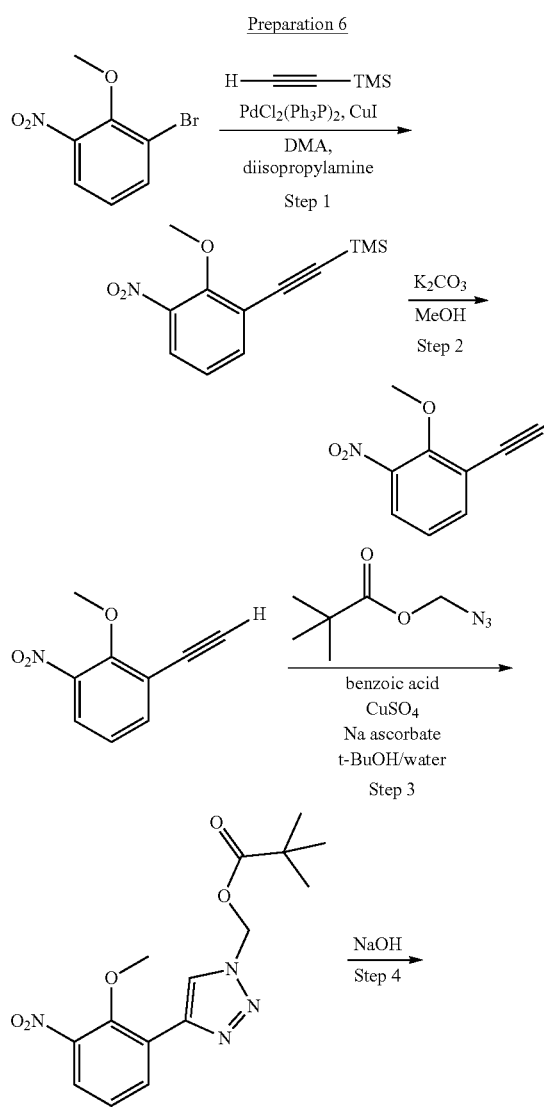

Preparation 6

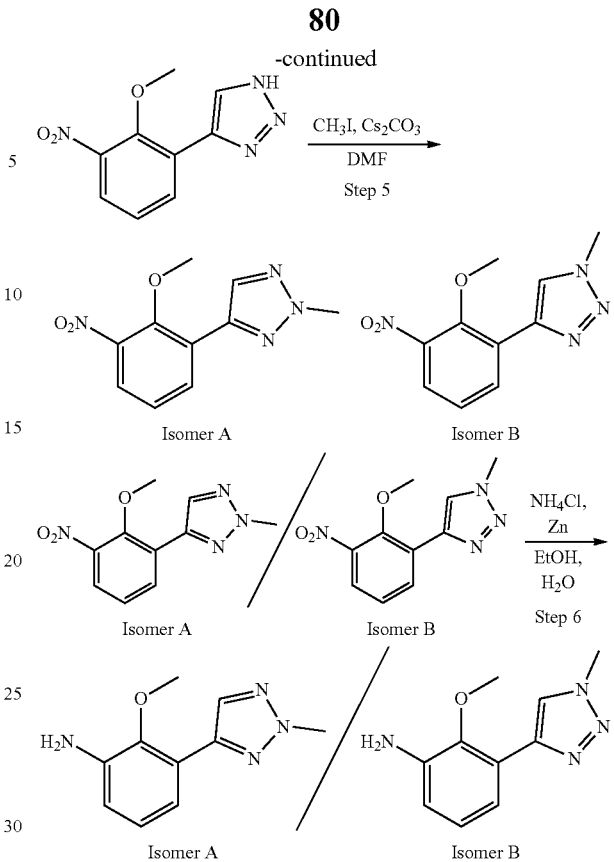

Step 1

A mixture of 1-bromo-2-methoxy-3-nitrobenzene (577 mg, 2.487 mmol), bis(triphenylphosphine)palladium(II) chloride (175 mg, 0.249 mmol), and copper(I) iodide (189 mg, 0.995 mmol) in DMA (10 mL) in a pressure vessel was stirred at room temperature and degassed by bubbling dry nitrogen through it for 5 minutes. Then ethynyltrimethylsilane (1.757 mL, 12.43 mmol) and bis(isopropyl)amine (7.74 mL, 54.7 mmol) were added and the reaction mixture immediately became a yellow solution. The vessel was then sealed and placed into a warm 105° C. bath. Stirred at 105° C. overnight. After stirring overnight, evaporated away the diisopropylamine and the excess TMS-acetylene, then diluted with 150 mL ethyl acetate. Washed the organic solution once with 1:1 ammonium hydroxide:sat. ammonium chloride, once with saturated ammonium chloride, once with 10% aqueous LiCl, and once with brine. The organic layer was then dried over sodium sulfate, filtered, concentrated, and loaded onto a 24 g silica gel column for purification by flash chromatography, eluting with 0-100% EtOAc in hexanes. Afforded ((2-methoxy-3-nitrophenyl)ethynyl)trimethylsilane (177 mg, 28% yield) as an impure brown oil.

Step 2

A mixture of ((2-methoxy-3-nitrophenyl)ethynyl)trimethylsilane (177 mg, 0.710 mmol) and potassium carbonate (294 mg, 2.130 mmol) in methanol (7 mL) was stirred at room temperature for 30 minutes. At which point the reaction was partitioned between EtOAc (50 mL) and water (25 mL). The layers were separated and the aqueous layer was extracted once with EtOAc, the combined organic layers were then washed saturated ammonium chloride and brine. The organic layer was dried over sodium sulfate, filtered and concentrated. The resultant oil was loaded onto a 12 g silica gel column, then purified by flash chromatography, eluting with 0-10% MeOH in dichloromethane. Afforded 1-ethynyl-2-methoxy-3-nitrobenzene (74 mg, 0.397 mmol, 55.9% yield) as a brown oil.

Step 3

Benzoic acid (2 mg, 0.016 mmol), L-ascorbic acid sodium salt (2 mg, 10.10 mol), and copper(II) sulfate (2 mg, 0.013 mmol) were all weighed into the small flask containing 1-ethynyl-2-methoxy-3-nitrobenzene (74 mg, 0.418 mmol). A solution of azidomethyl pivalate (197 mg, 1.253 mmol) in tert-butyl alcohol (1.5 mL) and water (1.5 mL) was added and the mixture was stirred at room temperature. After 20 minutes, the reaction was complete. The reaction was diluted with 50 mL dichloromethane, washed with water, and once with 1:1 water:brine. The organic layer was dried over sodium sulfate, then filtered, concentrated, and loaded onto a 12 g ISCO column for purification by flash chromatography, eluting with 0-100% EtOAc in hexanes. Afforded (4-(2-methoxy-3-nitrophenyl)-1H-1,2,3-triazol-1-yl)methyl pivalate (116 mg, 0.333 mmol, 80% yield) as a tan solid. $^1$H NMR (400 MHz, chloroform-d) δ 8.27 (s, 1H), 7.59 (dd, J=7.9, 1.5 Hz, 1H), 7.06-7.01 (m, 1H), 6.76 (dd, J=7.9, 1.5 Hz, 1H), 6.32 (s, 2H), 3.66 (s, 3H), 1.20 (s, 9H).

Step 4

To a solution of (4-(2-methoxy-3-nitrophenyl)-1H-1,2,3-triazol-1-yl)methyl pivalate (76 mg, 0.227 mmol) in methanol (1 mL) and tetrahydrofuran (1.000 mL) was added sodium hydroxide (1N in water, 0.491 mL, 0.491 mmol). The solution was stirred at room temperature. After 10 minutes, the de-protection was complete. The reaction was neutralized with 0.75 mL 1M (aq.) HCl, and then concentrated to a solid. Afforded 4-(2-methoxy-3-nitrophenyl)-1H-1,2,3-triazole (50 mg, 0.204 mmol, 90% yield) as an off-white solid.

Step 5

To a solution of 4-(2-methoxy-3-nitrophenyl)-1H-1,2,3-triazole (50 mg, 0.227 mmol) in DMF (2 mL) was added portionwise cesium carbonate (222 mg, 0.681 mmol), followed by iodomethane (0.031 mL, 0.500 mmol). The mixture was stirred for 1 hour at room temperature. The reaction was quenched with water (10 mL) and extracted with ethyl acetate. Washed combined organic layers with brine, then dried over sodium sulfate. The material was filtered, concentrated, and loaded onto a 12 g silica column for purification by flash chromatography. Eluted with 0-100% EtOAc in hexanes. (Note: regiochemistry was confirmed by crystallography).

Afforded Isomer A: 4-(2-Methoxy-3-nitrophenyl)-1-methyl-2H-1,2,3-triazole (19 mg, 0.081 mmol, 36% yield).

$^1$H NMR (400 MHz, chloroform-d) δ 8.04 (s, 1H), 7.27 (d, J=1.6 Hz, 1H), 7.04-6.98 (m, 1H), 6.78 (dd, J=7.8, 1.6 Hz, 1H), 4.27 (s, 3H), 3.70 (s, 3H).

Isomer B: 4-(2-Methoxy-3-nitrophenyl)-2-methyl-1H-1,2,3-triazole (6 mg, 0.026 mmol, 11% yield). $^1$H NMR (400 MHz, chloroform-d) δ 8.02 (s, 1H), 7.62-7.58 (m, 1H), 7.05 (t, J=7.8 Hz, 1H), 6.77 (dd, J=7.8, 1.6 Hz, 1H), 4.19 (s, 3H), 3.70 (s, 3H).

Step 6

Isomer A: A mixture of 4-(2-methoxy-3-nitrophenyl)-1-methyl-2H-1,2,3-triazole (20 mg, 0.085 mmol), zinc (55.8 mg, 0.854 mmol) and ammonium chloride (45.7 mg, 0.854 mmol) in EtOH (1 mL) and water (0.143 mL) was stirred at room temperature for 1 hr. The reaction was then diluted with dichloromethane (50 ml), and filtered. The filtrate was washed with water (50 ml), dried over sodium sulfate, and concentrated to afford 2-methoxy-3-(1-methyl-2H-1,2,3-triazol-4-yl)aniline (16 mg, 0.074 mmol, 87% yield). This was used without further purification in the next step.

Isomer B: A mixture of 4-(2-methoxy-3-nitrophenyl)-1-methyl-1H-1,2,3-triazole (21 mg, 0.09 mmol), zinc (58.6 mg, 0.897 mmol) and ammonium chloride (48 mg, 0.897 mmol) in EtOH (1 mL) and water (0.143 mL) was stirred at room temperature for 1 hr. The reaction was then diluted with dichloromethane (50 ml), and filtered. The filtrate was washed with water (50 ml), dried over sodium sulfate, and concentrated to afford 2-methoxy-3-(1-methyl-1H-1,2,3-triazol-4-yl)aniline (19 mg, 0.084 mmol, 93% yield). Used as is in the next step.

Preparation 7

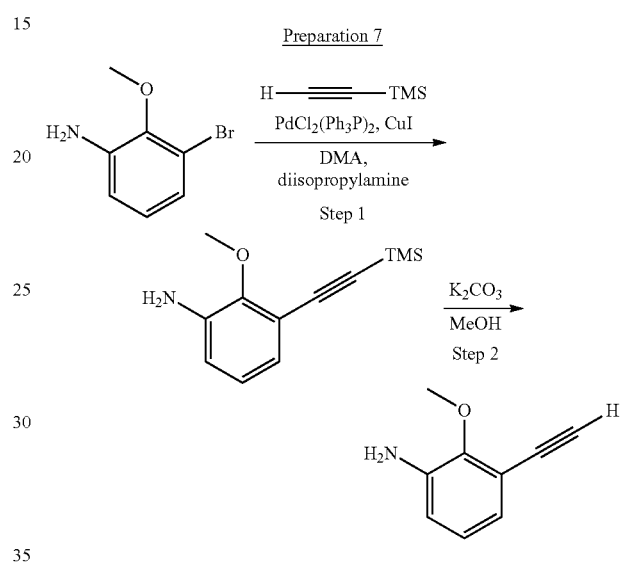

Step 1

2-Methoxy-3-((trimethylsilyl)ethynyl)aniline (231 mg, 0.79 mmol, 59% yield) was prepared in exactly the same manner as Preparation 6, substituting 3-bromo-2-methoxyaniline (268 mg, 1.326 mmol) as the starting material in place of the 1-bromo-2-methoxy-3-nitrobenzene.

Step 2

A mixture of 2-methoxy-3-((trimethylsilyl)ethynyl)aniline (253 mg, 1.153 mmol) and potassium carbonate (478 mg, 3.46 mmol) in methanol (5 mL) was stirred at room temperature for 30 minutes. After 30 minutes, the reaction was complete. The reaction was partitioned between EtOAc (50 mL) and water (25 mL). The layers were separated and the aqueous layer extracted with EtOAc, then the combined organic layers were washed with saturated ammonium chloride and brine. The organic layer was dried over sodium sulfate, then filtered and concentrated. The resulting oil was loaded onto a 12 g silica gel column, and then purified by flash chromatography, eluting with 0-10% MeOH indichloromethane. Afforded 3-ethynyl-2-methoxyaniline (75 mg, 0.510 mmol, 44.2% yield) as a brown oil.

Preparation 8

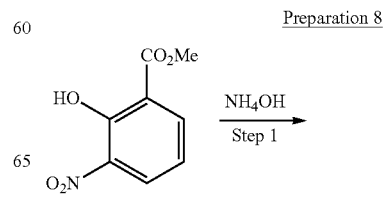

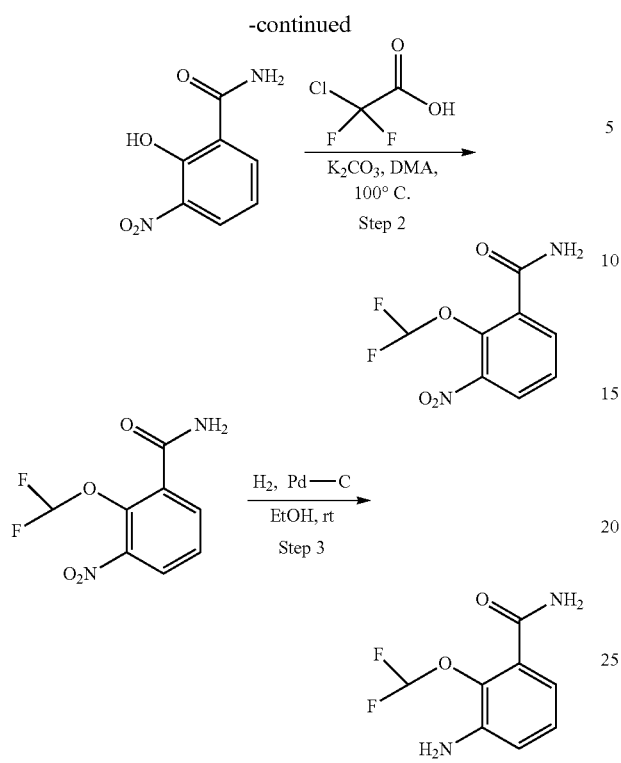

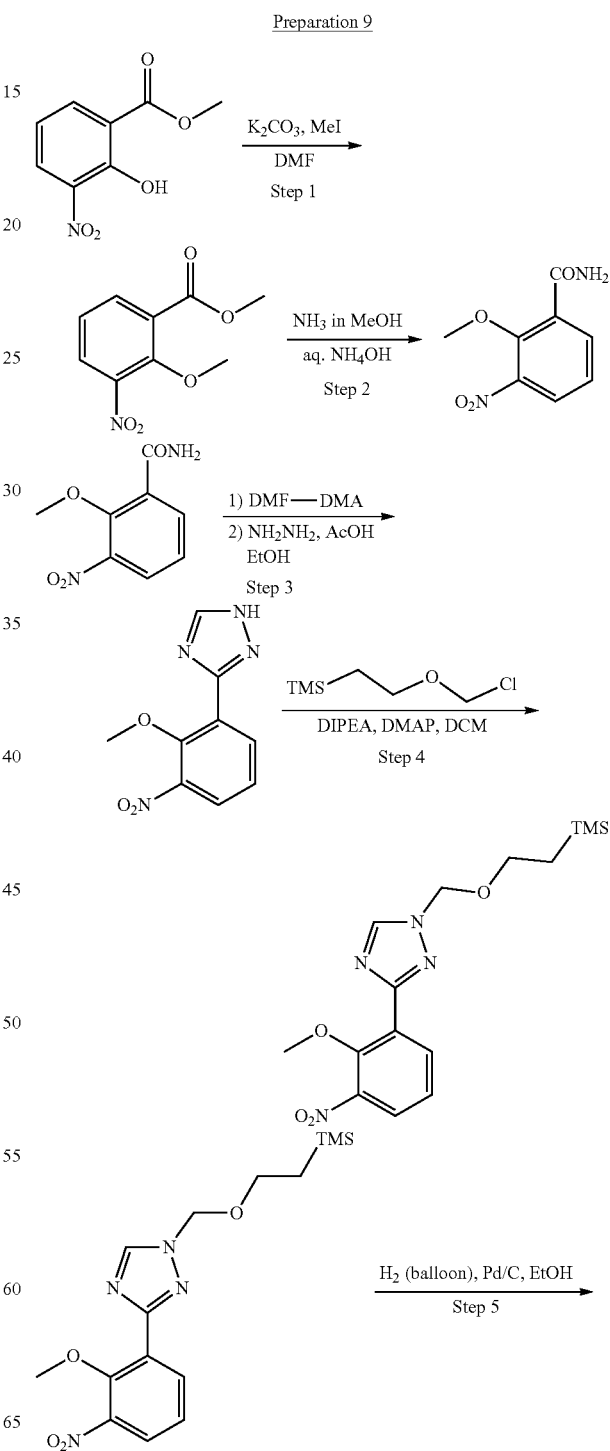

Step 1
Concentrated (30-35%) aqueous ammonium hydroxide (100 mL) was added to methyl 2-hydroxy-3-nitrobenzoate (12 g, 60.9 mmol) and the resulting orange partial slurry was allowed to stir at room temperature overnight. The reaction was worked up by concentrating under vacuum to yield a red-orange semi-solid to which was added water (~200 mL) and acetic acid (~15 mL) and the slurry was stirred for 1-2 hours and filtered to collect the solid, which was rinsed with water and dried to afford 9.42 g (85%) of a pale yellow solid as the pure product. LC retention time 0.59 minutes [J].

Step 2
To a solution of 2-hydroxy-3-nitrobenzamide (1 g, 5.49 mmol) in DMF (10 mL) was added potassium carbonate (2.276 g, 16.47 mmol) and the mixture was stirred at room temperature for 5 min giving an orange slurry. 2-chloro-2,2-difluoroacetic acid (0.603 mL, 7.14 mmol) was then slowly added causing some effervescence. The reaction was stirred at room temperature for an additional 5 minutes, and then heated to 100° C. for ~1 h. The reaction was then cooled to room temperature, diluted with water (~25 mL) and extracted with EtOAc (3×20 mL) and the combined extracts were dried over anhydrous sodium sulfate. The extracts were concentrated to give the crude product as a brown liquid containing residual DMA. The crude product was dissolved into a minimal amount of dichloromethane and was loaded onto a 4 g silica gel cartridge and was eluted with EtOAc/hexanes as the eluent. Afforded 0.58 g (46%) of a yellow solid. $^1$H NMR (400 MHz, DMSO-$d_6$) δ 8.12 (dd, J=8.0, 1.7 Hz, 1H), 8.03 (br. s., 1H), 7.87 (dd, J=7.7, 1.5 Hz, 1H), 7.80 (br. s., 1H), 7.62 (t, J=7.9 Hz, 1H), 7.34-6.89 (m, 1H).

Step 3
A solution of 2-(difluoromethoxy)-3-nitrobenzamide (0.58 g, 2.498 mmol) in EtOH (20 mL) was sparged with nitrogen for a few minutes before adding Pd/C (0.266 g, 0.125 mmol) then the flask was purged with hydrogen gas using a balloon and the mixture was stirred at room temperature for ~2 h under hydrogen. The mixture was sparged with nitrogen to remove the hydrogen and the mixture was filtered through CELITE® and the resulting clear, nearly colorless filtrate was concentrated under vacuum overnight. Afforded 503 mg of a light grey colored solid as the product. Material was used as is without any further purification. $^1$H NMR (400 MHz, methanol-$d_4$) δ 7.11-7.04 (m, 1H), 6.94 (dd, J=8.0, 1.7 Hz, 1H), 6.90-6.85 (m, 1H), 6.68 (t, J=75.2 Hz, 1H).

Preparation 9

-continued

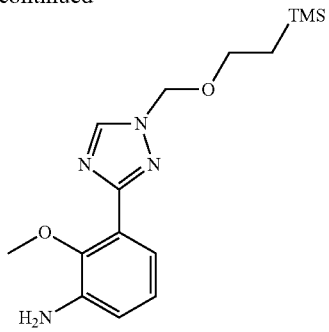

Step 1

To a solution of methyl 2-hydroxy-3-nitrobenzoate (10 g, 50.7 mmol) in DMF (100 mL) at room temperature was added potassium carbonate (14.02 g, 101 mmol) followed by addition of methyl iodide (6.34 mL, 101 mmol) and the resulting orange mixture was heated to 60° C. for 1 h. The reaction was cooled to room temperature and then crushed ice (~100 mL) was added, followed by water to a total volume of ~400 mL causing a yellow solid to crystallize from solution. The slurry was stirred for a few minutes and then collected by vacuum filtration and the resulting initially yellow solid was rinsed with additional water (~100 mL) until all of the yellow color was rinsed into the filtrate giving a near white solid in the funnel. Partially air-dried solid in funnel then transferred to a flask and further dried under vacuum overnight to afford 10.5 g (98%) of a yellow solid as the desired product. LC retention time 0.83 [J].

Step 2

Methyl 2-methoxy-3-nitrobenzoate (11 g, 52.1 mmol) was dissolved in a cold solution of ammonia in methanol (7N, 250 mL) and conc. aqueous ammonium hydroxide (100 mL) was added. The flask was sealed and the resulting solution was allowed to gently stir at room temperature overnight (~17 h). The reaction mixture was concentrated on the rotovap using a slightly warm water bath to yield an aqueous slurry of the product. This slurry was diluted with additional water (~300 mL) and was sonicated briefly then the solid was collected by vacuum filtration and the resulting yellow solid was rinsed with additional water (~100 mL). The solid was air dried in the funnel for several hours then under vacuum to afford 7.12 g of a yellow solid as the pure product. A second crop of product was obtained by extracting the filtrate with EtOAc (3×100 mL) followed by washing the extracts with brine, drying over anhydrous sodium sulfate, decanting and concentration under vacuum to afford 1.67 g of additional product as a yellow solid (86% overall combined yield). LC retention time 0.58 [J]. MS (E+) m/z: 197 (MH+).

Step 3

2-Methoxy-3-nitrobenzamide (7.1 g, 36.2 mmol) was slurried in dimethyl formamide dimethyl acetal (48.5 mL, 362 mmol) and the mixture was heated to 95° C. giving a clear, pale yellow solution. After heating for ~30 min at this temp the reaction was cooled and was concentrated on the rotovap and the resulting yellow oil was azeotroped twice with 1,2-dichloroethane (40 mL portions) to ensure complete removal of any residual dimethyl formamide dimethyl acetal. The crude oil thus obtained was immediately dissolved in 35 mL of ethanol and was immediately used in the following step.

In a separate flask was prepared a mixture of ethanol (150 mL) and acetic acid (AcOH, 35 mL) and the resulting solution was cooled in an ice bath. Once cooled, hydrazine hydrate (17.59 mL, 362 mmol) was added dropwise. At this time, the solution containing the crude dimethyl formamide dimethyl acetal adduct as prepared above was transferred dropwise over ~15 min by cannula into the previously prepared well-stirred ice-cold mixture containing the hydrazine. During the addition, a pale yellow solid formed in the solution. After the addition was complete, the resulting cloudy yellow mixture was allowed to warm to room temperature and stir for ~4 h. The reaction mixture at this time was concentrated on the rotovap to remove some of the ethanol, diluted with additional water and filtered to collect the solid. The solid was washed with additional portions of water, air dried in the funnel then under vacuum to afford 5.5 g (69%) of a pale yellow solid as the desired product. LC retention time 0.62 [J]. MS (E+) m/z: 221 (MH+).

Step 4

To a solution of 3-(2-methoxy-3-nitrophenyl)-4H-1,2,4-triazole (1.76 g, 7.99 mmol), diisopropylethylamine (DIPEA, Hunig's base, 1.954 mL, 11.19 mmol) and N,N'-dimethylaminopyridine (DMAP, 0.098 g, 0.799 mmol) in dichloromethane (25 mL) at room temperature was added 2-(trimethylsilyl)ethoxymethyl chloride (SEM-Cl, 1.701 mL, 9.59 mmol) and the reaction mixture was stirred at room temperature for 3 h. Mixture was then concentrated to remove the solvent, water was added and the mixture was extracted with EtOAc (100 mL×4). The combined extracts were washed with brine, dried over anhydrous sodium sulfate, filtered and concentrated to afford a tan semi-solid as the crude product. This material was purified by silica gel chromatography (hex/EtOAc; 40 g column) to afford fractions containing the major product. These fractions were concentrated to afford 1.26 g (45%) of a clear oil as the desired product (1.26 g, 3.60 mmol, 45% yield) as an apparent 2:3 mixture of regioisomers. HPLC RT=3.44 and 3.53 min. LCMS (m+1)=351. Major isomer: 1H NMR (400 MHz, chloroform-d) δ 8.34 (s, 2H), 8.25 (dd, J=7.8, 1.7 Hz, 2H), 7.82 (dd, J=8.0, 1.7 Hz, 2H), 7.31 (t, J=8.0 Hz, 2H), 5.59 (s, 4H), 3.96 (s, 7H), 3.76-3.71 (m, 5H), 1.02-0.92 (m, 4H), 0.01 (s, 9H).

Step 5

To a slurry of 3-(2-methoxy-3-nitrophenyl)-1-((2-(trimethylsilyl)ethoxy)methyl)-1H-1,2,4-triazole (1.26 g, 3.60 mmol) in EtOH (50 mL) was added Pd/C (10% on carbon) (0.115 g, 0.108 mmol). The flask was evacuated and supplied with hydrogen gas from a balloon for 4 hours. At this time, the balloon was removed and reaction was flushed with nitrogen, then filtered through a pad of CELITE® to remove the catalyst and the resulting clear colorless filtrate was concentrated to afford 1.12 g (97%) of the product as a clear oil which solidified on standing. HPLC and LCMS analysis indicated an ~2:3 mixture of regioisomers. HPLC Peak RT=2.70 min (major) and 3.01 min (minor).

Preparation 10

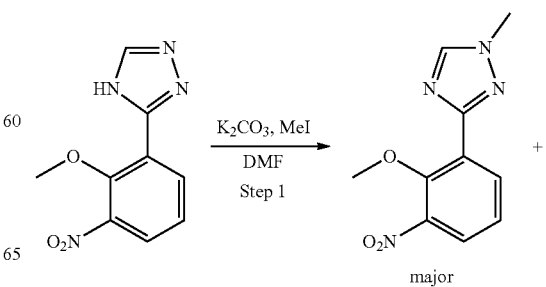

major

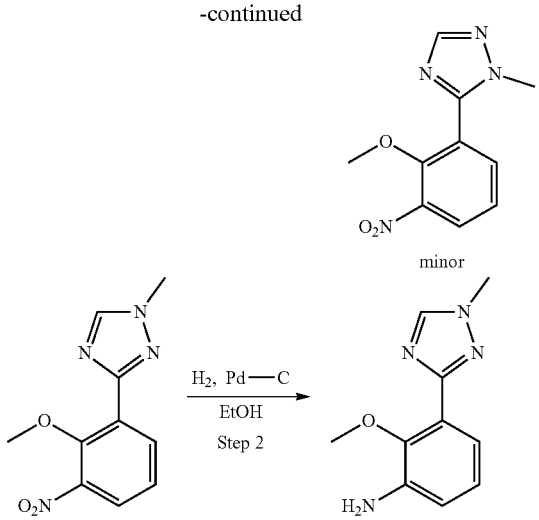

minor

Step 1

A solution of 3-(2-methoxy-3-nitrophenyl)-4H-1,2,4-triazole from Step 3 of Preparation 9 (2.23 g, 10.13 mmol) in DMF (20 mL) was treated with potassium carbonate (4.20 g, 30.4 mmol). After cooling the resulting mixture in an ice bath, a solution of iodomethane (0.855 mL, 13.67 mmol) in DMF (5 mL) was slowly added dropwise by syringe over 2 min. After the addition was complete, the ice bath was removed and the reaction mixture was allowed to warm to rt. After stirring at room temperature for ~4 h, LCMS analysis indicated complete and clean conversion to the regioisomeric mixture of products in ~2:1 ratio, respectively. The reaction was cooled in an ice bath and was diluted with water (~50 mL) and the solution was extracted with EtOAc (3×40 mL) and the combined extracts were washed with 10% aq. LiCl (2×20 mL), water (20 mL) then brine before concentrating to afford 2.17 g (91%) of a yellow oil as the crude product which solidified to a yellow solid upon standing. This crude material was combined with another batch of additional crude product (~0.45 g) from a previous similar reaction and the material was purified by supercritical fluid chromatograph (SFC) to resolve the isomers (Conditions: column=chiral IC 3×25 cm, 5 μm; column temp.=35° C.; flow rate=200 mL/min; mobile phase=CO$_2$/MeOH=80/20; injection program=stacked (2.3 min/cycle), 2.5 ml/per injection; sampler conc. (mg/mL): 60 mg/mL; detector wavelength=220 nm) to afford 1.87 g (65%) of the major isomer as a pale yellow solid. $^1$H NMR (400 MHz, methanol-d$_4$) δ 8.50 (s, 1H), 8.11 (dd, J=7.9, 1.8 Hz, 1H), 7.85 (dd, J=8.1, 1.8 Hz, 1H), 7.38 (t, J=8.0 Hz, 1H), 4.03 (s, 3H), 3.83 (s, 3H). LC retention time 0.74 [J]. MS (E$^+$) m/z: 235 (MH$^+$).

Step 2

A solution of 3-(2-methoxy-3-nitrophenyl)-1-methyl-1H-1,2,4-triazole (1.87 g, 7.98 mmol) in EtOH (50 mL) was sparged with nitrogen for a few minutes before adding 5% Pd—C (0.850 g, 0.399 mmol) followed by sparging with hydrogen from a balloon for a few minutes then allowing the mixture to stir under a balloon of hydrogen for 1.5 h at rt. The mixture was then sparged with nitrogen to deactivate the catalyst and the mixture was filtered through a pad of CELITE® washing with additional amounts of EtOH and the resulting clear, colorless filtrate containing the product was concentrated under vacuum to afford a colorless oil. This material was azeotroped with two portions of dry toluene (~25 mL each) to afford an off-white solid which was dried further under vacuum to afford 1.5 g (92%) of a free-flowing white solid as the pure product. $^1$H NMR (400 MHz, chloroform-d) δ 8.09 (s, 1H), 7.35 (dd, J=7.8, 1.7 Hz, 1H), 7.00 (t, J=7.8 Hz, 1H), 6.82 (dd, J=7.8, 1.7 Hz, 1H), 4.00 (s, 3H), 3.94 (br. s., 2H), 3.78 (s, 3H). LC retention time 0.44 [J]. MS (E$^+$) m/z: 205 (MH$^+$).

Preparation 11

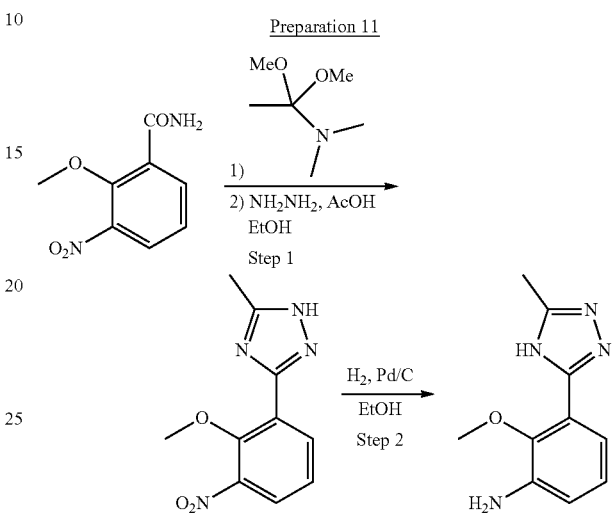

Step 1

Prepared using the procedure previously described in Step 3 of Preparation 9 by replacing dimethyl formamide dimethyl acetal with 1,1-dimethoxy-N,N-dimethylethanamine to afford 1.32 g (74%) of the product, 3-(2-methoxy-3-nitrophenyl)-5-methyl-4H-1,2,4-triazole as a dark solid. $^1$H NMR (400 MHz, chloroform-d) δ 8.45 (dd, J=7.9, 1.5 Hz, 1H), 7.93 (dd, J=8.1, 1.8 Hz, 1H), 7.42-7.33 (m, 1H), 3.97 (s, 3H), 2.53 (s, 3H). LC retention time 1.58 [A]. MS (E$^+$) m/z: 235 (MH$^+$).

Step 2

Prepared using the procedure previously described in Step 5 of Preparation 9 to afford 0.97 g (86%) of the product as a clear oil which solidified upon standing (not characterized)

Preparation 12

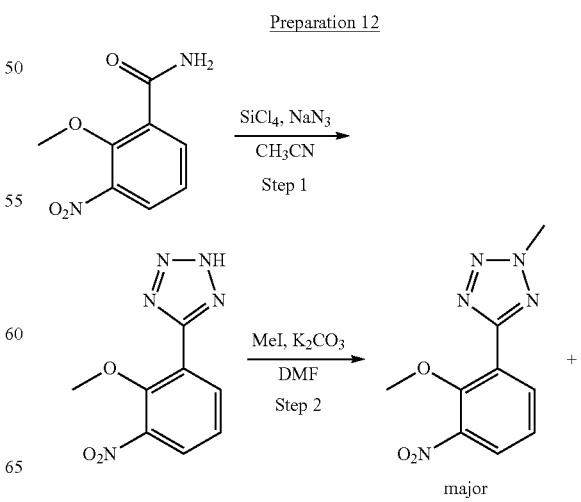

major

-continued

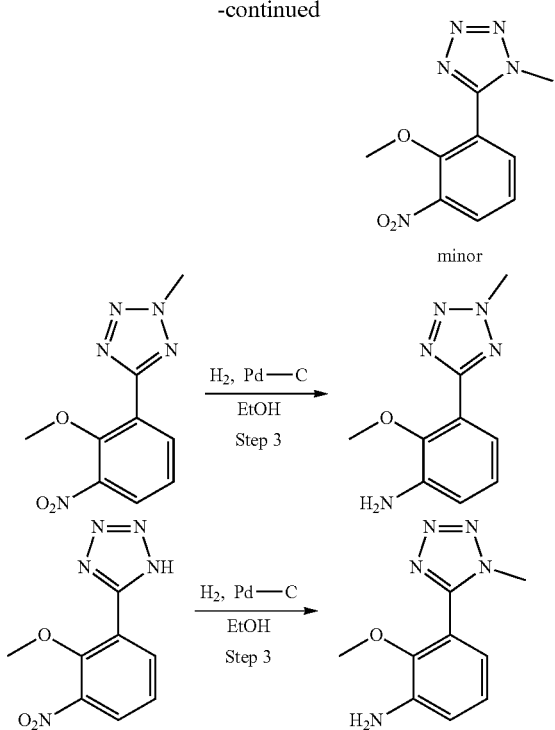

Step 1

Sodium azide (497 mg, 7.65 mmol) was suspended in acetonitrile (5.0 mL) at room temperature, silicon tetrachloride (0.322 mL, 2.80 mmol) was added and the reaction mixture became milky white. The amide substrate (500 mg, 2.55 mmol) was added as solid at this time and the mixture was heated under nitrogen at 75° C. for 4 h. The reaction was then allowed to cool to room temperature and stirred overnight. Water (50 mL) was added and after sonication, the solid was collected by filtration, rinsed with water and dried on the filter to afford 556 mg (99%) of a yellow solid as the desired product. LC retention time 0.65 [J]. MS (E$^+$) m/z: 222 (MH$^+$).

Step 2

To a solution of 5-(2-methoxy-3-nitrophenyl)-2H-tetrazole (535 mg, 2.419 mmol) in DMF (1.0 mL) was added iodomethane (0.303 mL, 4.84 mmol) and $K_2CO_3$ and the resulting mixture was stirred at room temperature for 3 h. The reaction was cooled in an ice bath and was diluted with water (~100 mL) and the solution was extracted with EtOAc (3×100 mL). The combined extracts were washed with 10% aq. LiCl (2×40 mL), water (40 mL) then brine, then dried over sodium sulfate before concentrating to afford 0.6 g of a yellow oil as the crude product as a ~3:1 mixture of regioisomers. This material was purified by SFC to resolve the regioisomers. The major regioisomer was the first eluted product (Conditions: column=cell 45×25 cm, 5 µm; column temp.=40° C.; flow rate=250 mL/min; mobile phase=$CO_2$/MeOH=70/30; injection program=stacked (2.5 min/cycle), 1.0 ml/per injection; sampler conc. (mg/mL)=60; detector wavelength=220 nm).

Major regioisomer (372 mg, 65% yield). $^1$H NMR (400 MHz, chloroform-d) δ 8.35-8.26 (m, 1H), 7.98-7.85 (m, 1H), 7.44-7.32 (m, 1H), 4.48 (s, 3H), 3.99 (s, 3H). LC retention time 0.79 [J]. MS (E$^+$) m/z: 236 (MH$^+$).

Minor regioisomer (139 mg, 24% yield). $^1$H NMR (400 MHz, chloroform-d) δ 8.11 (dd, J=8.3, 1.7 Hz, 1H), 7.83 (dd, J=7.8, 1.7 Hz, 1H), 7.46 (t, J=8.0 Hz, 1H), 4.05 (s, 3H), 3.68 (s, 3H). LC retention time 0.70[J]. MS (E$^+$) m/z: 236 (MH$^+$).

Step 3

A solution of 5-(2-methoxy-3-nitrophenyl)-2-methyl-2H-tetrazole (0.37 g, 1.573 mmol) in EtOH (10 mL) was sparged with nitrogen for a few minutes before adding 5% Pd—C (10% on Carbon) (0.084 g, 0.079 mmol) followed by sparging with hydrogen from a balloon for a few minutes then letting mixture stir under a balloon of hydrogen for 1.5 h at room temperature. The mixture was then sparged with nitrogen to deactivate the catalyst and the mixture was filtered through Millipore 45µ filter washing with additional amounts of EtOH and the resulting clear, colorless filtrate containing the product was concentrated under vacuum to afford a colorless oil. After further concentrating under vacuum, a solid was obtained and this material was azeotroped with two portions of dry toluene (~25 mL each), then further dried under vacuum to afford 0.286 g (89%) of a colorless oil as the pure product. $^1$H NMR (400 MHz, chloroform-d) δ 7.41 (dd, J=7.7, 1.5 Hz, 1H), 7.05 (t, J=7.8 Hz, 1H), 6.89 (dd, J=7.8, 1.7 Hz, 1H), 4.44 (s, 3H), 3.98 (br. s., 2H), 3.81 (s, 3H). LC retention time 0.54 [J]. MS (E$^+$) m/z: 206 (MH$^+$).

The corresponding minor regioisomer was reduced in a similar manner providing 119 mg (98%) of the corresponding aniline. LC retention time 0.52 [J]. MS (E$^+$) m/z: 206 (MH$^+$).

Preparation 13

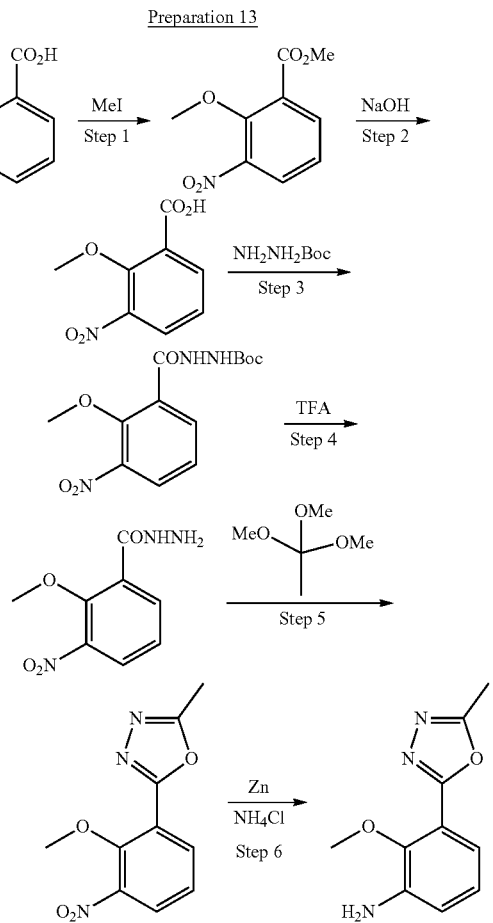

Step 1

A mixture of 2-hydroxy-3-nitrobenzoic acid (1.0 g, 5.46 mmol), iodomethane (1.02 mL, 16.4 mmol) and potassium carbonate (3.02 g, 21.8 mmol) in DMF (25 mL) was heated at 50° C. overnight. The reaction mixture was cooled to room temperature, then diluted with ice-water [100 mL] with vigorous stirring, then filtered. The solid product was dried to give 0.962 g white solid product (83% yield). $^1$H NMR (400 MHz, DMSO-d6) □δ 8.12 (dd, J=8.1, 1.5 Hz, 1H), 8.03 (dd, J=7.8, 1.5 Hz, 1H), 7.44 (t, J=7.9 Hz, 1H), 3.90 (s, 3H), 3.88 (s, 3H). LC retention time 2.22 [A]. MS (E$^+$) m/z: 212 (MH$^+$).

Step 2

A stirred solution of methyl 2-methoxy-3-nitrobenzoate (0.962 g, 4.56 mmol) in methanol (10 mL) was heated to 75° C. 1.0 N (aq.) sodium hydroxide (9.57 mL, 9.57 mmol) was added dropwise and the reaction mixture heated at 75° C. for fifteen minutes. The reaction mixture was cooled to room temperature and concentrated to remove the methanol solvent. The residue was acidified with 1N (aq.) HCl solution to pH~1, stirred and filtered. The solid residue was air-dried to give 0.841 g white solid product (94% yield). $^1$H NMR (400 MHz, DMSO-d$_6$) □δ 8.06 (dd, J=7.9, 1.5 Hz, 1H), 8.01 (dd, J=7.7, 1.5 Hz, 1H), 7.40 (t, J=7.9 Hz, 1H), 3.89 (s, 3H). LC retention time 1.78 min [A].

Step 3

A mixture of 2-methoxy-3-nitrobenzoic acid (0.841 g, 4.27 mmol), tert-butyl carbazate (0.677 g, 5.12 mmol), (benzotriazol-1-yloxy)tris(dimethylamino)phosphonium hexafluorophosphate (BOP) (1.52 g, 5.12 mmol) and N,N-diisopropylethylamine (0.892 ml, 5.12 mmol) in DMF (10 ml) was stirred at room temperature for overnight. The reaction mixture was concentrated under vacuum. The residue was partitioned between ethyl acetate and water. The ethyl acetate extract was separated and concentrated. The residue was triturated with cold water. A white solid precipitated. The mixture was filtered. The solid residue was air-dried to give 1.12 g off-white solid product (84% yield). LC retention time 0.77 [J]. MS (E$^+$) m/z: 312 (MH$^+$).

Step 4

Trifluoroacetic acid (0.787 mL, 10.60 mmol) was added to a stirred solution of tert-butyl 2-(2-methoxy-3-nitrobenzoyl) hydrazinecarboxylate (1.10 g, 3.53 mmol) in dichloromethane (10 mL) at room temperature. The reaction mixture was stirred for one hour at room temperature. The reaction mixture was concentrated under vacuum with repeated additions of dichloromethane to evaporate of residual TFA to give 0.730 g tan solid product. (Yield 98%). LC retention time 0.70 [A]. MS (E$^+$) m/z: 212 (MH$^+$).

Step 5

A stirred mixture of 2-methoxy-3-nitrobenzohydrazide (0.050 g, 0.237 mmol) and trimethylorthoacetate (0.603 ml, 4.74 mmol) was heated at 105° C. for overnight. LC-MS indicated complete conversion to the desired product. The reaction mixture was concentrated under high vacuum to remove excess reactant/solvent. The crude residue partitioned between ethyl acetate and saturated sodium bicarbonate solution. The ethyl acetate extract was dried over sodium sulfate and concentrated to give 0.049 g product as a viscous tan liquid (yield 88%). LC retention time 0.75 [J]. MS (E$^+$) m/z: 236 (MH$^+$).

Step 6

A mixture of 2-(2-methoxy-3-nitrophenyl)-5-methyl-1,3,4-oxadiazole (0.510 g, 2.168 mmol), zinc (1.418 g, 21.68 mmol) and ammonium chloride (1.160 g, 21.68 mmol) in methanol (25 mL) and THF (8.33 mL) was stirred at room temperature for 2 hours. The reaction mixture was diluted with ethyl acetate and filtered through a CELITE® pad. The filtrate was concentrated under vacuum. The residue was dissolved in 100 mL ethyl acetate and washed with water and brine, filtered, dried and concentrated to give 0.412 g product as a tan solid (yield 93%). LC retention time 0.58 [J]. MS (E$^+$) m/z: 206 (MH$^+$).

Preparation 14

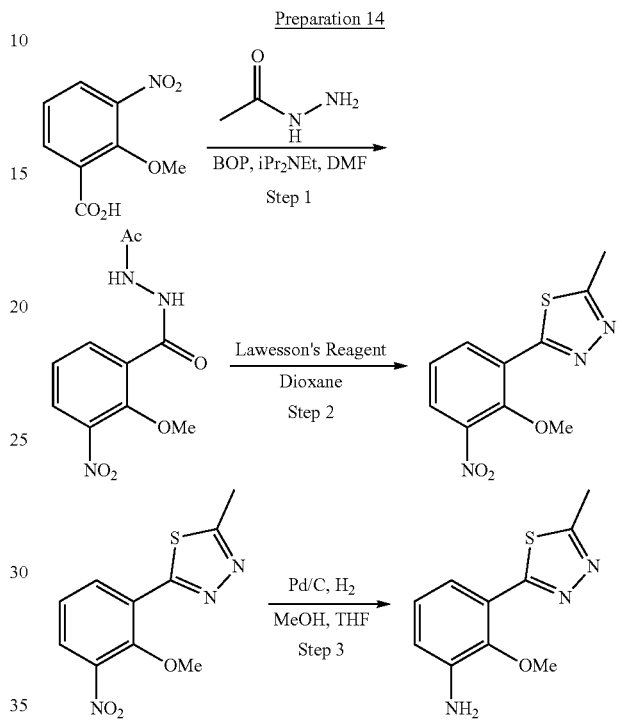

Step 1

To a stirred solution of 2-methoxy-3-nitrobenzoic acid (850 mg, 4.31 mmol) in DMF (9 mL), acetohydrazide (639 mg, 8.62 mmol), diisopropylethylamine (1.506 mL, 8.62 mmol) and BOP (1907 mg, 4.31 mmol) were added. The reaction mixture was stirred at room temperature for 2 hours and then water was added to crash out the crude product. The solid was filtered off, washed with water and then with petroleum ether to give N'-acetyl-2-methoxy-3-nitrobenzohydrazide (750 mg, 67% yield). $^1$H NMR (400 MHz, DMSO-d$_6$) □δ 10.31 (s, 1H), 10.04 (s, 1H), 8.01 (dd, J=8.0, 1.6 Hz, 1H), 7.72 (dd, J=8.0, 1.6 Hz, 1H), 7.40 (t, J=8.0 Hz, 1H), 3.93 (s, 3H), 1.92 (s, 3H).

Step 2

To a solution of N'-acetyl-2-methoxy-3-nitrobenzohydrazide (500 mg, 1.975 mmol) in dioxane (20 mL) was added Lawesson's reagent (2.00 g, 4.94 mmol) and the reaction was heated to 110° C. for 12 hours. The reaction was then cooled to room temperature and concentrated and partitioned between water and ethyl acetate. The two layers were separated and the aqueous layer extracted three times with ethyl acetate. The combined organic layers were washed with 10% sodium bicarbonate solution followed by brine. The organic layer was then dried over sodium sulfate, filtered, concentrated and purified by silica gel chromatography to provide 2-(2-methoxy-3-nitrophenyl)-5-methyl-1,3,4-thiadiazole (400 mg, 60% yield). LC retention time 1.92 [R]. MS (E$^+$) m/z: 252 (MH$^+$).

Step 3

To a stirred solution of 2-(2-methoxy-3-nitrophenyl)-5-methyl-1,3,4-thiadiazole (50 mg, 0.199 mmol) in methanol (1 mL), 10% palladium on carbon (212 mg, 0.199 mmol) was added and kept under hydrogen atmosphere of 10 psi at room temperature for 2 hours. The reaction mixture was filtered through CELITE® and the organic layer was concentrated under vacuum to dryness. The crude residue was purified by automated chromatography to get the desired 2-methoxy-3-(5-methyl-1,3,4-thiadiazol-2-yl)aniline (35 mg, 43% yield). LC retention time 1.63 [R]. MS (E$^+$) m/z: 222 (MH$^+$).

Example 52

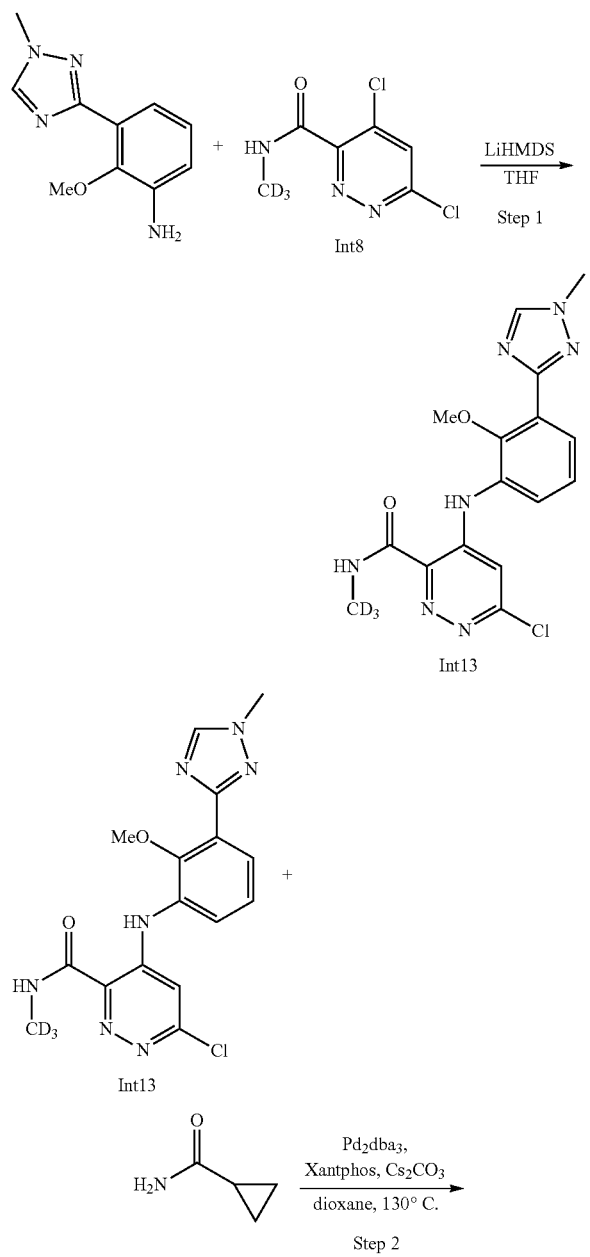

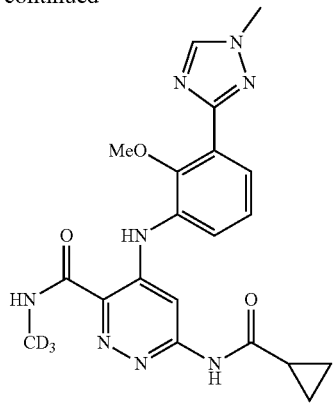

Step 1

To a solution of 2-methoxy-3-(1-methyl-1H-1,2,4-triazol-3-yl)aniline (10.26 g, 50.2 mmol) and Int8 (10.5 g, 50.2 mmol) in THF (120 mL) was added lithium bis(trimethylsilyl)amide (LiHMDS, 1M in THF, 151 mL, 151 mmol) in a dropwise manner using a pressure equalized addition funnel. The reaction was run for 10 minutes after the completion of the addition and then quenched with HCl (1M aq., 126 mL, 126 mmol). The reaction was concentrated on a rotary evaporator until the majority of the THF was removed and a precipitate prevailed throughout the vessel. Water (~500 mL) was then added and the slurry sonicated for 5 minutes and stirred for 15 min. The solid was filtered off, rinsing with water and then air dried for 30 minutes. The powder was collected and dissolved in dichloromethane. The organic layer was washed with water and brine and then dried over sodium sulfate, filtered and concentrated to provide the product (12.5 g, 66% yield) (carried on as is). $^1$H NMR (400 MHz, DMSO-d$_6$) δ 11.11 (s, 1H), 9.36 (s, 1H), 8.56 (s, 1H), 7.72 (dd, J=7.8, 1.6 Hz, 1H), 7.60 (dd, J=7.9, 1.5 Hz, 1H), 7.29 (t, J=7.9 Hz, 1H), 7.19 (s, 1H), 3.95 (s, 3H), 3.72 (s, 3H). LC retention time 1.18 [E]. MS (E$^+$) m/z: 377 (MH$^+$).

Step 2

Int13 (2.32 g, 6.16 mmol) and cyclopropanecarboxamide (1.048 g, 12.31 mmol) were dissolved in dioxane (62 mL) and Pd$_2$(dba)$_3$ (564 mg, 0.616 mmol), Xantphos (534 mg, 0.924 mmol) and cesium carbonate (4.01 g, 12.3 mmol) were added. The vessel was evacuated three times (backfilling with nitrogen) and then sealed and heated to 130° C. for 140 minutes. The reaction was filtered through CELITE® (eluting with ethyl acetate) and concentrated (on smaller scale this material could then be purified using preparative HPLC). The crude product was adsorbed onto CELITE® using dichloromethane, dried and purified using automated chromatography (100% EtOAc) to provide example 52 (1.22 g, 46% yield). $^1$H NMR (500 MHz, chloroform-d) δ 10.99 (s, 1H), 8.63 (s, 1H), 8.18 (s, 1H), 8.10 (d, J=0.5 Hz, 2H), 7.81 (dd, J=7.9, 1.7 Hz, 1H), 7.51 (dd, J=7.9, 1.4 Hz, 1H), 7.33-7.20 (m, 1H), 4.01 (d, J=0.3 Hz, 3H), 3.82 (s, 3H), 1.73-1.60 (m, 1H), 1.16-1.06 (m, 2H), 0.97-0.84 (m, 2H). LC retention time 6.84 [N]. MS (E$^+$) m/z: 426 (MH$^+$).

Example 53

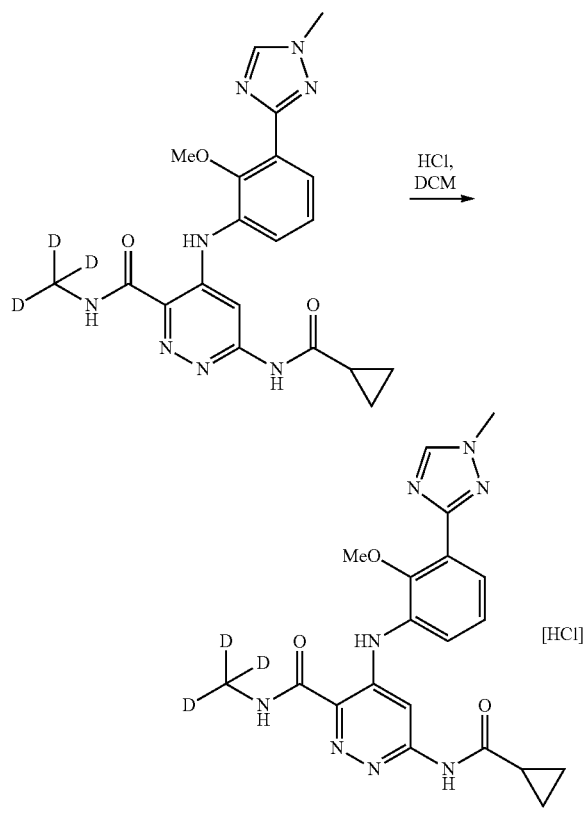

To a homogeneous solution of Example 52 (50 mg, 0.12 mmol) in dichloromethane (3 mL) was added HCl (1M aq., 0.13 mL, 0.13 mmol) resulting in the solution turning yellow. The homogenous solution was concentrated down and then re-concentrated from dichloromethane twice to remove residual water, resulting in a white powder. The powder was suspended in dichloromethane and sonicated for 15 minutes, the powder was then collected via filtration, rinsing with dichloromethane to provide the corresponding HCl salt (38 mg, 70% yield). $^1$H NMR (500 MHz, chloroform-d) δ 12.02 (s, 1H), 8.35 (s, 1H), 8.16 (s, 1H), 8.01 (dd, J=7.9, 1.5 Hz, 1H), 7.57 (br. s., 1H), 7.52-7.46 (m, 1H), 7.36 (t, J=7.9 Hz, 1H), 4.03 (s, 3H), 3.83 (s, 3H), 2.05-1.95 (m, 1H), 1.16-1.09 (m, 2H), 1.03 (dd, J=7.4, 3.6 Hz, 2H). LC retention time 0.62 [J]. MS (E$^+$) m/z: 426 (MH$^+$).

Compare to NMR of parent free base: $^1$H NMR (500 MHz, chloroform-d) δ 10.99 (s, 1H), 8.63 (s, 1H), 8.18 (s, 1H), 8.10 (d, J=0.5 Hz, 2H), 7.81 (dd, J=7.9, 1.7 Hz, 1H), 7.51 (dd, J=7.9, 1.4 Hz, 1H), 7.33-7.20 (m, 1H), 4.01 (d, J=0.3 Hz, 3H), 3.82 (s, 3H), 1.73-1.60 (m, 1H), 1.16-1.06 (m, 2H), 0.97-0.84 (m, 2H).

The following Examples were prepared in a similar manner to the product of Example 52. The aniline used in each case was prepared following the preparation number, or in a manner similar to it, as denoted for each entry:

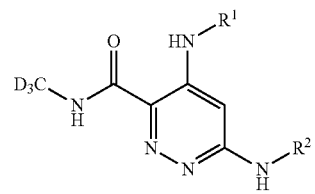

| Example No. | Preparation No. | R$^1$ | R$^2$ | Rt (min) [Method] | m/z [M + H]$^+$ |
|---|---|---|---|---|---|
| 54 | 4 | 3-(1-methyl-1H-pyrazol-3-yl)-2-methoxyphenyl | cyclopropylcarbonyl | 1.44 [E] | 425 |
| 55 | 4 | 3-(1-methyl-1H-pyrazol-3-yl)-2-methoxyphenyl | 5-fluoropyridin-2-yl | 1.82 [E] | 466 |

-continued

| Example No. | Preparation No. | R¹ | R² | Rt (min) [Method] | m/z [M + H]⁺ |
|---|---|---|---|---|---|
| 56 | 10 | | | 1.49 [E] | 467 |
| 57 | 4 | | | 1.44 [E] | 463 |
| 58 | 4 | | | 1.63 [E] | 434 |
| 59 | 4 | | | 1.76 [E] | 466 |
| 60 | 10 | | | 1.28 [E] | 452 |

-continued
| Example No. | Preparation No. | R¹ | R² | Rt (min) [Method] | m/z [M + H]⁺ |
|---|---|---|---|---|---|
| 61 | 4 | 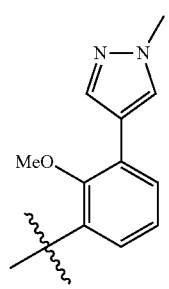 | 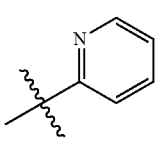 | 1.57 [E] | 434 |
| 62 | 10 | 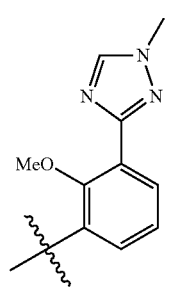 | 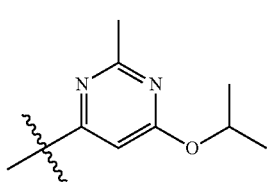 [SMILES: *c1cc(OC(C)C)nc(C)n1] | 1.58 [E] | 508 |
| 63 | 4 | 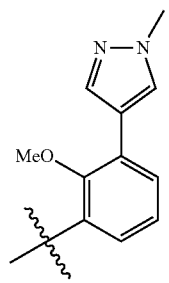 [SMILES: *c1cccc(-c2cnn(C)c2)c1OC] | 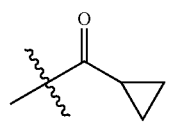 [SMILES: *C(=O)C1CC1] | 1.42 [E] | 425 |
| 64 | 5 | 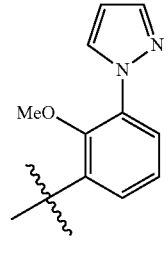 [SMILES: *c1cccc(-n2cccn2)c1OC] | 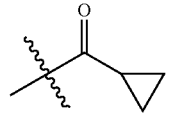 [SMILES: *C(=O)C1CC1] | 1.45 [E] | 411 |
| 65 | 5 | 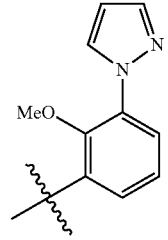 [SMILES: *c1cccc(-n2cccn2)c1OC] | 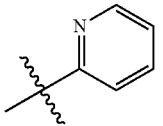 [SMILES: *c1ccccn1] | 1.58 [E] | 420 |

-continued

| Example No. | Preparation No. | R¹ | R² | Rt (min) [Method] | m/z [M + H]⁺ |
|---|---|---|---|---|---|
| 66 | 5 | 1-pyrazolyl-2-methoxyphenyl | 2-pyridyl | 1.86 [E] | 452 |
| 67 | 4 | 4-methyl-1H-imidazol-2-yl-2-methoxyphenyl | cyclopropyl ketone | 1.18 [E] | 425 |
| 68 | 10 | 1-methyl-1,2,4-triazol-3-yl-2-methoxyphenyl | 6-ethylpyrimidin-4-yl | 1.26 [E] | 464 |
| 69 | 4 | 6-methylpyridazin-3-yl-2-methoxyphenyl | cyclopropyl ketone | 2.29 [A] | 437 |
| 70 | 4 | pyrimidin-2-yl-2-methoxyphenyl | cyclopropyl ketone | 2.07 [A] | 423 |

-continued

| Example No. | Preparation No. | R¹ | R² | Rt (min) [Method] | m/z [M + H]⁺ |
|---|---|---|---|---|---|
| 71 | 4 | 3-(pyrimidin-2-yl)-2-methoxyphenyl | 5-fluoropyridin-2-yl | 2.15 [A] | 450 |
| 72 | 4 | 3-(pyridin-2-yl)-2-methoxyphenyl | cyclopropylcarbonyl | 1.86 [A] | 422 |
| 73 | 4 | 3-(4-methylthiazol-2-yl)-2-methoxyphenyl | pyridin-2-yl | 1.86 [E] | 451 |
| 74 | 4 | 3-(pyrazin-2-yl)-2-methoxyphenyl | 5-fluoropyridin-2-yl | 2.35 [A] | 450 |
| 75 | 4 | 3-(pyrazin-2-yl)-2-methoxyphenyl | cyclopropylcarbonyl | 2.35 [A] | 423 |

-continued

| Example No. | Preparation No. | R¹ | R² | Rt (min) [Method] | m/z [M + H]⁺ |
|---|---|---|---|---|---|
| 76 | 10 | 1-methyl-1,2,4-triazol-3-yl on MeO-phenyl | 2-pyridyl | 1.29 [E] | 435 |
| 77 | 4 | 2-pyridyl on MeO-phenyl | 5-fluoropyridin-2-yl | 1.76 [A] | 449 |
| 78 | 4 | pyridazin-3-yl on MeO-phenyl | cyclopropyl ketone | 2.11 [A] | 423 |
| 79 | 4 | pyridazin-3-yl on MeO-phenyl | 5-fluoropyridin-2-yl | 1.35 [E] | 450 |
| 80 *CD₃ replaced with CH₃* | 4 | 2,4-dimethylthiazol-5-yl on MeO-phenyl | 2-pyridyl | 11.14 [O] | 462 |

-continued

| Example No. | Preparation No. | R¹ | R² | Rt (min) [Method] | m/z [M + H]⁺ |
|---|---|---|---|---|---|
| 81 *CD₃ replaced with CH₃* | 4 | 2-methylthiazol-5-yl on MeO-phenyl | pyridin-2-yl | 6.64 [P] | 448 |
| 82 | 4 | 4-methylpyrimidin-2-yl on MeO-phenyl | cyclopropyl ketone | 2.42 [A] | 437 |
| 83 | 4 | 4-methylpyrimidin-2-yl on MeO-phenyl | 5-fluoropyridin-2-yl | 2.36 [A] | 464 |
| 84 | 10 | 1-methyl-1,2,4-triazol-3-yl on MeO-phenyl | 4-(1-hydroxyethyl)pyridin-2-yl | 1.09 [E] | 479 |
| 85 | 4 | 1-methylpyrazol-4-yl on MeO-phenyl | 1,5-dimethylpyrazol-3-yl | 1.41 [E] | 451 |

-continued

| Example No. | Preparation No. | R¹ | R² | Rt (min) [Method] | m/z [M + H]⁺ |
|---|---|---|---|---|---|
| 86 | 4 | pyrimidine-MeO-phenyl | cyclopropyl ketone | 2.65 [A] | 423 |
| 87 | 10 | N-methyl-triazole-MeO-phenyl | 2-methyl-4-(methoxymethyl)pyrimidine | 1.14 [E] | 494 |
| 88 | 10 | N-methyl-triazole-MeO-phenyl | 4-methoxypyrimidine | 1.27 [E] | 466 |
| 89 | 4 | pyrimidine-MeO-phenyl | 5-fluoropyridine | 1.43 [E] | 450 |
| 90 *CD₃ replaced with CH₃* | 4 | 2-methylthiazole-MeO-phenyl | cyclopropyl ketone | 7.04 [P] | 439 |

-continued

| Example No. | Preparation No. | R¹ | R² | Rt (min) [Method] | m/z [M + H]⁺ |
|---|---|---|---|---|---|
| 91 | 4 | 2-(pyrimidin-2-yl)-3-methoxyphenyl | pyridin-2-yl | 2.20 [A] | 432 |
| 92 | 4 | 2-(pyrimidin-2-yl)-3-methoxyphenyl | 1,5-dimethyl-1H-pyrazol-3-yl | 2.29 [A] | 449 |
| 93 | 4 | 2-(1-methyl-1H-pyrazol-3-yl)-3-methoxyphenyl | 1,5-dimethyl-1H-pyrazol-3-yl | 1.44 [E] | 451 |
| 94 | 10 | 2-(1-methyl-1H-1,2,4-triazol-3-yl)-3-methoxyphenyl | pyrimidin-4-yl | 1.07 [E] | 436 |
| 95 | 4 | 2-(4-methylthiazol-2-yl)-3-methoxyphenyl | cyclopropanecarbonyl | 1.67 [E] | 442 |

-continued
| Example No. | Preparation No. | R¹ | R² | Rt (min) [Method] | m/z [M + H]⁺ |
|---|---|---|---|---|---|
| 96 | 4 | 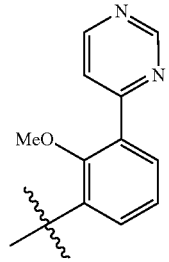 [SMILES: *c1cccc(-c2ccncn2)c1OC] | 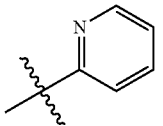 [SMILES: *c1ccccn1] | 1.38 [E] | 432 |
| 97 | 4 | 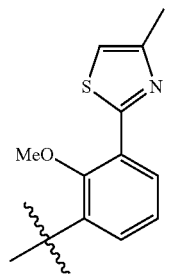 [SMILES: *c1cccc(-c2nc(C)cs2)c1OC] | 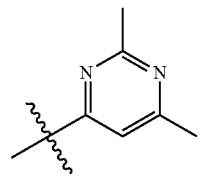 [SMILES: *c1cc(C)nc(C)n1] | 1.71 [E] | 480 |
| 98 | 10 | 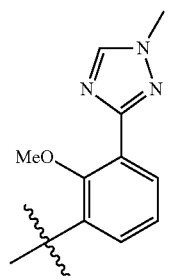 [SMILES: *c1cccc(-c2ncn(C)n2)c1OC] | 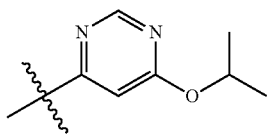 [SMILES: *c1cc(OC(C)C)ncn1] | 1.47 [E] | 494 |
| 99 | 10 | 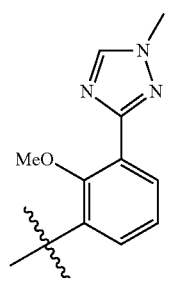 | 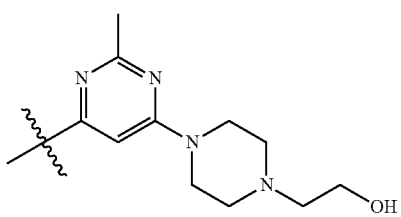 [SMILES: *c1cc(N2CCN(CCO)CC2)nc(C)n1] | 1.05 [E] | 578 |
| 100 | 4 | 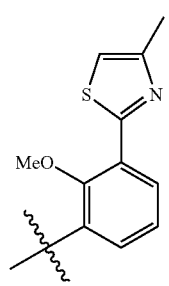 [SMILES: *c1cccc(-c2nc(C)cs2)c1OC] | 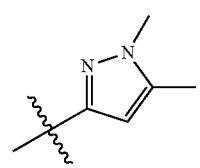 [SMILES: *c1cc(C)n(C)n1] | 1.74 [E] | 468 |

-continued

| Example No. | Preparation No. | R¹ | R² | Rt (min) [Method] | m/z [M + H]⁺ |
|---|---|---|---|---|---|
| 101 | 4 | 5-methylthiazol-2-yl, 2-methoxyphenyl | cyclopropyl ketone | 1.70 [E] | 442 |
| 102 | 10 | 1-methyl-1,2,4-triazol-3-yl, 2-methoxyphenyl | (6-pyridin-3-yl)methanol | 1.05 [E] | 465 |
| 103 | 10 | 1-methyl-1,2,4-triazol-3-yl, 2-methoxyphenyl | 2-methylpyrimidin-4-yl | 1.04 [E] | 450 |
| 104 | 4 | 5-methylthiazol-2-yl, 2-methoxyphenyl | 1,5-dimethylpyrazol-3-yl | 1.68 [E] | 468 |
| 105 | 4 | thiazol-2-yl, 2-methoxyphenyl | cyclopropyl ketone | 1.44 [E] | 428 |

-continued

| Example No. | Preparation No. | R¹ | R² | Rt (min) [Method] | m/z [M + H]⁺ |
|---|---|---|---|---|---|
| 106 | 4 | thiazole-MeO-phenyl | 5-fluoro-4-methylpyridin-2-yl | 1.76 [E] | 469 |
| 107 | 4 | thiazole-MeO-phenyl | 1,5-dimethyl-1H-pyrazol-3-yl | 1.43 [E] | 454 |
| 108 | 10 | 1-methyl-1H-1,2,4-triazol-3-yl-MeO-phenyl | 2,6-dimethylpyrimidin-4-yl | 1.19 [E] | 464 |
| 109 | 10 | 1-methyl-1H-1,2,4-triazol-3-yl-MeO-phenyl | 6-methylpyrimidin-4-yl | 1.14 [E] | 450 |
| 110 | 10 | 1-methyl-1H-1,2,4-triazol-3-yl-MeO-phenyl | 4-(hydroxymethyl)pyridin-2-yl | 1.09 [E] | 465 |

-continued
| Example No. | Preparation No. | R¹ | R² | Rt (min) [Method] | m/z [M + H]⁺ |
|---|---|---|---|---|---|
| 111 | 4 | 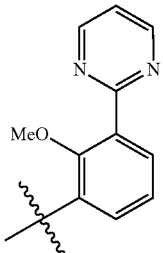 [SMILES: *c1cccc(-c2ncccn2)c1OC] | 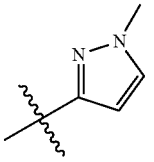 [SMILES: *c1ccn(C)n1] | 2.16 [A] | 435 |
| 112 | 4 | 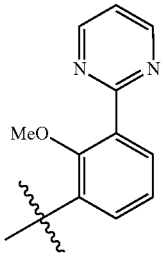 [SMILES: *c1cccc(-c2ncccn2)c1OC] | 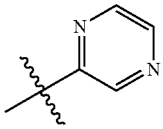 [SMILES: *c1cnccn1] | 2.03 [A] | 433 |
| 113 | 4 | 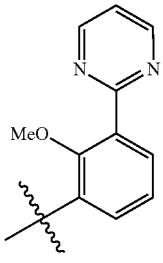 [SMILES: *c1cccc(-c2ncccn2)c1OC] | 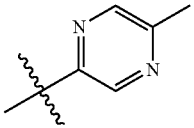 [SMILES: *c1cnc(C)cn1] | 2.18 [A] | 447 |
| 114 | 10 | 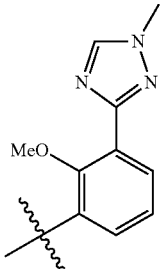 | 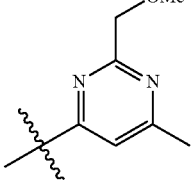 | 1.08 [E] | 494 |
| 115 | 10 | 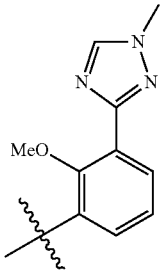 | 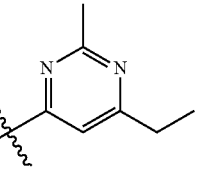 | 1.23 [E] | 478 |

-continued

| Example No. | Preparation No. | R¹ | R² | Rt (min) [Method] | m/z [M + H]⁺ |
|---|---|---|---|---|---|
| 116 | 4 | 5-fluoropyrimidin-2-yl attached to 2-methoxyphenyl | cyclopropyl ketone | 2.62 [A] | 441 |
| 117 | 4 | 5-methylthiazol-2-yl attached to 2-methoxyphenyl | pyridin-2-yl | 1.83 [E] | 451 |
| 118 | 4 | pyrimidin-2-yl attached to 2-methoxyphenyl | pyrimidin-4-yl | 1.94 [A] | 433 |
| 119 | 4 | pyrimidin-2-yl attached to 2-methoxyphenyl | 6-methylpyrimidin-4-yl | 2.03 [A] | 447 |
| 120 | 10 | 1-methyl-1H-1,2,4-triazol-3-yl attached to 2-methoxyphenyl | 4-(2-hydroxypropan-2-yl)pyridin-2-yl | 1.16 [E] | 493 |

-continued

| Example No. | Preparation No. | R¹ | R² | Rt (min) [Method] | m/z [M + H]⁺ |
|---|---|---|---|---|---|
| 121 | 4 | 2-methoxy-3-(pyrimidin-2-yl)phenyl | 2,6-dimethylpyrimidin-4-yl | 2.09 [A] | 461 |
| 122 | 4 | 2-methoxy-3-(pyrimidin-2-yl)phenyl | 6-methylpyridazin-3-yl | 2.06 [A] | 447 |
| 123 | 4 | 2-methoxy-3-(pyrimidin-2-yl)phenyl | pyridazin-3-yl | 1.96 [A] | 433 |
| 124 | 4 | 2-methoxy-3-(5-methylthiazol-2-yl)phenyl | 5-fluoro-4-methylpyridin-2-yl | 2.03 [E] | 483 |
| 125 | commercial source | 2-methoxyphenyl | cyclopropylcarbonyl | 1.45 [E] | 345 |
| 126 | 4 | 2-methoxy-3-(thiazol-4-yl)phenyl | cyclopropylcarbonyl | 1.54 [E] | 428 |

| Example No. | Preparation No. | R¹ | R² | Rt (min) [Method] | m/z [M + H]⁺ |
|---|---|---|---|---|---|
| 127 | 10 | 1-methyl-1,2,4-triazol-3-yl, 2-MeO-phenyl | 4-ethoxypyridazin-2-yl | 1.53 [E] | 479 |
| 128 | 10 | 1-methyl-1,2,4-triazol-3-yl, 2-MeO-phenyl | 4-ethylpyridin-2-yl | 1.45 [E] | 463 |
| 129 | 4 | thiazol-4-yl, 2-MeO-phenyl | 5-fluoro-4-methylpyridin-2-yl | 1.89 [E] | 469 |
| 130 | 4 | thiazol-4-yl, 2-MeO-phenyl | 2,6-dimethylpyrimidin-4-yl | 1.51 [E] | 466 |
| 131 | 4 | thiazol-4-yl, 2-MeO-phenyl | 1,5-dimethylpyrazol-3-yl | 1.53 [E] | 454 |
| 132 | 4 | thiazol-4-yl, 2-MeO-phenyl | pyridin-2-yl | 1.68 [E] | 437 |

-continued

| Example No. | Preparation No. | R¹ | R² | Rt (min) [Method] | m/z [M + H]⁺ |
|---|---|---|---|---|---|
| 133 | 10 | 1-methyl-1,2,4-triazol-3-yl, 2-methoxyphenyl | 4-methoxypyridin-2-yl | 1.32 [E] | 465 |
| 134 | 10 | 1-methyl-1,2,4-triazol-3-yl, 2-methoxyphenyl | 6-(cyclopropanecarbonylamino)-2-methylpyrimidin-4-yl | 1.30 [E] | 533 |
| 135 | 10 | 1-methyl-1,2,4-triazol-3-yl, 2-methoxyphenyl | 4-(methoxymethyl)pyridin-2-yl | 1.30 [E] | 479 |
| 136 | 6 | 2-methyl-2H-1,2,3-triazol-4-yl, 2-methoxyphenyl | cyclopropanecarbonyl | 1.42 [E] | 426 |
| 137 | 6 | 2-methyl-2H-1,2,3-triazol-4-yl, 2-methoxyphenyl | 2,6-dimethylpyrimidin-4-yl | 1.43 [E] | 464 |

-continued

| Example No. | Preparation No. | R¹ | R² | Rt (min) [Method] | m/z [M + H]⁺ |
|---|---|---|---|---|---|
| 138 | 6 | 1-methyl-1,2,3-triazol-4-yl linked to MeO-phenyl | cyclopropyl ketone | 1.24 [E] | 426 |
| 139 | 7 | ethynyl-MeO-phenyl | cyclopropyl ketone | 1.66 [E] | 369 |
| 140 | 8 | 2-(difluoromethoxy)-benzamide | 5-fluoro-4-methylpyridin-2-yl | 1.37 [E] | 465 |
| 141 | 11 | 5-methyl-1H-1,2,4-triazol-3-yl linked to MeO-phenyl | cyclopropyl ketone | 1.11 [E] | 426 |
| 142 | 11 | 5-methyl-1H-1,2,4-triazol-3-yl linked to MeO-phenyl | 5-fluoro-4-methylpyridin-2-yl | 1.43 [E] | 467 |
| 143 | 12 | 1-methyl-1H-tetrazol-5-yl linked to MeO-phenyl | cyclopropyl ketone | 1.26 [E] | 427 |

-continued

| Example No. | Preparation No. | R¹ | R² | Rt (min) [Method] | m/z [M + H]⁺ |
|---|---|---|---|---|---|
| 144 | 12 | 2-methyltetrazol-5-yl, MeO-phenyl | 2,6-dimethylpyrimidin-4-yl | 0.63 [J] | 465 |
| 145 | 12 | 1-methyltetrazol-5-yl, MeO-phenyl | pyridin-2-yl | 1.37 [E] | 436 |
| 146 | 12 | 2-methyltetrazol-5-yl, MeO-phenyl | cyclopropylcarbonyl | 1.30 [E] | 427 |
| 147 | 12 | 2-methyltetrazol-5-yl, MeO-phenyl | pyridin-2-yl | 1.43 [E] | 436 |
| 148 | 11 | 5-methyl-1H-1,2,4-triazol-3-yl, MeO-phenyl | 1,5-dimethyl-1H-pyrazol-3-yl | 1.09 [E] | 452 |

-continued
| Example No. | Preparation No. | R¹ | R² | Rt (min) [Method] | m/z [M + H]⁺ |
|---|---|---|---|---|---|
| 149 | 13 | 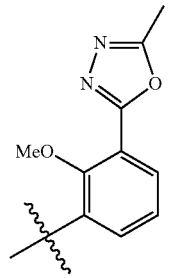 | 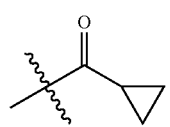 [SMILES: *C(=O)C1CC1] | 1.29 [E] | 427 |
| 150 | 13 | 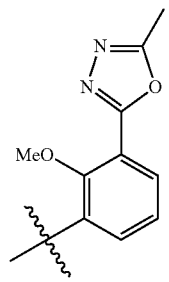 | 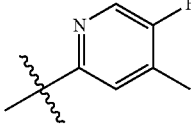 | 1.63 [E] | 468 |
| 151 | 13 | 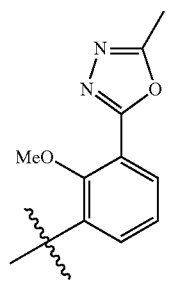 | 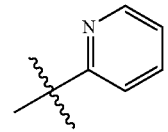 [SMILES: *c1ccccn1] | 1.34 [E] | 436 |
| 152 | 13 | 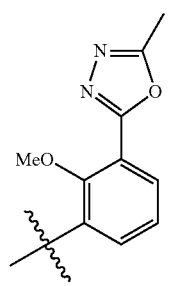 | 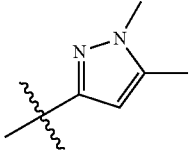 [SMILES: *c1cc(C)n(C)n1] | 1.31 [E] | 453 |
| 153 | 13 | 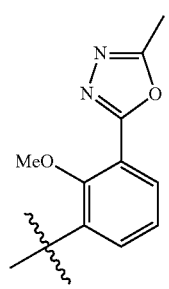 | 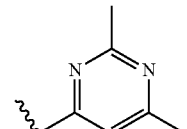 | 1.19 [E] | 465 |

-continued

| Example No. | Preparation No. | R¹ | R² | Rt (min) [Method] | m/z [M + H]⁺ |
|---|---|---|---|---|---|
| 154 *CD₃ replaced with CH₃* | 14 | 2-methyl-1,3,4-thiadiazole attached to MeO-phenyl | cyclopropyl ketone | 1.92 [R] | 440 |
| 155 *CD₃ replaced with CH₃* | 14 | 2-methyl-1,3,4-thiadiazole attached to MeO-phenyl | 2-pyridyl | 2.01 [R] | 449 |
| 156 *CD₃ replaced with CH₃* | 13 | 2-methyl-1,3,4-oxadiazole attached to MeO-phenyl | 2-pyridyl | 2.04 [R] | 433 |
| 157 | 4 | thiazole attached to MeO-phenyl | 1-(pyridin-4-yl)ethanol | 1.50 [E] | 481 |
| 158 | 4 | pyrimidin-2-yl attached to MeO-phenyl | 2-methylpyrimidin-4-yl | 2.02 [A] | 447 |

-continued
| Example No. | Preparation No. | R¹ | R² | Rt (min) [Method] | m/z [M + H]⁺ |
|---|---|---|---|---|---|
| 159 | 4 | | | 1.19 [E] | 425 |
| 160 | 4 | | | 1.53 [E] | 442 |
| 161 | 4 | | | 1.51 [E] | 468 |
Preparation 15
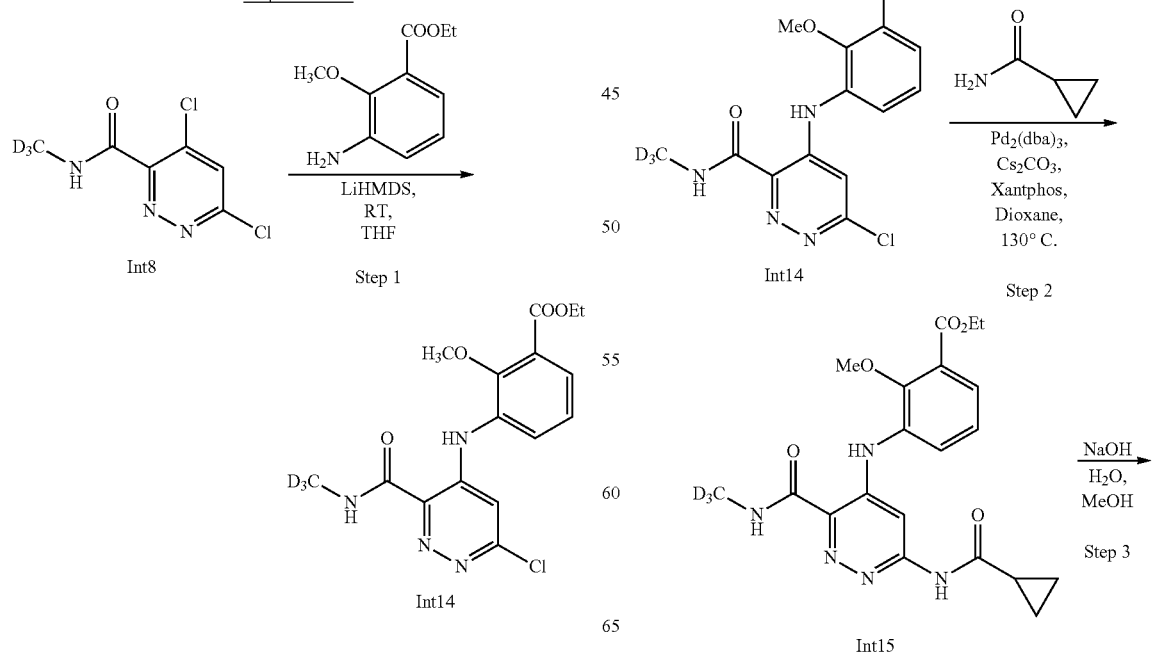

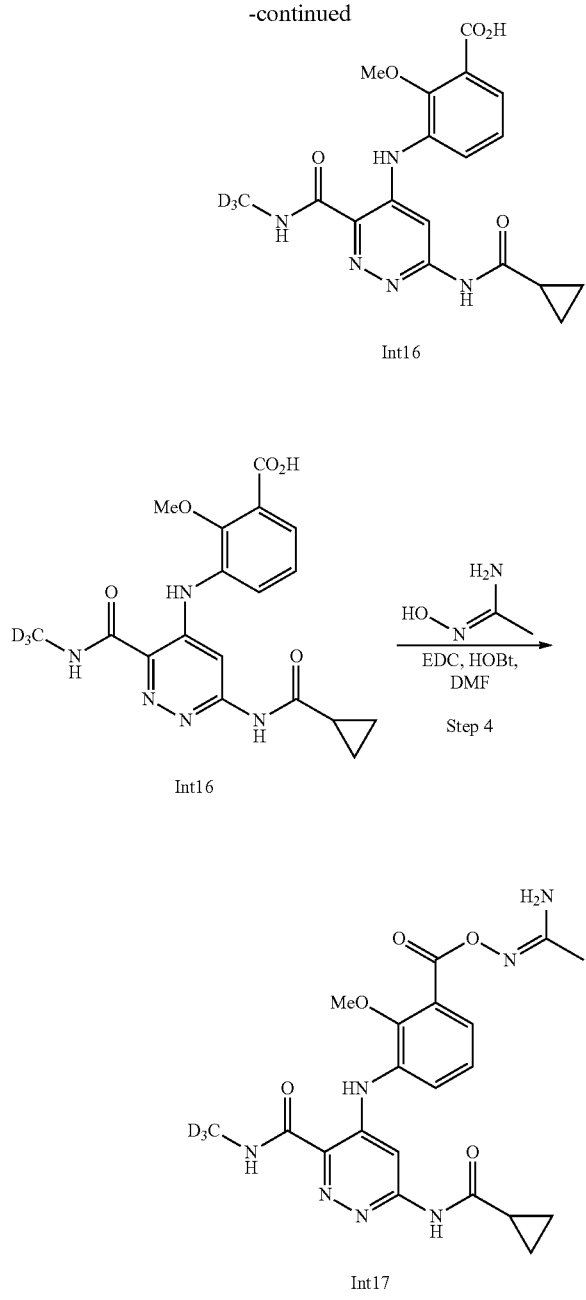

Step 1

To a solution of Int8 (200 mg, 0.957 mmol) and ethyl 3-amino-2-methoxybenzoate (187 mg, 0.957 mmol) in THF (9 mL) at room temperature was added dropwise over 1 minute LiHMDS (1M in THF, 2.392 mL, 2.392 mmol). The resulting solution was stirred at room temperature for 1 hr. The reaction mixture was quenched with saturated ammonium chloride solution (2 ml). The mixture was partitioned between EtOAc (40 ml) and saturated ammonium chloride solution (40 ml). The organic layer was washed with brine (40 ml), dried ($Na_2SO_4$) and concentrated to afford a solid residue that was purified on a 12 gm ISCO silica gel cartridge, eluting with a 0-100% EtOAc/hex gradient. The pure fractions were concentrated to afford ethyl 3-((6-chloro-3-(trideuteromethylcarbamoyl)pyridazin-4-yl) amino)-2-methoxybenzoate (301 mg, 0.818 mmol, 86% yield) as an tan solid. LC retention time 2.28 minutes [Q]. MS (ESI$^+$) m/z: 368.2/370.2 (MH$^+$), chlorine pattern. $^1$H NMR (400 MHz, DMSO-$d_6$) δ 11.11 (s, 1H), 9.37 (s, 1H), 7.76 (dd, J=7.9, 1.3 Hz, 1H), 7.57 (dd, J=7.9, 1.5 Hz, 1H), 7.30 (t, J=7.9 Hz, 1H), 7.20 (s, 1H), 4.33 (q, J=7.1 Hz, 2H), 3.74 (s, 3H), 1.33 (t, J=7.0 Hz, 3H).

Step 2

A mixture of ethyl 3-((6-chloro-3-(trideuteromethylcarbamoyl)pyridazin-4-yl)amino)-2-methoxybenzoate (240 mg, 0.653 mmol), cyclopropanecarboxamide (111 mg, 1.305 mmol), $Pd_2(dba)_3$ (59.8 mg, 0.065 mmol), Xantphos (76 mg, 0.131 mmol) and $Cs_2CO_3$ (850 mg, 2.61 mmol) in dioxane (5 mL) was degassed by bubbling nitrogen through the mixture for 5 minutes. The reaction vessel was sealed and heated to 130° C. for 8 hr. After cooling to room temperature, the reaction mixture was partitioned between EtOAc (50 ml) and water (50 ml). The aqueous layer was extracted with EtOAc (30 ml) and the combined organics were dried ($Na_2SO_4$) and concentrated to afford a semisolid that was purified on a 24 gm ISCO silica gel cartridge, eluting with a 0-100% EtOAc/hex gradient. The pure fractions were concentrated to afford ethyl 3-((6-(cyclopropanecarboxamido)-3-(trideuteromethylcarbamoyl)pyridazin-4-yl) amino)-2-methoxybenzoate (115 mg, 0.276 mmol, 42.3% yield) as a tan solid. Used as is. LC retention time 2.02 minutes [Q]. MS (ESI$^+$) m/z: 417.5 (MH$^+$).

Step 3

A mixture of ethyl 3-((6-(cyclopropanecarboxamido)-3-(trideuteromethylcarbamoyl)pyridazin-4-yl)amino)-2-methoxybenzoate (114 mg, 0.274 mmol) and NaOH, 1M (1.369 mL, 1.369 mmol) in MeOH (2.5 mL) and THF (1 mL) was stirred at room temperature for 3.5 hr. The reaction was diluted with water (10 ml) and the pH was adjusted to ~1 with 1N HCl. The mixture was extracted with EtOAc (30 ml). The organic layer was washed with brine (30 ml), dried ($MgSO_4$) and concentrated to afford 3-((6-(cyclopropanecarboxamido)-3-(trideuteromethylcarbamoyl)pyridazin-4-yl)amino)-2-methoxybenzoic acid (74 mg, 0.191 mmol, 69.6% yield) as a yellow solid. Used as is. LC retention time 1.55 minutes [Q]. MS (ESI$^+$) m/z: 389.3 (MH$^+$).

Step 4

A mixture of 3-((6-(cyclopropanecarboxamido)-3-(trideuteromethylcarbamoyl)pyridazin-4-yl)amino)-2-methoxybenzoic acid (73 mg, 0.188 mmol), hydroxybenzotriazole (HOBt) (34.5 mg, 0.226 mmol) and 1-ethyl-3-(3-dimethylaminopropyl)carbodiimide (EDC) (43.2 mg, 0.226 mmol) in DMF (1.5 mL) was stirred at room temperature for 30 minutes. At this time, (Z)—N'-hydroxyacetimidamide (13.92 mg, 0.188 mmol) was added and stirring was continued at room temperature for 1.5 hr. The reaction mixture was partitioned between EtOAc (20 ml) and saturated sodium bicarbonate solution (20 ml). The organic layer was washed with water (2×20 ml) and brine (20 ml). After drying ($Na_2SO_4$) and filtration the organic layer was concentrated to afford (Z)-4-((3-((((1-aminoethylidene)amino)oxy)carbonyl)-2-methoxyphenyl)amino)-6-(cyclopropanecarboxamido)-N-trideuteromethylpyridazine-3-carboxamide (57 mg, 0.128 mmol, 68.2% yield) as a light yellow oil. Used as is. LC retention time 1.65 minutes [Q]. MS (ESI$^+$) m/z: 445.4 (MH$^+$).

Example 162

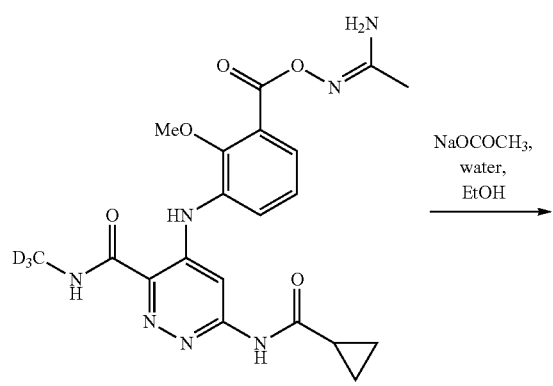

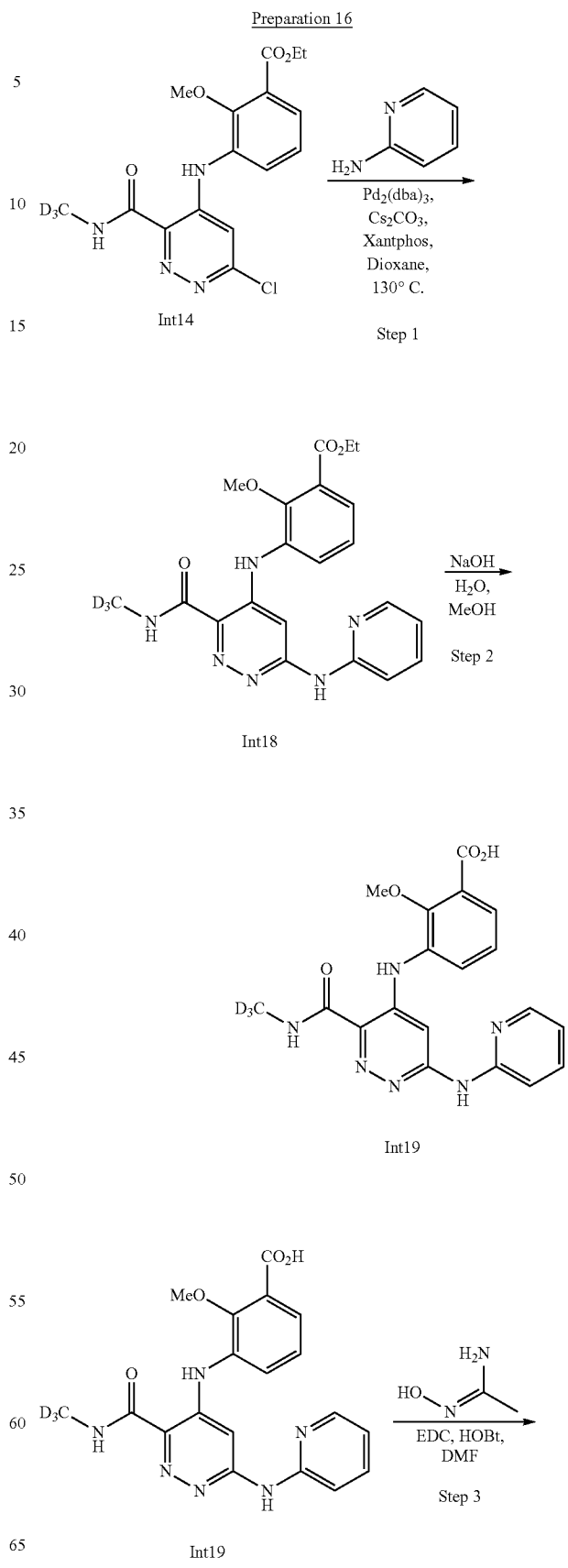

To a solution of (Z)-4-((3-((((1-aminoethylidene)amino)oxy)carbonyl)-2-methoxyphenyl)amino)-6-(cyclopropanecarboxamido)-N-trideuteromethylpyridazine-3-carboxamide (51 mg, 0.115 mmol) in ethanol (3 mL) was added sodium acetate, trihydrate (39.1 mg, 0.287 mmol) as a solution in water (0.5 mL) and the resulting mixture was heated to 80° C. for 20 hours. After cooling to room temperature, the reaction mixture was filtered and the resulting solid was washed with water and EtOH. The solid was triturated with EtOH with heating and sonication and overnight stirring. Filtration and drying afforded 6-(cyclopropanecarboxamido)-4-((2-methoxy-3-(3-methyl-1,2,4-oxadiazol-5-yl)phenyl)amino)-N-trideuteromethylpyridazine-3-carboxamide (10 mg, 0.022 mmol, 18.80% yield) as a light yellow solid. LC retention time 2.05 minutes [Q]. MS (ESI$^{+}$) m/z: 427.4 (MH$^{+}$). $^1$H NMR (400 MHz, DMSO-$d_6$) δ 11.36 (s, 1H), 11.06 (s, 1H), 9.17 (s, 1H), 8.13 (s, 1H), 7.79 (ddd, J=17.6, 8.0, 1.4 Hz, 2H), 7.42 (t, J=7.9 Hz, 1H), 3.78 (s, 3H), 2.45 (s, 3H), 2.16-2.02 (m, 1H), 0.89-0.68 (m, 4H).

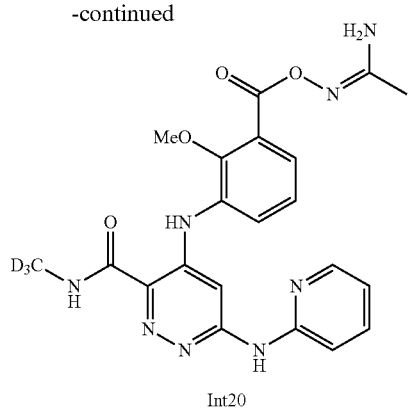

Int20

Step 1

A mixture of Int14 (120 mg, 0.326 mmol), pyridin-2-amine (61.4 mg, 0.653 mmol), Pd$_2$(dba)$_3$ (29.9 mg, 0.033 mmol), Xantphos (37.8 mg, 0.065 mmol) and Cs$_2$CO$_3$ (425 mg, 1.305 mmol) in dioxane (2.5 mL) was degassed by bubbling nitrogen through the mixture for 5 minutes. The reaction vessel was sealed and heated to 130° C. for 8 hr. After cooling to room temperature, the reaction mixture was partitioned between EtOAc (50 ml) and water (50 ml). The aqueous layer was extracted with EtOAc (30 ml) and the combined organics were dried (Na$_2$SO$_4$) and concentrated to afford ethyl 2-methoxy-3-((3-(trideuteromethylcarbamoyl)-6-(pyridin-2-ylamino)pyridazin-4-yl)amino)benzoate (139 mg, 0.327 mmol, 99% yield) a yellow solid. Attempts to purify were unsuccessful and the crude product mixture was taken on as is. LC retention time 2.13 minutes [Q]. MS (ESI$^+$) m/z: 426.4 (MH$^+$).

Step 2

A mixture of Int18 (92 mg, 0.232 mmol) and NaOH, 1N NaOH (1.634 mL, 1.634 mmol) in MeOH (3 mL) and THF (1 mL) was stirred at room temperature for 22 hr. The organic solvents were removed in vacuo and the residue was diluted with 20 ml of water the pH was adjusted to ~1 with 1N HCl and the resulting mixture was extracted with EtOAc (2×50 ml) and EtOAc:THF, 1:1 (50 ml). After drying (Na$_2$SO$_4$) and filtration the organic layer was concentrated to afford Int19 (92 mg, 0.232 mmol, 70.9% yield) as a yellow solid. Used as is. LC retention time 1.88 minutes [Q]. MS (ESI$^+$) m/z: 398.3 (MH$^+$).

Step 3

A mixture of 2-methoxy-3-((3-(trideuteromethylcarbamoyl)-6-(pyridin-2-ylamino)pyridazin-4-yl)amino)benzoic acid (90 mg, 0.226 mmol), HOBt (41.6 mg, 0.272 mmol) and EDC (52.1 mg, 0.272 mmol) in DMF (2 mL) was stirred at room temperature for 30 minutes. At this time, (Z)—N'-hydroxyacetimidamide (16.78 mg, 0.226 mmol) was added and stirring was continued at room temperature for 18 hr. The reaction mixture was partitioned between EtOAc (20 ml) and saturated sodium bicarbonate solution (20 ml). The organic layer was washed with 10% LiCl solution (2×20 ml) and brine (20 ml). After drying (Na$_2$SO$_4$) and filtration the organic layer was concentrated to afford Int20 (69 mg, 0.152 mmol, 67.2% yield) as a light yellow solid. Used as is. LC retention time 1.88 minutes [Q]. MS (ESI$^+$) m/z: 454.4 (MH$^+$).

Example 163

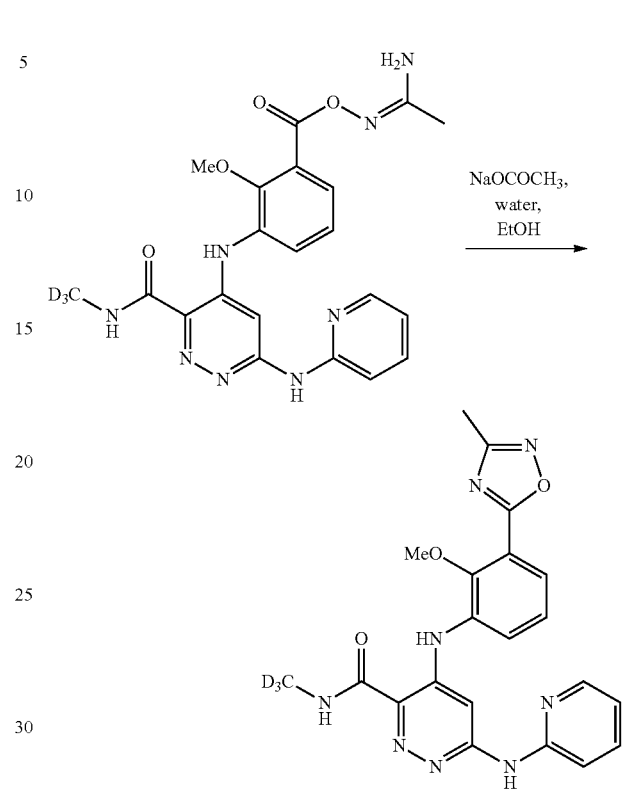

To a solution of Int20 (68 mg, 0.150 mmol) in ethanol (3 mL) was added sodium acetate trihydrate (51.1 mg, 0.375 mmol) as a solution in water (0.5 mL) and the resulting mixture was heated to 80° C. for 30 hr. After cooling to room temperature, the reaction mixture was filtered and the filter cake was washed with water followed by EtOH. Drying afforded 4-((2-methoxy-3-(3-methyl-1,2,4-oxadiazol-5-yl)phenyl)amino)-N-trideutero-methyl-6-(pyridin-2-ylamino)pyridazine-3-carboxamide (12 mg, 0.026 mmol, 17.55% yield) as a white solid. LC retention time 2.23 minutes [Q]. MS (ESI$^+$) m/z: 436.4 (MH$^+$). $^1$H NMR (400 MHz, DMSO-d$_6$) δ 11.09 (s, 1H), 10.19 (s, 1H), 9.12 (s, 1H), 8.27-8.13 (m, 2H), 7.95-7.87 (m, 1H), 7.79 (dd, J=7.9, 1.3 Hz, 1H), 7.74-7.65 (m, 1H), 7.58 (d, J=8.4 Hz, 1H), 7.47 (t, J=8.0 Hz, 1H), 6.93 (dd, J=6.4, 5.1 Hz, 1H), 3.82 (s, 3H), 2.46 (s, 3H).

Example 164

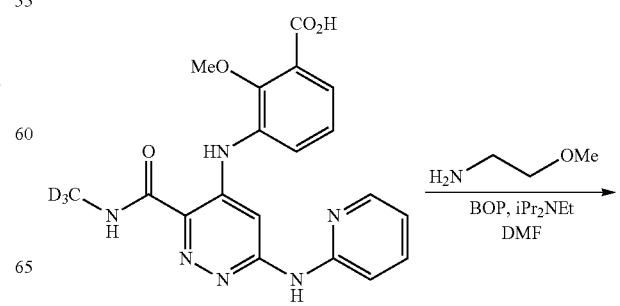

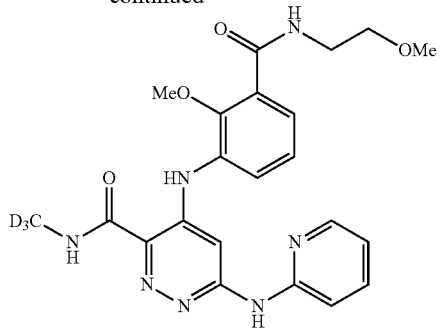

Int19

To a solution of Int19 (40 mg, 0.1 mmol) and 2-methoxyethanamine (10.4 mg, 0.128 mmol) in DMF (1 mL) was added (benzotriazol-1-yloxy)tris(dimethylamino)phosphonium hexafluorophosphate (BOP, 45 mg, 0.10 mmol) and N,N'-diisopropylethylamine (0.064 mL, 0.37 mmol). The reaction was stirred for 10 minutes and then filtered through a micropore filter and purified by preparative HPLC to provide 164 (4.4 mg, 10.5% yield). $^1$H NMR (500 MHz, DMSO-$d_6$) δ 10.97 (s, 1H), 10.18 (s, 1H), 9.10 (s, 1H), 8.37 (t, J=5.2 Hz, 1H), 8.25-8.15 (m, 2H), 7.73-7.65 (m, 2H), 7.56 (d, J=7.9 Hz, 1H), 7.39-7.34 (m, 1H), 7.33-7.26 (m, 1H), 6.96-6.90 (m, 1H), 3.74 (s, 3H), 3.53-3.42 (m, 4H), 3.29 (s, 3H). LC retention time 1.28 [E]. MS (E$^+$) m/z: 455 (MH$^+$).

The following Examples were prepared in a similar manner to the product of Example 164:

| Example No. | R | Rt (min) [Method] | m/z [M + H]$^+$ |
|---|---|---|---|
| 165 | cyclopropyl-CH$_2$- | 1.32 [E] | 437 |
| 166 | -CH$_2$C(CH$_3$)$_2$OH | 1.23 [E] | 469 |
| 167 | -CH$_2$CH$_2$-n-C$_4$H$_9$ | 1.89 [E] | 481 |
| 168 | -CH$_2$CH$_2$C(CH$_3$)$_2$OH | 1.27 [E] | 483 |
| 169 | -C(CH$_3$)$_2$Me | 1.18 [E] | 411 |
| 170 | -CH(CH$_3$)CH$_2$CH$_2$OH | 1.21 [E] | 455 |
| 171 | -C(CH$_3$)$_2$CH$_2$CF$_3$ | 1.08 [E] | 479 |

Example 172

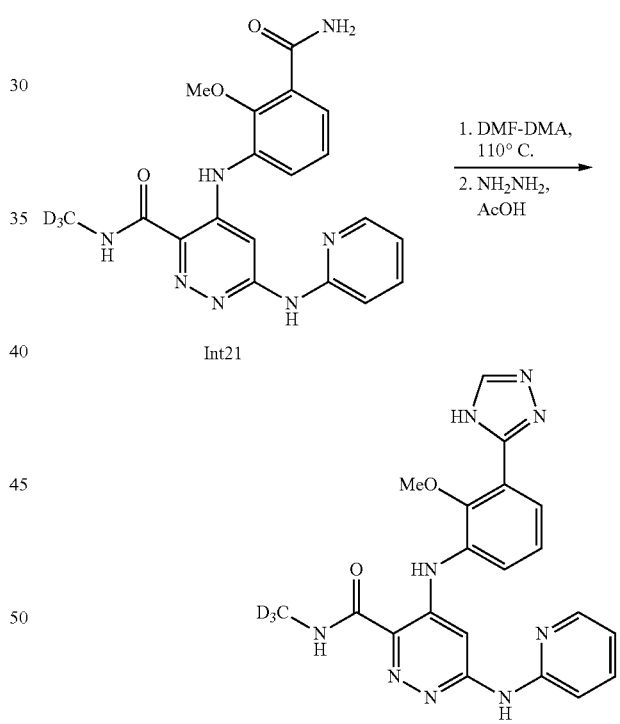

Int21 (prepared in a similar manner to Example 164) (30 mg, 0.076 mmol) was slurried in N,N-dimethylformamide dimethyl acetal (DMF-DMA, 1.5 mL, 11.2 mmol) and heated to 110° C. The reaction was run for 30 minutes and then dried, at which point acetic acid (0.12 mL) and ethanol (0.6 mL) were added, providing a clear solution. To this solution was added hydrazine hydrate (0.024 mL, 0.76 mmol) and the reaction was stirred for 30 minutes. The solution was filtered and purified using preparative HPLC to provide 172 (2.5 mg, 7.5% yield). $^1$H NMR (500 MHz, DMSO-$d_6$) δ 11.01 (s, 1H), 10.18 (s, 1H), 9.11 (s, 1H), 8.26-8.15 (m, 2H), 7.73-7.65 (m, 2H), 7.57 (d, J=8.5 Hz, 1H), 7.37 (br. s., 1H), 6.92 (dd, J=6.7, 5.5 Hz, 1H), 3.71 (s, 3H). LC retention time 1.16 [E]. MS (E⁺) m/z: 421 (MH⁺).

Step 1

Int 8 (311 mg, 1.486 mmol) and 2-methoxy-3-(1-((2-(trimethylsilyl)ethoxy)methyl)-1H-1,2,4-triazol-3-yl)aniline (Preparation 9, 500 mg, 1.560 mmol) were dissolved in THF (2 mL) and LHMDS (1 M in THF) (3.71 mL, 3.71 mmol) was added dropwise by syringe at room temperature over ~5 minutes causing a slight exotherm. The reaction mixture was stirred at room temperature for 15 min whereupon LCMS showed reaction was complete and starting material had been consumed. Crushed ice was added followed by saturated aqueous ammonium chloride until pH ~7 was obtained. The mixture was stirred for 30 min, then extracted with EtOAc (80 mL×3) and the combined organic extracts were washed with brine, dried over sodium sulfate, filtered and concentrated to afford 730 mg of tan solid as the desired product as a mixture of regioisomers. HPLC RT=3.67 and 3.78 min. MS (E⁺) m/z: 493 (MH⁺).

Step 2

A mixture of the SEM-protected substrate (420 mg, 0.852 mmol), cyclopropanecarboxamide (145 mg, 1.704 mmol), Xantphos (99 mg, 0.170 mmol) and cesium carbonate (833 mg, 2.56 mmol) in dioxane (3 mL) was sparged with nitrogen for 5 minutes, then Pd$_2$(dba)$_3$ (54.9 mg, 0.06 mmol) was added and the reaction was placed into a preheated 130° C. heating block for 1 h. The reaction was cooled and was partitioned between EtOAc and water and the layers were separated. The aqueous portion was extracted with EtOAc and the combined extracts were washed with water, brine, dried over sodium sulfate, filtered and concentrated to afford tan oil which was purified via silica gel chromatography (hex/EtOAc; 12 g column) to afford 383 mg (83%) of a tan semi-solid as the desired product as a mixture of regioisomers. HPLC RT=3.62 min. MS (E⁺) m/z: 542.6 (MH⁺).

Example 173

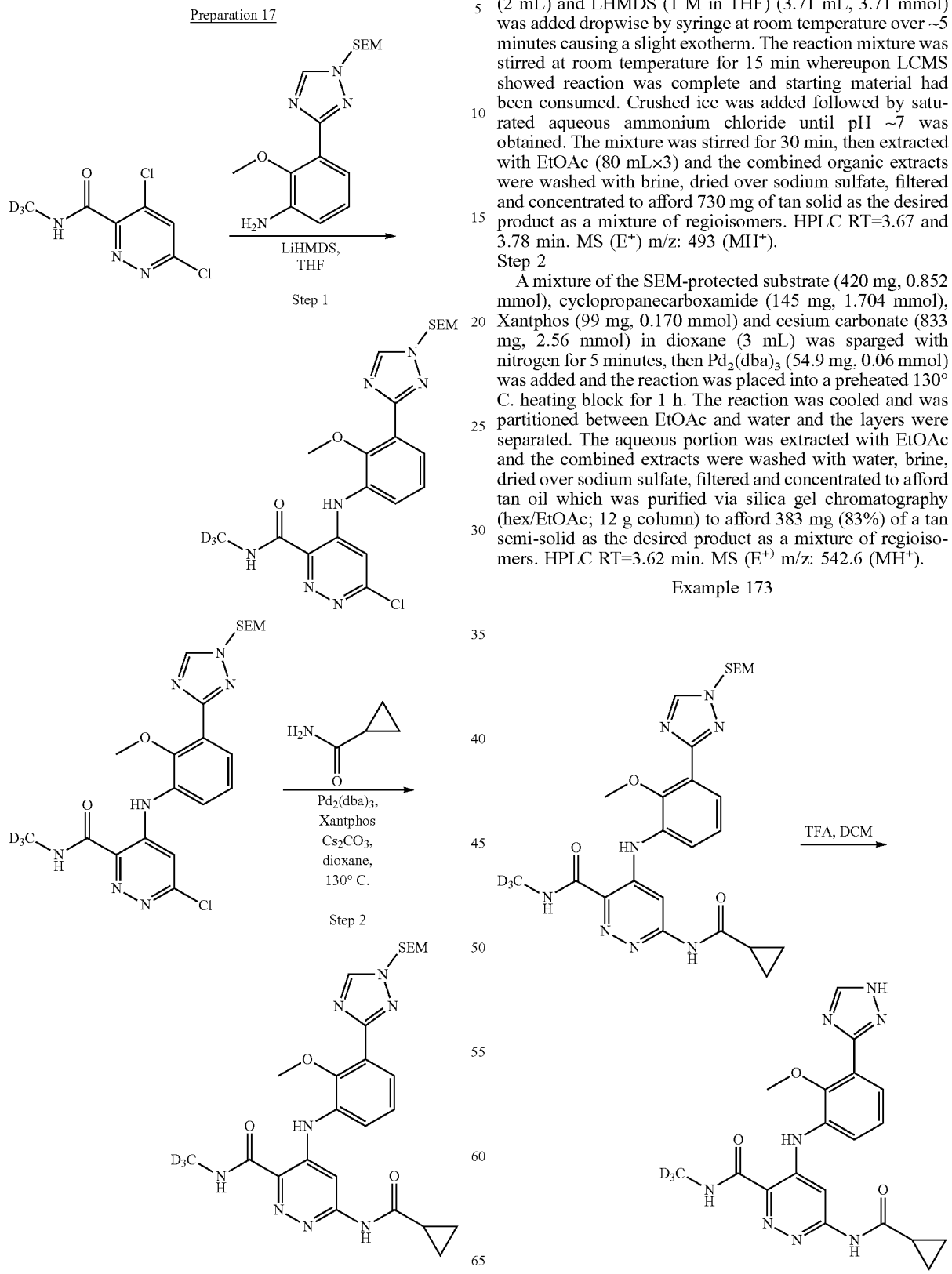

Preparation 17

To solution of the substrate (383 mg, 0.707 mmol) in dichloromethane (2 mL) was added TFA (1.089 mL, 14.14 mmol) and the mixture was allowed to stir overnight at room temperature then concentrated to remove the TFA and the resulting residue was partitioned between EtOAc and water. The layers were separated and the aqueous portion was extracted with additional EtOAc and the combined organics were washed with aq. sat sodium bicarbonate, brine, dried over sodium sulfate, filtered and concentrated to afford 290 mg of a tan semi-solid as Example 173. A portion of this material was purified using preparative HPLC to provide an analytical sample for testing. $^1$H NMR (500 MHz, DMSO-$d_6$) δ 11.33 (br. s., 1H), 10.98 (br. s., 1H), 9.16 (br. s., 1H), 8.22-8.01 (m, 2H), 7.86-7.65 (m, 1H), 7.57 (br. s., 1H), 7.39-7.17 (m, 1H), 3.67 (br. s., 3H), 2.06 (d, J=4.9 Hz, 1H), 0.87-0.73 (m, 4H).). LC retention time 1.05 [E]. MS (E$^+$) m/z: 412 (MH$^+$).

Example 174

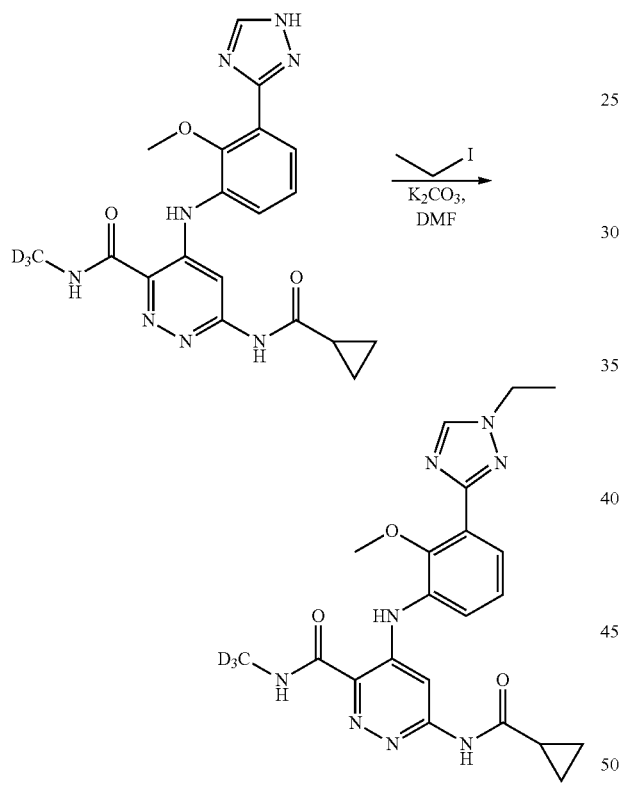

To slurry of Example 173 (50 mg, 0.085 mmol) and potassium carbonate (47.0 mg, 0.340 mmol) in DMF (0.3 mL) at room temperature was added iodoethane (19.90 mg, 0.128 mmol) and the resulting mixture was allowed to stir at room temperature for 3 h. A mixture of two regioisomers was seen; however, these were typically separable by preparative HPLC (exceptions noted in the table). Structural assignment was made by analysis of $^1$H NMR compared to compounds with known (by synthesis or crystal structure) regiochemistry. The crude reaction mixture was diluted with DMSO and was subjected to purification by reverse-phase HPLC to afford fractions containing the major product. Concentration and drying under vacuum afforded 6.4 mg (17%) of a solid as Example 174. $^1$H NMR (500 MHz, DMSO-$d_6$) □ δ 11.29 (s, 1H), 10.94 (s, 1H), 9.10 (s, 1H), 8.58 (s, 1H), 8.12 (s, 1H), 7.65 (d, J=6.7 Hz, 1H), 7.50 (d, J=6.7 Hz, 1H), 7.26 (t, J=7.6 Hz, 1H), 4.26 (q, J=7.3 Hz, 2H), 3.70 (s, 3H), 2.04 (d, J=4.9 Hz, 1H), 1.44 (t, J=7.3 Hz, 3H), 0.88-0.75 (m, 4H). LC retention time 1.30 [E]. MS (E$^+$) m/z: 440 (MH$^+$).

The following Examples were prepared using similar conditions as described for the preparation of Example 173 and Example 174:

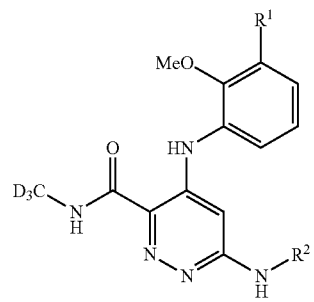

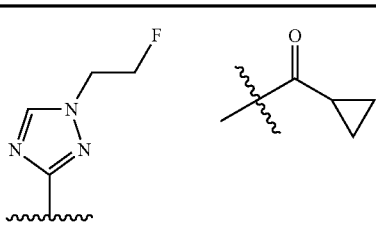

| Example No. | R$^1$ | R$^2$ | Rt (min) [Method] | m/z [M + H]$^+$ |
|---|---|---|---|---|
| 175 | ![F-ethyl triazole] | ![cyclopropyl ketone] | 1.21 [E] | 458 |

-continued
| Example No. | R¹ | R² | Rt (min) [Method] | m/z [M + H]⁺ |
|---|---|---|---|---|
| 176 (as a mixture of regioisomers) | 1,2,4-triazole with N-CH₂CHF₂ substituent | cyclopropyl ketone | 1.08 [E] 1.12 [E] | 476 |
| 177 | 1-ethyl-1,2,4-triazole | 2-pyridyl | 1.38 [E] | 449 |
| 178 | 1-methyl-1,2,4-triazole with 2-methoxyphenyl | 2-pyridyl | 1.30 [E] | 435 |
| 179 | 1-methyl-1,2,4-triazole with 2-methoxyphenyl | cyclopropyl ketone | 1.18 [E] | 426 |
| 180 | 1-methyl-1,2,4-triazole with 2-methoxyphenyl | 5-fluoro-4-methyl-2-pyridyl | 1.53 [E] | 467 |
Examples 181 and 182
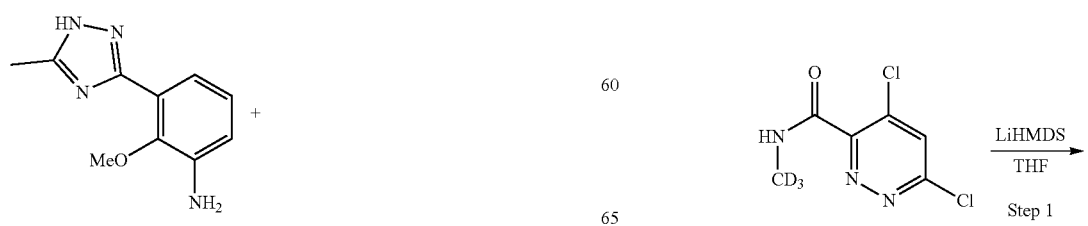
-continued

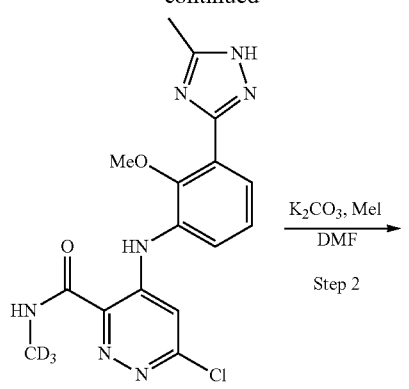

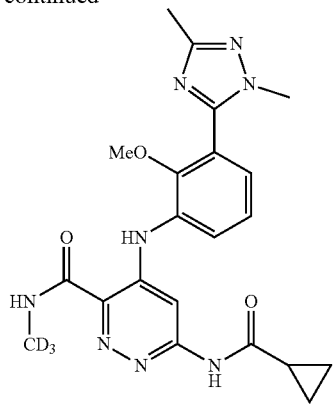

Step 1

To a solution of 4,6-dichloro-N-trideuteromethylpyridazine-3-carboxamide (Preparation 2, 700 mg, 3.35 mmol) and 2-methoxy-3-(5-methyl-4H-1,2,4-triazol-3-yl)aniline (Preparation 11, 752 mg, 3.68 mmol) in THF (10 mL) was added lithium bis(trimethylsilyl)amide (1M in THF, 11.7 mL, 11.7 mmol) in a dropwise manner. The reaction was stirred for 15 minutes and then quenched with 1N HCl to pH ~2. The suspension was stirred for 1 hour at 0° C., filtered and rinsed with water to afford the intermediate as a brown solid (832 mg, 66% yield). LC retention time 0.53 [J]. MS (E$^+$) m/z: 377 (MH$^+$).

Step 2

To a solution of the above intermediate (60 mg, 0.16 mmol) in DMF (0.5 mL) was added potassium carbonate (22 mg, 0.16 mmol) followed by iodomethane (0.013 mL, 0.21 mmol) in 0.1 mL DMF. The reaction was stirred at room temperature for 3 hours, filtered and concentrated. Regioisomers were not separated. $^1$H NMR major regioisomer only (400 MHz, methanol-d$_4$) δ 7.75 (dd, J=7.7, 1.5 Hz, 1H), 7.57 (dd, J=7.9, 1.5 Hz, 1H), 7.38-7.32 (m, 1H), 7.19 (s, 1H), 3.95 (s, 3H), 3.72 (s, 3H), 2.57 (s, 3H).

Step 3

The mixture of regioisomers obtained from the above methylation (18 mg, 0.046 mmol) were dissolved in dioxane (0.4 mL) along with cyclopropanecarboxamide (7.8 mg, 0.092 mmol), Xantphos (5.3 mg, 0.009 mmol) and cesium carbonate (30 mg, 0.092 mmol). The suspension was sparged with nitrogen for 5 minutes and then Pd$_2$(dba)$_3$ (8.4 mg, 0.009 mmol) was added, the vessel sealed, and then heated to 130° C. for 1 hour. After cooling to room temperature the reaction was filtered, diluted with DMSO and purified using preparative HPLC (isolating the two regioisomers separately).

181 (10.9 mg, 43% yield):
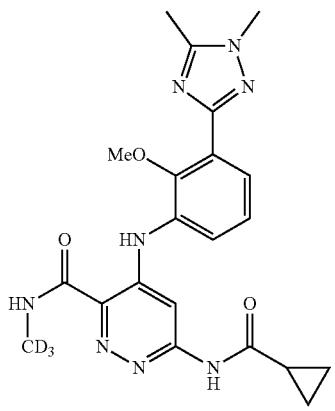 [SMILES: [2H]C([2H])([2H])NC(=O)c1nnc(NC(=O)C2CC2)cc1Nc1cccc(-c2nc(C)n(C)n2)c1OC]
¹H NMR (500 MHz, DMSO-d₆) δ 11.33 (s, 1H), 10.96 (s, 1H), 9.12 (s, 1H), 8.10 (s, 1H), 7.62 (d, J=7.9 Hz, 1H), 7.50 (d, J=7.9 Hz, 1H), 7.26 (t, J=7.9 Hz, 1H), 3.84 (s, 3H), 3.70 (s, 3H), 2.46 (s, 3H), 2.13-1.98 (m, 1H), 0.86-0.78 (m, 4H). LC retention time 0.94 [E]. MS (E⁺) m/z: 440 (MH⁺).
182 (1.9 mg, 7.4% yield):
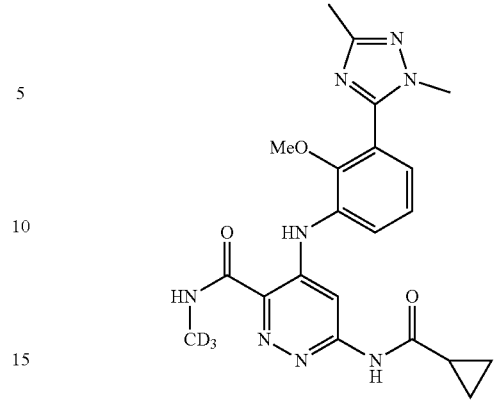
¹H NMR (500 MHz, DMSO-d₆) δ 11.34 (s, 1H), 10.94 (s, 1H), 9.13 (s, 1H), 8.08 (s, 1H), 7.62 (d, J=7.9 Hz, 1H), 7.38-7.21 (m, 2H), 3.64 (s, 3H), 3.42 (s, 3H), 2.29 (s, 3H), 2.06 (br. s., 1H), 0.88-0.72 (m, 4H). LC retention time 1.22 [E]. MS (E⁺) m/z: 440 (MH⁺).
The following Examples were prepared using similar conditions as described for the preparation of Example 181 and Example 182:
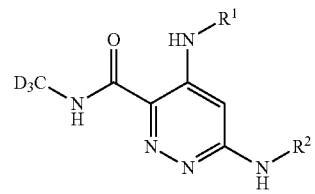
| Example No. | R¹ | R² | Rt (min) [Method] | m/z [M + H]⁺ |
|---|---|---|---|---|
| 183 | | | 0.84 [E] | 478 |
| 184 | | | 1.23 [E] | 478 |

Preparation 18

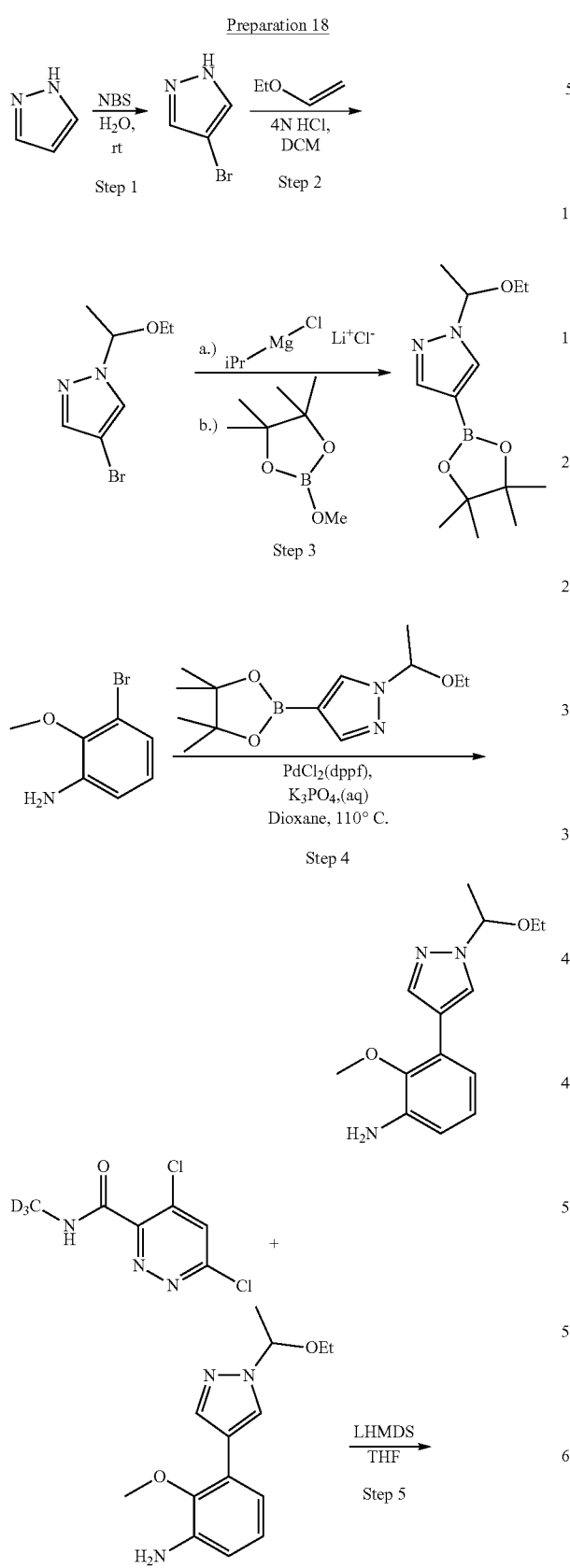

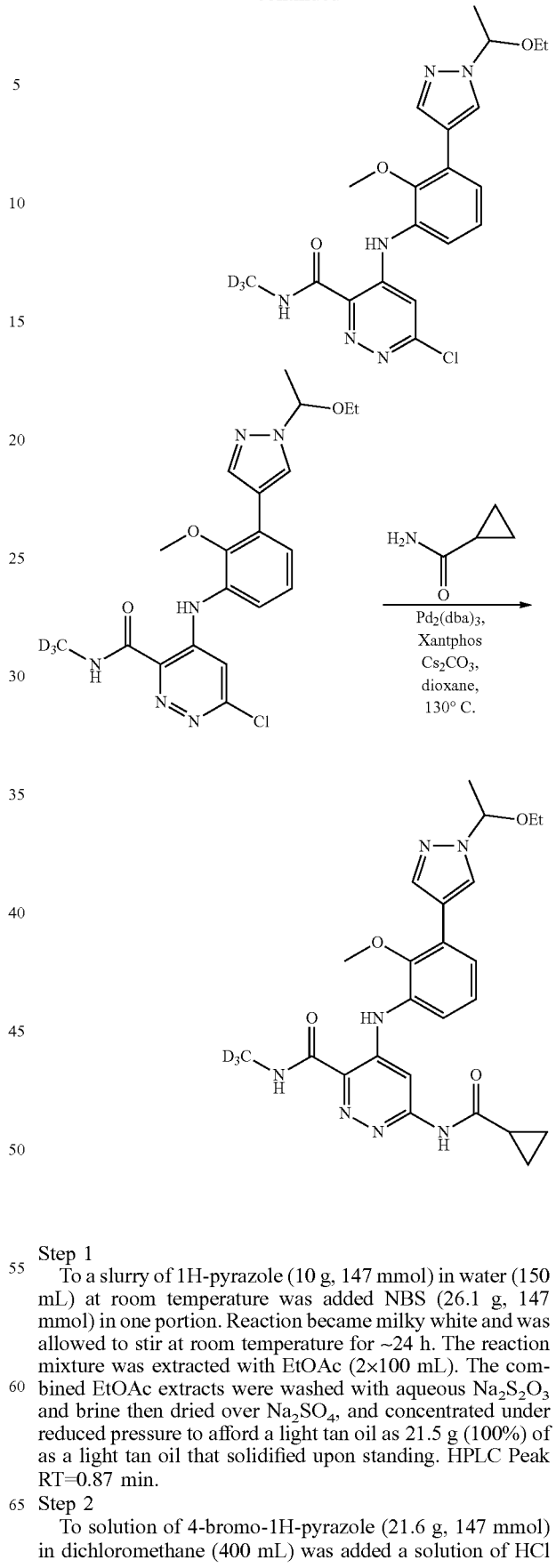

Step 1

To a slurry of 1H-pyrazole (10 g, 147 mmol) in water (150 mL) at room temperature was added NBS (26.1 g, 147 mmol) in one portion. Reaction became milky white and was allowed to stir at room temperature for ~24 h. The reaction mixture was extracted with EtOAc (2×100 mL). The combined EtOAc extracts were washed with aqueous $Na_2S_2O_3$ and brine then dried over $Na_2SO_4$, and concentrated under reduced pressure to afford a light tan oil as 21.5 g (100%) of as a light tan oil that solidified upon standing. HPLC Peak RT=0.87 min.

Step 2

To solution of 4-bromo-1H-pyrazole (21.6 g, 147 mmol) in dichloromethane (400 mL) was added a solution of HCl (4 N in dioxane) (2.204 mL, 8.82 mmol) and ethoxyethene (12.72 g, 176 mmol). After 30 min, the reaction was quenched with aqueous NaHCO$_3$ (30 mL), stirred at room temperature for 1 h, and the two layers were separated. The organic layer was washed with water, dried over Na$_2$SO$_4$, and concentrated under reduced pressure to dryness to afford the crude product (28 g). This material was purified by silica gel chromatography using a solvent gradient of EtOAc in hexanes to afford after concentration 13.2 g (41%) of the product as a clear oil. $^1$H NMR (400 MHz, chloroform-d) δ 7.61 (s, 1H), 7.47 (s, 1H), 5.48 (q, J=5.9 Hz, 1H), 3.53-3.41 (m, 1H), 3.35 (dq, J=9.5, 7.0 Hz, 1H), 1.68-1.62 (m, 3H), 1.21-1.12 (m, 3H).

Step 3

To an oven-dried vial was charged a solution of isopropyl magnesium/lithium chloride solution (1.0 M in THF) (6.32 ml, 8.22 mmol) at room temperature, and to this solution was added 4-bromo-1-(1-ethoxyethyl)-1H-pyrazole (1.00 g, 4.56 mmol) dropwise and the resulting mixture was stirred at room temperature for ~16 h. The resulting solution was then cooled to −20° C. and 2-methoxy-4,4,5,5-tetramethyl-1,3,2-dioxaborolane (1.731 g, 10.95 mmol) was added via syringe and the resulting mixture was allowed to warm to rt. After 2 h at room temperature, the reaction was quenched by addition of aq. sat. ammonium chloride (15 mL) causing a white precipitate to form. After diluting with additional water (~20 mL), the mixture was extracted with hexanes (140 mL×2) and the combined extracts were washed with aq. sat. sodium bicarbonate, brine, then dried over sodium sulfate, filtered and concentrated to afford 1.20 g (99%) of the product as a colorless oil.

Step 4

To a reaction vial charged with 3-bromo-2-methoxyaniline (0.30 g, 1.485 mmol) and 1-(1-ethoxyethyl)-4-(4,4,5,5-tetramethyl-1,3,2-dioxaborolan-2-yl)-1H-pyrazole (0.435 g, 1.633 mmol) in dioxane (2 ml) was added 2 M aqueous potassium phosphate (1.485 ml, 2.97 mmol) and the resulting mixture was deoxygenated by bubbling argon through the mixture for ~5 min. PdCl$_2$(dppf) (0.033 g, 0.045 mmol) was then added and the mixture was heated at 110° C. for 3 h. The reaction was cooled, diluted with EtOAc (100 mL), washed with water then brine and dried over sodium sulfate. The resulting dried solution was filtered and concentrated to afford a black oil which was purified via silica gel flash column chromatography using a gradient elution of ethyl acetate in hexanes. Fractions containing the desired product were concentrated under vacuum to afford 3-(1-(1-ethoxyethyl)-1H-pyrazol-4-yl)-2-methoxyaniline (355 mg, 1.358 mmol, 91% yield) as an oil which solidified upon standing. HPLC Peak RT=1.58 min. and MS (m+1)=262.1.

Step 5

Preparation as previously described in Example 52 to afford 530 mg (98%) of a tan solid as the product.

Step 6

Preparation as previously described in Example 52 to afford 390 mg (94%) of a solid as the product.

Example 185

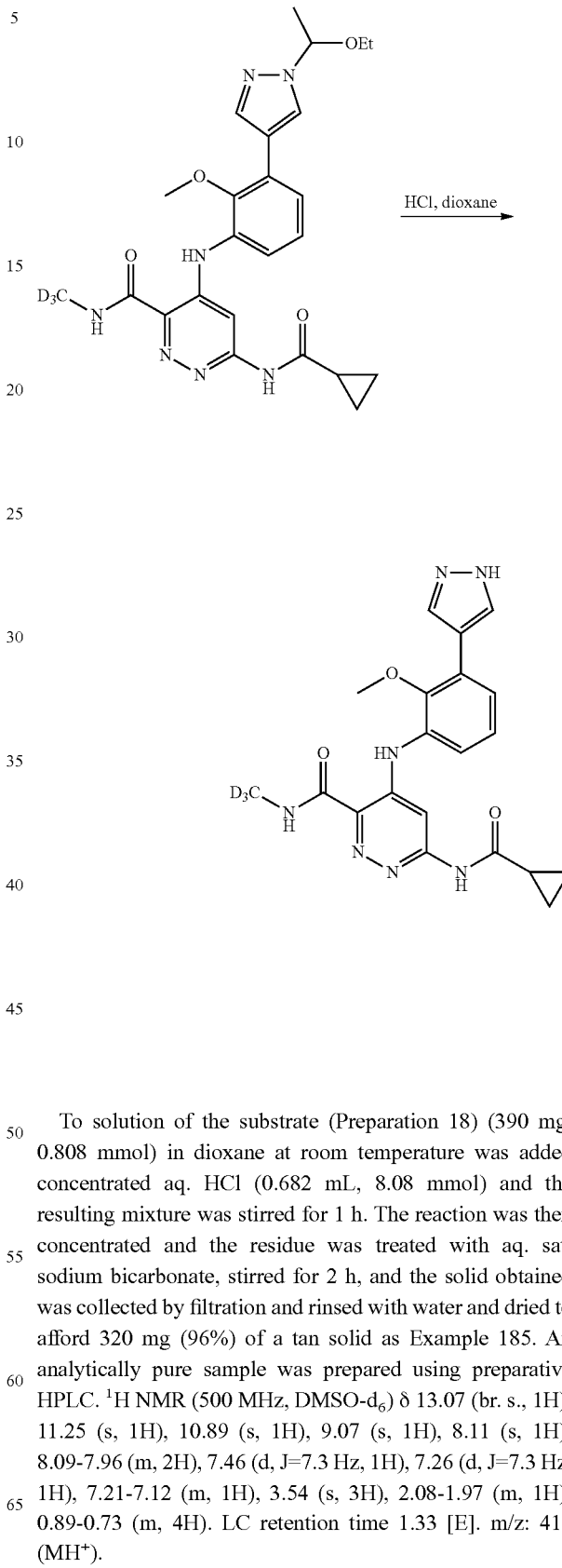

To solution of the substrate (Preparation 18) (390 mg, 0.808 mmol) in dioxane at room temperature was added concentrated aq. HCl (0.682 mL, 8.08 mmol) and the resulting mixture was stirred for 1 h. The reaction was then concentrated and the residue was treated with aq. sat. sodium bicarbonate, stirred for 2 h, and the solid obtained was collected by filtration and rinsed with water and dried to afford 320 mg (96%) of a tan solid as Example 185. An analytically pure sample was prepared using preparative HPLC. $^1$H NMR (500 MHz, DMSO-d$_6$) δ 13.07 (br. s., 1H), 11.25 (s, 1H), 10.89 (s, 1H), 9.07 (s, 1H), 8.11 (s, 1H), 8.09-7.96 (m, 2H), 7.46 (d, J=7.3 Hz, 1H), 7.26 (d, J=7.3 Hz, 1H), 7.21-7.12 (m, 1H), 3.54 (s, 3H), 2.08-1.97 (m, 1H), 0.89-0.73 (m, 4H). LC retention time 1.33 [E]. m/z: 411 (MH$^+$).

Example 186

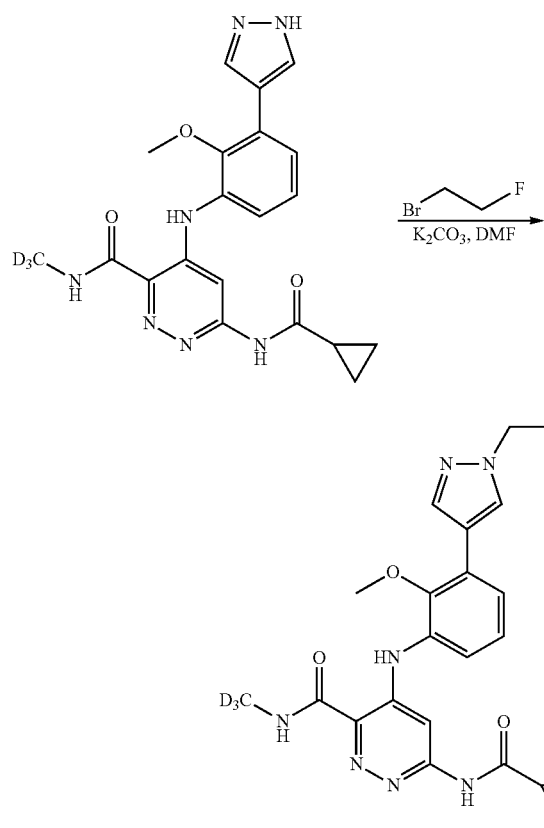

To slurry of the substrate Example 185 (25 mg, 0.061 mmol) and 1-bromo-2-fluoroethane (15.47 mg, 0.122 mmol) in DMF (0.3 mL) at room temperature was added 1-bromo-2-fluoroethane (15.47 mg, 0.122 mmol) stirred at room temperature for 3 h and 60° C. for an additional 3 h. The crude reaction mixture was diluted with DMSO and was subjected to reverse-phase HPLC to afford fractions containing the desired product which were concentrated under vacuum to afford 2.5 mg of Example 186. $^1$H NMR (500 MHz, DMSO-$d_6$) δ 11.29 (s, 1H), 10.93 (s, 1H), 9.11 (s, 1H), 8.24 (s, 1H), 8.12 (s, 1H), 7.99 (s, 1H), 7.46 (d, J=7.9 Hz, 1H), 7.28 (d, J=7.9 Hz, 1H), 7.23-7.14 (m, 1H), 4.91-4.70 (m, 2H), 4.61-4.36 (m, 2H), 3.57 (s, 3H), 2.05 (br. s., 1H), 0.94-0.69 (m, 4H). LC retention time 1.42 [E]. m/z: 457 (MH$^+$).

The following Examples were prepared in a similar manner to Example 186:

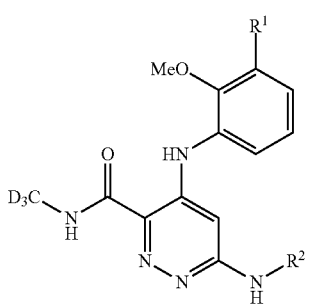

| Example No. | R$^1$ | R$^2$ | Rt (min) [Method] | m/z [M + H]$^+$ |
|---|---|---|---|---|
| 187 | 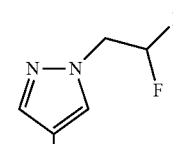 | 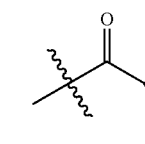 | 1.51 [E] | 475 |
| 188 | 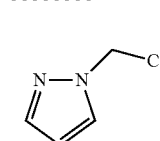 | 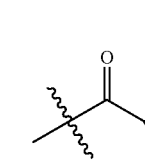 | 1.62 [E] | 493 |
| 189 | 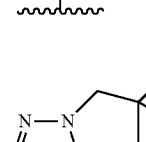 | 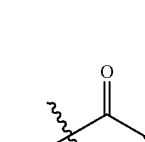 | 1.37 [E] | 483 |

Example 190

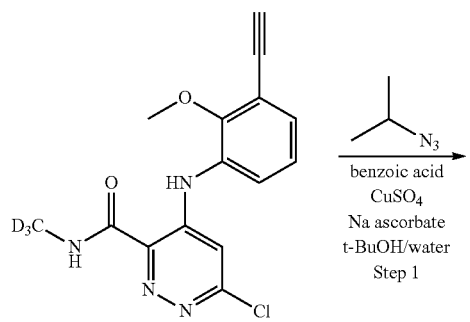

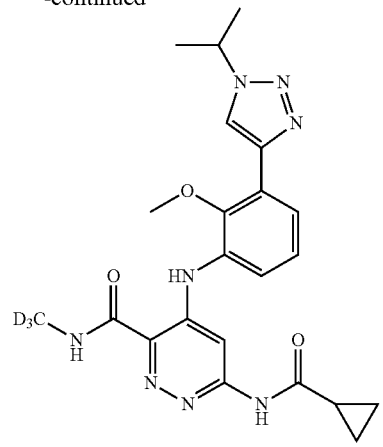

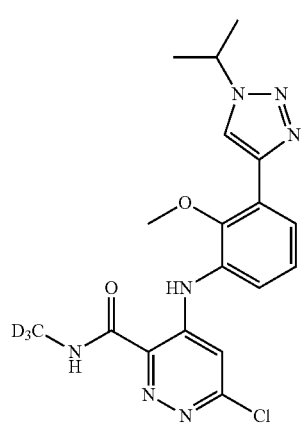

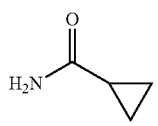

Step 1

6-Chloro-4-((3-ethynyl-2-methoxyphenyl)amino)-N-methylpyridazine-3-carboxamide (prepared in Preparation 7) (25 mg, 0.078 mmol) was combined with benzoic acid (2 mg, 0.016 mmol), L-Ascorbic acid sodium salt (2 mg, 0.0010 mmol) and copper(II) sulfate (2 mg, 0.013 mmol) in a small flask. A solution of 2-azidopropane (6.65 mg, 0.078 mmol) in tert-butyl alcohol (0.5 mL) and water (0.5 mL) was subsequently added and the reaction was stirred at room temperature for 1 hour. The reaction was diluted with dichloromethane (50 mL), washed with water (×1) and with a 1:1 mixture of water and brine solution. The organic layer was dried over sodium sulfate, filtered, concentrated and purified via automated chromatography to provide 6-chloro-4-((3-(1-isopropyl-1H-1,2,3-triazol-4-yl)-2-methoxyphenyl)amino)-N-trideuteromethylpyridazine-3-carboxamide (24 mg, 72.0% yield). LC retention time 0.87 [J]. MS (E+) m/z: 405 (MH+).

Step 2

A mixture of 6-chloro-4-((3-(1-isopropyl-1H-1,2,3-triazol-4-yl)-2-methoxyphenyl)amino)-N-trideuteromethylpyridazine-3-carboxamide (24 mg, 0.059 mmol), cyclopropanecarboxamide (10.1 mg, 0.119 mmol), and Xantphos (6.9 mg, 0.012 mmol) were degassed by sparging with nitrogen for 5 minutes. Cesium carbonate (77 mg, 0.24 mmol) and $Pd_2(dba)_3$ (5.4 mg, 0.0059 mmol) were then added, the reaction was sealed and heated to 130° C. for 60 minutes. The reaction was diluted with ethyl acetate, washed with water, saturated aqueous ammonium chloride and brine, and then dried over sodium sulfate, filtered and concentrated. The crude product was re-dissolved in DMF and purified by preparative HPLC to provide 190 (15.4 mg, 57%). $^1$H NMR (500 MHz, DMSO-$d_6$) δ 11.32 (s, 1H), 10.97 (s, 1H), 9.14 (s, 1H), 8.47 (s, 1H), 8.12 (s, 1H), 7.92 (d, J=7.7 Hz, 1H), 7.42 (d, J=7.7 Hz, 1H), 7.33-7.26 (m, 1H), 4.91 (dt, J=13.5, 6.7 Hz, 1H), 3.65 (s, 3H), 2.11-2.02 (m, 1H), 1.56 (d, J=6.7 Hz, 6H), 0.88-0.77 (m, 4H). LC retention time 1.48 [E]. m/z: 454 (MH+).

Example 191

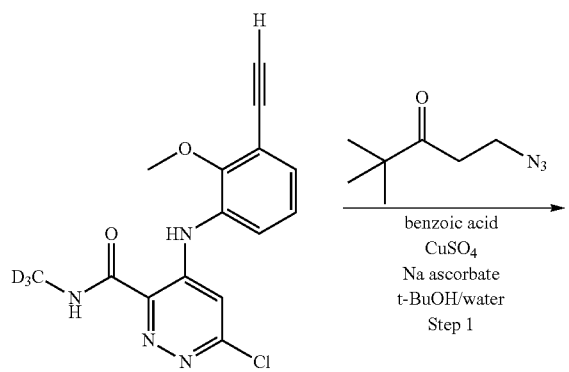

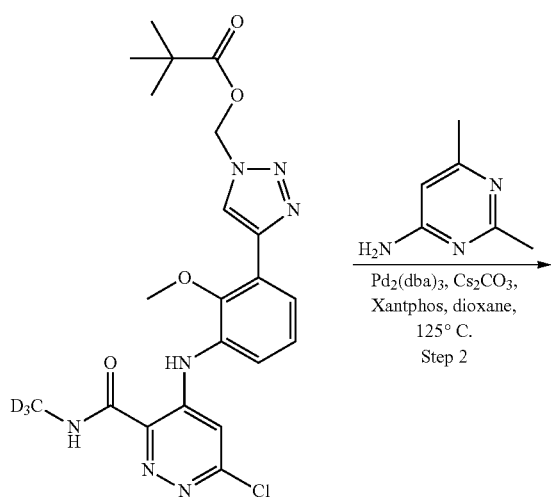

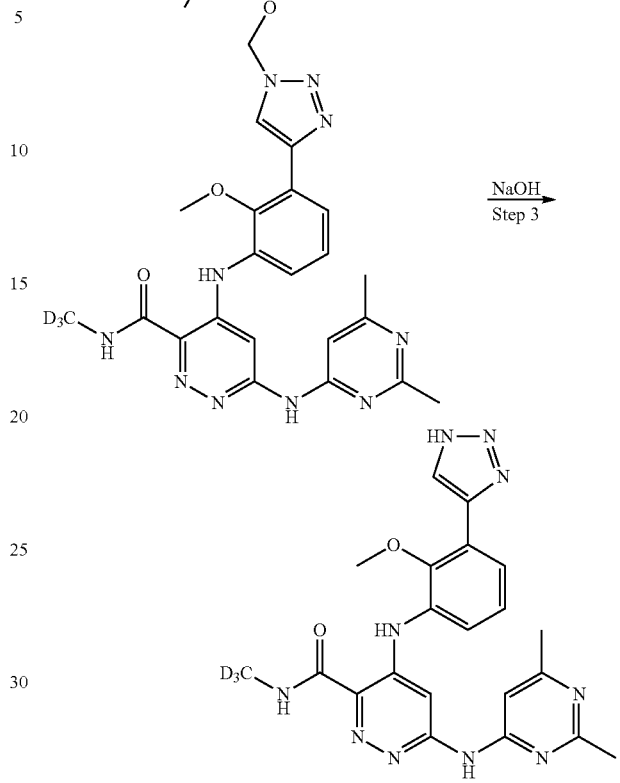

Step 1
(4-(3-((6-Chloro-3-(trideuteromethylcarbamoyl)pyridazin-4-yl)amino)-2-methoxyphenyl)-1H-1,2,3-triazol-1-yl)methyl pivalate (118 mg, 0.235 mmol, 79% yield) was prepared in the identical manner to Step 1 of Example 190, starting from 6-chloro-4-((3-ethynyl-2-methoxyphenyl)amino)-N-trideuteromethylpyridazine (95 mg, 0.297 mmol) and azido-methyl pivalate. LC retention time 0.98 [J]. m/z: 477 (MH$^+$).

Step 2
(4-(3-((6-Chloro-3-(trideuteromethylcarbamoyl)pyridazin-4-yl)amino)-2-methoxyphenyl)-1H-1,2,3-triazol-1-yl)methyl pivalate (22 mg, 0.046 mmol), Xantphos (5.3 mg, 0.009 mmol) and 2,6-dimethylpyrimidin-4-amine (11 mg, 0.092 mmol) were combined in dioxane (1.5 mL). The solution was degassed by sparging with nitrogen for 5 minutes and then cesium carbonate (60 mg, 0.18 mmol) and Pd$_2$(dba)$_3$ (4.2 mg, 0.0046 mmol) were added. The vessel was sealed and heated to 125° C. for 1 hour, after which it was diluted with ethyl acetate, washed with water, saturated ammonium chloride and brine. The organic layer was dried over sodium sulfate, filtered and concentrated to afford the crude product which was carried on to the final step as is. LC retention time 0.77 [J]. m/z: 564 (MH$^+$).

Step 3
(4-(3-((6-((2,6-Dimethylpyrimidin-4-yl)amino)-3-(trideuteromethylcarbamoyl)pyridazin-4-yl)amino)-2-methoxyphenyl)-1H-1,2,3-triazol-1-yl)methyl pivalate (23 mg, 0.041 mmol) was dissolved in THF (0.5 mL) and sodium hydroxide (1 M aqueous, 0.098 mL, 0.098 mmol) was added. The reaction was stirred at room temperature for 10 minutes and then neutralized with 0.11 mL of 1 M (aq.)

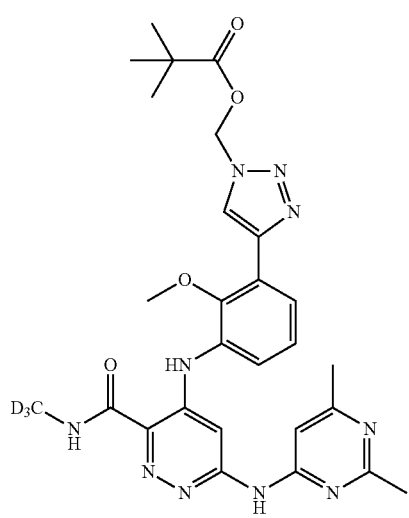

HCl. The resultant solution was concentrated, re-dissolved in DMF, filtered and purified using preparative HPLC to provide Example 191 (1.8 mg, 9.2% yield). $^1$H NMR (500 MHz, DMSO-d$_6$) δ 11.05 (br. s., 2H), 10.50 (s, 1H), 9.16 (s, 1H), 8.38 (br. s., 1H), 8.32-8.14 (m, 1H), 7.99-7.76 (m, 1H), 7.61 (d, J=6.7 Hz, 1H), 7.35 (t, J=7.9 Hz, 1H), 7.13 (s, 1H), 3.67 (s, 3H), 2.36 (s, 3H), 2.31 (s, 3H). LC retention time 1.16 [E]. m/z: 450 (MH$^+$).

The following Examples were prepared in a similar manner to Example 191:

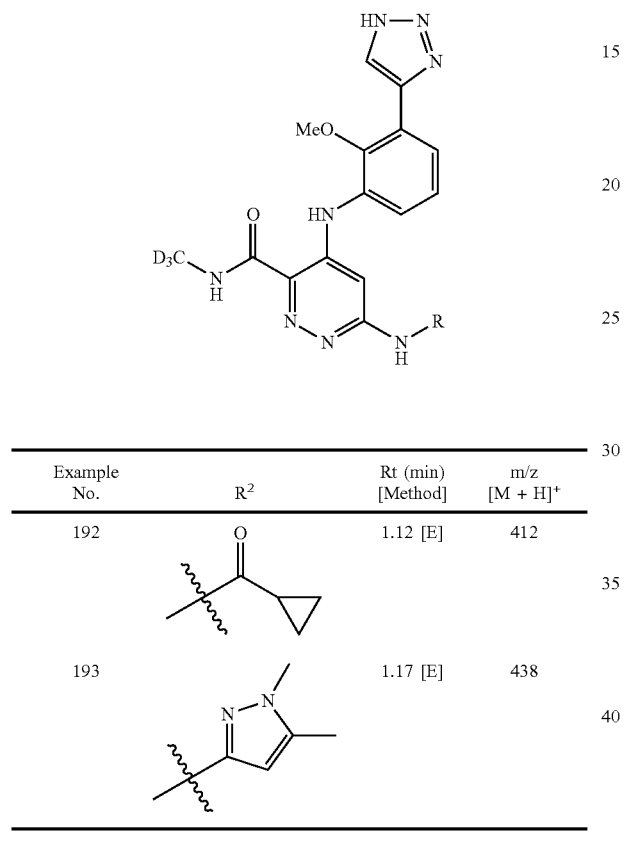

| Example No. | R$^2$ | Rt (min) [Method] | m/z [M + H]$^+$ |
|---|---|---|---|
| 192 | (cyclopropyl ketone) | 1.12 [E] | 412 |
| 193 | (1,5-dimethylpyrazol-3-yl) | 1.17 [E] | 438 |

Example 192 was prepared in a similar manner to Example 191.

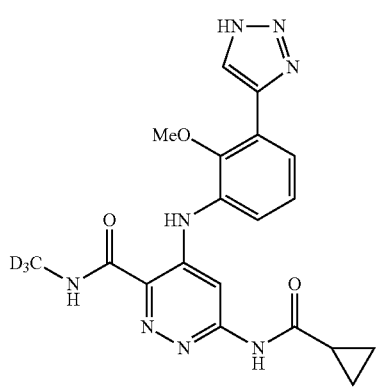 [SMILES: [2H]C([2H])([2H])NC(=O)c1nnc(NC(=O)C2CC2)cc1Nc1cccc(-c2c[nH]nn2)c1OC]

$^1$H NMR (500 MHz, DMSO-d$_6$) δ 10.98 (s, 1H), 9.14 (s, 1H), 8.25 (s, 1H), 8.14 (s, 1H), 7.81 (d, J=7.7 Hz, 1H), 7.44 (d, J=7.7 Hz, 1H), 7.29 (t, J=7.9 Hz, 1H), 3.63 (s, 3H), 2.06 (t, J=4.7 Hz, 1H), 0.90-0.69 (m, 4H). LC retention time 1.12 [E]. m/z: 412 (MH$^+$).

Example 194

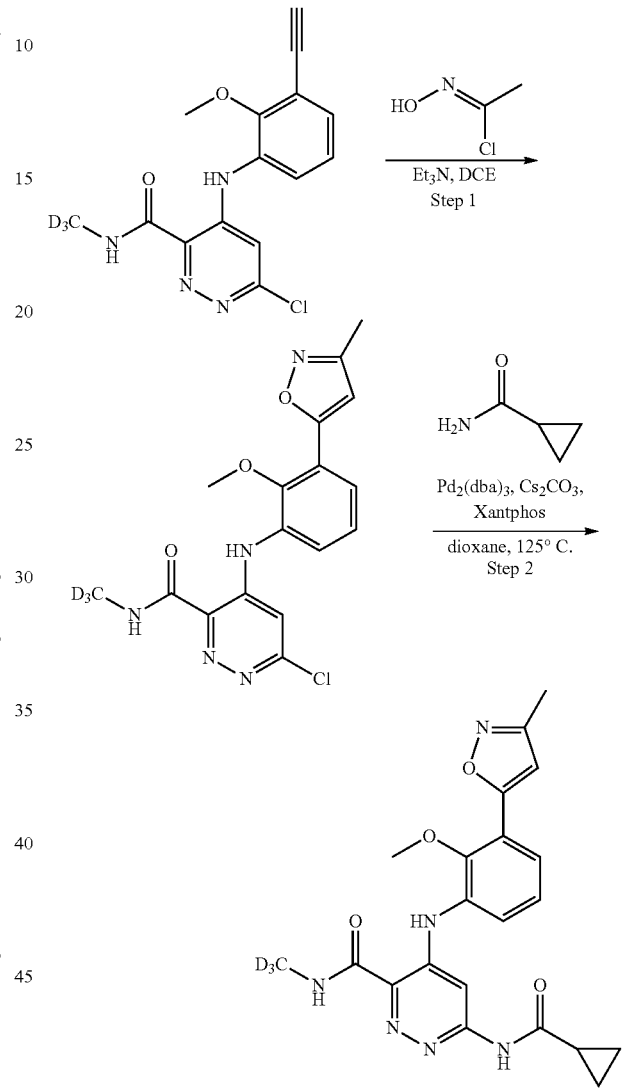

Step 1

To a solution of 6-chloro-4-((3-ethynyl-2-methoxyphenyl)amino)-N-trideuteromethylpyridazine (obtained using Preparation 7) (48 mg, 0.150 mmol) in 1,2-dichloroethane (1.5 mL) and (Z)—N-hydroxyacetimidoyl chloride (84 mg, 0.9 mmol) was added triethylamine (0.252 mL, 1.8 mmol). The mixture was stirred overnight at 65° C. Diluted with 50 mL dichloromethane, washed with ammonium chloride and 1:1 water:brine. The organic layer was dried over sodium sulfate, filtered and concentrated. The crude product was loaded onto a 12 g silica gel column, and then purified by flash chromatography, eluting with 0-100% EtOAc in hexanes. Afforded 6-chloro-4-((2-methoxy-3-(3-methylisoxazol-5-yl)phenyl)amino)-N-trideuteromethylpyridazine-3-carboxamide (41 mg, 0.109 mmol, 72.5% yield) as a white solid. $^1$H NMR (400 MHz, chloroform-d)

δ 11.02 (s, 1H), 8.27 (br. s., 1H), 7.87 (dd, J=7.8, 1.7 Hz, 1H), 7.44-7.31 (m, 2H), 7.00 (s, 1H), 6.71 (s, 1H), 3.76 (s, 3H), 2.42 (s, 3H).

Step 2

6-Chloro-4-((2-methoxy-3-(3-methylisoxazol-5-yl)phenyl)amino)-N-trideuteromethylpyridazine-3-carboxamide (40 mg, 0.106 mmol), Xantphos (12 mg, 0.021 mmol) and cyclopropanecarboxamide (18 mg, 0.21 mmol) were combined in dioxane (1 mL). The solution was degassed by sparging with nitrogen for 5 minutes and then cesium carbonate (138 mg, 0.42 mmol) and $Pd_2(dba)_3$ (9.7 mg, 0.011 mmol) were added. The vessel was sealed and heated to 125° C. for 1 hour. The reaction was diluted with dichloromethane and then concentrated directly onto CELITE® and purified using automated chromatography. The resulting material required additional purification (preparative HPLC) before providing 194 (18 mg, 38% yield). $^1$H NMR (400 MHz, chloroform-d) □δ 11.12 (s, 1H), 8.67 (s, 1H), 8.24 (s, 1H), 8.17 (br. s., 1H), 7.75 (dd, J=7.9, 1.5 Hz, 1H), 7.55 (dd, J=8.1, 1.5 Hz, 1H), 7.35-7.30 (m, 1H), 6.70 (s, 1H), 3.78 (s, 3H), 2.40 (s, 3H), 1.71-1.63 (m, 1H), 1.17-1.11 (m, 2H), 0.99-0.93 (m, 2H). LC retention time 0.83 [J]. m/z: 426 (MH$^+$).

Preparation 19

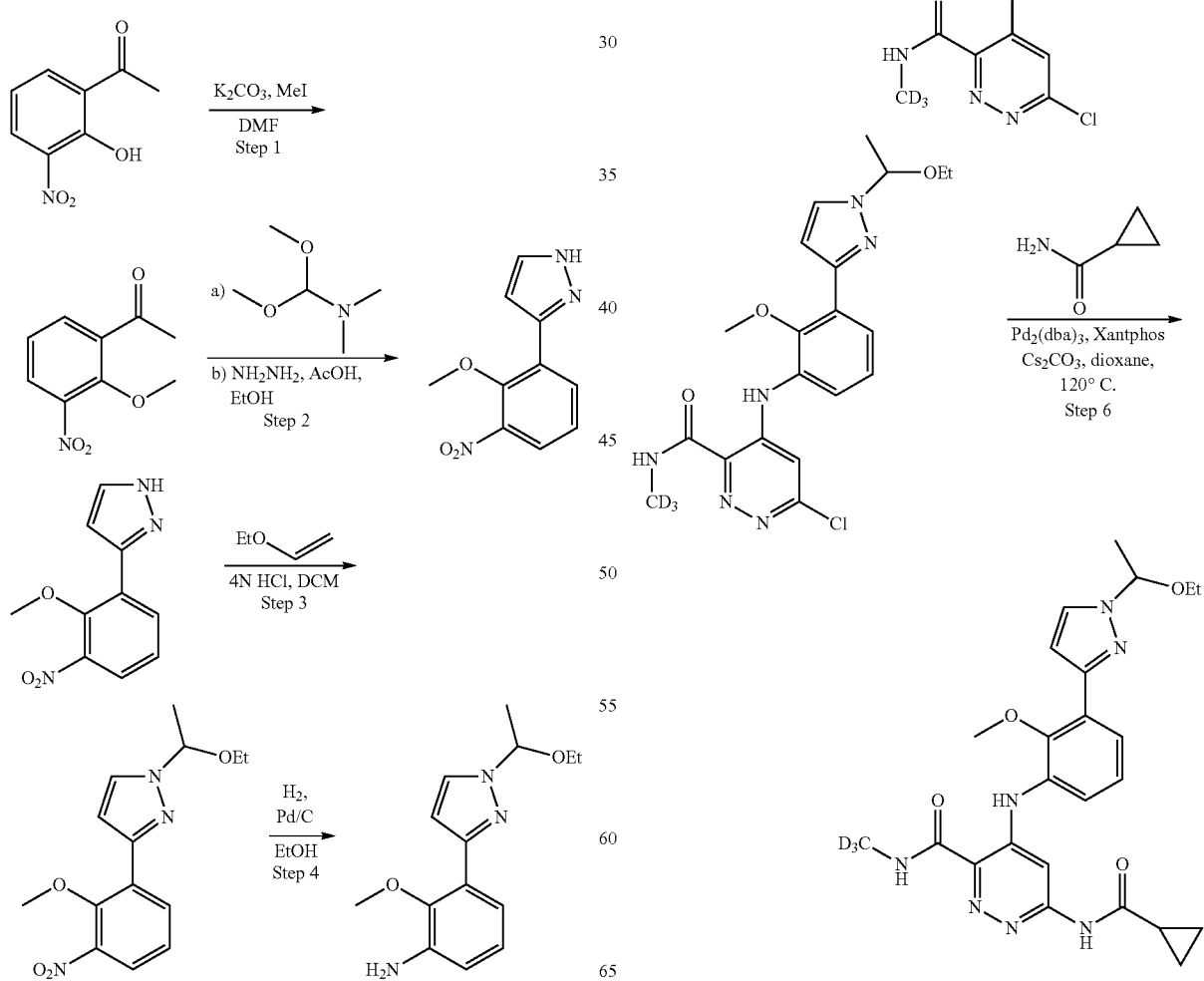

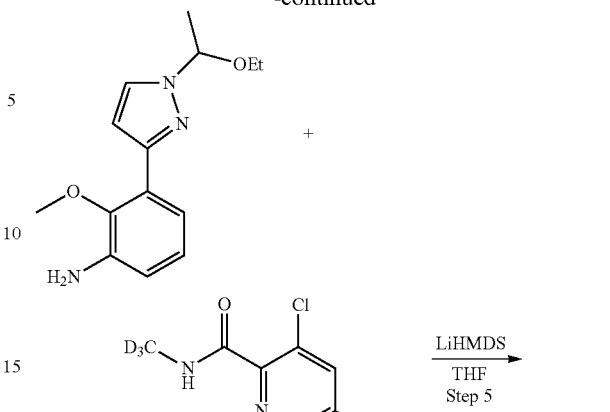

Step 1

A slurry of 1-(2-hydroxy-3-nitrophenyl)ethanone (1.00 g, 5.52 mmol) and potassium carbonate (3.05 g, 22.08 mmol) in DMF (20 mL) was stirred at room temperature for 30 min, then iodomethane (1.03 mL, 16.56 mmol) was added dropwise followed by stirring overnight (~16 h) at rt. Additional iodomethane (1.03 mL, 16.56 mmol) was added and the reaction was warmed to 50° C. for an additional 48 h. Ice cold water was added and the mixture was extracted with EtOAc (80 mL×3) and the combined extracts were washed with brine, dried over sodium sulfate, filtered and concentrated to afford 1.05 g (97%) of a tan oil as the product (not characterized).

Step 2

A solution of the ketone substrate (1 g, 5.12 mmol) in 1,1-dimethoxy-N,N-dimethylmethanamine (12.21 g, 102 mmol) was heated to 80° C. for 2 h then at reflux (120° C. oil bath temp) for an additional 2 h. The reaction was cooled slightly and was concentrated on the rotovap to remove the dimethyl formamide dimethyl acetal. The resulting reddish-orange oil was dissolved in toluene (~10 mL) and re-concentrated under vacuum and this process was repeated one additional time to ensure complete removal of any residual dimethyl formamide dimethyl acetal. The resulting reddish-orange oil was then dissolved in ethanol (4 mL) and AcOH (4 mL) and cooled in an ice bath before adding hydrazine (as a monohydrate) (0.482 mL, 7.69 mmol). Let warm to room temperature then resulting solution was heated to 80° C. for 30 minutes before cooling and concentrating on the rotovap. The resulting material was diluted with water (~25 mL) which caused an oil to form from the solution. The mixture was cooled in an ice bath, sonicated, and then stirred vigorously which eventually cause the oil to solidify. After stirring vigorously overnight, the solid was collected by vacuum filtration, rinsed with water and was allowed to air dry in the funnel then under vacuum overnight to afford 1.05 g (93%) of a pale yellow solid as 3-(2-methoxy-3-nitrophenyl)-1H-pyrazole. LC retention time 0.76 [J]. m/z: 220 (MH$^+$).

Step 3

To solution of 3-(2-methoxy-3-nitrophenyl)-1H-pyrazole (100 mg, 0.456 mmol) in dichloromethane (1 mL) at room temperature was added ethoxyethene (39.5 mg, 0.547 mmol) followed by HCl (4 N in dioxane) (6.84 µl, 0.027 mmol) and the resulting clear yellow solution was stirred at room temperature for 2 h. The mixture was then concentrated in vacuo to afford the product as a red oil. This oil was purified by dissolving into a minimum of dichloromethane and loading onto a silica gel cartridge (4 g) and eluting with a standard gradient of EtOAc in hexanes. The major UV-active product was collected near 30% EtOAc in hexanes concentration and the fractions were concentrated under vacuum to afford 104 mg (78%) of a clear pale yellow oil as the pure product. Material used as is in next reaction. LC retention time 0.96 [J]. m/z: 292 (MH$^+$).

Step 4

A solution of 1-(1-ethoxyethyl)-3-(2-methoxy-3-nitrophenyl)-1H-pyrazole (104 mg, 0.357 mmol) was sparged with nitrogen for a few minutes before adding Pd/C (38.0 mg, 0.018 mmol) followed by sparging with hydrogen gas from a balloon. Let stir under a balloon of hydrogen at room temperature for 1.5 h whereupon LCMS analysis indicated completion of the reaction. The reaction was sparged with nitrogen and the mixture was filtered through a Millipore filter to remove the catalyst. The resulting filtrate was concentrated under vacuum and azeotroped with toluene then dried under vacuum overnight to afford 90 mg (96%) of a clear, pale yellow oil as the pure product. Material was used as is without any further purification. LC retention time 0.67 [J]. m/z: 262 (MH$^+$).

Step 5

3-(1-(1-Ethoxyethyl)-1H-pyrazol-3-yl)-2-methoxyaniline (90 mg, 0.344 mmol) and 4,6-dichloro-N-d$_3$-methylpyridazine-3-carboxamide (68.6 mg, 0.328 mmol) were dissolved in THF (2 mL) at room temperature and the resulting solution was cooled in an ice bath whereupon LiHMDS (1 M in THF) (0.820 mL, 0.820 mmol) was added dropwise via syringe over ~1 min. After addition was complete, the ice bath was removed and the reaction was allowed to stir at room temperature for ~15 min. The reaction was quenched with a few drops of MeOH and the solution was concentrated and the resulting oil was dissolved into a minimal amount of dichloromethane (~1.5 mL) and was loaded onto a 4 g silica gel cartridge and eluted with EtOAc/hexanes as the eluent. Afforded 134 mg (94%) of the product as a pale yellow semi-solid. Was used as is without any further purification. LC retention time 0.98 [J]. m/z: 434 (MH$^+$).

Step 6

A mixture of the substrate (134 mg, 0.309 mmol), cyclopropanecarboxamide (52.6 mg, 0.618 mmol), Xantphos (35.7 mg, 0.062 mmol) and cesium carbonate (302 mg, 0.926 mmol) in dioxane (2 mL) was sparged with nitrogen for a few minutes before adding Pd$_2$(dba)$_3$ (56.6 mg, 0.062 mmol) and heating to reflux using a preheated 120° C. oil bath. Let continue at reflux for a total of ~4 h. Reaction was cooled to room temperature and partitioned between water (~8 mL) and EtOAc (20 mL). The aqueous portion was extracted with additional EtOAc (2×10 mL) and the combined extracts were washed with brine, dried over anhydrous sodium sulfate, decanted and concentrated under vacuum to afford a yellow sticky semi-solid as the crude product mixture. This material was dissolved into a minimum amount of dichloromethane (~2 mL) and was loaded onto a 4 g silica gel cartridge and was eluted with EtOAc in hexanes using a standard gradient elution. Afforded the product (112 mg, 75%) of a yellow semi-solid as the product. LC retention time 0.84 [J]. m/z: 483 (MH$^+$).

Example 195

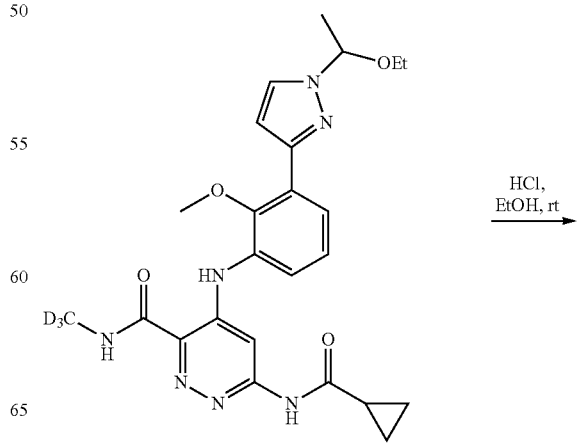

-continued

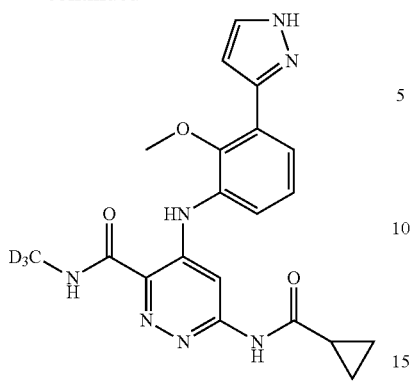

To the substrate (Preparation 19, 112 mg, 0.232 mmol) was added EtOH (1.5 mL) giving a fine slurry. To this mixture at room temperature was then added HCl (2.5 M in EtOH) (1 mL, 2.500 mmol) giving a clear, yellow solution. After stirring at room temperature for ~2 h total, the solution was concentrated under vacuum to yield a yellow oil which was dissolved in MeOH and re-concentrated and repeating this process two more times. Diethyl ether was added to the resulting oil and the mixture was sonicated which caused some of the material to solidify on the sides of the flask. Material was concentrated to yield a yellow semi-solid which was dried under high vacuum to yield a yellow solid. This sample was slurried in water (~3 mL) and saturated aqueous sodium bicarbonate (~1 mL) was added. The resulting slurry obtained was sonicated for a few minutes giving a fine slurry of the product which was collected by vacuum filtration followed by air drying in the funnel then slurrying the resulting moist solid in MeOH and concentrating then drying overnight under vacuum to afford 65 mg (67%) of a fine, pale yellow solid as Example 195. $^1$H NMR (400 MHz, DMSO-$d_6$) δ 11.30 (br. s., 1H), 10.97 (br. s., 1H), 9.12 (br. s., 1H), 8.16 (s, 1H), 7.82 (br. s., 1H), 7.72 (d, J=8.6 Hz, 1H), 7.63-7.34 (m, 2H), 7.23 (d, J=7.9 Hz, 1H), 6.75 (br. s., 1H), 3.59 (s, 3H), 2.14-2.01 (m, 1H), 0.94-0.74 (m, 4H). LC retention time 0.70 [J]. m/z: 411 (MH$^+$).

Example 196

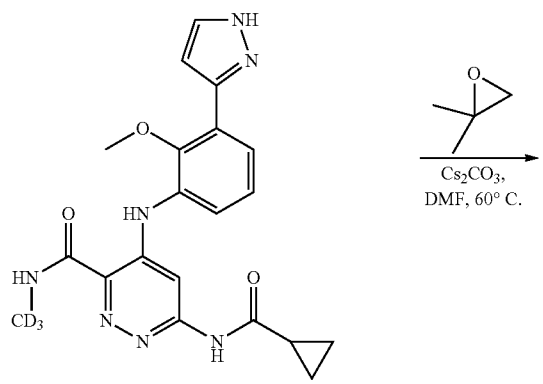

-continued

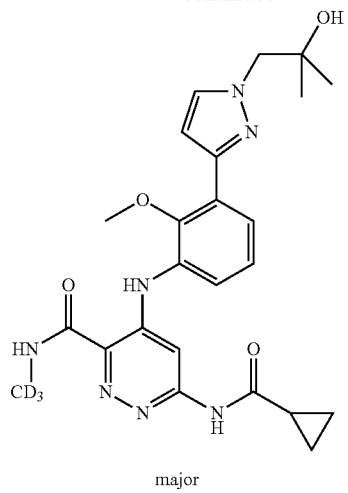

major

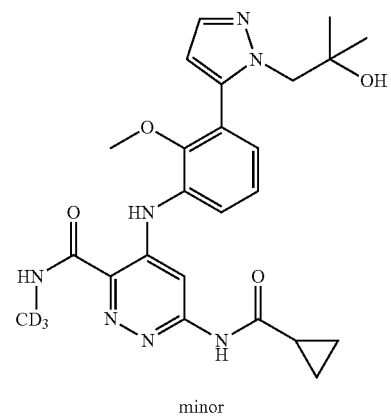

minor

Example 195 (35 mg, 0.085 mmol) and cesium carbonate (83 mg, 0.256 mmol) were mixed in DMF (0.3 mL) and 2,2-dimethyloxirane (12.30 mg, 0.171 mmol) was added followed by heating the resulting mixture at 60° C. for overnight (~16 h). The mixture was cooled, dissolved in DMSO, filtered and was purified via preparative HPLC. Unless noted (table below) the major and minor regioisomers (assignment from unambiguous parallel synthesis of representative examples) were isolated and characterized separately containing the major product were combined and dried via centrifugal evaporation to afford 30.2 mg of Example 196. $^1$H NMR (500 MHz, DMSO-$d_6$) δ 11.32 (s, 1H), 10.97 (s, 1H), 9.12 (s, 1H), 8.12 (s, 1H), 7.94 (s, 1H), 7.75 (s, 1H), 7.65 (d, J=7.9 Hz, 1H), 7.37 (d, J=7.3 Hz, 1H), 7.22 (t, J=7.9 Hz, 1H), 6.71 (s, 1H), 4.08 (s, 2H), 2.05 (br. s., 1H), 1.09 (s, 6H), 0.89-0.72 (m, 4H). LC retention time 1.47 [E]. m/z: 483 (MH$^+$).

The following Examples were prepared in a similar manner to Example 196:

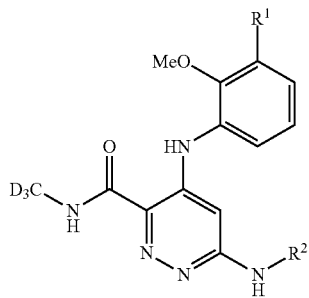

1H), 7.69 (dd, J=8.0, 1.4 Hz, 1H), 7.49 (t, J=8.0 Hz, 1H), 7.04 (s, 1H), 6.94 (s, 1H), 3.77 (s, 3H), 2.53 (s, 3H), 1.96-1.83 (m, 1H), 1.24-1.07 (m, 4H). LC retention time 0.67 [J]. m/z: 425 (MH+).

Example 201

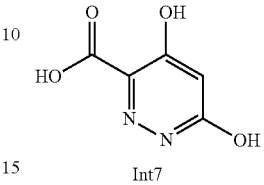 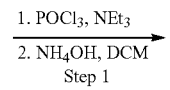

Int7

| Example No. | R¹ | R² | Rt (min) [Method] | m/z [M + H]+ |
|---|---|---|---|---|
| 197 | pyrazole-N-CH₃ | pyridine-F, CH₃ | 1.79 [E] | 466 |
| 198 mixture of regioisomers | pyrazole-N-CH₃ | pyrimidine-CH₃, CH₃ | 1.49 [E] | 463 |
| 199 | pyrazole-N-CH₃ | pyridine | 1.64 [E] | 434 |

Example 200

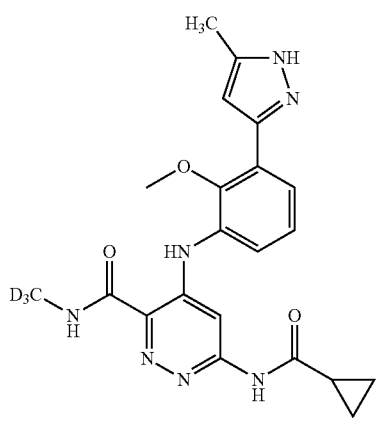 [SMILES: [2H]C([2H])([2H])NC(=O)c1nnc(NC(=O)C2CC2)cc1Nc1cccc(-c2cc(C)[nH]n2)c1OC]

Example 200 was prepared in a similar manner to Example 195 by using 1,1-dimethoxy-N,N-dimethylethanamine in place of 1,1-dimethoxy-N,N-dimethylmethanamine in Step 3. Afforded Example 200 as a tan solid. ¹H NMR (400 MHz, methanol-d₄) δ 7.82 (dd, J=7.9, 1.5 Hz, -continued

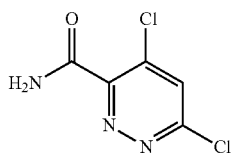

+

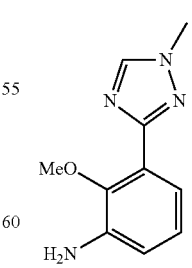  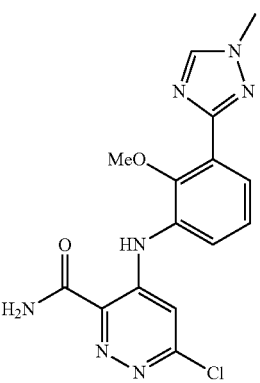

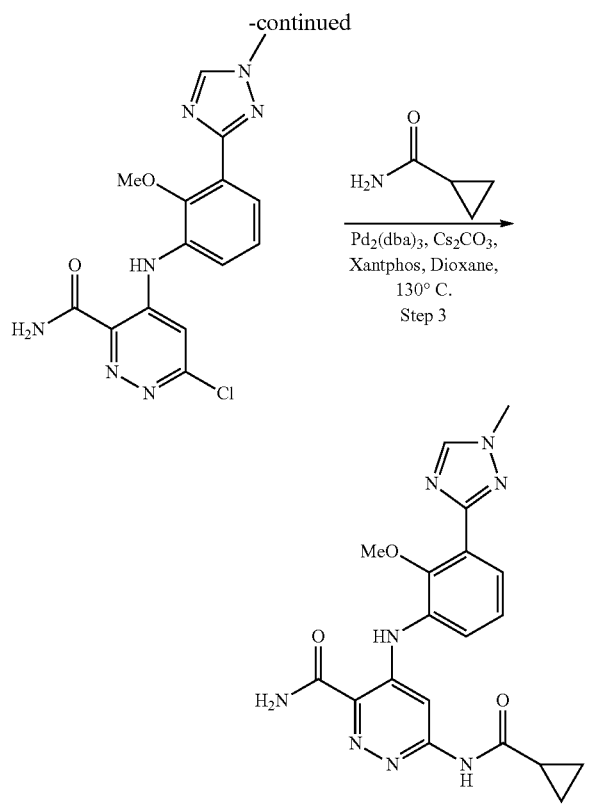

Step 1

Int7 (1.14 g, 7.3 mmol) was placed in a 500 mL RBF and triethylamine (1.02 mL, 7.3 mmol) was added, followed by phosphorus oxychloride (9 mL, 97 mmol). A water cooled condenser equipped with a drying tube (24/40 joint size) was then attached. The flask was placed in a room temperature oil bath and once self-reflux ceased, the temperature was raised to 80° C. Once that temperature was reached and the vigorous reflux subsided the temperature was raised again to 110° C. and the reaction run for 120 minutes. The heating was stopped and the reaction allowed to cool to ~90° C. (oil bath temperature), at which point 20 mL of anhydrous 1,2-dichloroethane was added and the flask was concentrated on the rotoevaporator, first under house vac and then under oil pump. Note that the evaporated material contains $POCl_3$ and must be disposed of carefully, in this case all of the distillates were poured into a rapidly stirred ethanol/ice bath. Next 20 mL of anhydrous 1,2-dichloroethane was added and the mixture sonicated and then concentrated. Finally 30 mL of anhydrous 1,2-dichloroethane was added and the sides of the vessel were scraped into the liqueur, the system was sonicated and stirred for ~10 minutes, and concentrated. This was slurried in 20 mL of dichloromethane. A solution of ammonium hydroxide in dichloromethane was prepared by extracting aqueous $NH_4OH$ with dichloromethane three times. This $NH_4OH$ solution was added gradually to the intermediate until LCMS confirmed complete conversion. The reaction was concentrated and then "re-dissolved" (majority of a black crude remained adhered to sides of flask) in DCM and decanted into a clean flask. This was absorbed onto CELITE®, dried and purified by automated chromatography to give 4,6-dichloropyridazine-3-carboxamide (405 mg, 29% yield). $^1$H NMR (400 MHz, DMSO-d$_6$) δ 8.47 (s, 1H), 8.40-8.03 (m, 2H). LC retention time 0.45 [J]. MS (E$^+$) m/z: 192 (MH$^+$).

Step 2

4,6-Dichloropyridazine-3-carboxamide (160 mg, 0.833 mmol) and 2-methoxy-3-(1-methyl-1H-1,2,4-triazol-3-yl)aniline (preparation described previously) (170 mg, 0.833 mmol) were dissolved in THF (2 mL). To this was added LiHMDS (1M in THF, 2.5 mL, 2.5 mmol) over c. 10 minutes. After an additional 10 minutes the reaction was complete, 1 mL of 1 M HCl (aqueous) was added and then the majority of the THF was removed in vacuo (until a precipitate prevailed). To this was added water (~50 mL) and the slurry sonicated. The slurry was filtered, rinsing with water, and then dried providing 6-chloro-4-((2-methoxy-3-(1-methyl-1H-1,2,4-triazol-3-yl)phenyl)amino)pyridazine-3-carboxamide (260 mg, 82%). $^1$H NMR (500 MHz, chloroform-d) δ 10.71 (s, 1H), 8.13 (s, 1H), 8.07 (br. s., 1H), 7.93 (dd, J=7.9, 1.7 Hz, 1H), 7.38 (dd, J=7.9, 1.3 Hz, 1H), 7.30-7.27 (m, 1H), 7.01 (s, 1H), 5.64 (br. s., 1H), 4.03 (d, J=0.5 Hz, 3H), 3.79 (s, 3H). LC retention time 0.68 [J]. MS (E$^+$) m/z: 360 (MH$^+$).

Step 3

6-Chloro-4-((2-methoxy-3-(1-methyl-1H-1,2,4-triazol-3-yl)phenyl)amino)pyridazine-3-carboxamide (75 mg, 0.21 mmol) and cyclopropanecarboxamide (53 mg, 0.62 mmol) were dissolved in dioxane (2.6 mL). To this was added Pd$_2$(dba)$_3$ (19 mg, 0.02 mmol), Xantphos (18 mg, 0.031 mmol) and cesium carbonate (136 mg, 0.42 mmol). The vessel was evacuated and backfilled with nitrogen three times and then heated to 130° C. for 90 minutes. The crude material was suspended in hot dichloromethane and absorbed onto CELITE®, the CELITE® was dried and the material was purified by automated chromatography. Following chromatography the collected product was suspended in hot dichloromethane, cooled and then filtered, rinsing with dichloromethane and then methanol, collecting the residual powder provided 201 (10 mg, 12% yield). $^1$H NMR (400 MHz, DMSO-d$_6$) δ 11.30 (s, 1H), 11.03 (s, 1H), 8.60-8.47 (m, 2H), 8.15 (s, 1H), 7.86 (s, 1H), 7.66 (dd, J=7.8, 1.4 Hz, 1H), 7.51 (dd, J=7.9, 1.3 Hz, 1H), 7.27 (t, J=7.9 Hz, 1H), 3.94 (s, 3H), 3.71 (s, 3H), 2.08 (quin, J=6.2 Hz, 1H), 0.89-0.75 (m, 4H). LC retention time 0.59 [J]. MS (E$^+$) m/z: 409 (MH$^+$).

Preparation 20

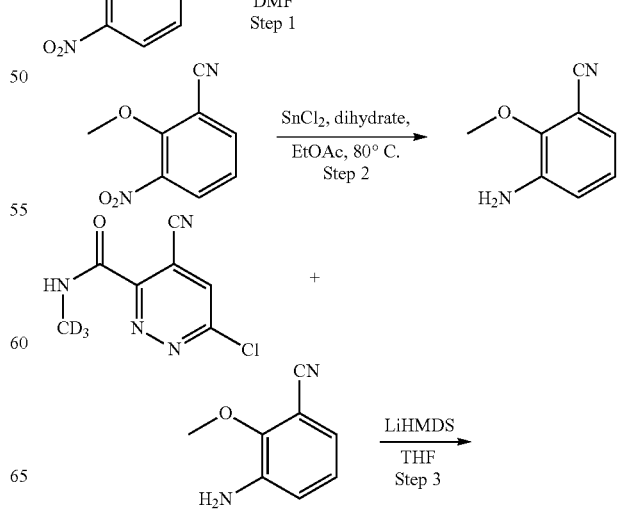

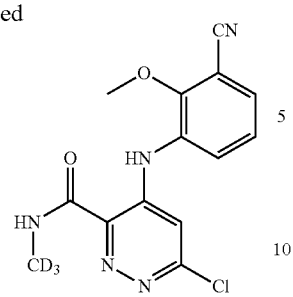

Step 1

A mixture of 2-hydroxy-3-nitrobenzonitrile (500 mg, 3.05 mmol), iodomethane (0.381 mL, 6.09 mmol) and potassium carbonate (1263 mg, 9.14 mmol) was stirred at room temperature for 16 hr. Additional potassium carbonate (1263 mg, 9.14 mmol) and iodomethane (0.381 mL, 6.09 mmol) were added and stirring was continued at room temperature for 24 hr. The reaction was poured into ~150 ml of water: 10% LiCl, 1:1. The resulting suspension was filtered, the filter cake was washed with water and dried to afford 740 mg of 2-methoxy-3-nitrobenzonitrile as an off-white solid. Drying was continued under high vacuum for 7 hr to afford 2-methoxy-3-nitrobenzonitrile (540 mg, 3.03 mmol, 99% yield) as an light yellow solid. $^1$H NMR (400 MHz, DMSO-$d_6$) δ 8.28 (dd, J=8.3, 1.7 Hz, 1H), 8.18 (dd, J=7.8, 1.7 Hz, 1H), 7.51 (t, J=8.0 Hz, 1H), 4.08 (s, 3H).

Step 2

A mixture of 2-methoxy-3-nitrobenzonitrile (540 mg, 3.03 mmol) and tin (II) chloride, dihydrate (2736 mg, 12.12 mmol) in EtOAc (30 mL) was heated to 80° C. for 1.5 hr. After cooling to room temperature, the reaction mixture was diluted with 30 ml of EtOAc and was washed with 2.5N NaOH (3×30 ml), water (30 ml) and brine (30 ml). After drying (MgSO$_4$) and filtration the organic layer was concentrated to afford 3-amino-2-methoxybenzonitrile (255 mg, 1.721 mmol, 56.8% yield) as an orange solid. $^1$H NMR (400 MHz, DMSO-$d_6$) δ 7.00-6.94 (m, 2H), 6.84 (dd, J=5.3, 4.0 Hz, 1H), 5.43 (s, 2H), 3.80 (s, 3H).

Step 3

To a solution of 4,6-dichloro-N-trideuteromethylpyridazine-3-carboxamide (325 mg, 1.555 mmol) and 3-amino-2-methoxybenzonitrile (255 mg, 1.721 mmol) in tetrahydrofuran (14 mL) at room temperature was added dropwise over 1 minute lithium bis(trimethylsilyl)amide (LiHMDS, 1M in THF, 3.89 mL, 3.89 mmol). The resulting solution was stirred at room temperature for 1 hr. The reaction mixture was quenched with saturated ammonium chloride solution (2 ml). The mixture was partitioned between EtOAc (40 ml) and saturated ammonium chloride solution (40 ml). The organic layer was washed with brine (40 ml), dried (Na$_2$SO$_4$) and concentrated to afford a solid residue that was purified on a 24 gm ISCO silica gel cartridge, eluting with a 0-100% EtOAc/hex gradient. The pure fractions were concentrated to afford a partially purified product that was triturated with ether and dried to afford 6-chloro-4-((3-cyano-2-methoxyphenyl)amino)-N-trideuteromethylpyridazine-3-carboxamide (385 mg, 1.200 mmol, 77% yield) as an tan solid. LC retention time 2.16 minutes [Q]. MS (ESI$^+$) m/z: 321.2/323.3 (MH$^+$), chlorine pattern. $^1$H NMR (400 MHz, DMSO-$d_6$) δ 11.10 (s, 1H), 9.39 (br. s., 1H), 7.87 (d, J=7.9 Hz, 1H), 7.67 (d, J=7.7 Hz, 1H), 7.35 (t, J=7.9 Hz, 1H), 7.22 (s, 1H), 3.91 (s, 3H).

Example 202

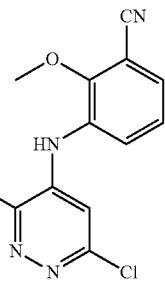
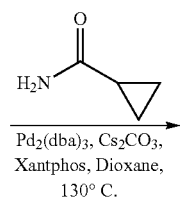

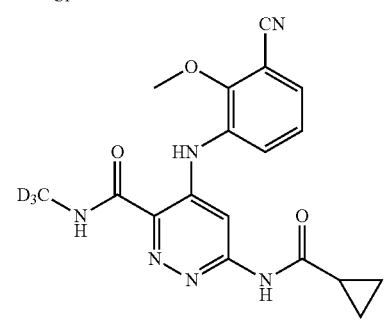

A mixture of 6-chloro-4-((3-cyano-2-methoxyphenyl)amino)-N-trideuteromethylpyridazine-3-carboxamide (240 mg, 0.748 mmol), cyclopropanecarboxamide (127 mg, 1.496 mmol), Pd$_2$(dba)$_3$, chloroform adduct (77 mg, 0.075 mmol), Xantphos (87 mg, 0.150 mmol) and Cs$_2$CO$_3$ (975 mg, 2.99 mmol) in dioxane (5 mL) was degassed by bubbling nitrogen through the mixture for 5 minutes. The reaction vessel was sealed and heated to 130° C. for 1.5 hr. The reaction mixture was filtered hot (~90° C.) through CELITE® and the filter cake was washed with EtOAc (100 ml). The filtrate was concentrated and the residue was triturated with MeOH. Filtration and drying afforded 4-((3-cyano-2-methoxyphenyl)amino)-6-(cyclopropanecarboxamido)-N-trideuteromethylpyridazine-3-carboxamide (215 mg, 0.582 mmol, 78% yield) as a tan solid. A small amount of 4-((3-cyano-2-methoxyphenyl)amino)-6-(cyclopropanecarboxamido)-N-trideutero-methylpyridazine-3-carboxamide (20 mg, 0.054 mmol) was dissolved in DMSO. The material was further purified via preparative LC/MS to afford 4-((3-cyano-2-methoxyphenyl)amino)-6-(cyclopropanecarboxamido)-N-trideuteromethylpyridazine-3-carboxamide (4.5 mg, 0.012 mmol, 22% yield). $^1$H NMR (500 MHz, DMSO-$d_6$) δ 11.37 (s, 1H), 10.97 (s, 1H), 9.16 (s, 1H), 8.03 (s, 1H), 7.77 (d, J=7.7 Hz, 1H), 7.60 (d, J=7.7 Hz, 1H), 7.35 (t, J=7.9 Hz, 1H), 3.90 (s, 3H), 2.06 (br. s., 1H), 0.98-0.62 (m, 4H). LC retention time 1.39 minutes [E]. MS (ESI$^+$) m/z: 370 (MH$^+$).

Preparation 21

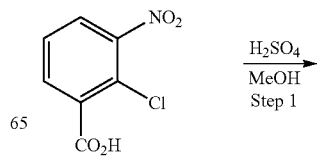

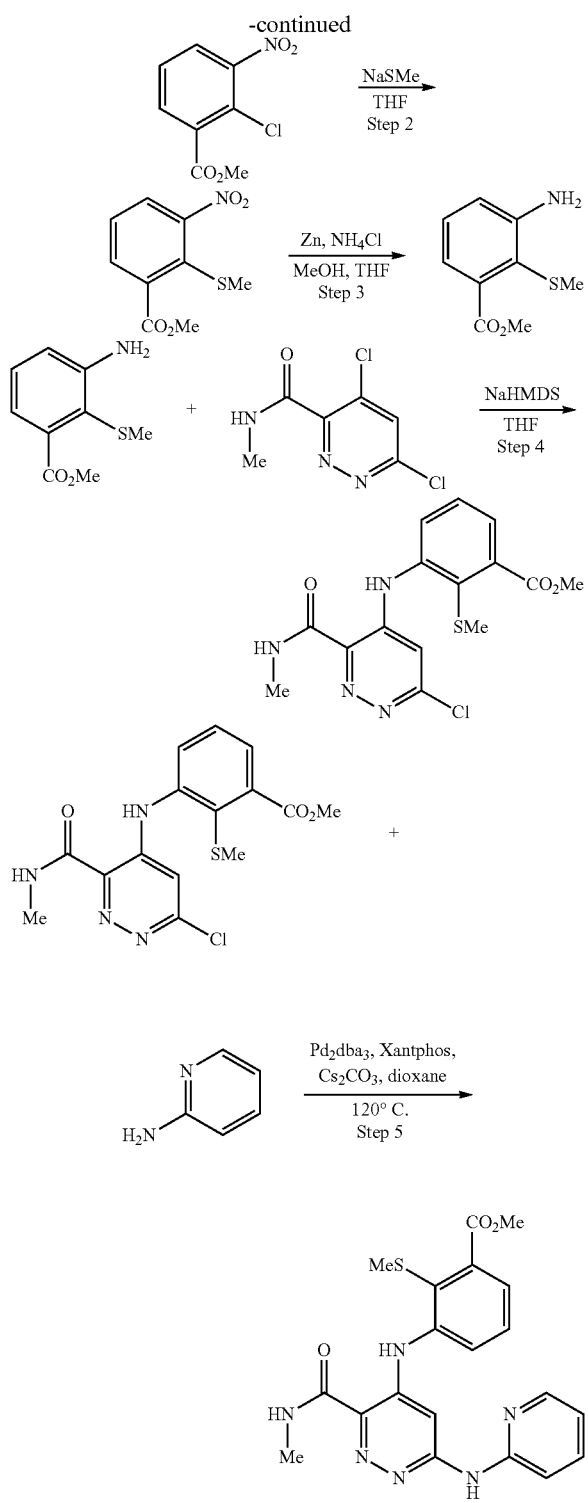

Step 1

Sulfuric acid (conc. 0.53 mL, 9.9 mmol) was added to 2-chloro-3-nitrobenzoic acid (2 g, 9.9 mmol) was dissolved in methyl alcohol (10 mL) and the reaction heated to reflux for 12 hours. The reaction was cooled to room temperature and then quenched with water. Ethyl acetate was added and the layers were separated, the organic layer was washed with brine and then dried over sodium sulfate. The crude product (2 g, 92% yield) was concentrated and carried on. $^1$H NMR (400 MHz, DMSO-$d_6$) δ 8.22 (dd, J=8.0, 1.6 Hz, 1H), 8.07 (dd, J=8.0, 1.6 Hz, 1H), 7.72 (t, J=8.0 Hz, 1H), 3.91 (s, 3H).

Step 2

To a cooled (0° C.) solution of sodium thiomethoxide (1.50 g, 21.3 mmol) in THF (40 mL) was added methyl 2-chloro-3-nitrobenzoate (2 g, 9.3 mmol) as a solution in THF (20 mL). The reaction was stirred for 2 hours at room temperature and then quenched with water. The product was extracted with ethyl acetate and the combined organic layers were washed with brine, dried over sodium sulfate, filtered and concentrated to provide the product (1 g, 47% yield). $^1$H NMR (400 MHz, DMSO-$d_6$) δ 8.05 (dd, J=8.0, 1.6 Hz, 1H), 7.90 (dd, J=8.0, 1.6 Hz, 1H), 7.69 (t, J=8.0 Hz, 1H), 3.91 (s, 3H), 2.40 (s, 3H).

Step 3

To a vessel containing methyl 2-(methylthio)-3-nitrobenzoate (1 g, 4.4 mmol), ammonium chloride (2.82 g, 52.8 mmol) and zinc (3.45 g, 52.8 mmol) was added methanol (15 mL) and THF (5 mL). The reaction was stirred at room temperature for 1 hour and then filtered through CELITE®. The crude product was purified via silica gel chromatography (EtOAc: petroleum ether) to provide methyl 3-amino-2(methylthio)benzoate (500 mg, 52% yield). $^1$H NMR (400 MHz, DMSO-$d_6$) δ 7.11 (dd, J=8.0, 0.8 Hz, 1H), 6.84 (dd, J=8.0, 1.2 Hz, 1H), 6.61 (dd, J=7.2, 1.2 Hz, 1H), 3.80 (s, 3H), 2.19 (s, 3H).

Step 4

To a solution of methyl 3-amino-2-(methylthio)benzoate (479 mg, 2.43 mmol) and 4,6-dichloro-N-methylpyridazine-3-carboxamide (500 mg, 2.43 mmol) in THF (20 mL) was added sodium bis(trimethylsilyl)amide (1M in THF, 6.1 mL, 6.1 mmol). The reaction was stirred at room temperature for 1 hour and then quenched with 1.5 M (aq.) HCl. The product was extracted using ethyl acetate and the combined organic layers were washed with brine, dried over sodium sulfate, filtered and concentrated. The crude product was purified via silica gel chromatography (EtOAc: petroleum ether) to provide methyl 3-((6-chloro-3-(methylcarbamoyl)pyridazin-4-yl)amino)-2-(methylthio)benzoate (250 mg, 25% yield). $^1$H NMR (400 MHz, DMSO-$d_6$) δ 11.30 (s, 1H), 9.40 (d, J=4.8 Hz, 1H), 7.30 (dd, J=8.0, 1.2 Hz, 1H), 7.53 (t, J=8.0, 1H), 7.40 (dd, J=7.2, 1.2 Hz, 1H), 7.28 (s, 1H), 3.87 (s, 3H), 2.86 (d, J=4.8 Hz, 3H), 2.26 (s, 3H).

Step 5

In a 10 mL pressure tube methyl 3-((6-chloro-3-(methylcarbamoyl)pyridazin-4-yl)amino)-2-(methylthio)benzoate (250 mg, 0.68 mmol) was dissolved in dioxane (2 mL) and the vessel purged with nitrogen for 10 minutes. Next pyridin-2-amine (128 mg, 1.36 mmol), Xantphos (59 mg, 0.10 mmol), Pd$_2$(dba)$_3$ (62 mg, 0.068 mmol) and cesium carbonate (444 mg, 1.36 mmol) were added. The vessel was sealed and heated in the microwave at 120° C. for 2.5 hours. Next the reaction mixture was filtered through CELITE® eluting with ethyl acetate. Water was added to the ethyl acetate and the layers were separated, the aqueous layer was extracted with ethyl acetate and then the combined organic layers were washed with brine, dried over sodium sulfate, filtered concentrated and purified using silica gel chromatography to provide the product (200 mg, 59% yield). LC retention time 2.15 [R]. MS (E$^+$) m/z: 425 (MH$^+$).

Example 203

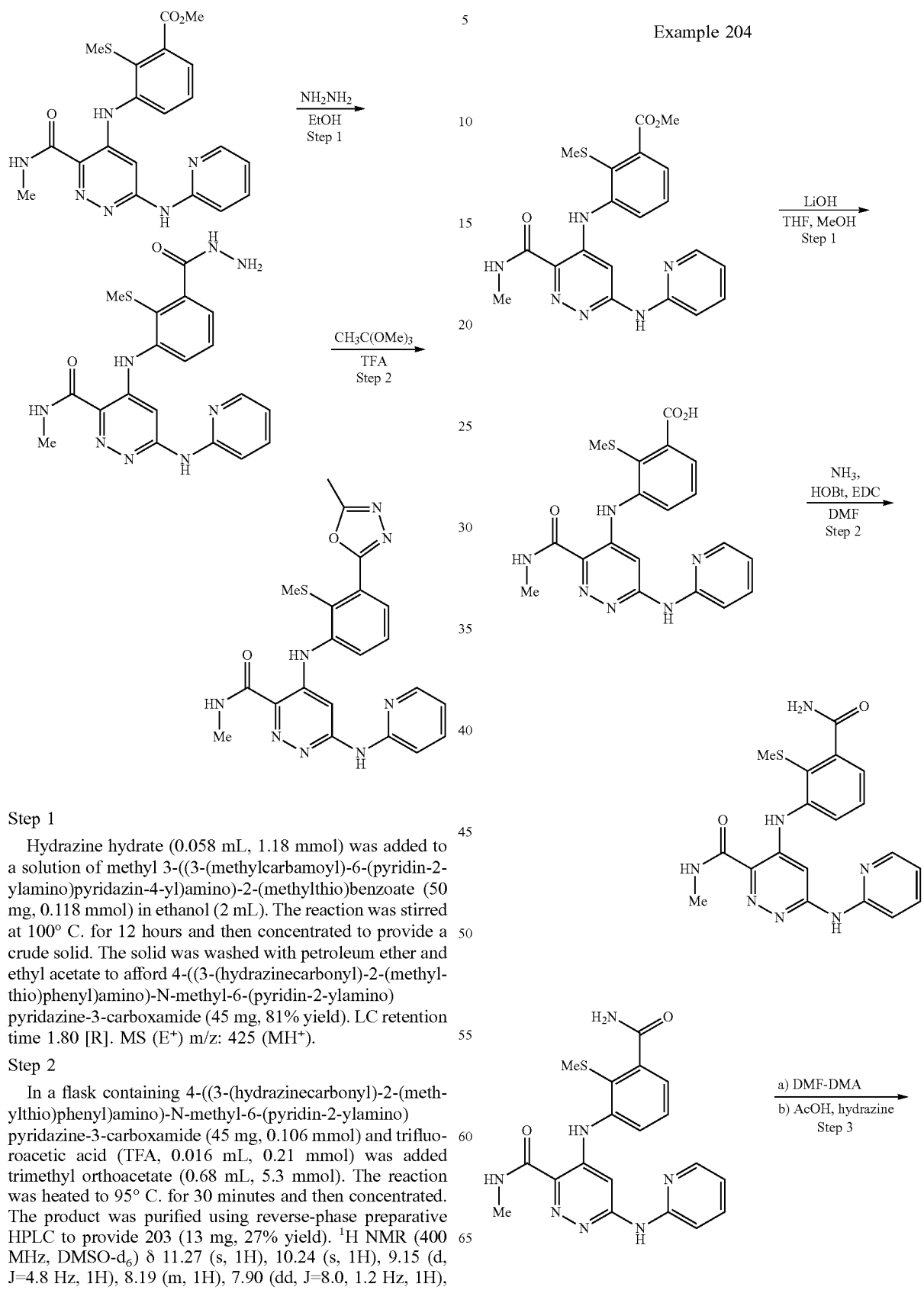

Step 1

Hydrazine hydrate (0.058 mL, 1.18 mmol) was added to a solution of methyl 3-((3-(methylcarbamoyl)-6-(pyridin-2-ylamino)pyridazin-4-yl)amino)-2-(methylthio)benzoate (50 mg, 0.118 mmol) in ethanol (2 mL). The reaction was stirred at 100° C. for 12 hours and then concentrated to provide a crude solid. The solid was washed with petroleum ether and ethyl acetate to afford 4-((3-(hydrazinecarbonyl)-2-(methylthio)phenyl)amino)-N-methyl-6-(pyridin-2-ylamino)pyridazine-3-carboxamide (45 mg, 81% yield). LC retention time 1.80 [R]. MS (E$^+$) m/z: 425 (MH$^+$).

Step 2

In a flask containing 4-((3-(hydrazinecarbonyl)-2-(methylthio)phenyl)amino)-N-methyl-6-(pyridin-2-ylamino)pyridazine-3-carboxamide (45 mg, 0.106 mmol) and trifluoroacetic acid (TFA, 0.016 mL, 0.21 mmol) was added trimethyl orthoacetate (0.68 mL, 5.3 mmol). The reaction was heated to 95° C. for 30 minutes and then concentrated. The product was purified using reverse-phase preparative HPLC to provide 203 (13 mg, 27% yield). $^1$H NMR (400 MHz, DMSO-d$_6$) δ 11.27 (s, 1H), 10.24 (s, 1H), 9.15 (d, J=4.8 Hz, 1H), 8.19 (m, 1H), 7.90 (dd, J=8.0, 1.2 Hz, 1H), 7.73 (m, 2H), 7.68 (m, 2H), 6.94 (m, 1H), 2.86 (d, J=4.8 Hz, 3H), 2.61 (s, 3H), 2.27 (s, 3H). LC retention time 2.03 [R]. MS (E$^+$) m/z: 449 (MH$^+$).

Example 204

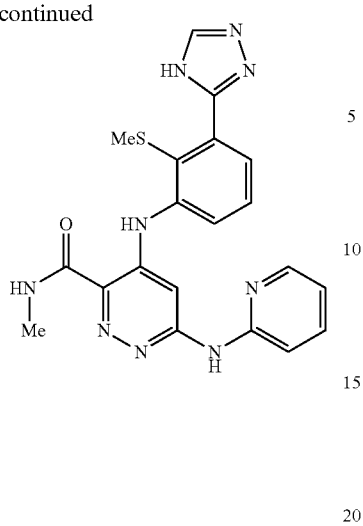

Step 1

Methyl 3-((3-(methylcarbamoyl)-6-(pyridin-2-ylamino)pyridazin-4-yl)amino)-2-(methylthio)benzoate (150 mg, 0.353 mmol) was dissolved in methanol (5 mL) and THF (5 mL) and then lithium hydroxide (85 mg, 3.53 mmol) in water (2.5 mL) was added. The reaction was run at room temperature for 4 hours and then acidified to pH ~2 using HCl. The resulting solid was collected via filtration to provide 3-((3-(methylcarbamoyl)-6-(pyridin-2-ylamino)pyridazin-4-yl)amino)-2-(methylthio)benzoic acid (110 mg, 64.5% yield). LC retention time 1.62 [R]. MS ($E^+$) m/z: 411 ($MH^+$).

Step 2

To a solution of 3-((3-(methylcarbamoyl)-6-(pyridin-2-ylamino)pyridazin-4-yl)amino)-2-(methylthio)benzoic acid (25 mg, 0.061 mmol), EDC (17.5 mg, 0.091 mmol) and HOBt (14 mg, 0.091 mmol) in DMF (3 mL) was added ammonia solution (0.044 mL, 0.61 mmol) and the reaction stirred for 2 hours. Water was added to the reaction and the product extracted with ethyl acetate. The organic layers were washed with brine, dried over sodium sulfate, filtered, and purified using silica gel chromatography to provide 4-((3-carbamoyl-2-(methylthio)phenyl)amino)-N-methyl-6-(pyridin-2-ylamino)pyridazine-3-carboxamide (20 mg, 72% yield). LC retention time 1.82 [R]. MS ($E^+$) m/z: 410 ($MH^+$).

Step 3

A solution of 4-((3-carbamoyl-2-(methylthio)phenyl)amino)-N-methyl-6-(pyridin-2-ylamino)pyridazine-3-carboxamide (25 mg, 0.061 mmol) dissolved in N,N-dimethylformamide dimethylacetal (2 mL) was heated 80° C. for 3 hours. The reaction was then concentrated and taken up in acetic acid (0.5 mL) and combined with hydrazine (0.1 mL, 0.061 mmol). This mixture was stirred at 95° C. for 1 hour and then water was added to quench the reaction. The product extracted with ethyl acetate. The organic layers were washed with brine, dried over sodium sulfate, filtered, and purified using preparative HPLC to provide 204 (8 mg, 30% yield). $^1$H NMR (400 MHz, DMSO-$d_6$) δ 11.19 (s, 1H), 10.20 (s, 1H), 9.12 (d, J=4.8 Hz, 1H), 8.26 (s, 1H), 8.19 (dd, J=8.0, 1.2 Hz, 1H), 7.74 (m, 2H), 7.68 (m, 2H), 7.36 (m, 1H), 6.94 (m, 1H), 2.86 (d, J=4.8 Hz, 3H), 2.18 (s, 3H). LC retention time 1.86 [R]. MS ($E^+$) m/z: 434 ($MH^+$).

Example 205

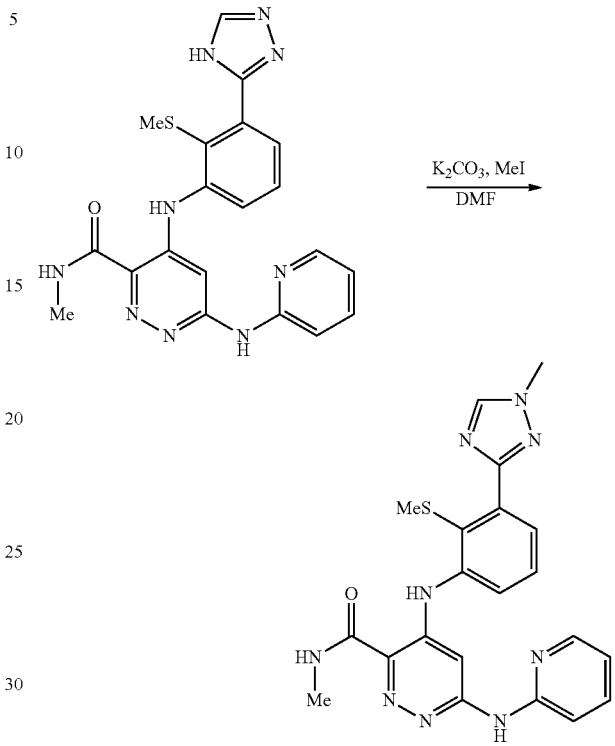

To a solution of N-methyl-4-((2-(methylthio)-3-(4H-1,2,4-triazol-3-yl)phenyl)amino)-6-(pyridin-2-ylamino)pyridazine-3-carboxamide (15 mg, 0.035 mmol) in DMF (1 mL) was added potassium carbonate (14.3 mg, 0.10 mmol) and then iodomethane (0.0026 mL, 0.042 mmol) in DMF (0.4 mL). The reaction was run for 15 minutes at room temperature and then diluted with water. The product extracted with ethyl acetate. The organic layers were washed with brine, dried over sodium sulfate, filtered, and purified using preparative HPLC to provide 205 (4 mg, 25% yield) (isolated as a single regioisomer). $^1$H NMR (400 MHz, DMSO-$d_6$) δ 11.15 (s, 1H), 10.17 (s, 1H), 9.10 (d, J=4.8 Hz, 1H), 8.55 (s, 1H), 8.19 (m, 2H), 7.72 (m, 2H), 7.68 (m, 2H), 7.55 (m, 1H), 6.91 (m, 1H), 3.95 (s, 3H), 2.86 (d, J=4.8 Hz, 3H), 2.21 (s, 3H). LC retention time 1.95 [R]. MS ($E^+$) m/z: 448 ($MH^+$).

Preparation 22

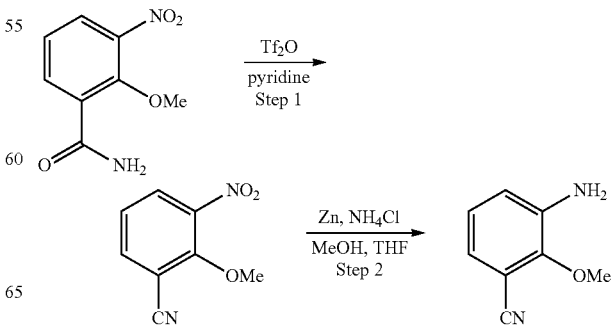

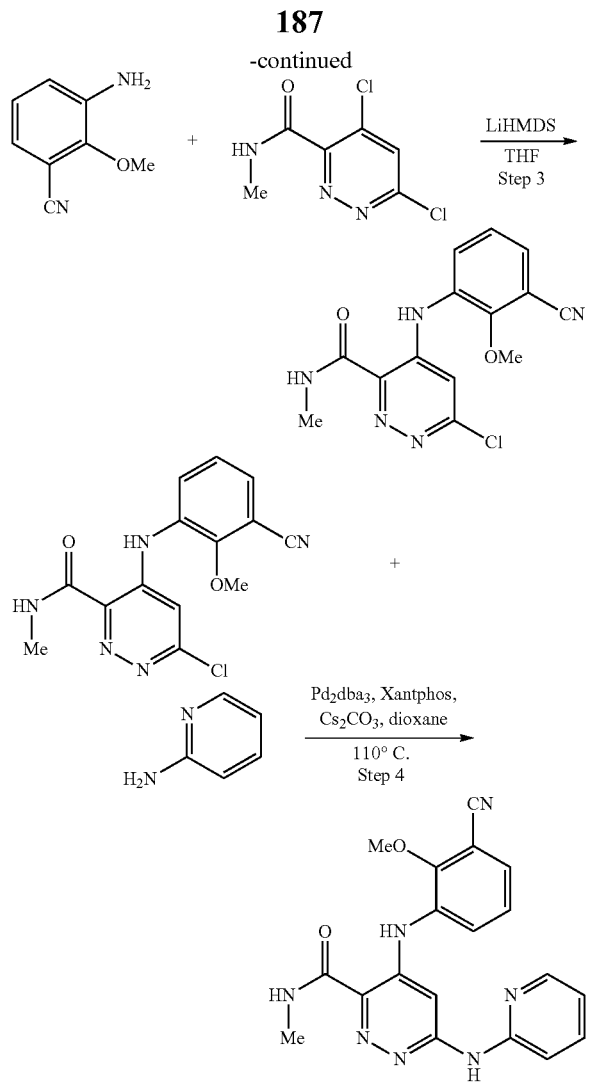

Step 1

To a suspension of 2-methoxy-3-nitrobenzamide (from Preparation 9, 500 mg, 2.55 mmol) in dioxane (20 mL) was added pyridine (0.62 mL, 7.65 mmol) followed by trifluoroacetic anhydride (0.72 mL, 5.1 mmol). The reaction was run at room temperature for 3 hours and then quenched with water. The product extracted with ethyl acetate. The organic layers were washed with brine, dried over sodium sulfate, filtered, and purified using silica gel chromatography to provide 2-methoxy-3-nitrobenzonitrile (310 mg, 68% yield). $^1$H NMR (400 MHz, CDCl$_3$) δ 8.03 (dd, J=8.0, 1.6 Hz, 1H), 7.84 (dd, J=8.0, 1.6 Hz, 1H), 7.32 (t, J=8.0 Hz, 1H), 4.20 (s, 3H).

Step 2

To a vessel containing methyl 2-methoxy-3-nitrobenzonitrile (300 mg, 1.684 mmol), ammonium chloride (1.08 g, 20.2 mmol) and zinc (1.32 g, 20.2 mmol) was added methanol (8 mL) and THF (3 mL). The reaction was stirred at room temperature for 1 hour and then filtered through CELITE®. The crude product was purified via silica gel chromatography (EtOAc: petroleum ether) to provide 3-amino-2-methoxybenzonitrile (219 mg, 88% yield). $^1$H NMR (400 MHz, CDCl$_3$) δ 6.93 (m, 3H), 4.02 (s, 3H). LC retention time 1.67 [R]. MS (E$^+$) m/z: 149 (MH$^+$).

Step 3

To a solution of 3-amino-2-methoxybenzonitrile (180 mg, 1.213 mmol) and 4,6-dichloro-N-methylpyridazine-3-carboxamide (250 mg, 1.21 mmol) in THF (6 mL) was added lithium bis(trimethylsilyl)amide (1M in THF, 3.6 mL, 3.6 mmol). The reaction was stirred at room temperature for 2 hour and then quenched with 1.5 M (aq.) HCl. The product was extracted using ethyl acetate and the combined organic layers were washed with brine, dried over sodium sulfate, filtered and concentrated. The crude product was purified via silica gel chromatography (EtOAc: petroleum ether) to provide 6-chloro-4-((3-cyano-2-methoxyphenyl)amino)-N-methylpyridazine-3-carboxamide (220 mg, 57% yield). $^1$H NMR (400 MHz, CDCl$_3$) δ 11.04 (s, 1H), 8.26 (bs, 1H), 7.54 (dd, J=8.0, 1.2 Hz, 1H), 7.50 (dd, J=8.0, 1.2 Hz, 1H), 7.23 (t, J=8.0 Hz, 1H), 6.93 (s, 1H), 4.05 (s, 3H), 3.06 (d, J=4.2 Hz, 3H).

Step 4

In a 10 mL pressure tube 6-chloro-4-((3-cyano-2-methoxyphenyl)amino)-N-methylpyridazine-3-carboxamide (200 mg, 0.629 mmol) was dissolved in dioxane (8 mL) and the vessel purged with nitrogen for 10 minutes. Next pyridin-2-amine (71.1 mg, 0.755 mmol), Xantphos (72.8 mg, 0.13 mmol), Pd$_2$(dba)$_3$ (58 mg, 0.063 mmol) and cesium carbonate (410 mg, 1.26 mmol) were added. The vessel was sealed and heated in the microwave at 110° C. for 1 hour. Next the reaction mixture was filtered through CELITE® eluting with ethyl acetate. Water was added to the ethyl acetate and the layers were separated, the aqueous layer was extracted with ethyl acetate and then the combined organic layers were washed with brine, dried over sodium sulfate, filtered concentrated and purified using silica gel chromatography to provide 4-((3-cyano-2-methoxyphenyl)amino)-N-methyl-6-(pyridin-2-ylamino)pyridazine-3-carboxamide (070 mg, 29% yield). LC retention time 2.64 [R]. MS (E$^+$) m/z: 376 (MH$^+$).

Example 206

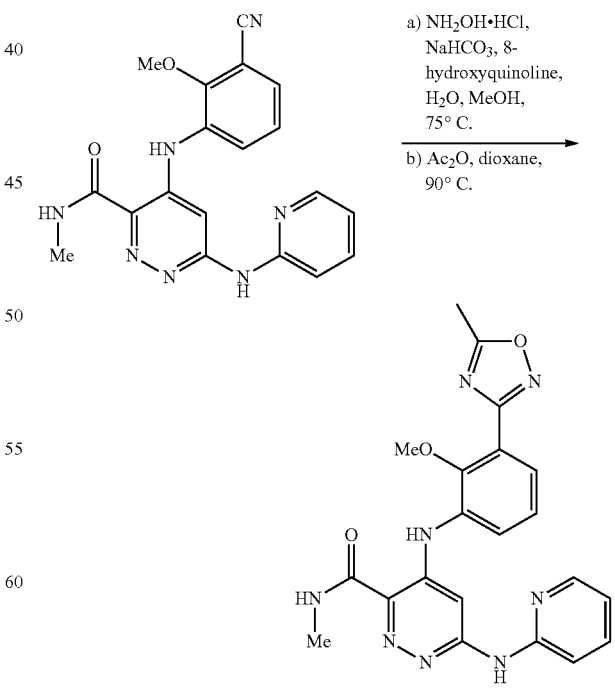

A solution of 4-((3-cyano-2-methoxyphenyl)amino)-N-methyl-6-(pyridin-2-ylamino)pyridazine-3-carboxamide (50 mg, 0.133 mmol), hydroxylamine hydrochloride (27.8 mg, 0.400 mmol) and sodium bicarbonate (33.6 mg, 0.400 mmol) in MeOH (3 mL) was refluxed for 6 h. Analysis of the crude mixture revealed that the starting material was intact. Next 8-hydroxyquinoline (19.33 mg, 0.133 mmol) in water (3 mL) was added and the reaction heated at 75° C. for 3 h, resulting in complete conversion to the intermediate. The reaction was concentrated and dissolved in dioxane and acetic anhydride (0.013 mL, 0.133 mmol) was added. The reaction was heated at 90° C. for 15 hours and then purified using preparative HPLC to provide 206 (7 mg, 12% yield). $^1$H NMR (400 MHz, DMSO-d$_6$) δ 11.04 (s, 1H), 10.18 (s, 1H), 9.12 (d, J=4.8 Hz, 1H), 8.20 (s, 1H), 8.19 (m, 1H), 7.81 (dd, J=8.0, 1.2 Hz, 1H), 7.68 (m, 2H), 7.57 (d, J=8.0 Hz, 1H), 7.42 (t, J=8.0 Hz, 1H), 6.92 (m, 1H), 3.76 (s, 3H), 2.86 (d, J=4.8 Hz, 3H), 2.69 (s, 3H). LC retention time 6.82 [P]. MS (E$^+$) m/z: 433 (MH$^+$).

6-Ethylpyrimidin-4-amine

A solution of 6-vinylpyrimidin-4-amine (prepared according to the procedure of PCT Patent Application WO 2012/035039, Example 8, Step 2; 100 mg, 0.825 mmol) in methanol (5 mL) was treated with 20% palladium hydroxide on carbon (50 mg, 0.071 mmol). The mixture was stirred at room temperature under a hydrogen atmosphere for 21.25 h. The mixture was filtered through CELITE®, the solids were rinsed with methanol and the combined filtrates were concentrated under vacuum to provide 6-ethylpyrimidin-4-amine as a white waxy solid (94 mg, 92% yield). $^1$H NMR (400 MHz, DMSO-d$_6$) δ 8.25 (d, J=1.1 Hz, 1H), 6.65 (br. s., 2H), 6.29-6.19 (m, 1H), 2.46 (q, J=7.6 Hz, 2H), 1.14 (t, J=7.6 Hz, 3H).

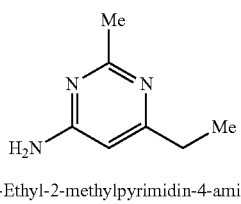

6-Ethyl-2-methylpyrimidin-4-amine

Step 1

A mixture of 6-chloro-2-methylpyrimidin-4-amine (300 mg, 2.09 mmol), 4,4,5,5-tetramethyl-2-vinyl-1,3,2-dioxaborolane (386 mg, 2.51 mmol) and sodium carbonate (886 mg, 8.36 mmol) in 1,4-dioxane (9.0 mL) and water (0.9 mL) was bubbled with argon with sonication for 1 min. The mixture was treated with tetrakis(triphenylphosphine)palladium (169 mg, 0.146 mmol) and the vessel was sealed and subjected to 5 evacuate-fill cycles with argon. The mixture was stirred on a heating block at 100° C. for 16.5 h, then was cooled to room temperature, diluted with water and extracted twice with ethyl acetate. The combined organic phases were washed with brine, dried over sodium sulfate and concentrated under vacuum. The residue was subjected to column chromatography (Isco Combiflash Companion, 24 g silica gel, 20-100% ethyl acetate-hexane, 8 min, then isocratic) to provide 2-methyl-6-vinylpyrimidin-4-amine as a white solid (189 mg, 67% yield). Mass spectrum m/z 271, (2M+H)$^+$. $^1$H NMR (400 MHz, DMSO-d$_6$) δ 6.71 (br. s., 2H), 6.54 (dd, J=17.2, 10.6 Hz, 1H), 6.26-6.20 (m, 1H), 6.20 (s, 1H), 5.53-5.40 (m, 1H), 2.31 (s, 3H).

Step 2

A solution of 2-methyl-6-vinylpyrimidin-4-amine (100 mg, 0.740 mmol) in methanol (5 mL) was treated with 20% palladium hydroxide on carbon (50 mg, 0.071 mmol). The mixture was stirred at room temperature under a hydrogen atmosphere for 15.25 h. The mixture was filtered through CELITE® and the solids were rinsed with methanol. The filtrate was concentrated under vacuum to provide 6-ethyl-2-methylpyrimidin-4-amine as a white waxy solid (101 mg, quantitative yield). $^1$H NMR (400 MHz, DMSO-d$_6$) δ 6.54 (br. s., 2H), 6.07 (s, 1H), 2.42 (q, J=7.6 Hz, 2H), 2.27 (s, 3H), 1.13 (t, J=7.6 Hz, 3H).

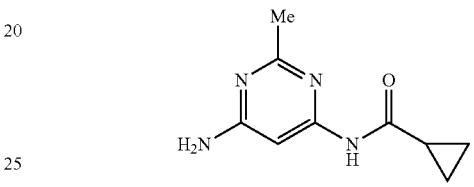

N-(6-Amino-2-methylprimidin-4-yl)cyclopropanecarboxamide

Step 1

A mixture of (6-chloro-2-methylpyrimidin-4-yl)-bis-carbamic acid tert-butyl ester (prepared according to the procedure of PCT Patent Application WO 2012/066061, Example 24, Step 1; 250 mg, 0.727 mmol), cyclopropanecarboxamide (93 mg, 1.09 mmol), Xantphos (42 mg, 0.073 mmol) and cesium carbonate (474 mg, 1.45 mmol) in 1,4-dioxane (3 mL) was sonicated while bubbling with argon for 1 min. The mixture was treated with Pd$_2$(dba)$_3$ (33 mg, 0.036 mmol) and the vessel was sealed and subjected to five evacuate-fill cycles with argon. The mixture was stirred on a heating block at 80° C. for 16 h. The mixture was cooled to room temperature and partitioned between water and ethyl acetate. The aqueous phase was extracted with ethyl acetate, and the combined organic phases were washed with brine, dried over sodium sulfate and concentrated under vacuum. The residue was subjected to column chromatography (Isco Combiflash Companion, 40 g silica gel, 0-40% ethyl acetate-hexane, 14 min, then isocratic) to provide (6-cyclopropanecarbonylamino-2-methylpyrimidin-4-yl)-bis-carbamic acid tert-butyl ester as an off-white glassy solid (182 mg, 64% yield). Mass spectrum m/z 393, (M+H)$^+$. $^1$H NMR (400 MHz, chloroform-d) δ 8.24 (s, 1H), 8.09 (s, 1H), 2.53 (s, 3H), 1.57-1.49 (s+m, 19H), 1.20-1.11 (m, 2H), 0.99-0.89 (m, 2H).

Step 2

A solution of (6-cyclopropanecarbonylamino-2-methylpyrimidin-4-yl)-bis-carbamic acid tert-butyl ester (179 mg, 0.455 mmol) in dichloromethane (2 mL) was treated with trifluoroacetic acid (2 mL) and let stand at room temperature for 2.25 h. The solution was concentrated under vacuum and the residue was partitioned between ethyl acetate and saturated aqueous sodium bicarbonate. The organic phase was dried over sodium sulfate and concentrated under vacuum to provide N-(6-amino-2-methylpyrimidin-4-yl)cyclopropanecarboxamide as a tan solid (90 mg, quantitative yield). Mass spectrum m/z 193, (M+H)$^+$.

¹H NMR (400 MHz, DMSO-d₆) δ 10.50 (s, 1H), 6.95 (s, 1H), 6.62 (br. s., 2H), 2.24 (s, 3H), 2.04-1.90 (m, 1H), 0.79 (s, 2H), 0.77 (s, 2H).

| Compound | ¹H NMR (methanol-d₄ equates CDCl₃:MeOD ~1:1 unless otherwise noted) Occasionally water suppression is used in DMSO-d₆ spectra |
|---|---|
| 2 | ¹H NMR (500 MHz, methanol-d₄) δ 8.30 (br. s., 1H), 8.09 (d, J = 7.9 Hz, 1H), 8.00 (br. s., 1H), 7.88-7.83 (m, 1H), 7.77 (t, J = 7.7 Hz, 1H), 7.51-7.39 (m, 2H), 7.29 (d, J = 5.9 Hz, 1H), 3.13 (s, 3H). |
| 3 | ¹H NMR (500 MHz, methanol-d₄) δ 8.28 (s, 1H), 8.09 (dd, J = 7.9, 1.5 Hz, 1H), 8.00 (d, J = 3.0 Hz, 1H), 7.84 (d, J = 7.9 Hz, 1H), 7.79-7.74 (m, 1H), 7.48-7.40 (m, 2H), 7.28 (dd, J = 8.9, 3.5 Hz, 1H), 3.14 (s, 3H), 3.03 (s, 3H). |
| 4 | ¹H NMR (500 MHz, methanol-d₄) δ 8.24 (s, 1H), 8.09 (dd, J = 7.9, 1.5 Hz, 1H), 8.00 (d, J = 3.0 Hz, 1H), 7.87-7.82 (m, 1H), 7.79-7.75 (m, 1H), 7.50-7.40 (m, 2H), 7.30 (dd, J = 9.2, 3.7 Hz, 1H), 3.51 (q, J = 7.3 Hz, 2H), 3.14 (s, 3H), 1.30 (t, J = 7.2 Hz, 3H) |
| 5 | ¹H NMR (500 MHz, methanol-d₄) δ 8.22 (s, 1H), 8.10 (dd, J = 7.9, 1.0 Hz, 1H), 7.99 (d, J = 2.5 Hz, 1H), 7.86-7.80 (m, 1H), 7.79-7.72 (m, 1H), 7.48-7.40 (m, 2H), 7.29 (dd, J = 8.9, 3.5 Hz, 1H), 3.14 (s, 3H), 2.94 (tf, J = 7.2, 3.7 Hz, 1H), 0.93-0.84 (m, 2H), 0.77-0.63 (m, 2H) |
| 6 | ¹H NMR (500 MHz, DMSO-d₆) δ 11.05 (s, 1H), 10.22 (s, 1H), 9.05 (s, 1H), 8.13 (d, J = 2.8 Hz, 1H), 7.98 (dd, J = 8.0, 1.4 Hz, 1H), 7.88 (s, 1H), 7.86-7.79 (m, 2H), 7.72-7.63 (m, 2H), 7.45 (t, J = 6.8 Hz, 1H), 3.18 (s, 3H) |
| 7 | ¹H NMR (500 MHz, methanol-d₄) δ 8.63 (s, 1H), 8.12 (dd, J = 7.9, 1.5 Hz, 1H), 7.90-7.84 (m, 1H), 7.79 (td, J = 7.8, 1.2 Hz, 1H), 7.50-7.42 (m, 1H), 6.83 (s, 1H), 3.14 (s, 3H), 2.41 (s, 3H), 2.40 (s, 3H) |
| 8 | N/A |
| 9 | ¹H NMR (400 MHz, DMSO-d₆) δ 11.10 (s, 1H), 10.35 (s, 1H), 9.10 (d, J = 4.8 Hz, 1H), 8.16 (d, J = 2.8 Hz, 1H), 8.00 (dd, J = 8.0, 1.6 Hz, 1H), 7.89-7.82 (m, 2H), 7.81 (s, 1H), 7.73 (m, 1H), 7.64 (dd, J = 9.2, 4.0 Hz, 1H), 7.48 (m, 1H), 3.20 (s, 3H), 2.86 (d, J = 4.8 Hz, 3H) |
| 10 | ¹H NMR (400 MHz, DMSO-d₆) δ 11.09 (s, 1H), 10.36 (s, 1H), 9.14 (d, J = 4.4 Hz, 1H), 8.88 (d, J = 1.6 Hz, 1H), 8.07 (s, 1H), 8.00 (d, J = 7.2 Hz, 1H), 7.83 (m, 3H), 7.49 (m, 1H), 3.20 (s, 3H), 2.86 (d, J = 4.8 Hz, 3H), 2.40 (s, 3H) |
| 11 | ¹H NMR (400 MHz, DMSO-d₆) δ 11.09 (s, 1H), 10.53 (s, 1H), 9.21 (d, J = 4.8 Hz, 1H), 8.40 (d, J = 1.2 Hz, 1H), 8.16 (s, 1H), 8.01 (d, J = 8.4 Hz, 1H), 7.84 (m, 2H), 7.76 (s, 1H), 7.50 (m, 1H), 7.34 (m, 1H), 3.19 (s, 3H), 2.86 (d, J = 4.8 Hz, 3H) |
| 12 | ¹H NMR (400 MHz, DMSO-d₆) δ 11.38 (s, 1H), 11.09 (s, 1H), 9.13 (dd, J = 9.2, 4.4 Hz, 1H), 8.09 (s, 1H), 7.99 (dd, J = 8.0, 1.6 Hz, 1H), 7.77 (m, 1H), 7.71 (d, J = 7.2 Hz, 1H), 7.47 (m, 1H), 3.17 (s, 3H), 2.85 (d, J = 4.8 Hz, 3H), 2.07 (m, 1H), 0.81 (m, 4H) |

-continued

| Compound | ¹H NMR (methanol-d₄ equates CDCl₃:MeOD ~1:1 unless otherwise noted) Occasionally water suppression is used in DMSO-d₆ spectra |
|---|---|
| 13 | ¹H NMR (400 MHz, DMSO-d₆) δ 11.03 (s, 1H), 10.16 (s, 1H), 9.19 (m, 1H), 9.08 (s, 1H), 8.35 (s, 1H), 8.01 (t, J = 8.8 Hz, 2H), 7.81 (m, 3H), 7.68 (m, 1H), 7.46 (m, 3H), 3.20 (s, 3H), 2.86 (d, J = 4.8 Hz, 3H) |
| 14 | ¹H NMR (400 MHz, DMSO-d₆) δ 11.05 (s, 1H), 10.10 (s, 1H), 9.09 (dd, J = 9.6, 4.8 Hz, 1H), 8.04 (s, 1H), 7.97 (m, 2H), 7.82 (m, 2H), 7.45 (m, 2H), 6.77 (dd, J = 4.8, 0.8 Hz, 1H), 3.18 (s, 3H), 2.85 (d, J = 4.8 Hz, 3H), 2.27 (s, 3H) |
| 15 | N/A |
| 16 | ¹H NMR (500 MHz, methanol-d₄) δ 8.39 (s, 1H), 8.14 (d, J = 4.0 Hz, 1H), 8.09 (dd, J = 7.9, 1.5 Hz, 1H), 7.87 (d, J = 7.9 Hz, 1H), 7.79-7.72 (m, 1H), 7.70-7.64 (m, 1H), 7.42 (t, J = 7.4 Hz, 1H), 7.22 (d, J = 8.4 Hz, 1H), 6.97-6.88 (m, 1H), 3.14 (s, 3H) |
| 17 | ¹H NMR (500 MHz, DMSO-d₆) δ 11.39 (s, 1H), 11.10 (s, 1H), 9.12 (s, 1H), 8.13-8.04 (m, 1H), 8.01-7.90 (m, 1H), 7.80-7.74 (m, 1H), 7.73-7.67 (m, 1H), 7.46 (t, J = 7.2 Hz, 1H), 3.17 (s, 3H), 2.16-1.92 (m, 1H), 0.88-0.63 (m, 4H) |
| 18 | ¹H NMR (500 MHz, methanol-d₄) δ 8.10 (d, J = 5.9 Hz, 1H), 8.00 (br. s., 1H), 7.95 (s, 1H), 7.76 (br. s., 2H), 7.52 (br. s., 2H), 7.06 (br. s., 1H), 3.12 (br. s., 3H), 2.31 (br. s., 3H) |
| 19 | ¹H NMR (500 MHz, DMSO-d₆) δ 11.12 (s, 1H), 10.41 (s, 1H), 9.11 (s, 1H), 8.08-7.91 (m, 2H), 7.88-7.70 (m, 4H), 7.56-7.36 (m, 2H), 3.21 (s, 3H), 2.56-2.45 (m, 3H) |
| 20 | N/A |
| 21 | N/A |
| 22 | ¹H NMR (500 MHz, DMSO-d₆) δ 11.08 (s, 1H), 10.15 (br. s., 1H), 9.06 (s, 1H), 8.02-7.92 (m, 1H), 7.89-7.73 (m, 4H), 7.53 (d, J = 9.4 Hz, 1H), 7.49-7.38 (m, 2H), 3.78 (s, 3H), 3.18 (s, 3H) |
| 23 | ¹H NMR (500 MHz, methanol-d₄) δ 8.16-8.05 (m, 2H), 7.82-7.75 (m, 1H), 7.75-7.69 (m, 1H), 7.52 (t, J = 7.7 Hz, 1H), 7.02 (s, 1H), 6.97 (br. s., 1H), 3.15 (s, 3H), 2.41 (s, 3H) |
| 24 | ¹H NMR (500 MHz, methanol-d₄) δ 8.04 (dd, J = 7.9, 1.5 Hz, 1H), 7.78 (d, J = 7.4 Hz, 1H), 7.74-7.66 (m, 1H), 7.61 (s, 1H), 7.42-7.33 (m, 1H), 5.86 (s, 1H), 3.60 (s, 3H), 3.08 (s, 3H), 2.23 (s, 3H) |
| 25 | ¹H NMR (500 MHz, methanol-d₄) δ 8.45 (br. s., 1H), 8.13 (d, J = 7.9 Hz, 1H), 7.95 (s, 1H), 7.88-7.67 (m, 2H), 7.58-7.45 (m, 4H), 7.29 (br. s., 1H), 3.16 (s, 3H) |
| 26 | ¹H NMR (500 MHz, DMSO-d₆) δ 11.11 (s, 1H), 10.65 (s, 1H), 9.15 (s, 1H), 8.52 (s, 1H), 7.98 (d, J = 7.9 Hz, 1H), 7.90-7.83 (m, 2H), 7.83-7.78 (m, 1H), 7.67 (s, 1H), 7.47 (t, J = 7.6 Hz, 1H), 3.18 (s, 3H), 2.41 (s, 3H) |
| 27 | ¹H NMR (500 MHz, methanol-d₄) δ 8.48-8.42 (m, 1H), 8.19 (dd, J = 8.0, 1.4 Hz, 1H), 7.97 (ddd, J = 8.5, 7.4, 1.9 Hz, 1H), 7.92-7.84 (m, 1H), 7.78 (dd, J = 7.9, 1.0 Hz, 1H), 7.67 (td, J = 7.8, 1.1 Hz, 1H), 7.27 (ddd, J = 7.3, 5.3, 0.7 Hz, 1H), 7.13 (d, J = 8.3 Hz, 1H), 6.75 (s, 1H), 3.22 (s, 3H) |

| Compound | ¹H NMR (methanol-d₄ equates CDCl₃:MeOD ~1:1 unless otherwise noted) Occasionally water suppression is used in DMSO-d₆ spectra |
|---|---|
| 28 | ¹H NMR (500 MHz, DMSO-d₆) δ 11.44 (s, 1H), 11.12 (s, 1H), 9.13 (s, 1H), 8.09 (s, 1H), 7.98 (dd, J = 7.9, 1.2 Hz, 1H), 7.82-7.76 (m, 1H), 7.75-7.70 (m, 1H), 7.47 (t, J = 7.6 Hz, 1H), 5.07-4.81 (m, 1H), 3.18 (s, 3H), 2.26 (dt, J = 13.7, 7.2 Hz, 1H), 1.71-1.50 (m, 1H), 1.17 (ddt, J = 12.5, 9.0, 6.3 Hz, 1H) |
| 29 | ¹H NMR (500 MHz, DMSO-d₆) δ 11.04 (s, 1H), 9.95 (s, 1H), 9.02 (s, 1H), 7.97 (d, J = 6.7 Hz, 1H), 7.90 (s, 1H), 7.86-7.76 (m, 3H), 7.56-7.47 (m, 1H), 7.46-7.39 (m, 2H), 3.78-3.69 (m, 4H), 3.17 (s, 3H), 3.08-3.00 (m, 4H) |
| 30 | ¹H NMR (500 MHz, DMSO-d₆) δ 11.03 (s, 1H), 10.21 (s, 1H), 9.03 (br. s., 1H), 8.36 (s, 1H), 7.99 (d, J = 7.9 Hz, 1H), 7.82 (d, J = 3.7 Hz, 2H), 7.66-7.38 (m, 2H), 7.15 (d, J = 7.9 Hz, 1H), 6.75 (d, J = 7.3 Hz, 1H), 3.17 (s, 3H), 2.19 (s, 3H) |
| 31 | ¹H NMR (400 MHz, DMSO-d₆) δ 11.06 (s, 1H), 10.20 (s, 1H), 9.08 (d, J = 2.8 Hz, 1H), 8.17-8.07 (m, 2H), 7.98 (d, J = 8.4 Hz, 1H), 7.88-7.78 (m, 2H), 7.72-7.64 (m, 1H), 7.51 (d, J = 7.9 Hz, 1H), 7.48-7.41 (m, 1H), 6.90 (dd, J = 6.7, 5.2 Hz, 1H), 3.18 (s, 3H), 2.85 (d, J = 4.8 Hz, 3H) |
| 32 | ¹H NMR (500 MHz, DMSO-d₆) δ 11.07 (s, 1H), 10.67 (s, 1H), 9.09 (s, 1H), 8.63 (s, 1H), 8.16 (dd, J = 8.5, 2.4 Hz, 1H), 8.03 (s, 1H), 7.99 (d, J = 8.5 Hz, 1H), 7.86-7.79 (m, 2H), 7.66 (d, J = 8.5 Hz, 1H), 7.49 (t, J = 7.3 Hz, 1H), 3.82 (s, 3H), 3.17 (s, 3H) |
| 33 | ¹H NMR (500 MHz, DMSO-d₆) δ 11.06 (s, 1H), 10.36 (s, 1H), 9.12 (s, 1H), 8.33 (d, J = 5.0 Hz, 1H), 8.13 (s, 1H), 7.98 (d, J = 7.7 Hz, 1H), 7.90 (s, 1H), 7.81 (br. s., 2H), 7.47 (d, J = 5.7 Hz, 1H), 7.36 (d, J = 4.4 Hz, 1H), 3.17 (s, 3H), 2.58 (s, 3H) |
| 34 | ¹H NMR (500 MHz, DMSO-d₆) δ 11.03 (s, 1H), 10.14 (s, 1H), 9.05 (s, 1H), 8.06-8.00 (m, 2H), 7.97 (d, J = 7.9 Hz, 1H), 7.81 (d, J = 3.7 Hz, 2H), 7.56 (s, 1H), 7.45 (dt, J = 7.9, 4.0 Hz, 1H), 6.84 (d, J = 4.9 Hz, 1H), 5.46 (t, J = 5.5 Hz, 1H), 4.48 (d, J = 4.9 Hz, 2H), 3.16 (s, 3H) |
| 35 | ¹H NMR (500 MHz, DMSO-d₆) δ 11.06 (s, 1H), 10.48 (s, 1H), 9.14 (s, 1H), 8.41 (d, J = 5.5 Hz, 1H), 8.16 (s, 1H), 7.98 (d, J = 7.3 Hz, 1H), 7.84-7.78 (m, 2H), 7.75 (s, 1H), 7.50-7.44 (m, 1H), 7.23 (d, J = 4.9 Hz, 1H), 3.17 (s, 3H) |
| 36 | ¹H NMR (500 MHz, DMSO-d₆) δ 11.11 (s, 1H), 10.65 (br. s., 1H), 9.06 (s, 1H), 8.13 (d, J = 4.9 Hz, 1H), 8.00 (d, J = 7.3 Hz, 1H), 7.87-7.78 (m, 2H), 7.60 (br. s., 1H), 7.51 (t, J = 7.3 Hz, 1H), 7.29 (br. s., 1H), 6.96 (br. s., 1H), 3.20 (s, 3H), 2.63 (q, J = 7.5 Hz, 2H), 1.18 (t, J = 7.3 Hz, 3H) |
| 37 | ¹H NMR (500 MHz, DMSO-d₆) δ 11.09 (s, 1H), 10.76 (br. s., 1H), 9.03 (s, 1H), 8.11 (d, J = 6.1 Hz, 1H), 8.01 (d, J = 7.9 Hz, 1H), 7.87-7.76 (m, 2H), 7.51 (t, J = 7.6 Hz, 1H), 7.43 (br. s., 1H), 6.91 (br. s., 1H), 6.76 (br. s., 1H), 4.15 (q, J = 6.7 Hz, 2H), 3.20 (s, 3H), 1.36 (t, J = 7.0 Hz, 3H) |
| 38 | ¹H NMR (500 MHz, DMSO-d₆) δ 11.10 (s, 1H), 10.88 (br. s., 1H), 9.03 (s, 1H), 8.14 (d, J = 6.7 Hz, 1H), 8.01 (d, J = 7.3 Hz, 1H), 7.86-7.76 (m, 2H), 7.52 (t, J = 7.3 Hz, 1H), 7.36 (br. s., 1H), 6.91 (br. s., 1H), 6.80 (d, J = 4.9 Hz, 1H), 3.88 (s, 3H), 3.20 (s, 3H) |
| 39 | ¹H NMR (400 MHz, DMSO-d₆) δ 11.33 (s, 1H), 10.99 (s, 1H), 9.15 (s, 1H), 9.07 (d, J = 1.5 Hz, 1H), 8.79 (dd, J = 2.6, 1.6 Hz, 1H), 8.65 (d, J = 2.6 Hz, 1H), 8.16 (s, 1H), 7.57 (ddd, J = 7.9, 6.8, 1.5 Hz, 2H), 7.45-7.28 (m, 1H), 3.51 (s, 3H), 2.16-2.02 (m, 1H), 0.87-0.76 (m, 4H) |
| 39 | ¹H NMR (500 MHz, DMSO-d₆) δ 11.10 (s, 1H), 10.64 (s, 1H), 9.12 (s, 1H), 8.34 (d, J = 5.5 Hz, 1H), 8.29 (s, 1H), 8.01 (d, J = 7.9 Hz, 1H), 7.85 (d, J = 4.3 Hz, 2H), 7.51 (dt, J = 8.1, 4.2 Hz, 1H), 7.21 (d, J = 5.5 Hz, 1H), 3.19 (s, 3H), 2.33 (s, 3H) |
| 40 | ¹H NMR (500 MHz, DMSO-d₆) δ 11.09 (s, 1H), 10.63 (s, 1H), 9.14 (s, 1H), 8.22 (br. s., 1H), 8.01 (d, J = 7.9 Hz, 1H), 7.84 (d, J = 3.7 Hz, 2H), 7.50 (dt, J = 8.1, 4.2 Hz, 1H), 7.34 (br. s., 1H), 4.35 (s, 2H), 3.38 (s, 3H), 3.19 (s, 3H), 2.32 (s, 3H) |
| 41 | ¹H NMR (500 MHz, DMSO-d₆) δ 11.07 (s, 1H), 10.61 (s, 1H), 9.12 (s, 1H), 8.11 (br. s., 1H), 8.01 (d, J = 7.9 Hz, 1H), 7.87-7.75 (m, 2H), 7.56-7.45 (m, 1H), 7.27 (s, 1H), 4.22 (s, 2H), 3.19 (s, 3H), 3.17 (s, 3H), 2.35 (s, 3H) |
| 42 | ¹H NMR (500 MHz, DMSO-d₆) δ 11.09 (s, 1H), 10.40 (s, 1H), 9.16 (s, 1H), 8.40 (s, 1H), 7.99 (d, J = 7.7 Hz, 1H), 7.87-7.78 (m, 2H), 7.74 (s, 1H), 7.48 (t, J = 7.1 Hz, 1H), 7.21 (s, 1H), 3.89 (s, 3H), 3.19 (s, 3H) |
| 43 | ¹H NMR (500 MHz, DMSO-d₆) δ 11.08 (s, 1H), 10.41 (s, 1H), 9.12 (s, 1H), 8.08 (s, 1H), 8.00 (d, J = 7.9 Hz, 1H), 7.88-7.76 (m, 2H), 7.56-7.43 (m, 1H), 6.75 (s, 1H), 3.84 (s, 3H), 3.19 (s, 3H), 2.30 (s, 3H) |
| 44 | ¹H NMR (500 MHz, DMSO-d₆) δ 11.05 (s, 1H), 10.38 (s, 1H), 9.08 (s, 1H), 8.12 (s, 1H), 8.00 (d, J = 7.3 Hz, 1H), 7.87-7.76 (m, 2H), 7.54-7.44 (m, 1H), 6.61 (s, 1H), 5.30-5.16 (m, 1H), 3.18 (s, 3H), 2.27 (s, 3H), 1.26 (d, J = 6.1 Hz, 6H) |
| 45 | ¹H NMR (500 MHz, DMSO-d₆) δ 11.06 (br. s., 1H), 10.36 (br. s., 1H), 9.10 (br. s., 1H), 8.36 (s, 1H), 7.99 (d, J = 7.7 Hz, 1H), 7.87-7.73 (m, 3H), 7.47 (t, J = 7.4 Hz, 1H), 7.07 (s, 1H), 5.31-5.14 (m, 1H), 3.18 (s, 3H), 1.29 (d, J = 6.1 Hz, 6H) |
| 46 | ¹H NMR (500 MHz, DMSO-d₆) δ 11.12 (s, 1H), 10.52 (s, 1H), 9.16 (s, 1H), 8.57 (s, 1H), 7.99 (d, J = 8.1 Hz, 1H), 7.94 (s, 1H), 7.88-7.79 (m, 2H), 7.54 (s, 1H), 7.48 (t, J = 6.6 Hz, 1H), 3.19 (s, 3H), 2.64 (q, J = 7.4 Hz, 2H), 1.20 (t, J = 7.6 Hz, 3H) |
| 47 | ¹H NMR (500 MHz, DMSO-d₆) δ 11.06 (s, 1H), 10.50 (s, 1H), 9.08 (s, 1H), 8.24 (s, 1H), 8.00 (d, J = 7.7 Hz, 1H), 7.82 (d, J = 7.5 Hz, 2H), 7.58-7.42 (m, 1H), 7.09 (s, 1H), 3.17 (s, 3H), 2.56 (q, J = 7.4 Hz, 2H), 2.30 (s, 3H), 1.16 (t, J = 7.6 Hz, 3H) |
| 48 | ¹H NMR (500 MHz, DMSO-d₆) δ 11.15 (s, 1H), 9.08 (s, 1H), 8.19 (d, |

| Compound | ¹H NMR (methanol-d₄ equates CDCl₃:MeOD ~1:1 unless otherwise noted) Occasionally water suppression is used in DMSO-d₆ spectra |
|---|---|
| | J = 5.4 Hz, 1H), 8.01 (d, J = 7.7 Hz, 1H), 7.89-7.77 (m, 2H), 7.57-7.41 (m, 3H), 7.07 (d, J = 5.0 Hz, 1H), 4.74 (q, J = 6.2 Hz, 1H), 3.59 (br. s., 1H), 3.21 (s, 3H), 1.32 (d, J = 6.4 Hz, 3H) |
| 49 | ¹H NMR (500 MHz, DMSO-d₆) δ 11.05 (s, 1H), 10.19 (s, 1H), 9.05 (s, 1H), 8.10 (s, 1H), 8.05 (s, 1H), 7.98 (d, J = 8.1 Hz, 1H), 7.82 (d, J = 3.7 Hz, 2H), 7.64 (d, J = 8.4 Hz, 1H), 7.51-7.43 (m, 2H), 4.41 (d, J = 5.0 Hz, 2H), 3.41 (d, J = 5.4 Hz, 1H), 3.17 (s, 3H) |
| 50 | ¹H NMR (500 MHz, DMSO-d₆) δ 11.06 (s, 1H), 10.13 (s, 1H), 9.07 (s, 1H), 8.10 (s, 1H), 8.03 (d, J = 5.4 Hz, 1H), 7.97 (d, J = 7.7 Hz, 1H), 7.81 (d, J = 3.4 Hz, 2H), 7.66 (s, 1H), 7.48-7.41 (m, 1H), 6.97 (d, J = 5.0 Hz, 1H), 5.21 (s, 1H), 3.18 (s, 3H), 1.39 (s, 6H) |
| 51 | ¹H NMR (500 MHz, DMSO-d₆) δ 11.14 (s, 1H), 9.09 (s, 1H), 8.19 (d, J = 5.4 Hz, 1H), 8.00 (d, J = 7.7 Hz, 1H), 7.88-7.78 (m, 2H), 7.62 (br. s., 1H), 7.51 (t, J = 7.4 Hz, 1H), 7.44 (s, 1H), 6.97 (d, J = 5.0 Hz, 1H), 4.46 (s, 2H), 3.34 (s, 3H), 3.21 (s, 3H) |
| 54 | ¹H NMR (500 MHz, DMSO-d₆) δ 11.30 (s, 1H), 10.96 (s, 1H), 9.12 (s, 1H), 8.16 (s, 1H), 7.77 (d, J = 1.8 Hz, 1H), 7.68 (d, J = 7.9 Hz, 1H), 7.37 (d, J = 7.9 Hz, 1H), 7.21 (t, J = 7.9 Hz, 1H), 6.72 (d, J = 2.4 Hz, 1H), 3.90 (s, 3H), 3.58 (s, 3H), 2.12-2.02 (m, 1H), 0.89-0.74 (m, 4H) |
| 55 | ¹H NMR (500 MHz, DMSO-d₆) δ 11.02 (s, 1H), 9.12 (s, 1H), 8.11 (s, 1H), 7.78 (br. s., 2H), 7.68 (d, J = 7.4 Hz, 1H), 7.57 (br. s., 1H), 7.48 (d, J = 7.7 Hz, 1H), 7.28 (t, J = 7.9 Hz, 1H), 6.74 (s, 1H), 3.91 (s, 3H), 3.61 (s, 3H), 2.27 (s, 3H) |
| 56 | ¹H NMR (500 MHz, DMSO-d₆) δ 11.05 (s, 1H), 10.40 (br. s., 1H), 9.12 (br. s., 1H), 8.56 (s, 1H), 8.13 (s, 1H), 7.76-7.57 (m, 3H), 7.51 (br. s., 1H), 7.33 (t, J = 7.9 Hz, 1H), 3.94 (s, 3H), 3.74 (s, 3H), 2.27 (s, 3H) |
| 57 | ¹H NMR (500 MHz, DMSO-d₆) δ 10.98 (s, 1H), 9.10 (s, 1H), 8.37 (s, 1H), 8.17 (s, 1H), 8.03-7.83 (m, 2H), 7.44 (t, J = 6.4 Hz, 2H), 7.31-7.16 (m, 1H), 7.09 (s, 1H), 3.89 (s, 6H), 3.16 (s, 6H) |
| 58 | ¹H NMR (500 MHz, DMSO-d₆) δ 11.11 (s, 1H), 10.84 (br. s., 1H), 9.13 (s, 1H), 8.30 (d, J = 4.9 Hz, 1H), 7.84 (t, J = 7.6 Hz, 1H), 7.78 (s, 1H), 7.74 (d, J = 7.9 Hz, 1H), 7.62 (br. s., 1H), 7.49 (d, J = 7.3 Hz, 1H), 7.38 (d, J = 7.9 Hz, 1H), 7.29 (t, J = 7.9 Hz, 1H), 7.09 (t, J = 6.1 Hz, 1H), 6.74 (d, J = 1.8 Hz, 1H), 3.91 (s, 3H), 3.63 (s, 3H) |
| 59 | ¹H NMR (500 MHz, DMSO-d₆) δ 10.93 (br. s., 1H), 10.05 (br. s., 1H), 9.08 (br. s., 1H), 8.22-8.01 (m, 1H), 7.90 (d, J = 12.8 Hz, 1H), 7.62 (br. s., 1H), 7.39 (br. s., 1H), 7.23 (br. s., 1H), 3.89 (br. s., 3H), 3.16 (d, J = 4.0 Hz, 3H), 2.25 (br. s., 3H) |
| 60 | ¹H NMR (500 MHz, DMSO-d₆) δ 10.94 (s, 1H), 9.69 (br. s., 1H), 8.99 (br. s., 1H), 8.56 (s, 1H), 7.81 (br. s., 1H), 7.61 (dd, J = 11.9, 8.2 Hz, 2H), 7.30 (t, J = 7.7 Hz, 1H), 5.95 (br. s., 1H), 3.95 (s, 3H), 3.74 (s, 3H), 3.59 (s, 3H), 2.19 (s, 3H) |
| 61 | ¹H NMR (500 MHz, DMSO-d₆) δ 10.95 (s, 1H), 10.14 (s, 1H), 9.07 (s, 1H), 8.26-8.07 (m, 3H), 7.92 (s, 1H), 7.69 (t, J = 7.1 Hz, 1H), 7.54 (d, J = 8.4 Hz, 1H), 7.41 (t, J = 6.7 Hz, 2H), 7.23 (t, J = 7.9 Hz, 1H), 6.97-6.85 (m, 1H), 3.89 (d, J = 2.4 Hz, 3H), 3.60 (s, 3H) |
| 62 | ¹H NMR (500 MHz, DMSO-d₆) δ 11.01 (s, 1H), 10.36 (s, 1H), 9.11 (s, 1H), 8.57 (s, 1H), 8.29 (br. s., 1H), 7.66 (d, J = 8.1 Hz, 2H), 7.31 (t, J = 7.7 Hz, 1H), 6.64 (br. s., 1H), 5.25 (dt, J = 12.4, 6.1 Hz, 1H), 3.96 (s, 3H), 3.75 (s, 3H), 2.36 (s, 3H), 1.27 (d, J = 6.1 Hz, 6H) |
| 63 | ¹H NMR (500 MHz, DMSO-d₆) δ 11.30 (s, 1H), 10.94 (s, 1H), 9.13 (s, 1H), 8.16 (s, 1H), 8.14 (s, 1H), 7.91 (s, 1H), 7.43 (d, J = 7.9 Hz, 1H), 7.27 (d, J = 7.3 Hz, 1H), 7.22-7.14 (m, 1H), 3.89 (s, 3H), 2.06 (t, J = 5.2 Hz, 1H), 0.86-0.74 (m, 4H) |
| 64 | ¹H NMR (500 MHz, DMSO-d₆) δ 11.36 (s, 1H), 11.04 (s, 1H), 9.16 (s, 1H), 8.25-8.14 (m, 2H), 7.78 (d, J = 1.2 Hz, 1H), 7.51-7.42 (m, 2H), 7.36-7.28 (m, 1H), 6.56 (t, J = 2.1 Hz, 1H), 3.45 (s, 3H), 2.08 (quin, J = 6.1 Hz, 1H), 0.87-0.76 (m, 4H) |
| 65 | ¹H NMR (500 MHz, DMSO-d₆) δ 11.17 (s, 1H), 9.14 (s, 1H), 8.30 (d, J = 4.4 Hz, 1H), 8.22 (d, J = 2.0 Hz, 1H), 7.85 (t, J = 7.2 Hz, 1H), 7.79 (s, 1H), 7.72 (br. s., 1H), 7.59 (d, J = 7.7 Hz, 1H), 7.52 (d, J = 7.7 Hz, 1H), 7.46-7.35 (m, 3H), 7.09 (t, J = 6.2 Hz, 1H), 6.58 (s, 1H) |
| 66 | ¹H NMR (500 MHz, DMSO-d₆) δ 11.08 (s, 1H), 10.25 (br. s., 1H), 9.13 (s, 1H), 8.22 (d, J = 2.4 Hz, 1H), 8.11 (s, 1H), 7.85 (s, 1H), 7.78 (s, 1H), 7.67-7.53 (m, 2H), 7.48-7.41 (m, 1H), 7.40-7.34 (m, 1H), 6.57 (s, 1H), 2.26 (s, 3H) |
| 67 | ¹H NMR (500 MHz, DMSO-d₆) δ 11.30 (s, 1H), 10.94 (br. s., 2H), 9.12 (s, 2H), 8.10 (s, 2H), 7.38 (d, J = 7.7 Hz, 2H), 7.24 (t, J = 7.9 Hz, 2H), 2.88 (s, 3H), 2.05 (br. s., 2H), 1.89 (s, 3H), 0.90-0.74 (m, 4H) |
| 68 | ¹H NMR (500 MHz, DMSO-d₆) δ 11.04 (s, 1H), 10.48 (s, 1H), 9.19 (s, 1H), 8.63 (s, 1H), 8.57 (s, 1H), 8.02 (s, 1H), 7.65 (d, J = 7.7 Hz, 2H), 7.61 (s, 1H), 7.33 (d, J = 7.9 Hz, 1H), 3.96 (s, 3H), 3.76 (s, 3H), 2.65 (q, J = 7.5 Hz, 2H), 1.21 (t, J = 7.6 Hz, 3H) |
| 69 | ¹H NMR (500 MHz, DMSO-d₆) δ 11.33 (s, 1H), 10.98 (s, 1H), 9.13 (s, 1H), 8.16 (s, 1H), 7.97 (d, J = 8.7 Hz, 1H), 7.69 (d, J = 8.7 Hz, 1H), 7.57 (ddd, J = 18.4, 7.8, 1.4 Hz, 2H), 7.44-7.30 (m, 2H), 3.47 (s, 3H), 2.69 (s, 3H), 2.14-2.04 (m, 1H), 0.79-0.64 (m, 2H) |
| 70 | ¹H NMR (400 MHz, DMSO-d₆) δ 11.31 (s, 1H), 10.94 (s, 1H), 9.12 (s, 1H), 8.95 (d, J = 4.8 Hz, 2H), 8.15 (s, 1H), 7.58 (dd, J = 7.9, 1.5 Hz, 1H), 7.55-7.49 (m, 2H), 7.31 (t, J = 7.9 Hz, 1H), 3.68 (s, 3H), 2.08 (quin, J = 6.1 Hz, 1H), 0.90-0.74 (m, 4H) |
| 71 | ¹H NMR (400 MHz, DMSO-d₆) δ 10.94 (s, 1H), 10.21 (s, 1H), 9.09 (s, 1H), 8.96 (d, J = 4.8 Hz, 2H), 8.19 (s, 1H), 7.99 (s, 1H), 7.74-7.65 (m, |

| Compound | ¹H NMR (methanol-d₄ equates CDCl₃:MeOD ~1:1 unless otherwise noted) Occasionally water suppression is used in DMSO-d₆ spectra |
|---|---|
| | 3H), 7.58-7.45 (m, 2H), 7.42-7.33 (m, 1H), 3.70 (s, 3H) |
| 72 | ¹H NMR (500 MHz, DMSO-d₆) δ 11.30 (s, 1H), 10.97 (s, 1H), 9.12 (s, 1H), 8.77-8.65 (m, 1H), 8.17 (s, 1H), 7.91-7.86 (m, 1H), 7.86-7.82 (m, 1H), 7.52 (td, J = 8.0, 1.6 Hz, 2H), 7.39 (ddd, J = 7.2, 4.9, 1.3 Hz, 1H), 7.30 (t, J = 7.9 Hz, 1H), 3.47 (s, 3H), 2.16-2.00 (m, 1H), 0.83 (d, J = 6.1 Hz, 4H) |
| 73 | ¹H NMR (500 MHz, DMSO-d₆) δ 11.08 (s, 1H), 9.16 (s, 1H), 8.26 (d, J = 4.7 Hz, 1H), 8.10 (d, J = 7.7 Hz, 1H), 7.84 (t, J = 7.4 Hz, 1H), 7.65-7.53 (m, 2H), 7.47-7.29 (m, 3H), 7.07 (t, J = 6.1 Hz, 1H), 3.79 (s, 3H), 2.45 (s, 3H) |
| 74 | ¹H NMR (400 MHz, DMSO-d₆) δ 11.01 (s, 1H), 10.23 (s, 1H), 9.17-9.06 (m, 2H), 8.83-8.76 (m, 1H), 8.66 (d, J = 2.6 Hz, 1H), 8.18 (d, J = 2.4 Hz, 1H), 7.98 (s, 1H), 7.78-7.65 (m, 3H), 7.55 (dd, J = 7.8, 1.5 Hz, 1H), 7.48-7.37 (m, 1H), 3.54 (s, 3H) |
| 75 | ¹H NMR (400 MHz, DMSO-d₆) δ 11.33 (s, 1H), 10.99 (s, 1H), 9.15 (s, 1H), 9.07 (d, J = 1.5 Hz, 1H), 8.79 (dd, J = 2.6, 1.6 Hz, 1H), 8.65 (d, J = 2.6 Hz, 1H), 8.16 (s, 1H), 7.57 (ddd, J = 7.9, 6.8, 1.5 Hz, 2H), 7.44-7.29 (m, 1H), 3.51 (s, 3H), 2.19-2.02 (m, 1H), 0.91-0.76 (m, 4H) |
| 76 | ¹H NMR (500 MHz, DMSO-d₆) δ 11.00 (s, 1H), 10.17 (s, 1H), 9.09 (s, 1H), 8.57 (s, 1H), 8.28-8.13 (m, 2H), 7.77-7.53 (m, 4H), 7.32 (t, J = 7.9 Hz, 1H), 6.98-6.86 (m, 1H), 3.95 (s, 3H), 3.75 (s, 3H) |
| 77 | ¹H NMR (500 MHz, DMSO-d₆) δ 10.99 (s, 1H), 10.20 (s, 1H), 9.08 (s, 1H), 8.80-8.63 (m, 1H), 8.18 (d, J = 2.6 Hz, 1H), 7.99 (s, 1H), 7.93-7.82 (m, 2H), 7.75-7.67 (m, 2H), 7.62 (dd, J = 8.0, 1.4 Hz, 1H), 7.51 (dd, J = 7.8, 1.5 Hz, 1H), 7.43-7.33 (m, 2H), 3.50 (s, 3H) |
| 78 | ¹H NMR (400 MHz, DMSO-d₆) δ 11.33 (s, 1H), 10.99 (s, 1H), 9.25 (dd, J = 5.0, 1.7 Hz, 1H), 9.14 (s, 1H), 8.17 (s, 1H), 8.05 (dd, J = 8.6, 1.5 Hz, 1H), 7.79 (dd, J = 8.6, 5.1 Hz, 1H), 7.59 (ddd, J = 11.5, 7.9, 1.5 Hz, 2H), 7.41-7.34 (m, 1H), 3.47 (s, 3H), 2.09 (quin, J = 6.2 Hz, 1H), 0.83 (d, J = 6.2 Hz, 4H) |
| 79 | ¹H NMR (500 MHz, DMSO-d₆) δ 10.98 (s, 1H), 10.22 (s, 1H), 9.25 (d, J = 3.7 Hz, 1H), 9.09 (s, 1H), 8.18 (s, 1H), 8.07 (d, J = 8.1 Hz, 1H), 7.97 (s, 1H), 7.80 (dd, J = 8.4, 5.0 Hz, 1H), 7.70 (d, J = 6.1 Hz, 3H), 7.55 (d, J = 7.1 Hz, 1H), 7.49-7.38 (m, 1H), 3.56-3.41 (m, 3H) |
| 80 | ¹H NMR (400 MHz, DMSO-d₆) δ 11.02 (s, 1H), 10.18 (s, 1H), 9.10 (m, 1H), 8.25 (s, 1H), 8.21 (m, 1H), 7.72 (m, 2H), 7.63 (m, 1H), 7.56 (d, J = 8.0 Hz, 1H), 7.33 (t, J = 8.0 Hz, 1H), 7.16 (m, 1H), 6.93 (m, 1H), 3.48 (s, 3H), 2.85 (d, J = 4.8 Hz, 3H), 2.65 (s, 3H), 2.29 (s, 3H) |
| 81 | ¹H NMR (400 MHz, DMSO-d₆) δ 11.01 (s, 1H), 10.18 (s, 1H), 10.49 (bs, 1H), 9.14 (m, 1H), 8.23 (d, J = 4.4 Hz, 1H), 8.18 (s, 1H), 7.89 (bs, 1H), 7.78 (t, J = 3.6 Hz, 1H), 7.63 (d, J = 8.0 Hz 1H), 7.56 (m, 1H), 7.49 (m, 1H), 7.33 (m, 1H), 7.00 (m, 1H), 3.72 (s, 3H), 2.88 (d, J = 4.4 Hz, 3H), 2.70 (s, 3H) |
| 82 | ¹H NMR (400 MHz, DMSO-d₆) δ 11.31 (s, 1H), 10.92 (s, 1H), 9.12 (s, 1H), 8.78 (d, J = 5.1 Hz, 1H), 8.14 (s, 1H), 7.56 (dd, J = 7.9, 1.5 Hz, 1H), 7.50 (dd, J = 7.8, 1.5 Hz, 1H), 7.38 (d, J = 5.1 Hz, 1H), 7.32-7.26 (m, 1H), 3.69 (s, 3H), 2.54 (s, 3H), 2.08 (quin, J = 6.1 Hz, 1H), 0.82 (d, J = 5.9 Hz, 4H) |
| 83 | ¹H NMR (400 MHz, DMSO-d₆) δ 10.93 (s, 1H), 10.21 (s, 1H), 9.09 (s, 1H), 8.78 (d, J = 5.1 Hz, 1H), 8.19 (t, J = 1.7 Hz, 1H), 7.99 (s, 1H), 7.75-7.61 (m, 3H), 7.47 (dd, J = 7.8, 1.5 Hz, 1H), 7.41-7.28 (m, 2H), 3.71 (s, 3H), 2.55 (s, 3H) |
| 84 | ¹H NMR (500 MHz, DMSO-d₆) δ 10.98 (s, 1H), 10.10 (s, 1H), 9.11 (s, 1H), 8.55 (s, 1H), 8.25-8.05 (m, 2H), 7.71-7.56 (m, 3H), 7.30 (t, J = 7.7 Hz, 1H), 6.89 (d, J = 4.7 Hz, 1H), 5.41 (d, J = 3.7 Hz, 1H), 4.67 (br. s., 1H), 3.95 (s, 3H), 3.75 (s, 3H), 1.31 (d, J = 6.4 Hz, 3H) |
| 85 | ¹H NMR (500 MHz, DMSO-d₆) δ 10.92 (s, 1H), 9.67 (s, 1H), 8.99 (s, 1H), 8.17 (s, 1H), 7.92 (s, 1H), 7.77 (br. s., 1H), 7.39 (d, J = 7.7 Hz, 2H), 7.21 (t, J = 7.7 Hz, 1H), 5.95 (br. s., 1H), 3.90 (s, 4H), 3.58 (d, J = 11.4 Hz, 6H), 2.19 (s, 3H) |
| 86 | ¹H NMR (400 MHz, DMSO-d₆) δ □□.33 (s, 1H), 11.00 (s, 1H), 9.31 (d, J = 1.2 Hz, 1H), 9.15 (s, 1H), 8.89 (d, J = 5.4 Hz, 1H), 8.15 (s, 1H), 7.99 (dd, J = 5.3, 1.4 Hz, 1H), 7.68 (dd, J = 7.8, 1.5 Hz, 1H), 7.62 (dd, J = 7.9, 1.5 Hz, 1H), 7.37 (t, J = 7.9 Hz, 1H), 3.55 (s, 3H), 2.09 (quin, J = 6.2 Hz, 1H), 0.87-0.77 (m, 4H) |
| 87 | ¹H NMR (500 MHz, DMSO-d₆) δ 11.04 (s, 1H), 9.16 (s, 1H), 8.57 (s, 1H), 8.38 (br. s., 1H), 7.67 (d, J = 7.7 Hz, 2H), 7.45-7.23 (m, 2H), 4.36 (s, 2H), 3.95 (s, 3H), 3.75 (s, 3H), 2.40 (s, 3H) |
| 88 | ¹H NMR (500 MHz, DMSO-d₆) δ 11.07 (s, 1H), 9.21 (s, 1H), 8.58 (s, 1H), 8.14 (br. s., 1H), 7.70 (d, J = 7.7 Hz, 1H), 7.64 (d, J = 8.1 Hz, 1H), 7.39 (br. s., 1H), 7.33 (t, J = 7.7 Hz, 1H), 3.96 (s, 3H), 3.75 (s, 3H), 2.50 (br. s., 3H), 2.45 (s, 3H) |
| 89 | ¹H NMR (500 MHz, DMSO-d₆) δ 11.01 (br. s., 1H), 10.23 (br. s., 1H), 9.31 (br. s., 1H), 9.11 (br. s., 1H), 8.89 (d, J = 4.4 Hz, 1H), 8.18 (br. s., 1H), 8.04-7.91 (m, 2H), 7.76-7.61 (m, 4H), 7.43 (t, J = 7.2 Hz, 1H), 3.56 (s, 3H) |
| 90 | ¹H NMR (400 MHz, DMSO-d₆) δ 11.33 (s, 1H), 10.96 (s, 1H), 10.49 (bs, 1H), 9.18 (m, 1H), 8.17 (s, 1H), 8.11 (s, 1H), 7.61 (dd, J = 8.0, 1.2 Hz, 1H), 7.42 (dd, J = 8.0, 1.2 Hz, 1H), 7.27 (t, J = 8.0 Hz, 1H), 3.62 (s, 3H), 2.87 (d, J = 4.8 Hz, 3H), 2.51 (s, 3H) 2.08 (m, 1H), 0.81 (m, 4H) |
| 91 | ¹H NMR (400 MHz, DMSO-d₆) δ 10.95 (s, 1H), 10.16 (s, 1H), 9.08 (s, |

| Compound | ¹H NMR (methanol-d₄ equates CDCl₃:MeOD ~1:1 unless otherwise noted) Occasionally water suppression is used in DMSO-d₆ spectra |
|---|---|
| | 1H), 8.96 (d, J = 4.9 Hz, 2H), 8.23 (s, 1H), 8.20 (dd, J = 5.0, 1.4 Hz, 1H), 7.78-7.64 (m, 2H), 7.57 (d, J = 8.4 Hz, 1H), 7.55-7.44 (m, 2H), 7.40-7.27 (m, 1H), 6.92 (dd, J = 6.7, 5.3 Hz, 1H), 3.70 (s, 3H) |
| 92 | ¹H NMR (400 MHz, DMSO-d₆) δ 10.91 (s, 1H), 9.69 (s, 1H), 8.99 (s, 1H), 8.95 (d, J = 4.9 Hz, 2H), 7.80 (br. s., 1H), 7.69 (dd, J = 7.9, 1.5 Hz, 1H), 7.51 (t, J = 4.9 Hz, 1H), 7.48 (dd, J = 7.8, 1.5 Hz, 1H), 7.37-7.26 (m, 1H), 3.69 (s, 3H), 3.59 (s, 3H), 2.20 (s, 3H) |
| 93 | ¹H NMR (500 MHz, DMSO-d₆) δ 10.94 (s, 1H), 9.68 (s, 1H), 9.00 (s, 1H), 7.95-7.72 (m, 2H), 7.65 (d, J = 7.7 Hz, 1H), 7.51 (d, J = 8.1 Hz, 1H), 7.26 (t, J = 7.7 Hz, 1H), 6.75 (d, J = 1.3 Hz, 1H), 5.96 (br. s., 1H), 3.92 (s, 4H), 3.59 (s, 6H), 2.20 (s, 3H) |
| 94 | ¹H NMR (500 MHz, DMSO-d₆) δ 11.04 (s, 1H), 10.61 (s, 1H), 9.18 (s, 1H), 8.72 (s, 1H), 8.57 (s, 1H), 8.49 (d, J = 5.7 Hz, 1H), 8.08 (s, 1H), 7.72-7.60 (m, 3H), 7.35 (t, J = 7.9 Hz, 1H), 3.96 (s, 3H), 3.75 (s, 3H) |
| 95 | ¹H NMR (500 MHz, DMSO-d₆) δ 11.34 (s, 1H), 10.96 (s, 1H), 9.17 (s, 1H), 8.09 (s, 1H), 8.04 (d, J = 7.7 Hz, 1H), 7.51 (d, J = 7.7 Hz, 1H), 7.41 (s, 1H), 7.32 (t, J = 8.1 Hz, 1H), 3.74 (s, 3H), 2.45 (s, 3H), 2.06 (d, J = 4.4 Hz, 1H), 0.85-0.77 (m, 4H) |
| 96 | ¹H NMR (500 MHz, DMSO-d₆) δ 11.00 (s, 1H), 10.18 (s, 1H), 9.31 (s, 1H), 9.10 (s, 1H), 8.89 (d, J = 5.0 Hz, 1H), 8.24-8.11 (m, 2H), 8.01 (d, J = 5.0 Hz, 1H), 7.79-7.63 (m, 3H), 7.56 (d, J = 8.1 Hz, 1H), 7.41 (t, J = 7.9 Hz, 1H), 6.97-6.87 (m, 1H), 3.57 (s, 3H) |
| 97 | ¹H NMR (500 MHz, DMSO-d₆) δ 11.02 (s, 1H), 9.24 (s, 1H), 8.09 (d, J = 8.1 Hz, 2H), 7.61 (d, J = 7.7 Hz, 1H), 7.46-7.29 (m, 3H), 3.77 (s, 3H), 2.44 (d, J = 7.7 Hz, 9H) |
| 98 | ¹H NMR (500 MHz, DMSO-d₆) δ 11.01 (s, 1H), 10.36 (s, 1H), 9.17 (s, 1H), 8.58 (s, 1H), 8.42 (s, 1H), 7.87 (s, 1H), 7.64 (t, J = 7.6 Hz, 2H), 7.32 (t, J = 7.7 Hz, 1H), 7.16 (s, 1H), 5.26 (dt, J = 12.2, 6.2 Hz, 1H), 3.96 (s, 3H), 3.75 (s, 3H), 1.30 (d, J = 6.1 Hz, 6H) |
| 99 | ¹H NMR (500 MHz, DMSO-d₆) δ 11.07 (s, 1H), 9.11 (s, 1H), 8.57 (s, 1H), 8.14 (br. s., 1H), 7.94 (s, 1H), 7.65 (dd, J = 14.5, 7.7 Hz, 2H), 7.36-7.23 (m, 1H), 6.62 (s, 1H), 3.95 (s, 3H), 3.80-3.70 (m, 4H), 3.31 (br. s., 1H), 3.23 (br. s., 2H), 2.33 (s, 3H) |
| 100 | ¹H NMR (500 MHz, DMSO-d₆) δ 10.90 (s, 1H), 9.69 (s, 1H), 9.02 (s, 1H), 8.01 (d, J = 7.7 Hz, 1H), 7.68 (br. s., 1H), 7.61 (d, J = 7.7 Hz, 1H), 7.40 (s, 1H), 7.35 (t, J = 7.9 Hz, 1H), 5.94 (br. s., 1H), 3.75 (s, 3H), 2.45 (s, 3H), 2.17 (s, 3H) |
| 101 | ¹H NMR (500 MHz, DMSO-d₆) δ 11.32 (s, 1H), 10.92 (s, 1H), 9.16 (s, 1H), 8.07 (s, 1H), 8.01 (d, J = 7.4 Hz, 1H), 7.66 (d, J = 7.4 Hz, 1H), 7.50 (d, J = 7.4 Hz, 1H), 7.31 (t, J = 7.9 Hz, 1H), 3.74 (s, 3H), 2.05 (t, J = 4.7 Hz, 1H), 0.88-0.72 (m, 4H) |
| 102 | ¹H NMR (500 MHz, DMSO-d₆) δ 11.05 (s, 1H), 9.10 (s, 1H), 8.57 (s, |

| Compound | ¹H NMR (methanol-d₄ equates CDCl₃:MeOD ~1:1 unless otherwise noted) Occasionally water suppression is used in DMSO-d₆ spectra |
|---|---|
| | 1H), 8.18 (br. s., 1H), 7.90 (br. s., 1H), 7.73 (d, J = 8.1 Hz, 1H), 7.65 (dd, J = 16.7, 7.9 Hz, 2H), 7.45 (d, J = 8.4 Hz, 1H), 7.33 (t, J = 7.7 Hz, 1H), 7.24-7.00 (m, 1H), 4.45 (s, 2H), 3.95 (s, 3H), 3.75 (s, 3H) |
| 103 | ¹H NMR (500 MHz, DMSO-d₆) δ 11.05 (s, 1H), 9.15 (s, 1H), 8.57 (s, 1H), 8.44-8.32 (m, 2H), 7.68 (d, J = 6.4 Hz, 2H), 7.33 (t, J = 7.9 Hz, 1H), 7.28 (d, J = 5.4 Hz, 1H), 3.96 (s, 3H), 3.75 (s, 3H), 2.43 (s, 3H) |
| 104 | ¹H NMR (500 MHz, DMSO-d₆) δ 11.02 (s, 1H), 9.08 (s, 1H), 8.05 (d, J = 8.1 Hz, 1H), 7.67 (s, 1H), 7.58 (d, J = 7.7 Hz, 1H), 7.46-7.31 (m, 2H), 5.91 (s, 1H), 3.77 (s, 3H), 2.88 (s, 3H), 2.72 (s, 3H), 2.18 (s, 3H) |
| 105 | ¹H NMR (500 MHz, DMSO-d₆) δ 11.34 (s, 1H), 10.98 (s, 1H), 9.16 (br. s., 2H), 8.45 (s, 1H), 8.13 (s, 1H), 7.67 (d, J = 8.1 Hz, 1H), 7.46 (d, J = 8.1 Hz, 1H), 7.34-7.24 (m, 1H), 3.62 (s, 3H), 2.07 (br. s., 1H), 0.90-0.67 (m, 4H) |
| 106 | ¹H NMR (500 MHz, DMSO-d₆) δ 11.11 (s, 1H), 9.17 (d, J = 11.4 Hz, 2H), 8.47 (s, 1H), 8.14 (s, 1H), 7.72 (d, J = 7.7 Hz, 1H), 7.54 (d, J = 7.1 Hz, 2H), 7.45-7.32 (m, 2H), 3.65 (s, 3H), 2.28 (s, 3H) |
| 107 | ¹H NMR (500 MHz, DMSO-d₆) δ 11.10 (s, 1H), 9.28-8.99 (m, 2H), 8.47 (s, 1H), 7.72 (d, J = 7.7 Hz, 1H), 7.58-7.43 (m, 2H), 7.35 (t, J = 7.9 Hz, 1H), 5.92 (br. s., 1H), 3.72-3.53 (m, 6H), 2.20 (s, 3H) |
| 108 | ¹H NMR (500 MHz, DMSO-d₆) δ 11.07 (s, 1H), 9.21 (s, 1H), 8.58 (s, 1H), 8.14 (br. s., 1H), 7.70 (d, J = 7.7 Hz, 1H), 7.64 (d, J = 8.1 Hz, 1H), 7.39 (br. s., 1H), 7.33 (t, J = 7.7 Hz, 1H), 3.96 (s, 3H), 3.75 (s, 3H), 2.50 (br. s., 3H), 2.45 (s, 3H) |
| 109 | ¹H NMR (500 MHz, DMSO-d₆) δ 11.04 (s, 1H), 10.48 (s, 1H), 9.20 (s, 1H), 8.59 (d, J = 13.8 Hz, 2H), 8.00 (s, 1H), 7.65 (d, J = 7.4 Hz, 2H), 7.60 (s, 1H), 7.34 (t, J = 7.9 Hz, 1H), 3.96 (s, 3H), 3.76 (s, 3H), 2.38 (s, 3H) |
| 110 | ¹H NMR (500 MHz, DMSO-d₆) δ 11.13 (s, 1H), 9.13 (s, 1H), 8.58 (s, 1H), 8.29 (d, J = 5.4 Hz, 1H), 7.75 (d, J = 7.4 Hz, 1H), 7.61 (d, J = 7.4 Hz, 1H), 7.39-7.30 (m, 2H), 7.24 (br. s., 1H), 7.11 (d, J = 5.4 Hz, 1H), 4.59 (s, 2H), 3.95 (s, 3H), 3.75 (s, 3H), 3.52 (br. s., 1H) |
| 111 | ¹H NMR (400 MHz, DMSO-d₆) δ 10.91 (s, 1H), 9.78 (s, 1H), 9.01 (s, 1H), 8.95 (d, J = 4.9 Hz, 2H), 7.74 (br. s., 1H), 7.69 (dd, J = 7.9, 1.5 Hz, 1H), 7.56-7.44 (m, 3H), 7.40-7.28 (m, 1H), 3.72 (s, 3H), 3.69 (s, 3H) |
| 112 | ¹H NMR (400 MHz, DMSO-d₆) δ 10.98 (s, 1H), 10.48 (s, 1H), 9.14 (s, 1H), 9.02-8.92 (m, 3H), 8.22 (dd, J = 2.6, 1.5 Hz, 1H), 8.13 (d, J = 2.7 Hz, 1H), 8.01 (s, 1H), 7.69 (dd, J = 7.9, 1.5 Hz, 1H), 7.56-7.48 (m, 2H), 7.43-7.31 (m, 1H), 3.70 (s, 3H) |
| 113 | ¹H NMR (500 MHz, DMSO-d₆) δ 10.96 (s, 1H), 10.31 (s, 1H), 9.13 (s, 1H), 8.96 (d, J = 4.9 Hz, 2H), 8.91 (d, J = 1.4 Hz, 1H), 8.12 (d, J = 0.8 Hz, |

| Compound | ¹H NMR (methanol-d₄ equates CDCl₃:MeOD ~1:1 unless otherwise noted) Occasionally water suppression is used in DMSO-d₆ spectra |
|---|---|
| 114 | 1H), 7.92 (s, 1H), 7.68 (dd, J = 7.9, 1.5 Hz, 1H), 7.55-7.45 (m, 2H), 7.35 (t, J = 7.9 Hz, 1H), 3.70 (s, 3H), 2.40 (s, 3H) ¹H NMR (500 MHz, DMSO-d₆) δ 11.06 (s, 1H), 10.59 (s, 1H), 9.17 (s, 1H), 8.57 (s, 1H), 8.22 (br. s., 1H), 7.67 (t, J = 8.2 Hz, 2H), 7.40-7.25 (m, 2H), 4.32 (s, 2H), 3.96 (s, 3H), 3.75 (s, 3H), 3.26 (s, 3H), 2.36 (s, 3H) |
| 115 | ¹H NMR (500 MHz, DMSO-d₆) δ 11.10 (s, 1H), 10.56 (s, 1H), 9.20 (s, 1H), 8.63 (s, 1H), 8.48 (br. s., 1H), 7.73 (dd, J = 7.7, 3.4 Hz, 2H), 7.38 (t, J = 7.7 Hz, 1H), 7.20 (s, 1H), 4.02 (s, 3H), 3.82 (s, 3H), 2.64 (q, J = 7.5 Hz, 2H), 2.46 (s, 3H), 1.24 (t, J = 7.4 Hz, 3H) |
| 116 | ¹H NMR (500 MHz, DMSO-d₆) δ 11.31 (s, 1H), 10.94 (s, 1H), 9.12 (s, 1H), 9.04 (s, 2H), 8.15 (s, 1H), 7.59 (dd, J = 7.9, 1.2 Hz, 1H), 7.52 (dd, J = 7.8, 1.5 Hz, 1H), 7.31 (t, J = 7.9 Hz, 1H), 3.67 (s, 3H), 2.08 (t, J = 6.0 Hz, 1H), 0.88-0.75 (m, 4H) |
| 117 | ¹H NMR (500 MHz, DMSO-d₆) δ 10.94 (s, 1H), 10.17 (s, 1H), 9.12 (s, 1H), 8.13 (br. s., 2H), 8.00 (d, J = 7.7 Hz, 1H), 7.72-7.65 (m, 2H), 7.65-7.50 (m, 2H), 7.36 (t, J = 7.9 Hz, 1H), 6.91 (t, J = 5.9 Hz, 1H), 3.77 (s, 3H) |
| 118 | ¹H NMR (400 MHz, DMSO-d₆) δ 11.00 (s, 1H), 10.59 (s, 1H), 9.17 (s, 1H), 8.96 (d, J = 4.8 Hz, 2H), 8.71 (d, J = 0.9 Hz, 1H), 8.48 (d, J = 5.9 Hz, 1H), 8.07 (s, 1H), 7.77-7.62 (m, 2H), 7.58-7.47 (m, 2H), 7.42-7.33 (m, 1H), 3.70 (s, 3H) |
| 119 | ¹H NMR (400 MHz, DMSO-d₆) δ 10.98 (s, 1H), 10.46 (s, 1H), 9.18 (s, 1H), 8.96 (d, J = 4.8 Hz, 2H), 8.59 (d, J = 0.9 Hz, 1H), 7.98 (s, 1H), 7.70 (dd, J = 7.9, 1.5 Hz, 1H), 7.60 (s, 1H), 7.55-7.47 (m, 2H), 7.41-7.32 (m, 1H), 3.70 (s, 3H), 2.37 (s, 3H) |
| 120 | ¹H NMR (500 MHz, DMSO-d₆) δ 10.99 (s, 1H), 10.09 (s, 1H), 9.10 (br. s., 1H), 8.56 (s, 1H), 8.22 (s, 1H), 8.10 (d, J = 5.0 Hz, 1H), 7.72 (s, 1H), 7.63 (dd, J = 17.2, 7.7 Hz, 2H), 7.31 (t, J = 7.9 Hz, 1H), 6.98 (d, J = 4.7 Hz, 1H), 5.22 (s, 1H), 3.95 (s, 3H), 3.75 (s, 3H), 1.40 (s, 6H) |
| 121 | ¹H NMR (400 MHz, DMSO-d₆) δ 10.99 (s, 1H), 10.48 (s, 1H), 9.12 (s, 1H), 8.95 (d, J = 4.8 Hz, 2H), 8.37 (s, 1H), 7.73 (dd, J = 7.9, 1.3 Hz, 1H), 7.58-7.47 (m, 2H), 7.35 (t, J = 7.9 Hz, 1H), 7.14 (s, 1H), 3.70 (s, 3H), 2.39 (s, 3H), 2.31 (s, 3H) |
| 122 | ¹H NMR (400 MHz, DMSO-d₆) δ 10.98 (s, 1H), 10.35 (s, 1H), 9.12 (s, 1H), 8.96 (d, J = 5.1 Hz, 2H), 7.99-7.91 (m, 2H), 7.69 (dd, J = 8.1, 1.5 Hz, 1H), 7.56-7.45 (m, 3H), 7.32 (t, J = 7.9 Hz, 1H), 3.71 (s, 3H) |
| 123 | ¹H NMR (400 MHz, DMSO-d₆) δ 10.99 (s, 1H), 10.46 (s, 1H), 9.14 (s, 1H), 8.96 (d, J = 4.8 Hz, 2H), 8.81 (dd, J = 4.6, 1.3 Hz, 1H), 8.07-7.96 (m, 2H), 7.70 (dd, J = 7.9, 1.5 Hz, 1H), 7.60 (dd, J = 9.0, 4.6 Hz, 1H), 7.55-7.49 (m, 2H), 7.32 (t, J = 7.9 Hz, 1H), 3.71 (s, 3H) |
| 124 | ¹H NMR (500 MHz, DMSO-d₆) δ 10.96 (s, 1H), 9.15 (br. s., 1H), 8.11- 7.96 (m, 2H), 7.79-7.51 (m, 4H), 7.37 (t, J = 7.9 Hz, 1H), 3.76 (s, 3H), 2.25 (s, 3H) |
| 125 | ¹H NMR (500 MHz, DMSO-d₆) δ 11.21 (s, 1H), 10.59 (s, 1H), 9.02 (s, 1H), 7.95 (s, 1H), 7.34 (d, J = 7.7 Hz, 1H), 7.22-7.16 (m, 1H), 7.15-7.11 (m, 1H), 6.99 (t, J = 7.4 Hz, 1H), 3.79 (s, 3H), 2.11-1.89 (m, 1H), 0.88-0.70 (m, 4H) |
| 126 | ¹H NMR (500 MHz, DMSO-d₆) δ 11.33 (s, 1H), 11.00 (s, 1H), 9.25-9.07 (m, 2H), 8.24-8.11 (m, 2H), 8.01-7.87 (m, 2H), 7.45 (d, J = 7.7 Hz, 1H), 7.30 (t, J = 7.9 Hz, 1H), 3.63 (s, 3H), 2.07 (d, J = 5.4 Hz, 1H), 0.90-0.69 (m, 4H) |
| 127 | ¹H NMR (500 MHz, DMSO-d₆) δ 10.95 (s, 1H), 10.00 (s, 1H), 9.05 (s, 1H), 8.54 (s, 1H), 8.18 (s, 1H), 8.00 (d, J = 5.7 Hz, 1H), 7.61 (dd, J = 12.6, 7.9 Hz, 2H), 7.30 (t, J = 7.7 Hz, 1H), 7.17 (s, 1H), 6.56-6.52 (m, 1H), 4.06 (q, J = 7.1 Hz, 2H), 3.94 (s, 3H), 3.73 (s, 3H), 1.33 (t, J = 6.9 Hz, 3H) |
| 128 | ¹H NMR (500 MHz, DMSO-d₆) δ 11.11 (s, 1H), 9.11 (s, 1H), 8.58 (s, 1H), 8.22 (d, J = 5.4 Hz, 1H), 7.71 (d, J = 7.4 Hz, 1H), 7.61 (d, J = 7.7 Hz, 1H), 7.51 (br. s., 1H), 7.33 (t, J = 7.9 Hz, 1H), 7.26 (br. s., 1H), 7.02 (d, J = 4.7 Hz, 1H), 3.95 (s, 3H), 3.75 (s, 3H), 2.65 (q, J = 7.1 Hz, 2H), 1.19 (t, J = 7.4 Hz, 3H) |
| 129 | ¹H NMR (500 MHz, DMSO-d₆) δ 11.06 (s, 1H), 9.22 (d, J = 1.3 Hz, 1H), 9.14 (s, 1H), 8.22 (d, J = 1.3 Hz, 1H), 8.11 (s, 1H), 7.93 (d, J = 7.7 Hz, 1H), 7.74 (br. s., 1H), 7.55 (d, J = 7.4 Hz, 2H), 7.36 (t, J = 7.9 Hz, 1H), 3.66 (s, 3H), 2.27 (s, 3H) |
| 130 | ¹H NMR (500 MHz, DMSO-d₆) δ 11.01 (s, 1H), 10.48 (s, 1H), 9.20 (s, 1H), 9.12 (s, 1H), 8.36 (br. s., 1H), 8.20 (s, 1H), 7.93 (d, J = 8.1 Hz, 1H), 7.59 (d, J = 7.7 Hz, 1H), 7.34 (t, J = 7.9 Hz, 1H), 7.10 (s, 1H), 3.65 (s, 3H), 2.34 (s, 3H), 2.29 (s, 3H) |
| 131 | ¹H NMR (500 MHz, DMSO-d₆) δ 11.14 (s, 1H), 9.21 (s, 1H), 9.08 (s, 1H), 8.21 (s, 1H), 8.02-7.87 (m, 1H), 7.54 (d, J = 7.7 Hz, 1H), 7.36 (t, J = 7.9 Hz, 1H), 5.91 (s, 1H), 3.66 (s, 3H), 2.21 (s, 4H) |
| 132 | ¹H NMR (500 MHz, DMSO-d₆) δ 11.00 (s, 1H), 10.16 (s, 1H), 9.21 (s, 1H), 9.10 (s, 1H), 8.26-8.13 (m, 3H), 7.90 (d, J = 7.7 Hz, 1H), 7.75-7.66 (m, 1H), 7.61-7.50 (m, 2H), 7.35 (t, J = 7.9 Hz, 1H), 6.99-6.85 (m, 1H), 3.65 (s, 3H) |
| 133 | ¹H NMR (500 MHz, DMSO-d₆) δ 11.06 (s, 1H), 9.07 (br. s., 1H), 8.58 (s, 1H), 8.20 (d, J = 6.1 Hz, 1H), 7.71 (d, J = 7.4 Hz, 1H), 7.60 (d, J = 7.7 Hz, 1H), 7.47-7.25 (m, 2H), 6.93 (br. s., 1H), 6.82 (br. s., 1H), 3.95 (s, 3H), 3.90 (s, 3H), 3.75 (s, 3H) |

| Compound | $^1$H NMR (methanol-d$_4$ equates CDCl$_3$:MeOD ~1:1 unless otherwise noted) Occasionally water suppression is used in DMSO-d$_6$ spectra |
|---|---|
| 134 | $^1$H NMR (500 MHz, DMSO-d$_6$) δ 11.00 (s, 1H), 10.87 (s, 1H), 10.53 (s, 1H), 9.11 (s, 1H), 8.56 (s, 1H), 8.40 (br. s., 1H), 7.94 (br. s., 1H), 7.66 (t, J = 7.9 Hz, 2H), 7.31 (t, J = 7.9 Hz, 1H), 3.95 (s, 3H), 3.74 (s, 3H), 2.36 (s, 3H), 2.07-1.91 (m, 1H), 0.83 (d, J = 4.7 Hz, 4H) |
| 135 | $^1$H NMR (500 MHz, DMSO-d$_6$) δ 11.11 (s, 1H), 9.13 (s, 1H), 8.57 (s, 1H), 8.26 (d, J = 5.4 Hz, 1H), 7.71 (d, J = 7.7 Hz, 1H), 7.62 (d, J = 7.7 Hz, 1H), 7.51 (br. s., 1H), 7.42-7.29 (m, 2H), 7.02 (d, J = 5.0 Hz, 1H), 4.48 (s, 2H), 3.95 (s, 3H), 3.75 (s, 3H), 3.35 (s, 3H) |
| 136 | $^1$H NMR (500 MHz, DMSO-d$_6$) δ 11.33 (s, 1H), 11.00 (s, 1H), 9.15 (s, 1H), 8.13 (d, J = 16.2 Hz, 2H), 7.69 (d, J = 7.4 Hz, 1H), 7.46 (d, J = 7.4 Hz, 1H), 7.29 (t, J = 7.7 Hz, 1H), 4.23 (s, 3H), 3.64 (s, 3H), 2.11-2.01 (m, 1H), 0.88-0.73 (m, 4H) |
| 137 | $^1$H NMR (500 MHz, DMSO-d$_6$) δ 10.99 (s, 1H), 10.47 (s, 1H), 9.10 (s, 1H), 8.35 (s, 1H), 8.11 (s, 1H), 7.93 (s, 1H), 7.70 (d, J = 7.4 Hz, 1H), 7.60 (d, J = 8.1 Hz, 1H), 7.33 (t, J = 7.9 Hz, 1H), 7.08 (s, 1H), 4.21 (s, 3H), 3.88 (s, 3H), 2.88 (s, 3H), 2.72 (s, 3H) |
| 138 | $^1$H NMR (500 MHz, DMSO-d$_6$) δ 11.32 (s, 1H), 10.95 (s, 1H), 9.15 (s, 1H), 8.45 (s, 1H), 8.11 (s, 1H), 7.93 (d, J = 7.4 Hz, 1H), 7.42 (d, J = 7.7 Hz, 1H), 7.29 (t, J = 7.9 Hz, 1H), 4.13 (s, 3H), 3.65 (s, 3H), 2.07 (d, J = 5.0 Hz, 1H), 0.88-0.71 (m, 4H) |
| 139 | $^1$H NMR (500 MHz, DMSO-d$_6$) δ 11.33 (s, 1H), 10.93 (s, 1H), 9.13 (s, 1H), 8.09 (s, 1H), 7.48 (d, J = 7.9 Hz, 1H), 7.28 (d, J = 7.3 Hz, 1H), 7.21-7.15 (m, 1H), 3.82 (s, 3H), 2.07 (br. s., 1H), 0.86-0.78 (m, 4H) |
| 140 | $^1$H NMR (500 MHz, DMSO-d$_6$) δ 10.85 (s, 1H), 10.08 (s, 1H), 9.07 (s, 1H), 8.06 (s, 1H), 7.94 (s, 1H), 7.85 (s, 1H), 7.79 (s, 1H), 7.73-7.56 (m, 4H), 7.49 (t, J = 7.9 Hz, 1H), 7.36 (d, J = 6.7 Hz, 1H), 2.25 (s, 3H) |
| 141 | $^1$H NMR (500 MHz, DMSO-d$_6$) δ 13.86-13.54 (m, 1H), 11.31 (br. s., 1H), 10.95 (br. s., 1H), 9.12 (br. s., 1H), 8.12 (br. s., 1H), 7.83-7.60 (m, 1H), 7.51 (d, J = 18.3 Hz, 1H), 7.26 (br. s., 1H), 3.68 (br. s., 3H), 2.45-2.25 (m, 3H), 2.10-1.98 (m, 1H), 0.91-0.71 (m, 4H) |
| 142 | $^1$H NMR (500 MHz, DMSO-d$_6$) δ 10.95 (s, 1H), 10.06 (s, 1H), 9.09 (br. s., 1H), 8.06 (s, 1H), 7.97-7.85 (m, 1H), 7.62 (d, J = 5.5 Hz, 2H), 7.33 (br. s., 1H), 3.69 (br. s., 3H), 2.24 (s, 3H) |
| 143 | $^1$H NMR (500 MHz, DMSO-d$_6$) δ 11.37 (s, 1H), 10.95 (s, 1H), 9.15 (br. s., 1H), 8.07 (s, 1H), 7.72 (d, J = 5.7 Hz, 1H), 7.41 (br. s., 2H), 7.25 (s, 1H), 7.15 (s, 1H), 7.04 (s, 1H), 3.97 (s, 3H), 2.07 (br. s., 1H), 0.91-0.69 (m, 4H) |
| 144 | $^1$H NMR (500 MHz, DMSO-d$_6$) δ 11.06 (br. s., 1H), 9.13 (br. s., 1H), 8.37 (br. s., 1H), 7.83-7.64 (m, 2H), 7.40 (br. s., 1H), 7.11 (br. s., 1H), 4.45 (s, 3H), 3.75 (s, 3H), 2.40-2.24 (m, 6H) |
| 145 | $^1$H NMR (500 MHz, DMSO-d$_6$) δ 11.13 (s, 1H), 9.14 (s, 1H), 8.30 (d, J = 4.4 Hz, 1H), 7.93-7.71 (m, 3H), 7.54-7.32 (m, 3H), 7.10-7.02 (m, 1H), 3.99 (s, 3H) |
| 146 | $^1$H NMR (500 MHz, DMSO-d$_6$) δ 11.34 (s, 1H), 11.01 (s, 1H), 9.15 (s, 1H), 8.15 (s, 1H), 7.70 (d, J = 7.4 Hz, 1H), 7.63 (d, J = 7.7 Hz, 1H), 7.37 (t, J = 7.9 Hz, 1H), 4.45 (s, 3H), 3.73 (s, 3H), 2.07 (br. s., 1H), 0.90-0.76 (m, 4H) |
| 147 | $^1$H NMR (500 MHz, DMSO-d$_6$) δ 11.03 (s, 1H), 10.18 (s, 1H), 9.10 (s, 1H), 8.33-8.11 (m, 2H), 7.77 (d, J = 8.1 Hz, 2H), 7.71-7.63 (m, 2H), 7.56 (d, J = 8.1 Hz, 1H), 7.41 (t, J = 7.9 Hz, 1H), 4.45 (s, 3H), 3.76 (s, 3H) |
| 148 | $^1$H NMR (500 MHz, DMSO-d$_6$) δ 11.21 (s, 1H), 9.11 (s, 1H), 7.96 (s, 1H), 7.79 (d, J = 7.7 Hz, 1H), 7.64 (d, J = 7.7 Hz, 1H), 7.38 (t, J = 7.9 Hz, 1H), 5.93 (s, 1H), 2.90 (s, 3H), 2.74 (s, 3H), 2.43 (s, 3H), 2.23 (s, 3H) |
| 149 | $^1$H NMR (500 MHz, DMSO-d$_6$) δ 11.36 (s, 1H), 11.05 (s, 1H), 9.17 (s, 1H), 8.14 (s, 1H), 7.69 (t, J = 6.4 Hz, 2H), 7.39 (t, J = 7.9 Hz, 1H), 3.76 (s, 3H), 2.60 (s, 3H), 2.08 (d, J = 4.9 Hz, 1H), 0.89-0.73 (m, 4H) |
| 150 | $^1$H NMR (500 MHz, DMSO-d$_6$) δ 11.04 (s, 1H), 10.09 (s, 1H), 9.11 (s, 1H), 8.08 (s, 1H), 7.98-7.86 (m, 2H), 7.78 (d, J = 7.7 Hz, 1H), 7.70-7.58 (m, 2H), 7.49-7.38 (m, 1H), 3.77 (s, 3H), 2.60 (s, 3H), 2.25 (s, 3H) |
| 151 | $^1$H NMR (500 MHz, DMSO-d$_6$) δ 11.07 (s, 1H), 10.20 (s, 1H), 9.12 (s, 1H), 8.26-8.14 (m, 2H), 7.83 (d, J = 7.3 Hz, 1H), 7.73-7.68 (m, 1H), 7.66 (d, J = 7.9 Hz, 1H), 7.57 (d, J = 7.9 Hz, 1H), 7.47-7.41 (m, 1H), 6.96-6.90 (m, 1H), 3.79 (s, 3H), 2.60 (s, 3H) |
| 152 | $^1$H NMR (500 MHz, DMSO-d$_6$) δ 11.05 (s, 1H), 9.75 (s, 1H), 9.03 (s, 1H), 7.81 (d, J = 7.7 Hz, 2H), 7.64 (d, J = 7.7 Hz, 1H), 7.42 (t, J = 7.9 Hz, 1H), 5.95 (br. s., 1H), 3.78 (s, 3H), 3.58 (s, 3H), 2.61 (s, 3H), 2.20 (s, 3H) |
| 153 | $^1$H NMR (500 MHz, DMSO-d$_6$) δ 11.10 (s, 1H), 10.53 (s, 1H), 9.16 (s, 1H), 8.37 (s, 1H), 7.85 (d, J = 7.7 Hz, 1H), 7.71 (d, J = 7.7 Hz, 1H), 7.44 (t, J = 7.9 Hz, 1H), 7.13 (s, 1H), 3.79 (s, 3H), 2.68-2.59 (m, 3H), 2.37 (s, 3H), 2.31-2.13 (m, 3H) |
| 154 | $^1$H NMR:400 MHz(DMSO-d$_6$) δ = 11.33 (s, 1 H), 10.96 (s, 1 H), 9.20 (q, J = 4.7 Hz, 1 H), 8.10-8.06 (m, 2 H), 8.08 (d, J = 9.5 Hz, 2 H), 7.63 (dd, J = 1.5, 8.0 Hz, 1 H), 7.39 (t, J = 8.0 Hz, 1 H), 3.74 (s, 3 H), 2.87 (d, J = 4.8 Hz, 3 H), 2.79 (s, 3 H), 2.13-2.03 (m, 1 H), 0.87-0.77 (m, 4 H) |
| 155 | $^1$H NMR:400 MHz(DMSO-d$_6$) δ = 11.04-10.99 (s, 1 H), 10.53 (s, 1 H), 9.16 (q, J = 4.5 Hz, 1 H), 8.22 (d, J = 4.0 Hz, 1 H), 8.12 (dd, J = 1.4, 7.9 Hz, 1 H), 7.83-7.72 (m, J = 1.4 Hz, 3 H), 7.50-7.41 (m, 2 H), 7.04-6.99 (m, J = 6.0 Hz, 1 H), 3.78 (s, 3 H), 2.88 (d, J = 4.8 Hz, 3 H), 2.80 (s, 3H) |
| 156 | $^1$H NMR:400 MHz(DMSO-d$_6$) δ = 11.14-11.09 (s, 1 H), 10.54 (s, 1H), 9.14 (d, J = 4.8 Hz, 1 H), 8.26 (d, J = 4.6 |

| Compound | ¹H NMR (methanol-d₄ equates CDCl₃:MeOD ~1:1 unless otherwise noted) Occasionally water suppression is used in DMSO-d₆ spectra |
|---|---|
| 157 | Hz, 1 H), 7.85-7.76 (m, 8.0 Hz, 3 H), 7.71 (dd, J = 1.4, 7.9 Hz, 1 H), 7.52-7.43 (m, 2 H), 7.02 (t, J = 6.1 Hz, 1 H), 3.80 (s, 3 H), 2.87 (d, J = 4.8 Hz, 3 H), 2.61 (s, 3 H) |
| 158 | ¹H NMR (500 MHz, DMSO-d₆) δ 11.13 (s, 1H), 9.23 (s, 1H), 9.15 (s, 1H), 8.33-8.18 (m, 2H), 8.00 (d, J = 7.7 Hz, 1H), 7.55 (d, J = 7.7 Hz, 1H), 7.46-7.28 (m, 3H), 7.10 (d, J = 5.0 Hz, 1H), 4.76 (d, J = 6.4 Hz, 1H), 3.68 (s, 3H), 1.33 (d, J = 6.4 Hz, 3H) |
| | ¹H NMR (400 MHz, DMSO-d₆) δ 11.00 (s, 1H), 10.59 (s, 1H), 9.13 (s, 1H), 8.96 (s, 1H), 8.95 (s, 1H), 8.42 (s, 1H), 8.35 (d, J = 5.9 Hz, 1H), 7.78-7.70 (m, 1H), 7.55 (dd, J = 7.9, 1.5 Hz, 1H), 7.52 (t, J = 5.0 Hz, 1H), 7.36 (t, J = 7.9 Hz, 1H), 7.24 (d, J = 5.7 Hz, 1H), 3.70 (s, 3H), 2.42 (s, 3H) |
| 159 | N/A |
| 160 | ¹H NMR (500 MHz, DMSO-d₆) δ 11.34 (s, 1H), 10.96 (s, 1H), 9.16 (s, 1H), 8.16 (s, 1H), 8.12 (s, 1H), 7.60 (d, J = 7.4 Hz, 1H), 7.42 (d, J = 7.7 Hz, 1H), 7.32-7.19 (m, 1H), 3.61 (s, 3H), 2.68 (s, 3H), 2.17-1.96 (m, 1H), 0.93-0.69 (m, 4H) |
| 161 | ¹H NMR (500 MHz, DMSO-d₆) δ 10.92 (s, 1H), 9.70 (s, 1H), 9.02 (s, 1H), 8.16 (s, 1H), 7.73 (br. s., 1H), 7.55 (dd, J = 19.0, 7.9 Hz, 2H), 7.36-7.25 (m, 1H), 5.94 (br. s., 1H), 3.63 (s, 3H), 3.56 (s, 3H), 2.69 (s, 3H), 2.18 (s, 3H) |
| 165 | ¹H NMR (500 MHz, DMSO-d₆) δ 10.96 (s, 1H), 10.18 (s, 1H), 9.09 (s, 1H), 8.33 (d, J = 4.3 Hz, 1H), 8.23 (s, 1H), 8.19 (d, J = 3.7 Hz, 1H), 7.74-7.68 (m, 1H), 7.65 (d, J = 6.7 Hz, 1H), 7.55 (d, J = 7.9 Hz, 1H), 7.29-7.24 (m, 1H), 7.23-7.19 (m, 1H), 6.96-6.89 (m, 1H), 3.72 (s, 3H), 2.91-2.81 (m, 1H), 0.75-0.65 (m, 2H), 0.59-0.50 (m, 2H) |
| 166 | ¹H NMR (500 MHz, DMSO-d₆) δ 10.98 (s, 1H), 10.19 (s, 1H), 9.11 (s, 1H), 8.26 (t, J = 5.5 Hz, 1H), 8.22 (s, 1H), 8.19 (d, J = 4.9 Hz, 1H), 7.75-7.65 (m, 2H), 7.55 (d, J = 8.5 Hz, 1H), 7.45 (d, J = 6.7 Hz, 1H), 7.32 (t, J = 7.6 Hz, 1H), 6.96-6.87 (m, 1H), 3.76 (s, 3H), 3.27 (d, J = 5.5 Hz, 2H), 3.16 (d, J = 4.9 Hz, 1H), 1.15 (s, 6H) |
| 167 | ¹H NMR (500 MHz, DMSO-d₆) δ 10.96 (s, 1H), 10.18 (s, 1H), 9.09 (s, 1H), 8.30 (t, J = 5.8 Hz, 1H), 8.22 (s, 1H), 8.19 (d, J = 4.9 Hz, 1H), 7.73-7.67 (m, 1H), 7.66 (dd, J = 6.7, 2.4 Hz, 1H), 7.55 (d, J = 7.9 Hz, 1H), 7.31-7.23 (m, 2H), 6.96-6.88 (m, 1H), 3.73 (s, 3H), 3.25 (q, J = 6.7 Hz, 2H), 3.16 (d, J = 4.9 Hz, 1H), 1.56-1.46 (m, 2H), 1.37-1.18 (m, 6H), 0.90-0.82 (m, 3H) |
| 168 | ¹H NMR (500 MHz, DMSO-d₆) δ 10.95 (s, 1H), 10.18 (s, 1H), 9.09 (s, 1H), 8.38 (t, J = 5.5 Hz, 1H), 8.24-8.16 (m, 2H), 7.73-7.64 (m, 2H), 7.55 (d, J = 8.5 Hz, 1H), 7.36-7.32 (m, 1H), 7.31-7.26 (m, 1H), 6.95-6.90 (m, 1H), 3.73 (s, 3H), 3.16 (d, J = 5.5 Hz, 2H), 1.67-1.60 (m, 2H), 1.14 (s, 6H) |
| 169 | ¹H NMR (500 MHz, DMSO-d₆) δ 10.98 (s, 1H), 10.33 (br. s., 1H), 9.08 (s, 1H), 8.30-8.15 (m, 2H), 8.06 (br. s., |

| Compound | ¹H NMR (methanol-d₄ equates CDCl₃:MeOD ~1:1 unless otherwise noted) Occasionally water suppression is used in DMSO-d₆ spectra |
|---|---|
| | 1H), 7.81-7.70 (m, 1H), 7.66 (dd, J = 7.9, 1.5 Hz, 1H), 7.53 (d, J = 8.6 Hz, 1H), 7.35-7.31 (m, 1H), 7.31-7.26 (m, 1H), 7.00-6.93 (m, 1H), 3.74 (s, 3H), 2.80 (d, J = 4.4 Hz, 3H) |
| 170 | ¹H NMR (500 MHz, DMSO-d₆) δ 10.97 (s, 1H), 10.18 (s, 1H), 9.10 (s, 1H), 8.34 (s, 1H), 8.26-8.13 (m, 2H), 7.74-7.62 (m, 2H), 7.56 (d, J = 8.5 Hz, 1H), 7.36-7.24 (m, 2H), 6.97-6.87 (m, 1H), 4.15-4.03 (m, 2H), 3.74 (s, 3H), 3.50 (d, J = 5.5 Hz, 2H), 1.68 (t, J = 6.4 Hz, 2H) |
| 171 | ¹H NMR (500 MHz, DMSO-d₆) δ 11.01 (s, 1H), 10.19 (s, 1H), 9.10 (s, 1H), 8.97 (t, J = 6.4 Hz, 1H), 8.24 (s, 1H), 8.19 (d, J = 4.3 Hz, 1H), 7.76-7.67 (m, 2H), 7.55 (d, J = 8.5 Hz, 1H), 7.37-7.29 (m, 2H), 6.97-6.84 (m, 1H), 4.13 (d, J = 4.9 Hz, 2H), 3.73 (s, 3H) |
| 175 | ¹H NMR (500 MHz, DMSO-d₆) δ 11.34 (s, 1H), 10.99 (s, 1H), 9.12 (s, 1H), 8.66 (s, 1H), 8.11 (s, 1H), 7.94 (s, 1H), 7.68 (d, J = 7.4 Hz, 1H), 7.52 (d, J = 7.7 Hz, 1H), 7.28 (t, J = 7.9 Hz, 1H), 4.97-4.74 (m, 2H), 4.67-4.50 (m, 2H), 3.71 (s, 3H), 2.06 (d, J = 5.4 Hz, 1H), 0.92-0.66 (m, 4H) |
| 176 (major regio- isomer only) | ¹H NMR (500 MHz, DMSO-d₆) δ 11.31 (s, 1H), 10.97 (s, 1H), 9.11 (s, 1H), 8.68 (s, 1H), 8.14 (s, 1H), 7.66 (d, J = 7.7 Hz, 1H), 7.53 (d, J = 7.7 Hz, 1H), 7.34-7.24 (m, 1H), 6.66-6.29 (m, 1H), 4.82 (td, J = 15.3, 3.0 Hz, 2H), 3.70 (s, 3H), 2.14-1.96 (m, 1H), 0.89-0.70 (m, 5H) |
| 177 | ¹H NMR (500 MHz, DMSO-d₆) δ 10.98 (s, 1H), 10.15 (s, 1H), 9.07 (s, 1H), 8.60 (s, 1H), 8.23 (s, 1H), 8.19 (d, J = 4.4 Hz, 1H), 7.75-7.60 (m, 3H), 7.56 (d, J = 8.4 Hz, 1H), 7.31 (t, J = 7.9 Hz, 1H), 6.99-6.83 (m, 1H), 4.27 (q, J = 7.4 Hz, 2H), 3.74 (s, 3H), 1.45 (t, J = 7.2 Hz, 3H) |
| 178 | ¹H NMR (500 MHz, DMSO-d₆) δ 11.04 (s, 1H), 10.21 (s, 1H), 9.11 (s, 1H), 8.24 (s, 1H), 8.23-8.19 (m, 1H), 8.08 (s, 1H), 7.79 (dd, J = 7.9, 1.2 Hz, 1H), 7.74-7.67 (m, 1H), 7.56 (d, J = 7.9 Hz, 1H), 7.41 (t, J = 7.9 Hz, 1H), 7.27 (dd, J = 7.3, 1.2 Hz, 1H), 6.93 (dd, J = 6.7, 5.5 Hz, 1H), 3.74 (s, 3H), 3.47 (s, 3H) |
| 179 | ¹H NMR (500 MHz, DMSO-d₆) δ 11.36 (s, 1H), 10.96 (s, 1H), 9.15 (s, 1H), 8.08 (d, J = 8.5 Hz, 2H), 7.95 (s, 1H), 7.64 (d, J = 7.3 Hz, 1H), 7.39-7.33 (m, 1H), 7.33-7.28 (m, 1H), 3.73 (s, 3H), 3.42 (s, 3H), 2.07 (br. s., 1H), 0.88-0.77 (m, 4H) |
| 180 | ¹H NMR (500 MHz, DMSO-d₆) δ 11.01 (s, 1H), 10.11 (s, 1H), 9.11 (s, 1H), 8.09 (d, J = 17.1 Hz, 2H), 7.93 (d, J = 4.3 Hz, 2H), 7.75 (d, J = 8.5 Hz, 1H), 7.62 (d, J = 5.5 Hz, 1H), 7.41 (t, J = 7.6 Hz, 1H), 7.26 (d, J = 7.9 Hz, 1H), 3.73 (s, 3H), 2.88 (s, 3H), 2.72 (s, 3H) |
| 183 | ¹H NMR (500 MHz, DMSO-d₆) δ 11.42 (br. s., 1H), 11.05 (s, 1H), 9.19 (s, 1H), 8.12 (br. s., 1H), 7.66 (d, J = 7.9 Hz, 1H), 7.60 (d, J = 7.9 Hz, 1H), 7.39 (br. s., 1H), 7.30 (t, J = 7.9 Hz, 1H), 3.84 (s, 3H), 3.73 (s, 3H), 2.45 (d, J = 6.1 Hz, 6H) |

| Compound | ¹H NMR (methanol-d₄ equates CDCl₃:MeOD ~1:1 unless otherwise noted) Occasionally water suppression is used in DMSO-d₆ spectra |
|---|---|
| 184 | ¹H NMR (500 MHz, DMSO-d₆) δ 11.28 (br. s., 1H), 11.11 (s, 1H), 9.20 (s, 1H), 8.18 (br. s., 1H), 7.77 (d, J = 7.9 Hz, 1H), 7.38 (t, J = 7.6 Hz, 2H), 7.30 (d, J = 7.3 Hz, 1H), 3.65 (s, 3H), 3.47 (br. s., 3H), 2.51 (s, 3H), 2.43 (s, 3H), 2.29 (s, 3H) |
| 187 | ¹H NMR (500 MHz, DMSO-d₆) δ 11.29 (s, 1H), 10.93 (s, 1H), 9.11 (s, 1H), 8.27 (s, 1H), 8.12 (s, 1H), 8.03 (s, 1H), 7.46 (d, J = 7.3 Hz, 1H), 7.30 (d, J = 7.3 Hz, 1H), 7.23-7.15 (m, 1H), 6.61-6.20 (m, 1H), 4.77-4.56 (m, 2H), 3.57 (s, 3H), 2.05 (br. s., 1H), 0.91-0.68 (m, 4H) |
| 188 | ¹H NMR (500 MHz, DMSO-d₆) δ 11.31 (s, 1H), 10.95 (s, 1H), 9.13 (s, 1H), 8.34 (s, 1H), 8.15-8.04 (m, 2H), 7.48 (d, J = 7.3 Hz, 1H), 7.32 (d, J = 7.9 Hz, 1H), 7.25-7.14 (m, 1H), 5.20 (q, J = 9.2 Hz, 2H), 3.57 (s, 3H), 2.06 (t, J = 5.2 Hz, 1H), 0.87-0.69 (m, 4H) |
| 189 | ¹H NMR (500 MHz, DMSO-d₆) δ 11.31 (s, 1H), 10.96 (s, 1H), 9.11 (s, 1H), 8.15 (s, 1H), 8.09 (d, J = 4.3 Hz, 1H), 7.93 (s, 1H), 7.92 (s, 1H), 7.45 (d, J = 7.9 Hz, 1H), 7.27 (d, J = 7.3 Hz, 1H), 7.22-7.16 (m, 1H), 4.06 (s, 2H), 2.04 (br. s., 1H), 1.08 (s, 6H), 0.86-0.71 (m, 4H |
| 192 | ¹H NMR (500 MHz, DMSO-d₆) δ 10.98 (s, 1H), 9.14 (s, 1H), 8.25 (s, 1H), 8.14 (s, 1H), 7.81 (d, J = 7.7 Hz, 1H), 7.44 (d, J = 7.7 Hz, 1H), 7.29 (t, J = 7.9 Hz, 1H), 3.63 (s, 3H), 2.06 (t, J = 4.7 Hz, 1H), 0.90-0.69 (m, 4H) |
| 193 | ¹H NMR (500 MHz, DMSO-d₆) δ 11.14 (s, 1H), 9.08 (br. s., 1H), 8.28 (br. s., 1H), 7.86 (br. s., 1H), 7.55 (d, J = 7.7 Hz, 2H), 7.36 (t, J = 7.7 Hz, 1H), 5.92 (br. s., 1H), 3.67 (s, 3H), 3.61 (s, 3H), 2.21 (s, 3H) |
| 197 | ¹H NMR (500 MHz, DMSO-d₆) δ 11.12 (s, 1H), 10.68 (br. s., 1H), 9.12 (s, 1H), 8.28 (d, J = 4.3 Hz, 1H), 7.82 (t, J = 7.9 Hz, 2H), 7.69 (d, J = 7.9 Hz, 1H), 7.52 (d, J = 1.2 Hz, 1H), 7.45 (d, J = 8.5 Hz, 1H), 7.37 (t, J = 7.6 Hz, 1H), 7.20 (d, J = 6.7 Hz, 1H), 7.05 (t, J = 6.1 Hz, 1H), 6.40 (d, J = 1.2 Hz, 1H), 3.70 (s, 3H), 3.41 (br. s., 3H) |
| 198 (major regio-isomer only) | ¹H NMR (500 MHz, DMSO-d₆) δ 11.01 (s, 1H), 10.48 (s, 1H), 9.12 (br. s., 2H), 8.39 (br. s., 1H), 7.81-7.63 (m, 2H), 7.53 (d, J = 8.1 Hz, 1H), 7.25 (t, J = 7.9 Hz, 1H), 7.15-7.05 (m, 1H), 6.73 (s, 1H), 3.90 (s, 3H), 3.61 (s, 3H), 2.37 (s, 3H), 2.34-2.24 (m, 3H) |
| 199 | ¹H NMR (500 MHz, DMSO-d₆) δ 11.16 (br. s., 1H), 9.14 (br. s., 1H), 8.18 (br. s., 1H), 7.66 (d, J = 8.8 Hz, 2H), 7.52 (br. s., 1H), 7.43 (br. s., 1H), 7.37 (d, J = 8.1 Hz, 1H), 7.22 (br. s., 1H), 6.40 (br. s., 1H), 3.70 (s, 3H), 3.40 (br. s., 3H), 2.29 (br. s., 3H) |

SEQUENCE LISTING

This application includes a Sequence Listing submitted electronically as an ASCII text file via EFS-Web. The text file, created Nov. 18, 2019, is named 20191118_SEQT_12052USCNT3.txt and is 3 KB in size. The material in the ASCII text file is hereby incorporated by reference in its entirety herein.

---

What is claimed is:

1. A method of treating psoriasis in a subject, the method comprising orally administering to the subject a composition comprising a compound of the following formula:

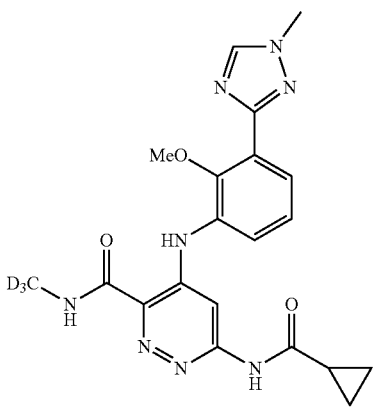

which is 6-(cyclopropaneamido)-4-((2-methoxy-3-(1-methyl-1H-1,2,4-triazol-3-yl)phenyl)amino)-N-(methyl-d3)pyridazine-3-carboxamide.

2. The method according to claim 1, wherein the composition is in the form of a tablet, a capsule, granules, a powder, or a liquid formulation.

3. The method according to claim 2, wherein the composition is in the form of a tablet.

4. The method according to claim 2, wherein the composition is in the form of a capsule.

5. The method according to claim 2, wherein the composition is in the form of granules.

6. The method according to claim 2, wherein the composition is in the form of a powder.

7. The method according to claim 2, wherein the composition is in the form of a liquid formulation.

8. The method according to claim 7, wherein the composition is in the form of a syrup.

9. The method according to claim 1, wherein the composition is orally administered to the subject 1 to 4 times per day.

10. The method according to claim 9, wherein the composition is in the form of a tablet.

11. A method of treating psoriasis in a subject, the method comprising orally administering to the subject, 1 to 2 times per day, a tablet comprising a compound of the following formula:

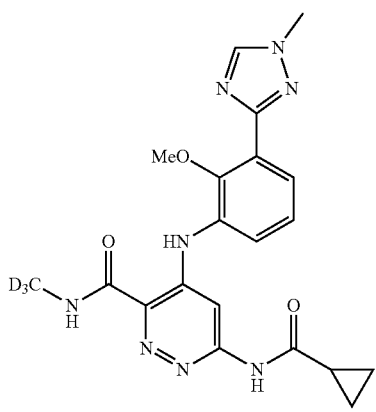 [SMILES: [2H]C([2H])([2H])NC(=O)c1nnc(NC(=O)C2CC2)cc1Nc1cccc(-c2ncn(C)n2)c1OC]

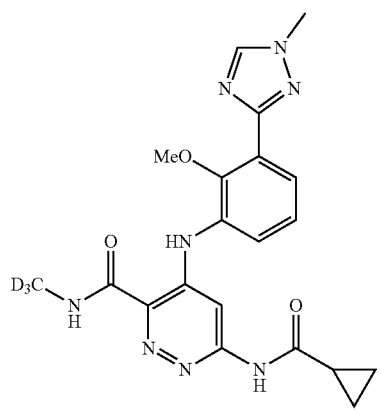 [SMILES: [2H]C([2H])([2H])NC(=O)c1nnc(NC(=O)C2CC2)cc1Nc1cccc(-c2ncn(C)n2)c1OC]

which is 6-(cyclopropaneamido)-4-((2-methoxy-3-(1-methyl-1H-1,2,4-triazol-3-yl)phenyl)amino)-N-(methyl-d3)pyridazine-3-carboxamide.

12. The method according to claim 11, wherein 1 tablet per day is administered to the subject.

13. The method according to claim 11, wherein 2 tablets per day are administered to the subject.

14. A method of treating psoriasis in a subject, the method comprising orally administering to the subject, 1 to 2 times per day, a tablet comprising a pharmaceutically acceptable salt of a compound of the following formula:

which is 6-(cyclopropaneamido)-4-((2-methoxy-3-(1-methyl-1H-1,2,4-triazol-3-yl)phenyl)amino)-N-(methyl-d3)pyridazine-3-carboxamide.

15. The method according to claim 14, wherein 1 tablet per day is administered to the subject.

16. The method according to claim 14, wherein 2 tablets per day are administered to the subject.

\* \* \* \* \*

SEQUENCE LISTING

<160> NUMBER OF SEQ ID NOS: 1

<210> SEQ ID NO 1
<211> LENGTH: 317
<212> TYPE: PRT
<213> ORGANISM: Homo sapiens

<400> SEQUENCE: 1

Met Gly Ser Ser His His His His His His Ser Ser Gly Glu Thr Val
1               5                   10                  15

Arg Phe Gln Gly His Met Asn Leu Ser Gln Leu Ser Phe His Arg Val
            20                  25                  30

Asp Gln Lys Glu Ile Thr Gln Leu Ser His Leu Gly Gln Gly Thr Arg
        35                  40                  45

Thr Asn Val Tyr Glu Gly Arg Leu Arg Val Glu Gly Ser Gly Asp Pro
    50                  55                  60

Glu Glu Gly Lys Met Asp Asp Glu Asp Pro Leu Val Pro Gly Arg Asp
65                  70                  75                  80

-continued

```
Arg Gly Gln Glu Leu Arg Val Val Leu Lys Val Leu Asp Pro Ser His
                85                      90                  95

His Asp Ile Ala Leu Ala Phe Tyr Glu Thr Ala Ser Leu Met Ser Gln
            100                 105                 110

Val Ser His Thr His Leu Ala Phe Val His Gly Val Cys Val Arg Gly
        115                 120                 125

Pro Glu Asn Ile Met Val Thr Glu Tyr Val Glu His Gly Pro Leu Asp
        130                 135                 140

Val Trp Leu Arg Arg Glu Arg Gly His Val Pro Met Ala Trp Lys Met
145                 150                 155                 160

Val Val Ala Gln Gln Leu Ala Ser Ala Leu Ser Tyr Leu Glu Asn Lys
                165                 170                 175

Asn Leu Val His Gly Asn Val Cys Gly Arg Asn Ile Leu Leu Ala Arg
            180                 185                 190

Leu Gly Leu Ala Glu Gly Thr Ser Pro Phe Ile Lys Leu Ser Asp Pro
        195                 200                 205

Gly Val Gly Leu Gly Ala Leu Ser Arg Glu Glu Arg Val Glu Arg Ile
    210                 215                 220

Pro Trp Leu Ala Pro Glu Cys Leu Pro Gly Gly Ala Asn Ser Leu Ser
225                 230                 235                 240

Thr Ala Met Asp Lys Trp Gly Phe Gly Ala Thr Leu Leu Glu Ile Cys
                245                 250                 255

Phe Asp Gly Glu Ala Pro Leu Gln Ser Arg Ser Pro Ser Glu Lys Glu
            260                 265                 270

His Phe Tyr Gln Arg Gln His Arg Leu Pro Glu Pro Ser Cys Pro Gln
        275                 280                 285

Leu Ala Thr Leu Thr Ser Gln Cys Leu Thr Tyr Glu Pro Thr Gln Arg
        290                 295                 300

Pro Ser Phe Arg Thr Ile Leu Arg Asp Leu Thr Arg Leu
305                 310                 315
```